US012565498B2

(12) United States Patent
Yang et al.

(10) Patent No.: US 12,565,498 B2
(45) Date of Patent: Mar. 3, 2026

(54) β-LACTAMASE INHIBITORS AND THEIR PREPARATION

(71) Applicant: NINGXIA ACADEMY OF AGRICULTURE AND FORESTRY SCIENCES, Ningxia (CN)

(72) Inventors: Zhixiang Yang, Ningxia (CN); Haikang Yang, Ningxia (CN); Jinbo Ji, Ningxia (CN); Yuanyu Gao, Ningxia (CN); Dong Tang, Ningxia (CN); Lijuan Zhai, Ningxia (CN); Zafar Iqbal, Ningxia (CN); Jian Sun, Ningxia (CN); Jingwen Ji, Ningxia (CN); Yangxiu Mu, Ningxia (CN); Lili He, Ningxia (CN); Yuanbai Liu, Ningxia (CN); Xueqin Ma, Ningxia (CN); Jianqiang Yu, Ningxia (CN)

(73) Assignee: NINGXIA ACADEMY OF AGRICULTURE AND FORESTRY SCIENCES, Ningxia (CN)

( * ) Notice: Subject to any disclaimer, the term of this patent is extended or adjusted under 35 U.S.C. 154(b) by 457 days.

(21) Appl. No.: 18/006,295

(22) PCT Filed: Sep. 1, 2020

(86) PCT No.: PCT/CN2020/112758

§ 371 (c)(1),
(2) Date: Jan. 20, 2023

(87) PCT Pub. No.: WO2022/047603

PCT Pub. Date: Mar. 10, 2022

(65) Prior Publication Data

US 2023/0365561 A1 Nov. 16, 2023

(51) Int. Cl.

| | |
|---|---|
| ***C07D 471/08*** | (2006.01) |
| ***A61K 45/06*** | (2006.01) |
| ***A61P 31/04*** | (2006.01) |
| *A61K 31/407* | (2006.01) |
| *A61K 31/439* | (2006.01) |
| *A61K 31/444* | (2006.01) |
| *A61K 31/4545* | (2006.01) |
| *A61K 31/501* | (2006.01) |
| *A61K 31/506* | (2006.01) |

(52) U.S. Cl.

CPC ............ *C07D 471/08* (2013.01); *A61K 45/06* (2013.01)

(58) Field of Classification Search

CPC .............................. C07D 471/08; A61P 31/04
See application file for complete search history.

(56) References Cited

FOREIGN PATENT DOCUMENTS

| | | | | |
|---|---|---|---|---|
| CN | 1655781 A | | 8/2005 | |
| WO | WO 2003063864 A2 | | 8/2003 | |
| WO | WO 2013030733 A1 | | 3/2013 | |
| WO | WO 2014141132 A1 | | 9/2014 | |
| WO | WO 2015110966 A1 | | 7/2015 | |
| WO | WO 2015150926 A1 | | 10/2015 | |
| WO | WO-2016116788 A1 | * | 7/2016 | .............. A61P 31/04 |
| WO | WO 2017045510 A1 | | 3/2017 | |

OTHER PUBLICATIONS

Kapoor G, Saigal S, Elongavan A. Action and resistance mechanisms of antibiotics: A guide for clinicians. J Anaesthesiol Clin Pharmacol. Jul.-Sep. 2017;33(3):300-305. doi: 10.4103/joacp.JOACP_349_15. PMID: 29109626; PMCID: PMC5672523. (Year: 2017).*

* cited by examiner

*Primary Examiner* — Bruck Kifle
*Assistant Examiner* — Kevin S Martin
(74) *Attorney, Agent, or Firm* — Haynes and Boone, LLP

(57) ABSTRACT

β-lactamase inhibitors, pharmaceutical compositions including the same, methods of preparing the same, and methods of treating bacterial infections in combination with β-lactam antibiotics, including infection caused by drug resistant organisms and especially multi-drug resistant organisms. The present invention includes compounds according to formula (I) or pharmaceutically acceptable salts thereof, wherein M and R are as defined herein.

[I]

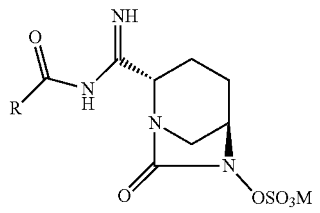

13 Claims, No Drawings

β-LACTAMASE INHIBITORS AND THEIR PREPARATION

CROSS-REFERENCE TO RELATED APPLICATION

This application claims priority to PCT International Application No. PCT/CN2020/112758, filed Sep. 1, 2020, the entire contents of which is hereby incorporated herein in its entirety by express reference thereto.

FIELD OF THE INVENTION

This invention relates to novel beta-lactamase inhibitors and their preparation and their use as antibacterial agents either alone or in combination with an antibiotic (or plural antibiotics) for the treatment of infections caused by β-lactamase-producing pathogenic bacteria. More particularly, the invention relates to compositions and methods for overcoming bacterial antibiotic resistance.

BACKGROUND OF THE INVENTION

Microbial drug resistance to β-lactam antibiotics, especially in Gram-negative bacterial, is most commonly mediated by β-lactamases. β-lactamases are enzymes that catalyze the hydrolysis of the β-lactam ring, which inactivate the antibacterial activity of the β-lactam antibiotic and allow the bacterial to become resistant. Inhibition of the β-lactamase with a β-lactamases inhibitor slows or prevents degradation of the β-lactam antibiotic and restores β-lactam antibiotic susceptibility to β-lactamase producing bacteria. Many of these β-lactamases are not effectively inhibited by β-lactamase inhibitors currently on the market rendering the β-lactam antibiotics ineffective in treating bacteria that producing these β-lactamases. There is an urgent need for novel β-lactamase inhibitors that inhibit β-lactamases that are not effectively inhibited by the current clinical β-lactamases (e.g. KPC, class C and class D β-lactamases) and that could be used in combination with β-lactam antibiotics to treat infection caused by β-lactam resistant bacteria.

Recently, certain diazabicyclic compounds have been disclosed in WO 2009/091856 which is hereby incorporated by reference in its entirety. In addition, a number of diazabicyclic heterocycles have been disclosed in the following patents or applications as β-lactamase inhibitors: US 2003/0199541 A1, US 2004/0157826 A1, US 2004/0097490 A1, US 2005/0020572 A1, US 2006/7112592 B2, US 2006/0189652 A1, US 2008/7439253 B2, US 2009/0018329 A1, EP 1307457 B1, EP 1537117 B1, WO 2002/100860 A2, WO 2002/10172 A1, WO 2003/063864 A2, WO 2004/052891 A1, WO 2004/022563 A1, WO 2008/142285 A1, WO 2009/090320 A1, US 2010/0092443 A1, WO 2010/126820 A2, WO 2013/038330 A1, US 2015/0031666 A1, US 2015/0239840 A1, US 2016/0297817 A1, US2016/0002235 A1, WO 2017037607 A1, WO 2018053057 A2, WO 2018053215 A1.

DETAILED DESCRIPTION OF THE INVENTION

In one aspect, the present invention relates to new diazabicyclic compounds (some of which have potent broad-spectrum β-lactamase inhibitory activity and others do not have such activity) that when used in combination with a β-lactam antibiotic or with other non β-lactam antibiotic enhance the activity of the antibiotic against class A, class B, class C, and class D enzyme producing organisms and thereby enhance the antibacterial properties. The inventive compounds are therefore useful in the treatment of bacterial infections in humans or animals either alone or in combination with β-lactam antibiotics.

In accordance with the present invention, there are provided (A) new compounds of general formula (I), (B) pharmaceutically acceptable salts of the compounds of formula (I), and (C) pharmaceutically acceptable solvates of the compounds of formula (I) and of their salts, and (D) deuterated compounds of compounds of (A), (B) and (C), (namely, (i) compounds of formula (I) modified in that they have been deuterated, (ii) pharmaceutically acceptable salts of the compounds of formula (I) modified in that they have been deuterated, (iii) pharmaceutically acceptable solvates of the compounds of formula (I) and of their salts modified in that they have been deuterated):

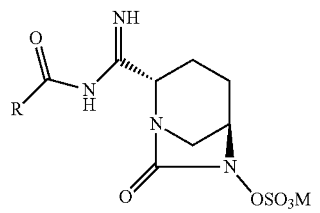

[I]

wherein:

M is hydrogen or a pharmaceutically acceptable salt forming cation,

- a "pharmaceutically acceptable salt" refers to a salt of a compound, which salt possesses the desired pharmacological activity of the parent compound,
- specified compounds "modified in that they have been deuterated" refer to compounds prepared by modifying the specified compounds so that one or more hydrogen atoms in the compound have been replaced with or converted to deuterium, R is optionally substituted with one or two substituents independently selected from the following:

- Lower alkyl, amino, substituted amino, alkoxy, hydroxyalkyl, halogen, hydroxy, carboxy, alkoxycarbonyl, haloalkyl, trifluoromethyl, trifluoromethyloxy, alkylamine, substituted alkylamine, carboxamide, thiocarboxamide, sulfonic acid, sulphate, acylamino, sulfonylamino, substituted or unsubstituted sulfonamide, substituted or unsubstituted urea, substituted or unsubstituted thiourea, oxyimino, hydroxamic acid, acyl, trifluoromethyl carbonyl, cyano, amidino, guanidino, aryloxy, heterocyclylalkyloxy, and heteroaryloxy.

The compounds of the present invention are new and the structural features are significantly distinct from the compounds described in the prior art.

In the formula (I), R is a radical selected from any of the following groups:
(1) $C_{1-6}$ straight, branched chain which is optionally substituted. Non-limiting examples of such compounds are:
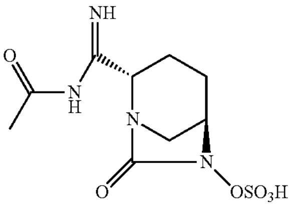
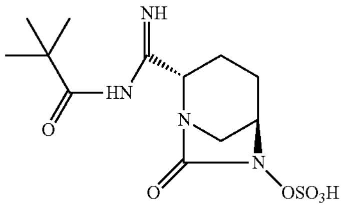
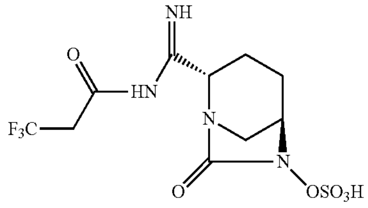
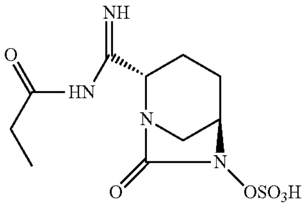
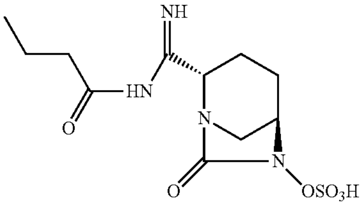
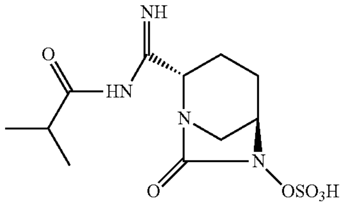
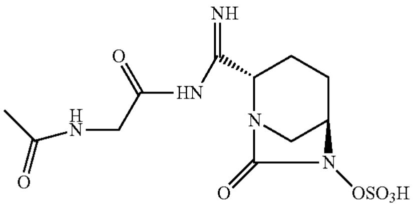
-continued
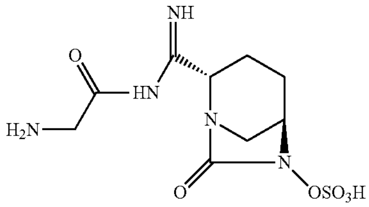
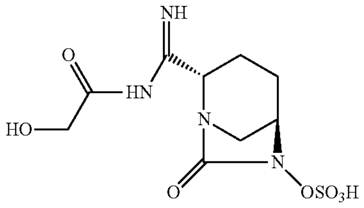
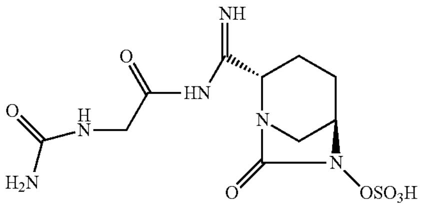
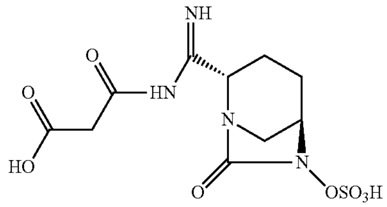
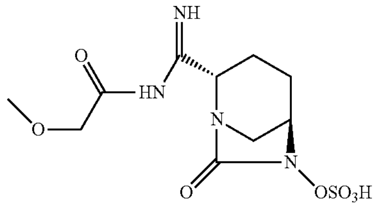
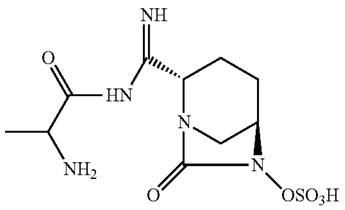
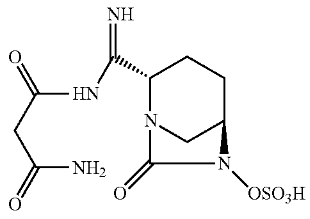
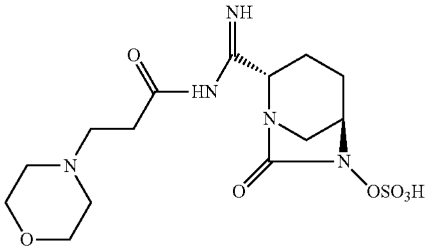

-continued
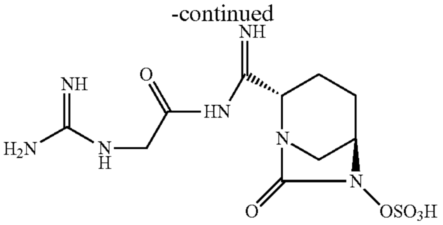
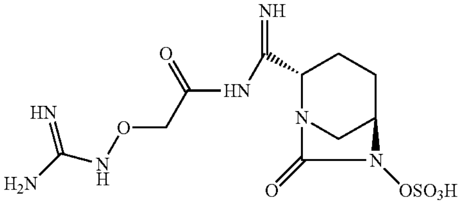
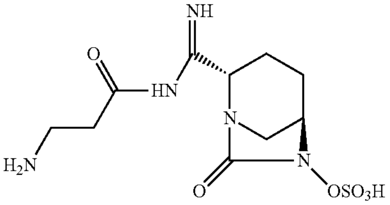
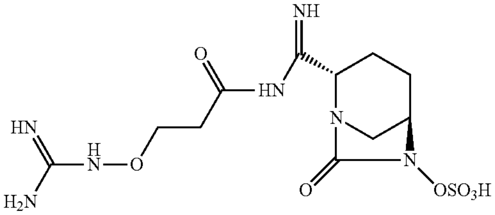
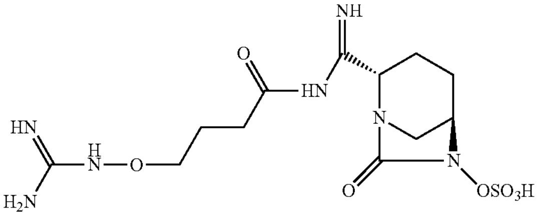
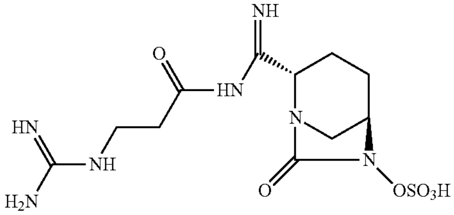
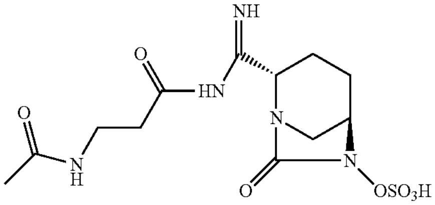
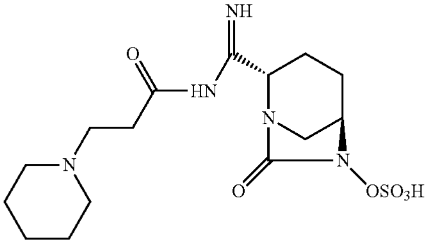
-continued
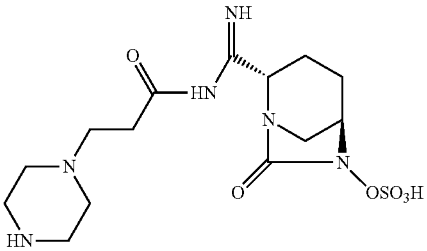
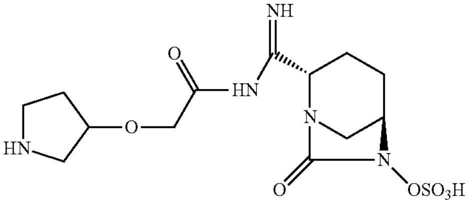
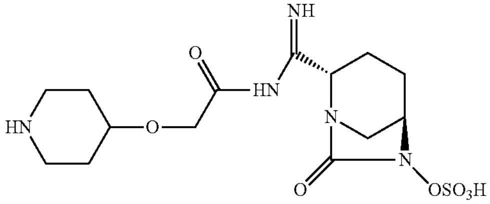
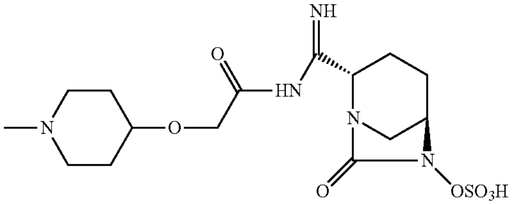
(2) $C_{3-7}$cycloalkyl which is optionally substituted. Non-limiting examples of such compounds are:
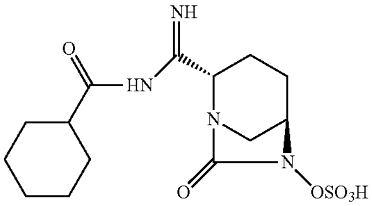
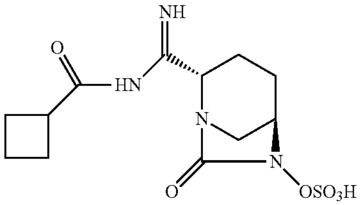
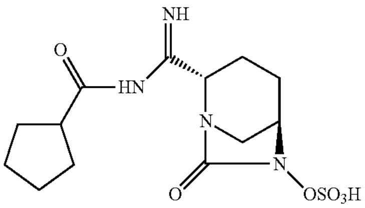

-continued
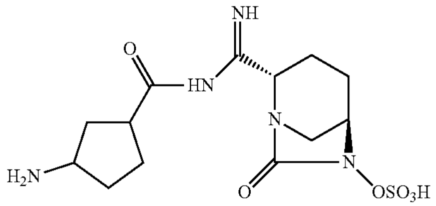
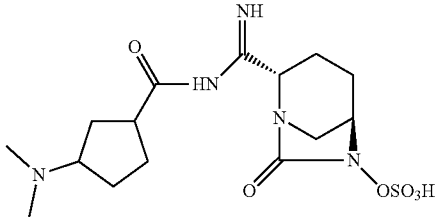
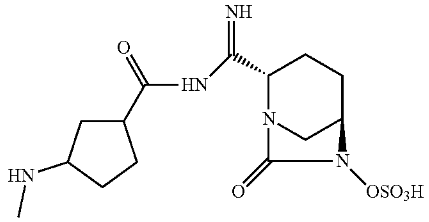
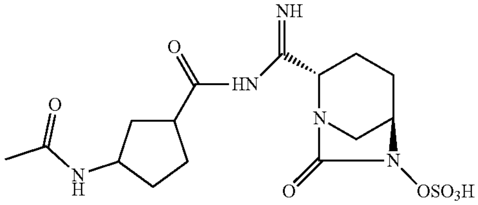
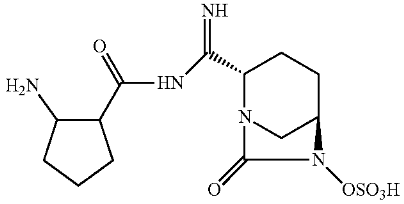
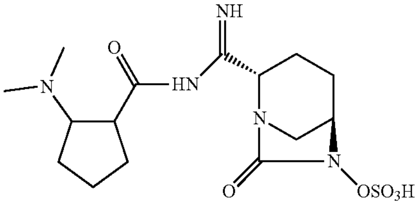
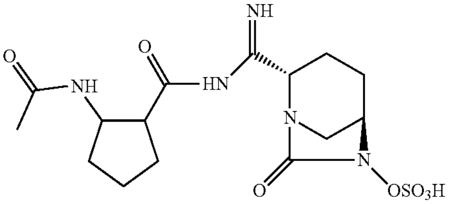
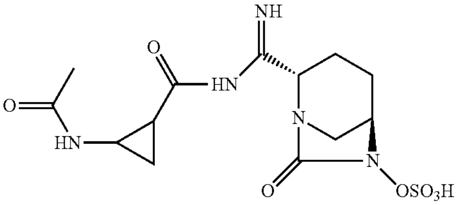
-continued
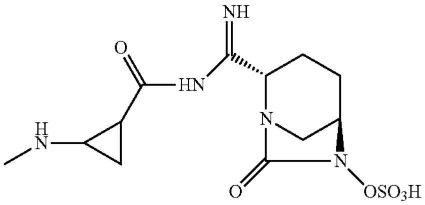
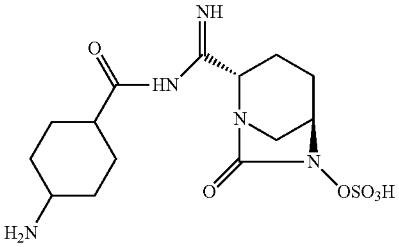
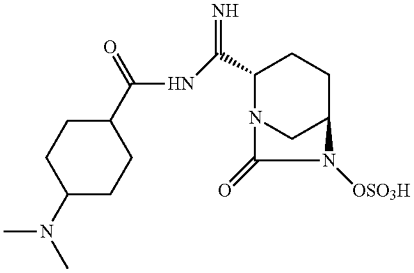
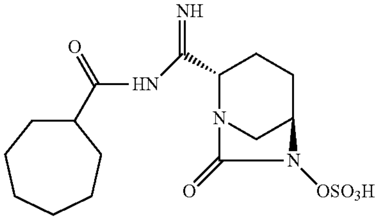
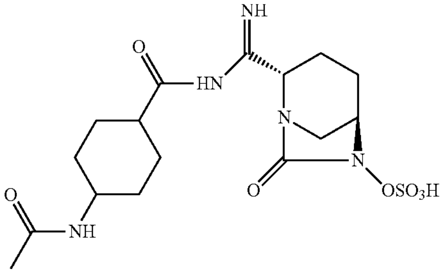
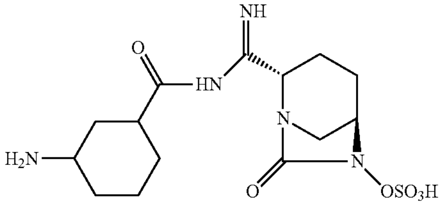
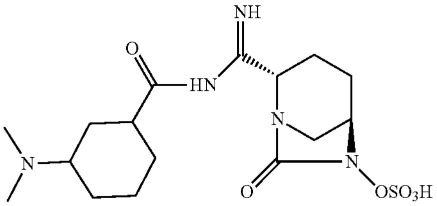

-continued
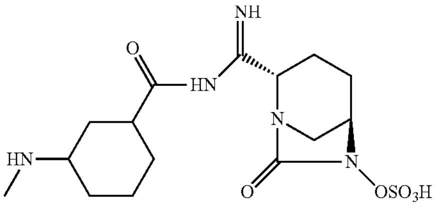
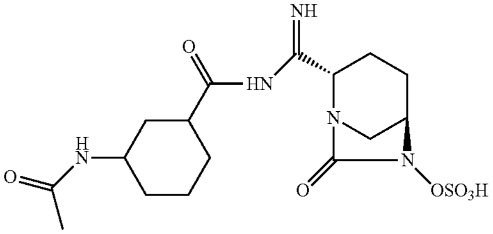
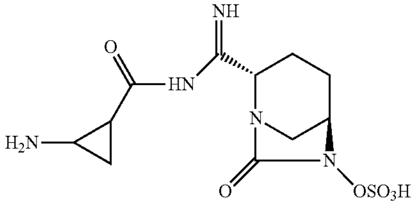
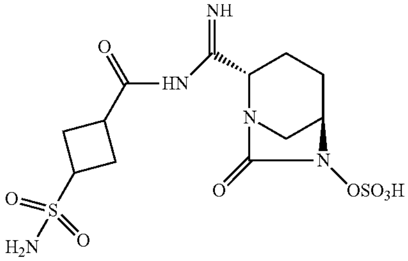
(3) $C_{4-7}$ saturated heterocycles containing at least one heteroatom selected from O, N and S wherein the said heterocycle is optionally substituted. Furthermore the ring S is optionally oxidized to S(O) or $S(O)_2$ and the free ring N atom may optionally take a substituent. Non-limiting examples of such compounds are:
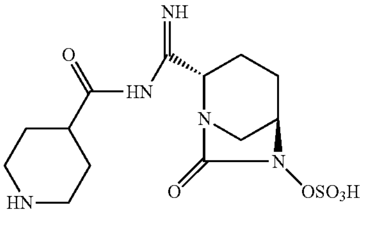
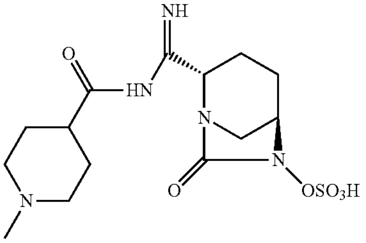
-continued
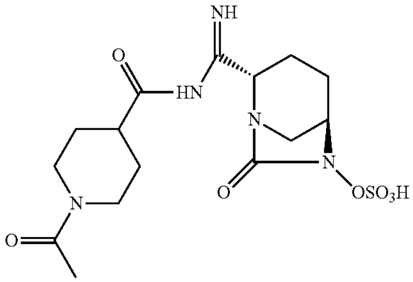
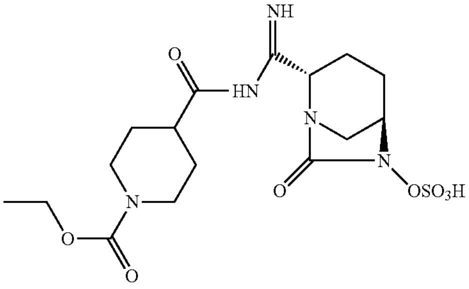
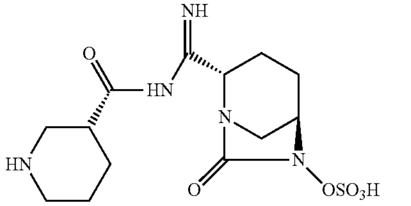
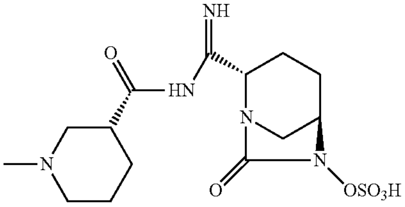
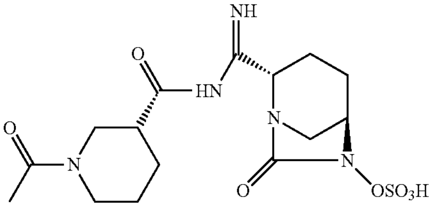
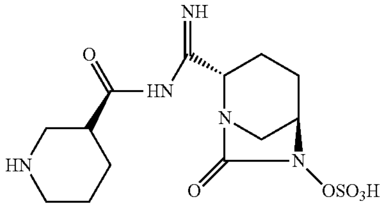
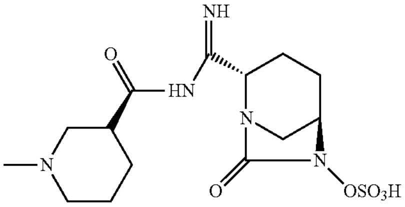

-continued
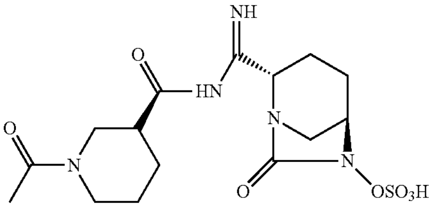
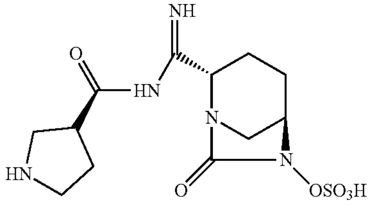
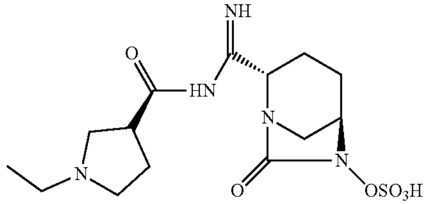
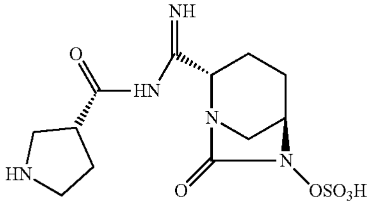
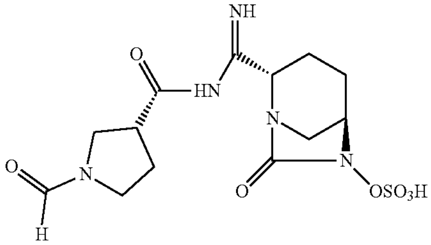
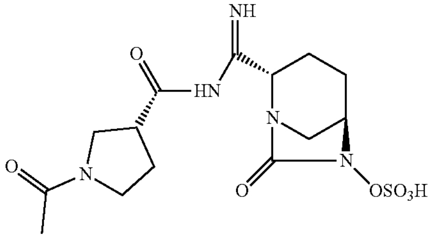
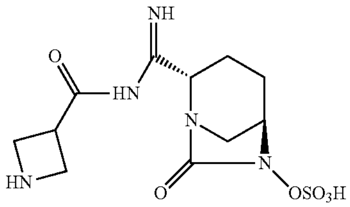
-continued
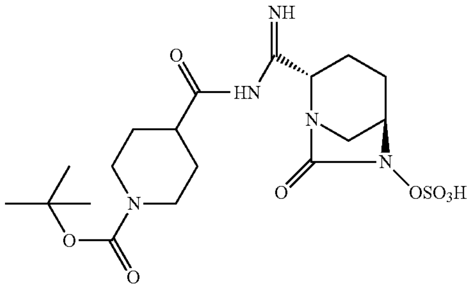
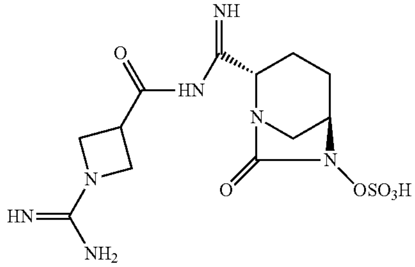
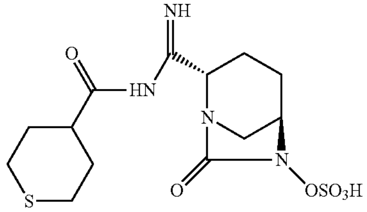
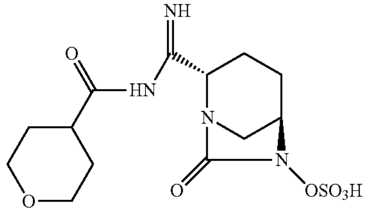
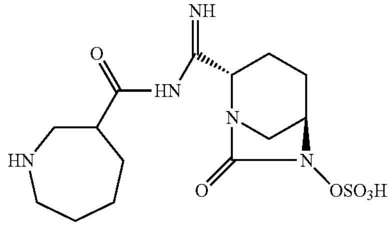
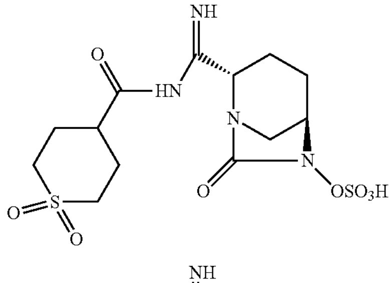
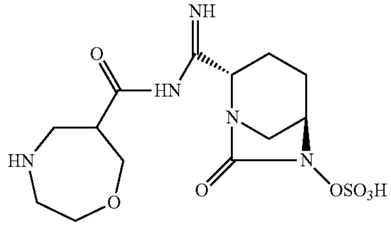

-continued
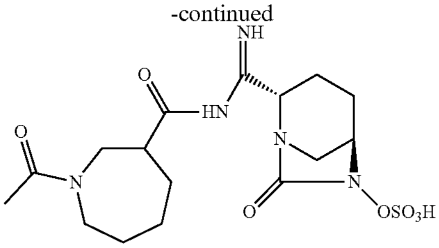
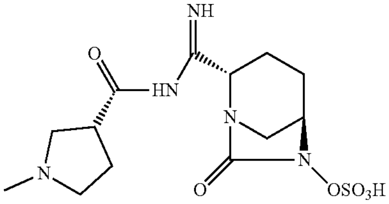
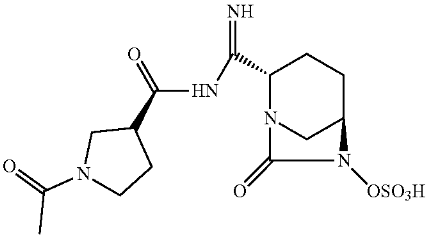
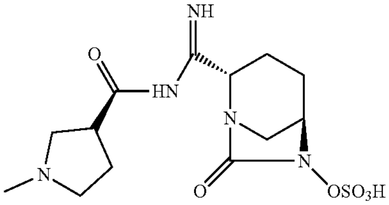
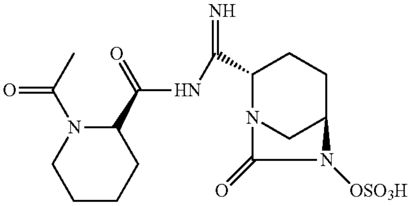
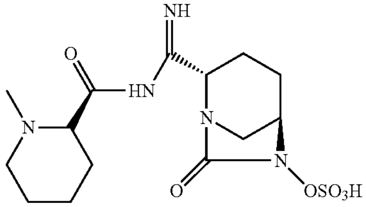
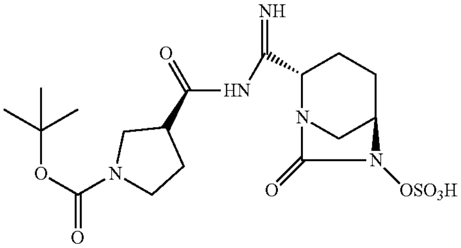
-continued
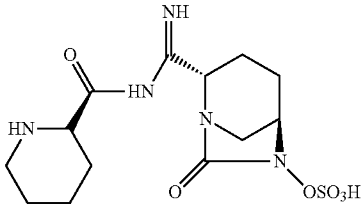
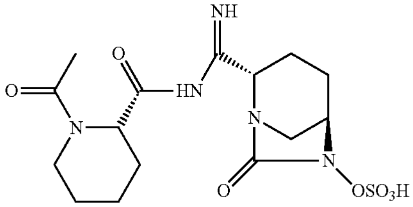
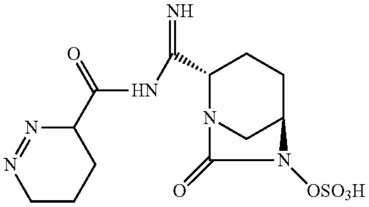
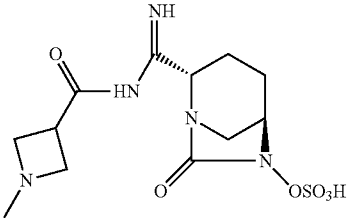
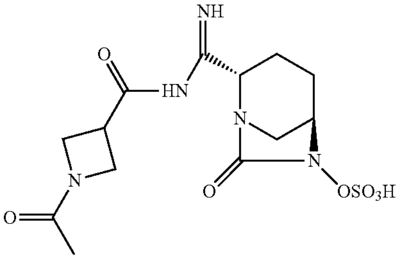
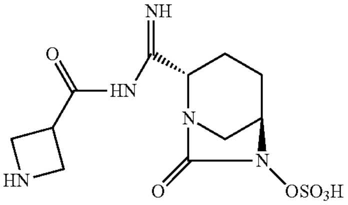
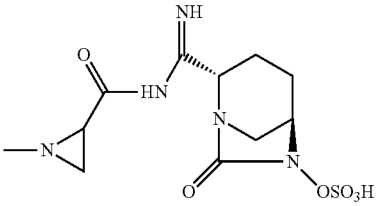
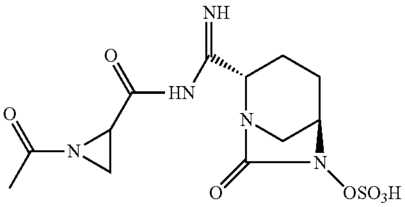

-continued
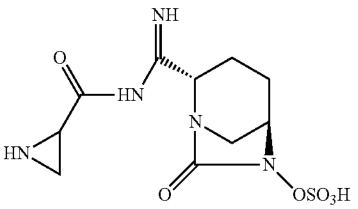
(4) Cyclic alkyl ($C_{1-6}$) or heterocyclyl ($C_{1-6}$) alkyl wherein the said heterocycle has the same definition as defined in (3). Furthermore, the said heterocycle is optionally substituted. Non-limiting examples of such compounds are:
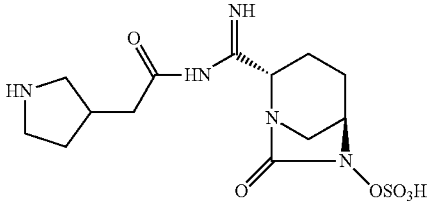
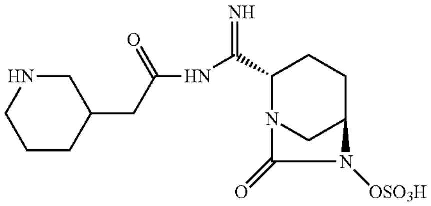
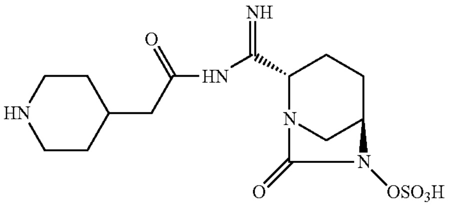
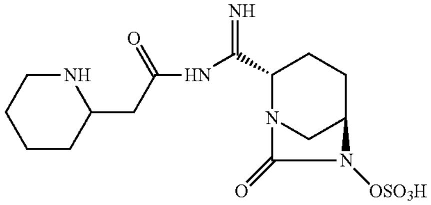
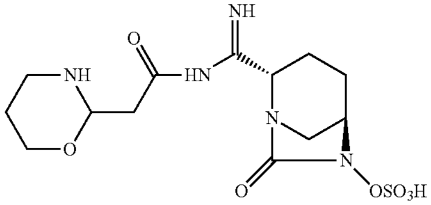
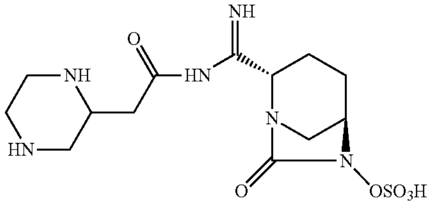
-continued
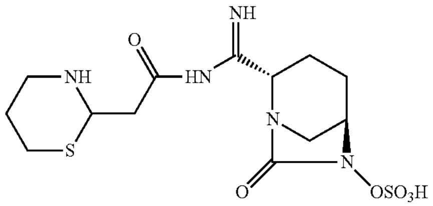
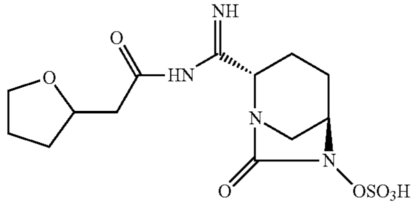
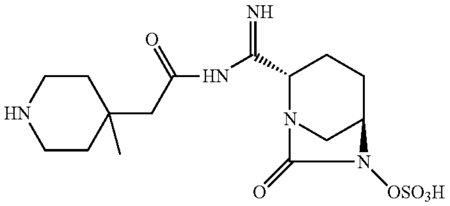
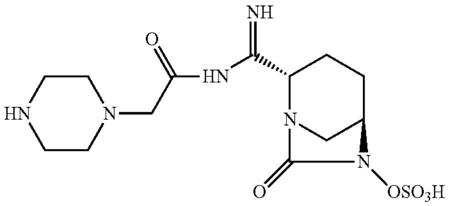
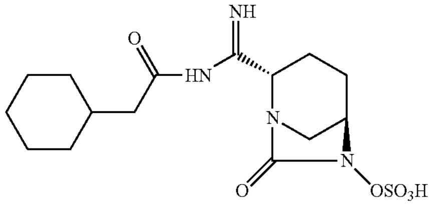
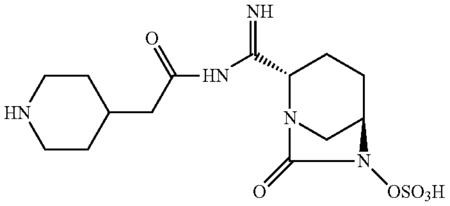
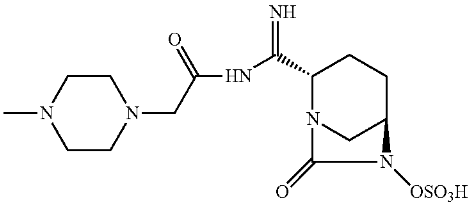
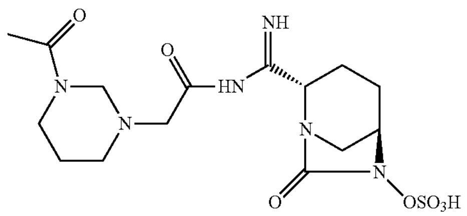

-continued
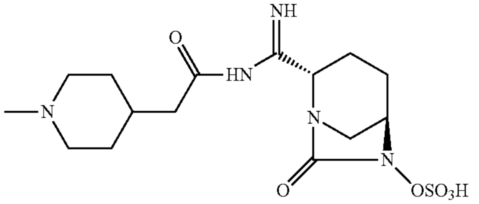
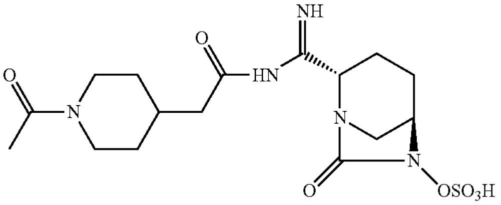
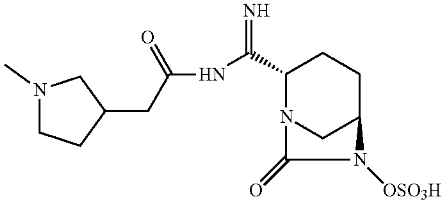
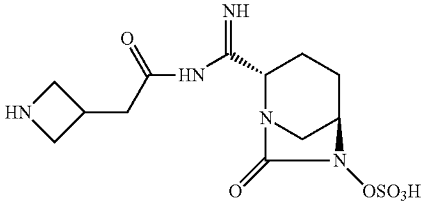
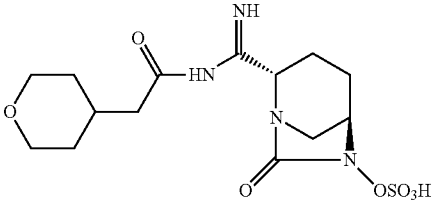
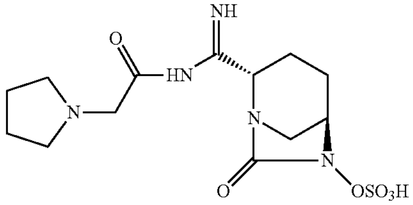
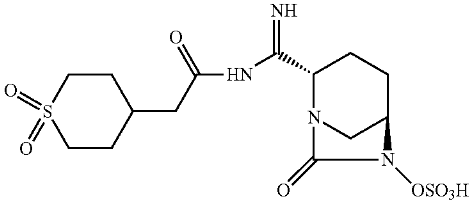
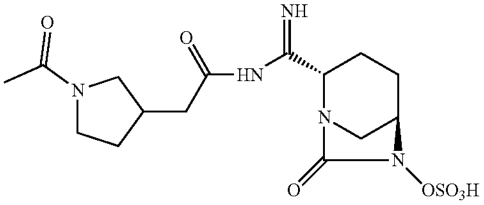
-continued
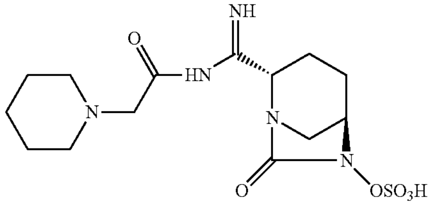
(5) $C_{5-7}$ membered heteroarylalkyl which is optionally substituted. Non-limiting examples of such compounds are:
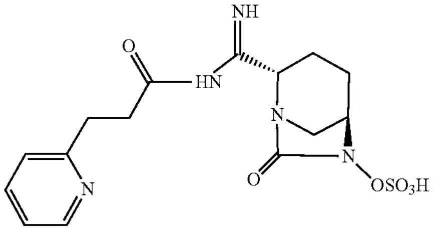
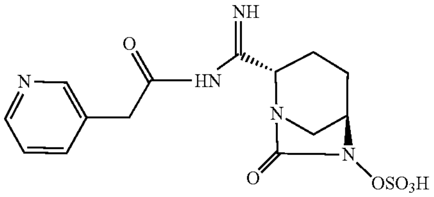
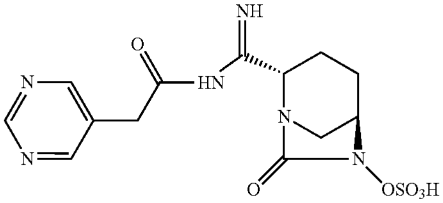
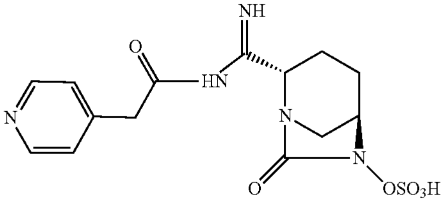
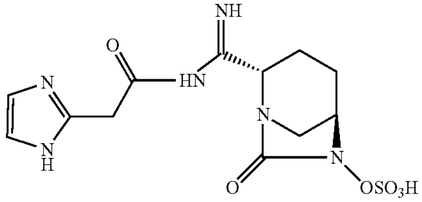
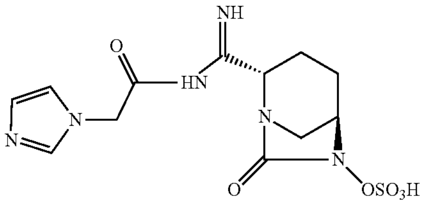

-continued
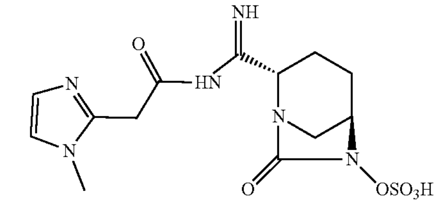
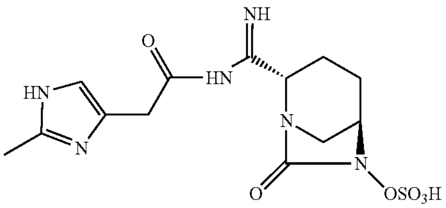
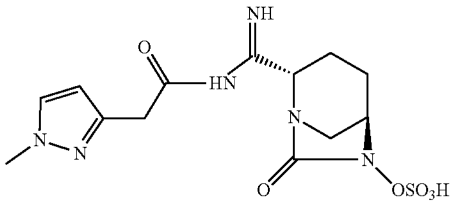
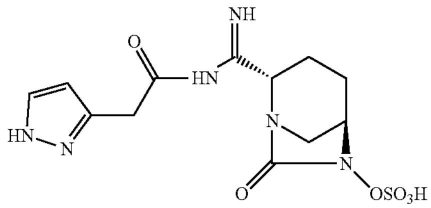
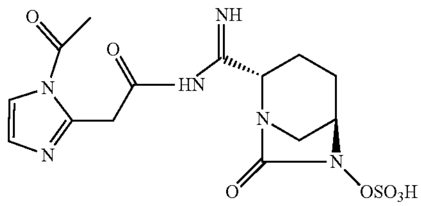
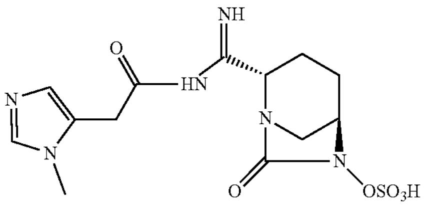
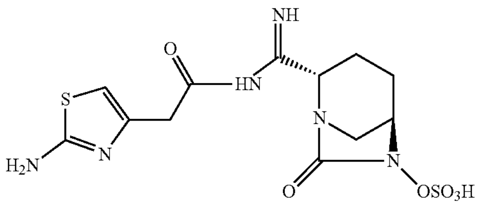
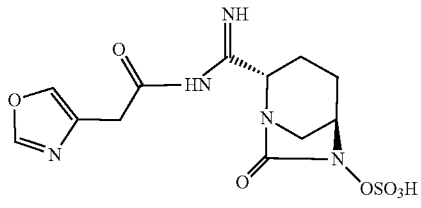
-continued
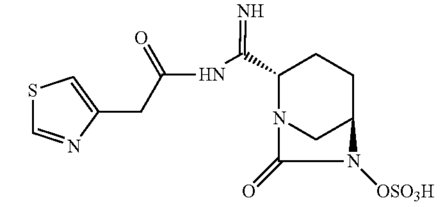
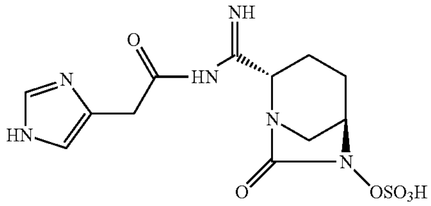
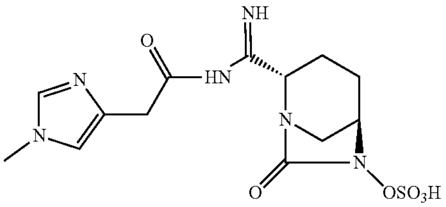
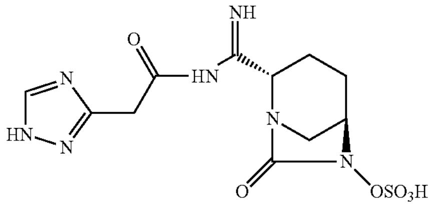
(6) $C_{5-6}$ membered aryl or heteroaryl which is optionally substituted. Non-limiting examples of such compounds are:
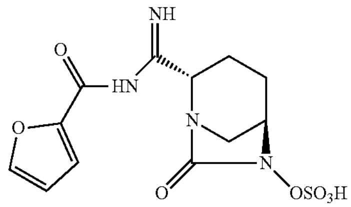
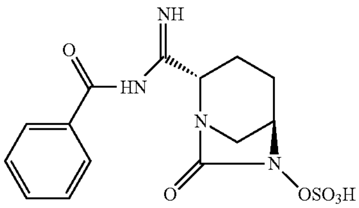
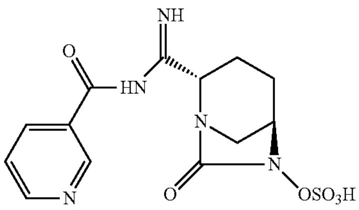

-continued
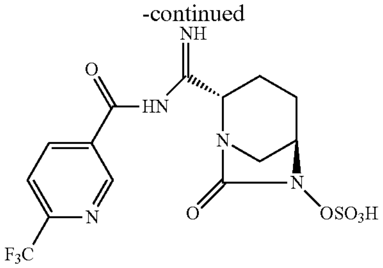
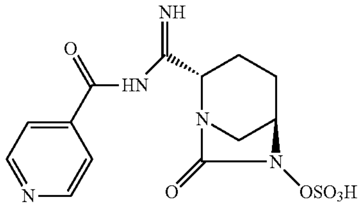
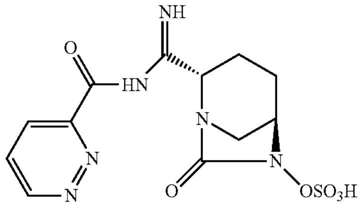
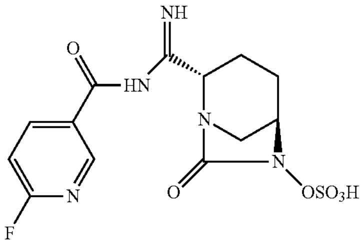
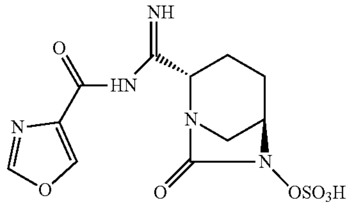
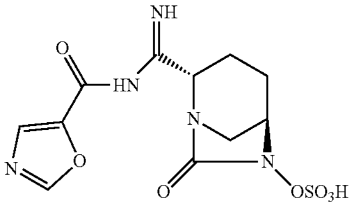
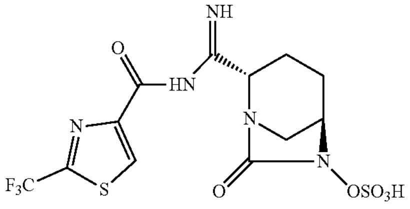
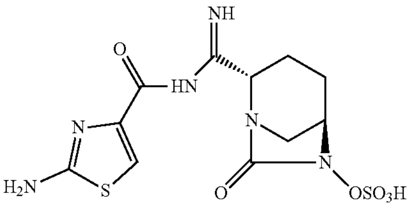
-continued
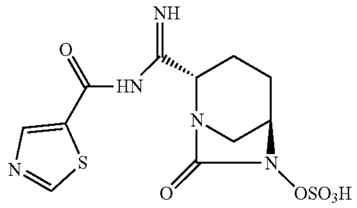
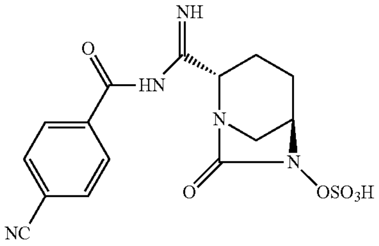
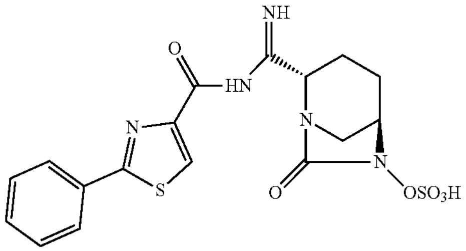
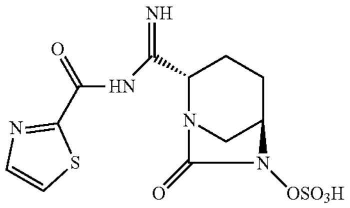
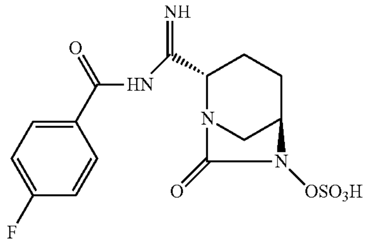
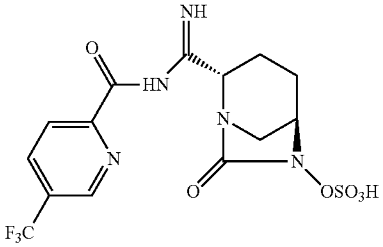
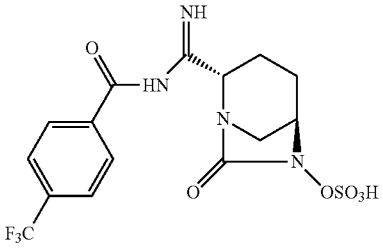

-continued
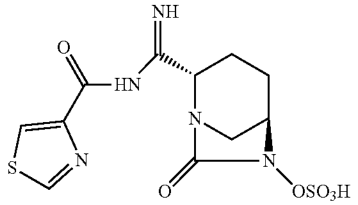
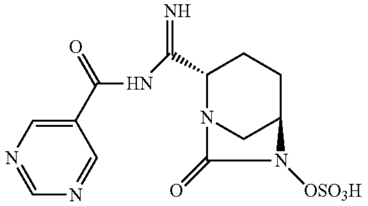
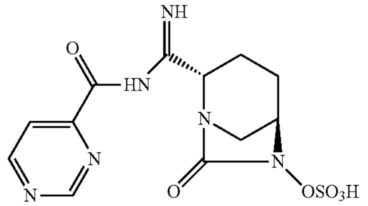
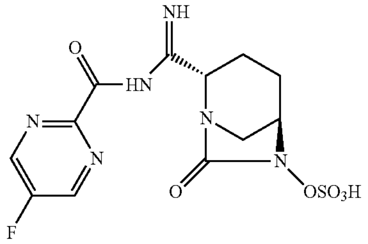
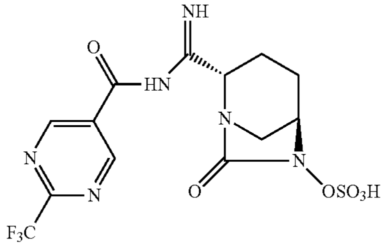
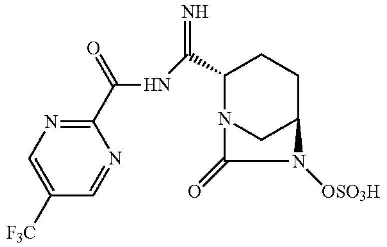
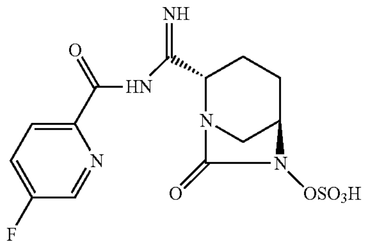
-continued
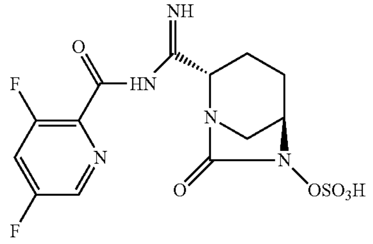
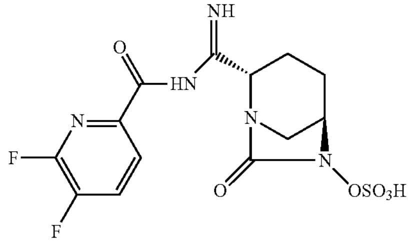
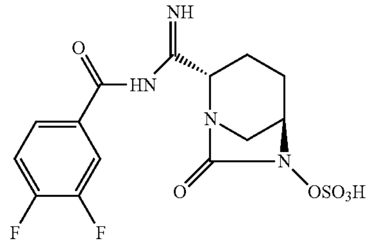
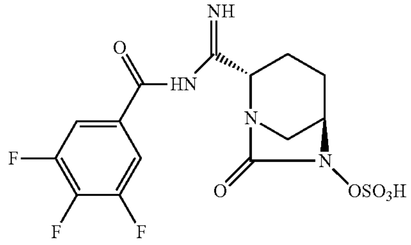
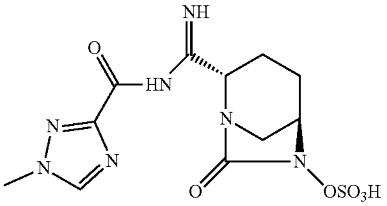
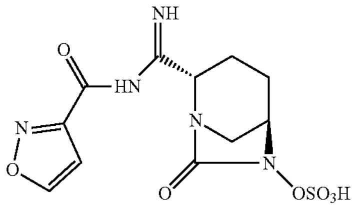
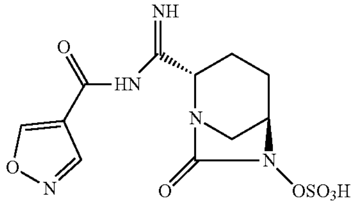

-continued

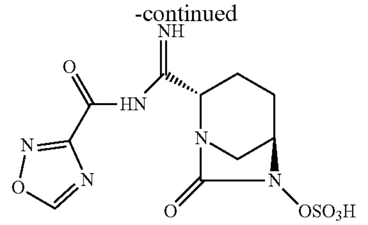

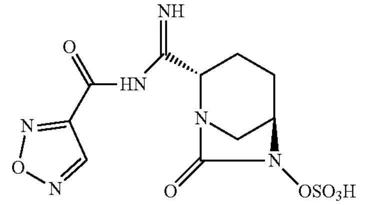

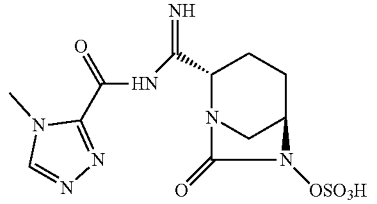

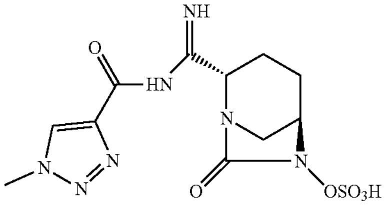

Examples of the groups for forming a pharmaceutically acceptable salt represented by M in the formula (I) include: inorganic base salts, ammonium salts, organic base salts, basic amino acid salts, inorganic acid addition salts, and organic acid addition salts. Inorganic bases that can form the inorganic base salts include alkali metals such as sodium, potassium, and lithium and alkaline earth metals such as calcium and magnesium. Organic bases that can form the organic base salts include n-propylamine, n-butylamine, cyclohexylamine, benzylamine, octylamine, ethanolamine, diethanolamine, diethylamine, triethylamine, dicyclohexylamine, procaine, choline, N-methylglucamine, morpholine, pyrrolidine, piperidine, N-ethylpiperidine and N-methylmorpholine.

Basic amino acids that can form the basic amino acid salts include lysine, arginine, ornithine and histidine. As will be appreciated by one skilled in the art, the compounds of formula (I) containing a basic nitrogen atom are capable of forming acid addition salts. Such salts with pharmaceutically acceptable acids are included in the invention. Examples of such acids are hydrochloric, hydrobromic, phosphoric, sulphuric, citric, oxalic, maleic, fumaric, glycolic, mandelic, tartaric, aspartic, succinic, malic, formic, acetic, p-toluenesulfonic, trifluoroacetic, methanesulfonic, ethanesulfonic, trifluoromethanesulfonic, benzenesulfonic and the like.

Moreover, some compounds of formula (I) when they contain a basic group such as NH, $NH_2$ or pyridine and the like may form an inner, zwitterionic salt with $OSO_3H$, such inner salts are also included in this invention.

Another aspect of the present invention is to include all possible isomers of formula (I). As used herein, the term 'isomers' refers to different compounds that have the same molecular formula but differ in arrangement and configuration of the atoms, such as geometrical isomers and optical isomers. For a given compound of the present invention, it is understood that a substituent may be attached at a chiral center of a carbon atom. Therefore the invention includes enantiomers, diastereomers or racemates of the compound. By definition, 'enantiomers' are a pair of stereoisomers that are non-superimposable mirror images of each other, and 1:1 mixture of a pair of enantiomers is a racemic mixture. By definition, 'diastereoisomers' are stereoisomers that have at least two asymmetric carbon atoms but which are not mirror-images of each other. When a compound of formula (I) is a pure enantiomer the stereochemistry at each chiral carbon may be specified by either R or S.

Compounds may also exist in several tautomeric forms including the enol form, the keto form, and mixtures of any of the foregoing. Accordingly, the chemical structures depicted herein encompass all possible tautomeric forms of the illustrated compounds.

A variety of protecting groups conventionally used in the β-lactam field to protect a reactive functional group present in the compound of formula (I) can be used. 'Protecting group' refers to a group of atoms that when attached to a reactive functional group in a molecule masks, reduces or prevents reactivity of the functional group. Examples of protecting groups can be found in "Protective Groups in Organic Synthesis", (Theodora W. Greene and Peter G. M. Wuts, John Wiley & Sons. Inc., $3^{rd}$, 1999). Representative amino protecting groups include, but are not limited to formyl, acetyl, trifluoroacetyl, benzyl, benzyloxycarbonyl (CBZ), tert-butoxycarbonyl (Boc), trimethylsilyl (TMS), 9-fluorenylmethyloxycarbonyl (FMOC), nitro-veratryoxycarbonyl (NVOC), and the like. Examples of hydroxy protecting groups include, but are not limited to, those where the hydroxyl group is either acylated or alkylated such as benzyl, and trityl ethers as well as alkyl ethers, tetrahydropyranyl ethers, trialkylsilyl ethers, and allyl ethers.

The term 'optionally substituted' refers to unsubstituted or substituted with one or two of the following substituents each of which is independently selected from:

Lower alkyl including from one to six carbon atoms in any arrangement, e.g., methyl, ethyl, i-propyl or t-butyl.

Amino,

Substituted amino such as $—NHCH_3$, $—N(CH_3)_2$, $—NHCH_2CH_3$, $—NHPr^i$, $—NHBu^t$,

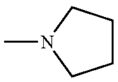

Alkoxy such as $—OCH_3$, $—OC_2H_5$, $—OPr^i$ (i.e., isopropyloxy), $—OBu^t$ (i.e., isobtutyloxy), Hydroxyalkyl such as $—CH_2OH$, $—CH_2CH_2OH$, Halogen such as F, Cl, Br, Hydroxy, Carboxy, Alkoxycarbonyl such as $—COOCH_3$, $—COOC_2H_5$, $—COOPr^i$, and $—COOBu^t$, Haloalkyl such as $—CH_2Cl$, $—CH_2F$, Trifluoromethyl, Trifluoromethyloxy, Alkylamine such as $—CH_2NH_2$, $—CH_2CH_2NH_2$, Substituted alkylamine such as $-CH_2CH_2NHCH_3$, $-CH_2CH_2N(CH_3)_2$, $-CH_2NHCH_3$, $-CH_2N(CH_3)_2$,

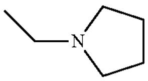

Carboxamide,

Thiocarboxamide,

Sulfonic acid,

Sulfate,

Acylamino,

Sulfonylamino,

Sulfonamide,

Substituted sulfonamide such as $-SO_2NHCH_3$, $-SO_2NHPr^i$, $-SO_2NHBu^t$, $-SO_2NHCH_2CH_3$,

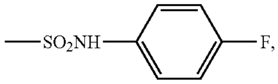,

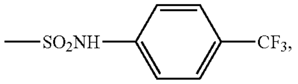,

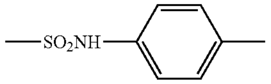

Urea ($-NHCONH_2$) which may be optionally substituted,

Thiourea ($-NHCSNH_2$), optionally substituted,

Sulfonylurea ($-NHSO_2NH_2$), optionally substituted,

Oxo (=O) when oxygen is bonded through double bond to a carbon atom,

Oxyimino (=N—O-A) where the nitrogen is bonded through double bond to a carbon atom which is attached to the rest of the molecule and A can be hydrogen, or optionally substituted straight or branched lower alkyl, cycloalkyl, aryl, heteroaryl and heterocyclyl, Hydroxamic acid ($-CONHOH$), Acyl ($-COCH_3$), Trifluoromethyl carbonyl ($-COCF_3$), Cyano ($-CN$), Amidino $-C(=NH)NH_2$ which may be optionally substituted, Guanidino $-NHC(=NH)NH_2$ which may be optionally substituted, Aryloxy, Heterocyclyl, Heteroaryl, Heterocyclyloxy, Heteroaryloxy, Heterocyclyalkyloxy, Trialkylammonium, The substituent mentioned above could be substituted at the carbon atom or at the free N-atom of the molecule as appropriate.

Among the compounds of formula (I), a particular subject of the invention is those in which M is hydrogen or a pharmaceutically acceptable salt forming cation.

A group of preferred examples of formula (I) are from the following Table 1

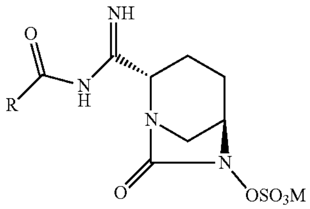

[I]

TABLE 1

| List of compounds | | |
|---|---|---|
| Compound No. | M | R |
| 1 | H | 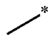 |
| 2 | H | 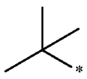 |
| 3 | H | 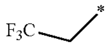 |
| 4 | Na | 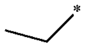 |
| 5 | H | 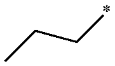 |
| 6 | H | 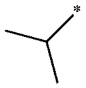 |
| 7 | H | 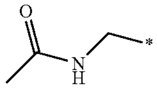 [SMILES: *CNC(C)=O] |
| 8 | Na | 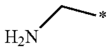 |
| 9 | H | 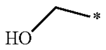 |
| 10 | H | 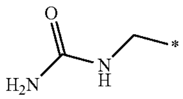 [SMILES: *CNC(N)=O] |
| 11 | H | 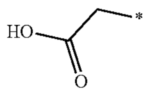 [SMILES: *CC(=O)O] |
| 12 | H | 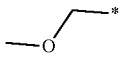 |
| 13 | H | 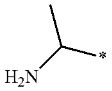 |
| 14 | H | 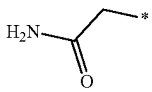 [SMILES: *CC(N)=O] |

TABLE 1-continued
List of compounds
| Compound No. | M | R |
|---|---|---|
| 15 | H | 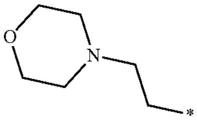 [SMILES: *CCN1CCOCC1] |
| 16 | H | 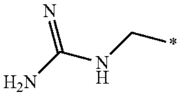 [SMILES: *CNC(=N)N] |
| 17 | H | 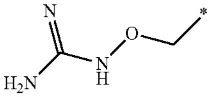 |
| 18 | Na | 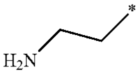 |
| 19 | Na | 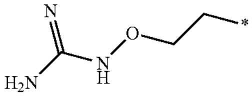 [SMILES: *CCONC(=N)N] |
| 20 | Na | 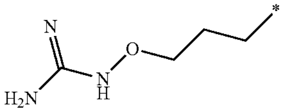 [SMILES: *CCCONC(=N)N] |
| 21 | Na | 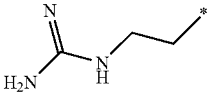 [SMILES: *CCNC(=N)N] |
| 22 | Na | 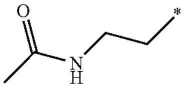 [SMILES: *CCNC(C)=O] |
| 23 | H | 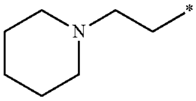 [SMILES: *CCN1CCCCC1] |
| 24 | H | 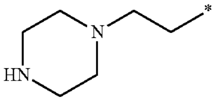 [SMILES: *CCN1CCNCC1] |
| 25 | Na | 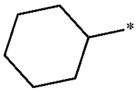 [SMILES: *C1CCCCC1] |
| 26 | H | 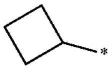 [SMILES: *C1CCC1] |
| 27 | H | 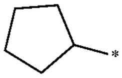 [SMILES: *C1CCCC1] |
| 28 | H | 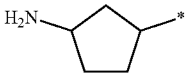 |
TABLE 1-continued
List of compounds
| Compound No. | M | R |
|---|---|---|
| 29 | H | 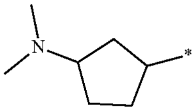 [SMILES: *C1CCC(N(C)C)C1] |
| 30 | H | 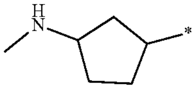 |
| 31 | H | 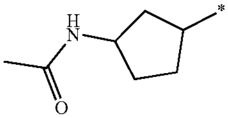 [SMILES: *C1CCC(NC(C)=O)C1] |
| 32 | H | 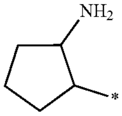 |
| 33 | H | 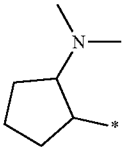 [SMILES: *C1CCCC1N(C)C] |
| 34 | H | 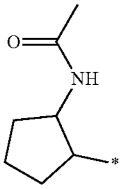 [SMILES: *C1CCCC1NC(C)=O] |
| 35 | H | 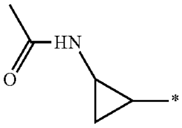 [SMILES: *C1CC1NC(C)=O] |
| 36 | H | 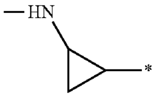 |
| 37 | H | 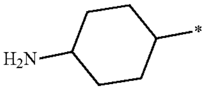 |
| 38 | H | 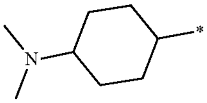 [SMILES: *C1CCC(N(C)C)CC1] |
| 39 | H | 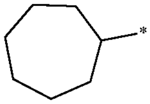 [SMILES: *C1CCCCCC1] |
| 40 | Na | 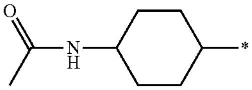 [SMILES: *C1CCC(NC(C)=O)CC1] |

TABLE 1-continued
| List of compounds | | |
|---|---|---|
| Compound No. | M | R |
| 41 | H | 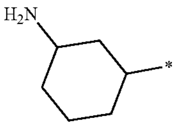 [SMILES: *C1CCCC(N)C1] |
| 42 | H | 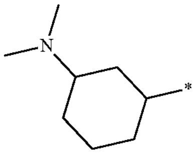 [SMILES: *C1CCCC(N(C)C)C1] |
| 43 | H | 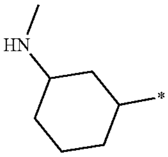 [SMILES: *C1CCCC(NC)C1] |
| 44 | H | 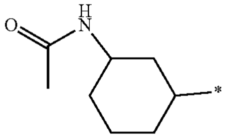 [SMILES: *C1CCCC(NC(C)=O)C1] |
| 45 | H | 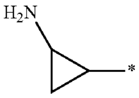 [SMILES: *C1CC1N] |
| 46 | Na | 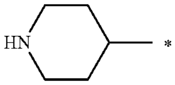 |
| 47 | Na | 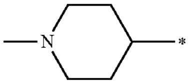 |
| 48 | Na | 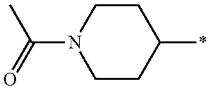 [SMILES: *C1CCN(C(C)=O)CC1] |
| 49 | H | 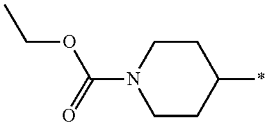 [SMILES: *C1CCN(C(=O)OCC)CC1] |
| 50 | H | 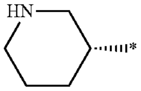 |
| 51 | Na | 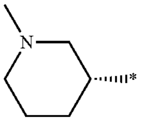 [SMILES: *[C@@H]1CCCN(C)C1] |
TABLE 1-continued
| List of compounds | | |
|---|---|---|
| Compound No. | M | R |
| 52 | Na | 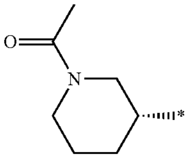 [SMILES: *[C@@H]1CCCN(C(C)=O)C1] |
| 53 | H | 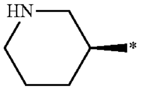 [SMILES: *[C@H]1CCCNC1] |
| 54 | Na | 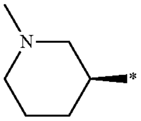 [SMILES: *[C@H]1CCCN(C)C1] |
| 55 | Na | 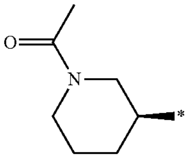 [SMILES: *[C@H]1CCCN(C(C)=O)C1] |
| 56 | Na | 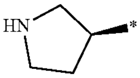 [SMILES: *[C@H]1CCNC1] |
| 57 | H | 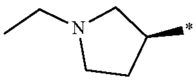 [SMILES: *[C@H]1CCN(CC)C1] |
| 58 | H | 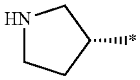 [SMILES: *[C@@H]1CCNC1] |
| 59 | H | 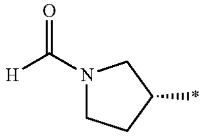 [SMILES: *[C@@H]1CCN(C=O)C1] |
| 60 | Na | 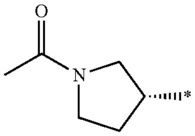 [SMILES: *[C@@H]1CCN(C(C)=O)C1] |
| 61 | H | 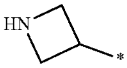 [SMILES: *C1CNC1] |
| 62 | Na | 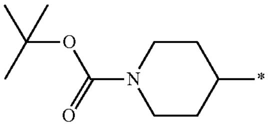 [SMILES: *C1CCN(C(=O)OC(C)(C)C)CC1] |
| 63 | H | 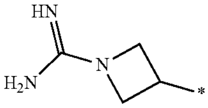 [SMILES: *C1CN(C(=N)N)C1] |

TABLE 1-continued
List of compounds
| Compound No. | M | R |
|---|---|---|
| 64 | H | 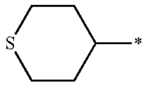 [SMILES: *C1CCSCC1] |
| 65 | H | 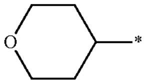 [SMILES: *C1CCOCC1] |
| 66 | H | 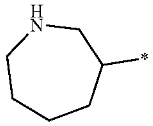 [SMILES: *C1CCCCNC1] |
| 67 | H | 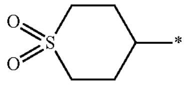 [SMILES: *C1CCS(=O)(=O)CC1] |
| 68 | H | 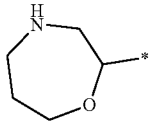 [SMILES: *C1CNCCCO1] |
| 69 | H | 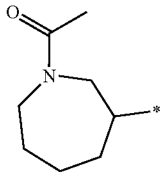 [SMILES: *C1CCCCN(C(C)=O)C1] |
| 70 | Na | 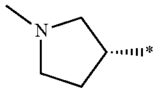 |
| 71 | Na | 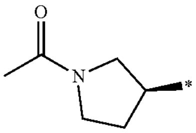 [SMILES: *[C@H]1CCN(C(C)=O)C1] |
| 72 | Na | 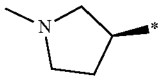 |
| 73 | Na | 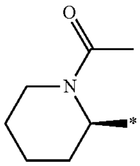 [SMILES: *[C@H]1CCCCN1C(C)=O] |
| 74 | H | 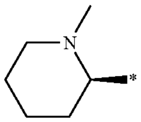 [SMILES: *[C@H]1CCCCN1C] |
| 75 | H | 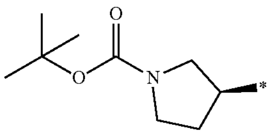 [SMILES: *[C@H]1CCN(C(=O)OC(C)(C)C)C1] |
TABLE 1-continued
List of compounds
| Compound No. | M | R |
|---|---|---|
| 76 | H | 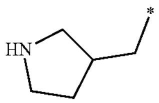 |
| 77 | H | 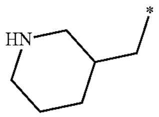 |
| 78 | H | 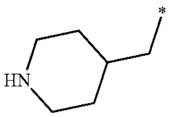 [SMILES: *CC1CCNCC1] |
| 79 | H | 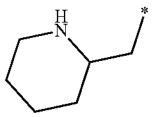 [SMILES: *CC1CCCCN1] |
| 80 | H | 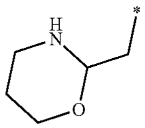 [SMILES: *CC1NCCCO1] |
| 81 | H | 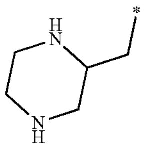 [SMILES: *CC1CNCCN1] |
| 82 | H | 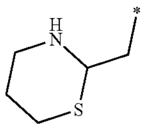 [SMILES: *CC1NCCCS1] |
| 83 | H | 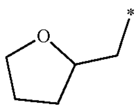 [SMILES: *CC1CCCO1] |
| 84 | H | 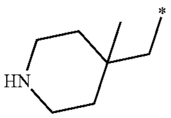 [SMILES: *CC1(C)CCNCC1] |
| 85 | H | 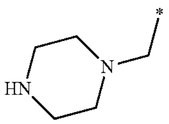 [SMILES: *CN1CCNCC1] |
| 86 | Na | 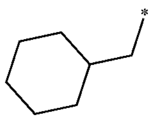 [SMILES: *CC1CCCCC1] |

TABLE 1-continued
List of compounds
| Compound No. | M | R |
|---|---|---|
| 87 | H | 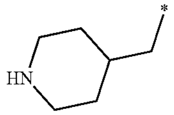 [SMILES: *CC1CCNCC1] |
| 88 | Na | 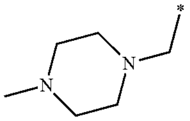 [SMILES: *CN1CCN(C)CC1] |
| 89 | H | 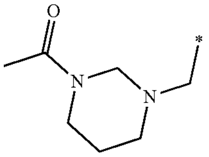 [SMILES: *CN1CCCN(C(C)=O)C1] |
| 90 | H | 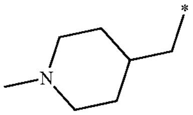 [SMILES: *CC1CCN(C)CC1] |
| 91 | H | 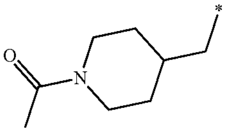 [SMILES: *CC1CCN(C(C)=O)CC1] |
| 92 | H | 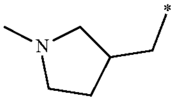 [SMILES: *CC1CCN(C)C1] |
| 93 | H | 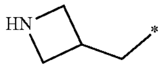 [SMILES: *CC1CNC1] |
| 94 | Na | 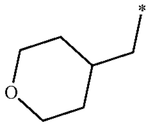 [SMILES: *CC1CCOCC1] |
| 95 | H | 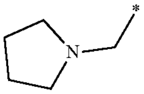 [SMILES: *CN1CCCC1] |
| 96 | H | 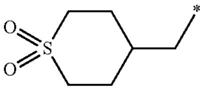 [SMILES: *CC1CCS(=O)(=O)CC1] |
| 97 | H | 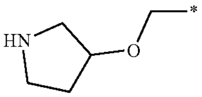 [SMILES: *COC1CCNC1] |
| 98 | H | 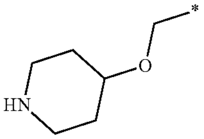 [SMILES: *COC1CCNCC1] |
| 99 | Na | 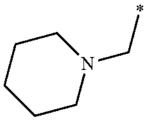 [SMILES: *CN1CCCCC1] |
| 100 | H | 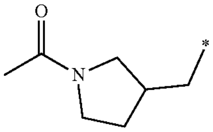 [SMILES: *CC1CCN(C(C)=O)C1] |
| 101 | H | 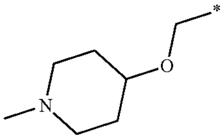 [SMILES: *COC1CCN(C)CC1] |
| 102 | H | 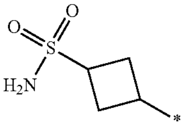 |
| 103 | Na | 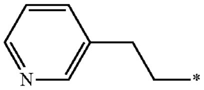 [SMILES: *CCc1cccnc1] |
| 104 | Na | 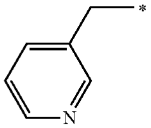 |
| 105 | Na | 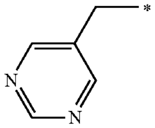 |
| 106 | H | 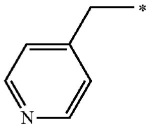 |
| 107 | H | 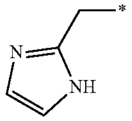 |
| 108 | Na | 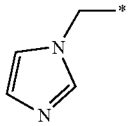 |
| 109 | H | 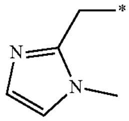 |

TABLE 1-continued
| List of compounds | | |
|---|---|---|
| Compound No. | M | R |
| 110 | H | 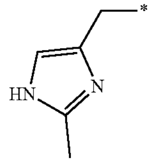 [SMILES: *Cc1c[nH]c(C)n1] |
| 111 | H | 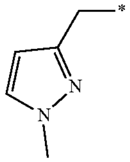 |
| 112 | H | 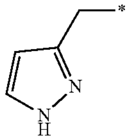 |
| 113 | H | 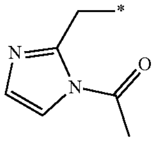 [SMILES: *Cc1nccn1C(C)=O] |
| 114 | H | 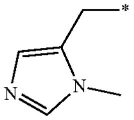 [SMILES: *Cc1cncn1C] |
| 115 | H | 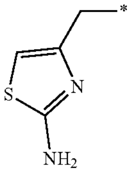 [SMILES: *Cc1csc(N)n1] |
| 116 | H | 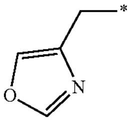 [SMILES: *Cc1cocn1] |
| 117 | H | 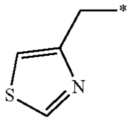 |
| 118 | H | 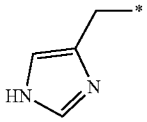 [SMILES: *Cc1c[nH]cn1] |
| 119 | H | 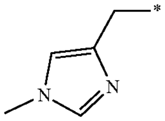 [SMILES: *Cc1cn(C)cn1] |
TABLE 1-continued
| List of compounds | | |
|---|---|---|
| Compound No. | M | R |
| 120 | H | 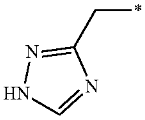 |
| 121 | H | 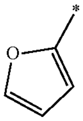 |
| 122 | H | 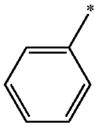 |
| 123 | H | 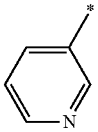 [SMILES: *c1cccnc1] |
| 124 | Na | 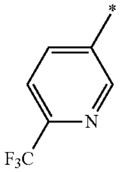 |
| 125 | H | 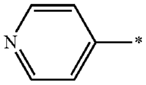 [SMILES: *c1ccncc1] |
| 126 | H | 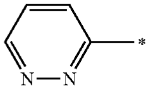 |
| 127 | H | 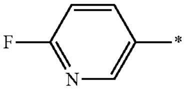 |
| 128 | Na | 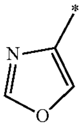 |
| 129 | Na | 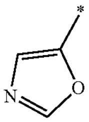 |
| 130 | Na | 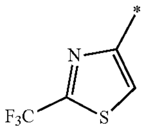 |

TABLE 1-continued
List of compounds
| Compound No. | M | R |
|---|---|---|
| 131 | Na | 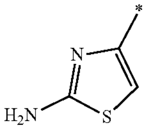 [SMILES: *c1csc(N)n1] |
| 132 | H | 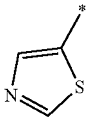 |
| 133 | Na | 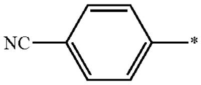 [SMILES: *c1ccc(C#N)cc1] |
| 134 | Na | 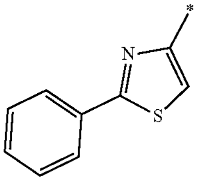 [SMILES: *c1csc(-c2ccccc2)n1] |
| 135 | Na | 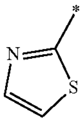 |
| 136 | H | 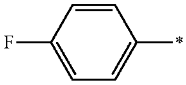 [SMILES: *c1ccc(F)cc1] |
| 137 | Na | 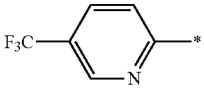 [SMILES: *c1ccc(C(F)(F)F)cn1] |
| 138 | Na | 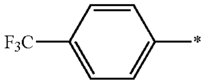 [SMILES: *c1ccc(C(F)(F)F)cc1] |
| 139 | Na | 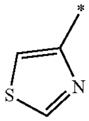 |
| 140 | Na | 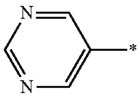 [SMILES: *c1cncnc1] |
| 141 | Na | 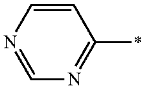 [SMILES: *c1ccncn1] |
| 142 | H | 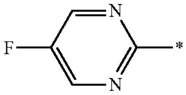 [SMILES: *c1ncc(F)cn1] |
| 143 | H | 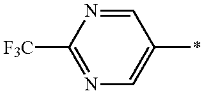 [SMILES: *c1cnc(C(F)(F)F)nc1] |
| 144 | H | 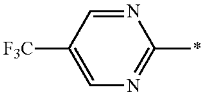 [SMILES: *c1ncc(C(F)(F)F)cn1] |
| 145 | H | 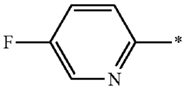 |
| 146 | H | 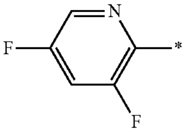 [SMILES: *c1ncc(F)cc1F] |
| 147 | H | 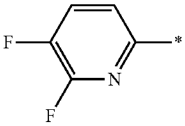 [SMILES: *c1ccc(F)c(F)n1] |
| 148 | H | 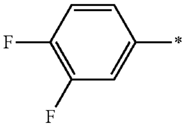 [SMILES: *c1ccc(F)c(F)c1] |
| 149 | H | 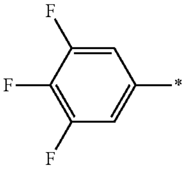 [SMILES: *c1cc(F)c(F)c(F)c1] |
| 150 | H | 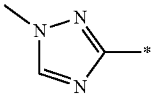 |
| 151 | H | 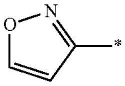 [SMILES: *c1ccon1] |
| 152 | H | 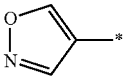 [SMILES: *c1cnoc1] |
| 153 | H | 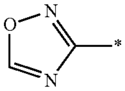 [SMILES: *c1ncon1] |
| 154 | H | 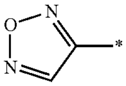 |

TABLE 1-continued

| List of compounds | | |
|---|---|---|
| Compound No. | M | R |
| 155 | H | 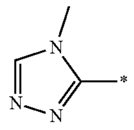 [SMILES: *c1nncn1C] |
| 156 | H | 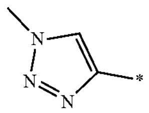 [SMILES: *c1cn(C)nn1] |
| 157 | H | 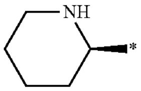 |
| 158 | H | 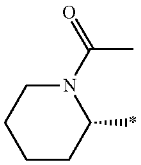 [SMILES: *[C@@H]1CCCCN1C(C)=O] |
| 159 | Na | 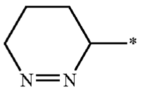 [SMILES: *C1CCCN=N1] |
| 160 | H | 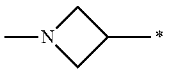 |
| 161 | H | 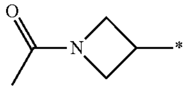 [SMILES: *C1CN(C(C)=O)C1] |
| 162 | H | 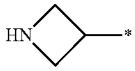 |
| 163 | H | 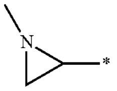 [SMILES: *C1CN1C] |
| 164 | H | 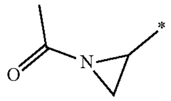 [SMILES: *C1CN1C(C)=O] |
| 165 | H | 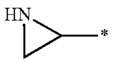 |

* = point of attachment with C

It is also an object of this invention to provide a combination of a compound of general formula (I) having antibacterial activity with another existing antibacterial agent, thus causing synergistic effect and the use of the same as drugs for the treatment of bacterial infections.

It is another object of the invention to provide methods for preparing the compounds of the invention of formula (I).

It is a further object of the invention to provide pharmaceutical compositions comprising a compound of formula (I) of this invention as an active ingredient in combination with an antibiotic (e.g., a β-lactam antibiotic or some other non β-lactam antibiotic) and a suitable amount of pharmaceutically acceptable carrier or diluent, so as to provide a form for proper administration to a patient. These compositions can be administered by parenteral, in particular intramascular route, oral, sublingual, rectal, aerosol or by local route in a topical application on the skin and the mucous membranes. Suitable pharmaceutical vehicles include excipients such as starch, glucose, lactose, sucrose, gelatin, gum arabic, malt, rice, flour, chalk, silica gel, sodium stearate, glycerol monostearate, talc, sodium chloride, dried skim milk, glycerol, propylene, glycol, water, ethanol, and the like. Other examples of suitable pharmaceutical vehicles have been described in the art (Remington's Science and Practice of Pharmacy, $21^{st}$ Edition, 2006). Compositions of the present disclosure, if desired, can also contain minor amounts of wetting, dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen. The present pharmaceutical compositions can take the form of injectable preparations, suspensions, emulsions, sugar-coated tablets, pellets, gelatin-capsules, capsules containing liquids, powders, granules, sustained-release formulations, suppositories, aerosols, sprays, ointments, creams or any other form suitable for use.

In another aspect, the present invention also provides for the use, in the manufacture of a medicament, of a compound within formula (I) above as an active ingredient in an antibacterial composition in admixture with a carrier.

In another aspect, the present invention also provides for the use, in the manufacture of a medicament, of a compound within formula (I) above as an active ingredient.

In another aspect, the present invention also provides for the use, in the manufacture of a medicament, of a compound within formula (I) above as an active ingredient, along with one or more β-lactam antibiotics (e.g., a β-lactam antibiotic or some other non β-lactam antibiotic), in an antibacterial composition in admixture with a carrier.

In another aspect, the present invention also provides for the use, in the manufacture of a medicament, of a compound within formula (I) above as an active ingredient, along with one or more β-lactam antibiotics (e.g., a β-lactam antibiotic or some other non β-lactam antibiotic).

For the parenteral administration which includes intramuscular, intraperitonial, subcutaneous and intravenous use, sterile solutions of the active ingredient are usually prepared and the pH of the solutions are suitably adjusted and buffered. For intravenous use, the total concentration of solutes should be controlled to render the preparation isotonic. Suitable solvents include saline solution (e.g., 0.9% NaCl solution) and apyrogenic sterile water. Pharmaceutical compositions for oral delivery can be, for example, in the form of tablets, lozenges, aqueous or oily suspensions, granules, powders, emulsions, capsules, syrups, or elixirs. Orally administered compositions can contain one or more optional agents, for example, sweetening agents such as fructose, aspartame, or saccharin, flavoring agents such as peppermint, oil of wintergreen, cherry, coloring agents, and preserving agents to provide a pharmaceutically palatable preparation. Moreover, when in tablet form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharin, cellulose, magnesium carbonate, and the like. For oral liquid preparations, for example, suspensions, elixirs, and solutions, suitable carriers, excipients, or diluents include water, saline, alkyleneglycols (e.g. propylene glycol), polyalkylene glycols (e.g., polyethylene glycol), oils, alcohols, slightly acidic buffers ranging from about pH 4 to about pH 6 (e.g., acetate, citrate, ascorbate ranging from about 5 mM to about 50 mM), and the like. Additionally, flavoring agents, preservatives, coloring agents, bile salts, acylcarnitines, and the like can be added.

For topical formulations of compounds of the present invention, creams, gels, ointments or viscous lotions can be used as appropriate delivery forms. Topical delivery systems also include transdermal patches containing at least one compound of formula (I) to be administered.

Delivery through the skin can be achieved by diffusion or by more active energy sources such as iontophoresis or electrotransport. Formulations of a compound of the present invention, for topical use, such as in creams, ointments, and gels, can include an oleaginous or water soluble ointment base, for example, topical compositions can include vegetable oils, animal fats, and in certain embodiments, semi-solid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, and glyceryl monostearate. Various water-soluble ointment bases can also be used, including glycol ethers and derivatives, polyethylene glycols, polyoxyl 40 stearate, and polysorbates.

In a pharmaceutical composition containing a compound of this invention, the weight ratio of active ingredient to carrier will normally be in the range of 1:30 to 30:1, for example, 1:25 to 25:1, 1:20 to 20:1, 1:15 to 15:1, 1:10 to 10:1, 1:5 to 5:1, 1:4 to 4:1, 1:3 to 3:1, 1:2 to 2:1, or 1:1. The administered daily dose varies according to the illness treated, and the administration route. However in most instances, an effective dose (e.g., in some instances, β-lactamase inhibiting dose) of a compound of formula (I) or a pharmaceutically acceptable salt thereof will be a daily dose in the range from about 1 to about 500 mg per kilogram of body weight orally, and from about 1 to about 500 mg per kilogram of body weight parenterally. The weight ratio of the compound of present invention to the antibiotic (if it is being administered with an antibiotic) will normally be in the range from 1:30 to 30:1, for example, 1:25 to 25:1, 1:15 to 15:1, 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1, or 1:1.

In some aspects of the present invention, an additional object is to provide an improved method for the treatment of bacterial infections caused by β-lactamase producing bacteria in a patient in need of such treatment comprising administering to the patient a therapeutically effective amount of at least one compound chosen from formula (I) or a pharmaceutically acceptable salt thereof in combination with a known β-lactam antibiotic. In such an aspect of the present invention, the compounds increase the antibacterial effectiveness of β-lactamase susceptible β-lactam antibiotics, that is, they increase the effectiveness of the antibiotic against infections caused by β-lactamase producing microorganisms in mammalian subjects, particularly in human. In these aspects of the present invention, this makes the compounds of formula (I) and pharmaceutically acceptable salts thereof, valuable for co-administration with β-lactam antibiotics. In the treatment of a bacterial infection in such an aspect of the present invention, said compounds of formula (I) or a pharmaceutically salt thereof can be mixed with the β-lactam antibiotic, and the two agents thereby administered simultaneously. When co-administered with a β-lactam antibiotic in such an aspect of the present invention, the combination of the compound of the invention and the antibiotic can provide a synergistic effect. The term 'synergystic effect' refers to the effect produced when two or more agents are co-administered is greater than the effect produced when the agents are administered individually. Alternatively, the compound of formula (I) or a salt thereof can be administered as a separate agent during a course of treatment with the antibiotic.

'Therapeutically effective amount' refers to the amount of a compound that, when administered to a subject for treating a disease, or at least one of the clinical symptoms of a disease, is sufficient to affect such treatment of the disease, disorder, or symptom. The therapeutically effective amount can vary depending, for example, on the compound, the disease, disorder, and/or symptoms of the disease, severity of the disease, disorder, and/or symptoms of the disease, the age, weight, and/or health of the patient to be treated, and the judgement of the prescribing physician.

The term 'β-lactam antibiotic' refers to a compound with antibiotic property that contains a β-lactam functionality. Examples of β-lactam antibiotics which can be used in combination with the compounds of the present invention represented by formula (I) are commonly marketed penicillins, cephalosporins, penems, carbapenems and monobactams.

Examples of β-lactam antibiotics which can be used in combination with the compounds of the present invention represented by formula (I) are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine and latamoxef (moxalactam). From the carbapenem class of β-lactam antibiotics such as imipenem, meropenem, panipenem, biapenem, doripenem, ertapenem and the like could be used. From monobactam class of β-lactam antibiotics such as aztreonam, carumonam, tigemonam, and the like could be used as the combination partner of antibiotic.

Examples of antibiotics (which are not β-lactam antibiotics) which can be used in combination with the compounds of the present invention (i.e., compounds of formula (I) above, salts, thereof, solvates of such compounds and salts, and deuterated compounds of any such compounds) include aminoglycosides, quinolones, tetracyclines, glycylcyclines, glycopeptides, lipopeptides, macrolides, ketolides, lincosamides, streptogramin, oxazolidinones, polymyxins, and other compounds known to have antibacterial properties.

'Pharmaceutically acceptable solvate' refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intra-molecular forces such as, for example, electrostatic forces, Van der Waals forces or hydrogen bonds. The term hydrate refers to a complex where the one or more solvent molecules are water.

Among the compounds of formula (I), a particular subject of the invention is the compounds with the following names. The following examples illustrate the invention, and are not intended to be limiting of its scope. To the contrary, the claims are intended to cover alternatives, modifications, and equivalents.

The non-limiting examples of the compounds of the present invention are:

(2S,5R)-2-(N-acetylcarbamimidoyl)-7-oxo-1,6-diazabicyclo[3.2.1]octan-6-yl hydrogen sulfate, (2S,5R)-7-oxo-2-(N-pivaloylcarbamimidoyl)-1,6-diazabicyclo[3.2.1]octan-6-yl hydrogen sulfate, (2S,5R)-7-oxo-2-(N-(3,3,3-trifluoropropanoyl)carbamimidoyl)-1,6-diazabicyclo[3.2.1]octan-6-yl hydrogen sulfate, (2S,5R)-7-oxo-2-(N-propionylcarbamimidoyl)-1,6-diazabicyclo[3.2.1]octan-6-yl hydrogen sulfate, (2S,5R)-2-(N-butyrylcarbamimidoyl)-7-oxo-1,6-diazabicyclo[3.2.1]octan-6-yl hydrogen sulfate, (2S,5R)-2-(N-isobutyrylcarbamimidoyl)-7-oxo-1,6-diazabicyclo[3.2.1]octan-6-yl hydrogen sulfate, (2S,5R)-2-(N-(acetylglycyl)carbamimidoyl)-7-oxo-1,6-diazabicyclo[3.2.1]octan-6-yl hydrogen sulfate, (2S,5R)-2-(N-glycylcarbamimidoyl)-7-oxo-1,6-diazabicyclo[3.2.1]octan-6-yl hydrogen sulfate, (2S,5R)-2-(N-(2-hydroxyacetyl)carbamimidoyl)-7-oxo-1,6-diazabicyclo[3.2.1]octan-6-yl hydrogen sulfate, (2S,5R)-2-(N-(carbamoylglycyl)carbamimidoyl)-7-oxo-1,6-diazabicyclo[3.2.1]octan-6-yl hydrogen sulfate, 3-oxo-3-((2S,5R)-7-oxo-6-(sulfooxy)-1,6-diazabicyclo[3.2.1]octane-2-carboximidamido)propanoic acid, (2S,5R)-2-(N-(2-methoxyacetyl)carbamimidoyl)-7-oxo-1,6-diazabicyclo[3.2.1]octan-6-yl hydrogen sulfate, (2S,5R)-2-(N-alanylcarbamimidoyl)-7-oxo-1,6-diazabicyclo[3.2.1]octan-6-yl hydrogen sulfate, (2S,5R)-2-(N-(3-amino-3-oxopropanoyl)carbamimidoyl)-7-oxo-1,6-diazabicyclo[3.2.1]octan-6-yl hydrogen sulfate, (2S,5R)-2-(N-(3-morpholinopropanoyl)carbamimidoyl)-7-oxo-1,6-diazabicyclo[3.2.1]octan-6-yl hydrogen sulfate, (2S,5R)-2-(N-(carbamimidoylglycyl)carbamimidoyl)-7-oxo-1,6-diazabicyclo[3.2.1]octan-6-yl hydrogen sulfate, (2S,5R)-2-(N-(2-(guanidinooxy)acetyl)carbamimidoyl)-7-oxo-1,6-diazabicyclo[3.2.1]octan-6-yl hydrogen sulfate, (2S,5R)-2-(N-(3-aminopropanoyl)carbamimidoyl)-7-oxo-1,6-diazabicyclo[3.2.1]octan-6-yl hydrogen sulfate, (2S,5R)-2-(N-(3-(guanidinooxy)propanoyl)carbamimidoyl)-7-oxo-1,6-diazabicyclo[3.2.1]octan-6-yl hydrogen sulfate, (2S,5R)-2-(N-(4-(guanidinooxy)butanoyl)carbamimidoyl)-7-oxo-1,6-diazabicyclo[3.2.1]octan-6-yl hydrogen sulfate, (2S,5R)-2-(N-(3-guanidinopropanoyl)carbamimidoyl)-7-oxo-1,6-diazabicyclo[3.2.1]octan-6-yl hydrogen sulfate, (2S,5R)-2-(N-(3-acetamidopropanoyl)carbamimidoyl)-7-oxo-1,6-diazabicyclo[3.2.1]octan-6-yl hydrogen sulfate, (2S,5R)-7-oxo-2-(N-(3-(piperidin-1-yl)propanoyl)carbamimidoyl)-1,6-diazabicyclo[3.2.1]octan-6-yl hydrogen sulfate, (2S,5R)-7-oxo-2-(N-(3-(piperazin-1-yl)propanoyl)carbamimidoyl)-1,6-diazabicyclo[3.2.1]octan-6-yl hydrogen sulfate, (2S,5R)-2-(N-(cyclohexanecarbonyl)carbamimidoyl)-7-oxo-1,6-diazabicyclo[3.2.1]octan-6-yl hydrogen sulfate, (2S,5R)-2-(N-(cyclobutanecarbonyl)carbamimidoyl)-7-oxo-1,6-diazabicyclo[3.2.1]octan-6-yl hydrogen sulfate, (2S,5R)-2-(N-(cyclopentanecarbonyl)carbamimidoyl)-7-oxo-1,6-diazabicyclo[3.2.1]octan-6-yl hydrogen sulfate, (2S,5R)-2-(N-(3-aminocyclopentane-1-carbonyl)carbamimidoyl)-7-oxo-1,6-diazabicyclo[3.2.1]octan-6-yl hydrogen sulfate, (2S,5R)-2-(N-(3-(dimethylamino)cyclopentane-1-carbonyl)carbamimidoyl)-7-oxo-1,6-diazabicyclo[3.2.1]octan-6-yl hydrogen sulfate, (2S,5R)-2-(N-(3-(methylamino)cyclopentane-1-carbonyl)carbamimidoyl)-7-oxo-1,6-diazabicyclo[3.2.1]octan-6-yl hydrogen sulfate, (2S,5R)-2-(N-(3-acetamidocyclopentane-1-carbonyl)carbamimidoyl)-7-oxo-1,6-diazabicyclo[3.2.1]octan-6-yl hydrogen sulfate, (2S,5R)-2-(N-(2-aminocyclopentane-1-carbonyl)carbamimidoyl)-7-oxo-1,6-diazabicyclo[3.2.1]octan-6-yl hydrogen sulfate, (2S,5R)-2-(N-(2-(dimethylamino)cyclopentane-1-carbonyl)carbamimidoyl)-7-oxo-1,6-diazabicyclo[3.2.1]octan-6-yl hydrogen sulfate, (2S,5R)-2-(N-(2-acetamidocyclopentane-1-carbonyl)carbamimidoyl)-7-oxo-1,6-diazabicyclo[3.2.1]octan-6-yl hydrogen sulfate, (2S,5R)-2-(N-(2-acetamidocyclopropane-1-carbonyl)carbamimidoyl)-7-oxo-1,6-diazabicyclo[3.2.1]octan-6-yl hydrogen sulfate (2S,5R)-2-(N-(2-(methylamino)cyclopropane-1-carbonyl)carbamimidoyl)-7-oxo-1,6-diazabicyclo[3.2.1]octan-6-yl hydrogen sulfate, (2S,5R)-2-(N-(4-aminocyclohexane-1-carbonyl)carbamimidoyl)-7-oxo-1,6-diazabicyclo[3.2.1]octan-6-yl hydrogen sulfate, (2S,5R)-2-(N-(4-(dimethylamino)cyclohexane-1-carbonyl)carbamimidoyl)-7-oxo-1,6-diazabicyclo[3.2.1]octan-6-yl hydrogen sulfate, (2S,5R)-2-(N-(cycloheptanecarbonyl)carbamimidoyl)-7-oxo-1,6-diazabicyclo[3.2.1]octan-6-yl hydrogen sulfate, (2S,5R)-2-(N-(4-acetamidocyclohexane-1-carbonyl)carbamimidoyl)-7-oxo-1,6-diazabicyclo[3.2.1]octan-6-yl hydrogen sulfate, (2S,5R)-2-(N-(3-aminocyclohexane-1-carbonyl)carbamimidoyl)-7-oxo-1,6-diazabicyclo[3.2.1]octan-6-yl hydrogen sulfate, (2S,5R)-2-(N-(3-(dimethylamino)cyclohexane-1-carbonyl)carbamimidoyl)-7-oxo-1,6-diazabicyclo[3.2.1]octan-6-yl hydrogen sulfate, (2S,5R)-2-(N-(3-(methylamino)cyclohexane-1-carbonyl)carbamimidoyl)-7-oxo-1,6-diazabicyclo[3.2.1]octan-6-yl hydrogen sulfate, (2S,5R)-2-(N-(3-acetamidocyclohexane-1-carbonyl)carbamimidoyl)-7-oxo-1,6-diazabicyclo[3.2.1]octan-6-yl hydrogen sulfate, (2S,5R)-2-(N-(2-aminocyclopropane-1-carbonyl)carbamimidoyl)-7-oxo-1,6-diazabicyclo[3.2.1]octan-6-yl hydrogen sulfate, (2S,5R)-7-oxo-2-(N-(piperidine-4-carbonyl)carbamimidoyl)-1,6-diazabicyclo[3.2.1]octan-6-yl hydrogen sulfate, (2S,5R)-2-(N-(1-methylpiperidine-4-carbonyl)carbamimidoyl)-7-oxo-1,6-diazabicyclo[3.2.1]octan-6-yl hydrogen sulfate, (2S,5R)-2-(N-(1-acetylpiperidine-4-carbonyl)carbamimidoyl)-7-oxo-1,6-diazabicyclo[3.2.1]octan-6-yl hydrogen sulfate, ethyl 4-((imino((2S,5R)-7-oxo-6-(sulfooxy)-1,6-diazabicyclo[3.2.1]octan-2-yl)methyl)carbamoyl)piperidine-1-carboxylate,
(2S,5R)-7-oxo-2-(N-((R)-piperidine-3-carbonyl)carbamimidoyl)-1,6-diazabicyclo[3.2.1]octan-6-yl hydrogen sulfate,
(2S,5R)-2-(N-((R)-1-methylpiperidine-3-carbonyl)carbamimidoyl)-7-oxo-1,6-diazabicyclo[3.2.1]octan-6-yl hydrogen sulfate,
(2S,5R)-2-(N-((R)-1-acetylpiperidine-3-carbonyl)carbamimidoyl)-7-oxo-1,6-diazabicyclo[3.2.1]octan-6-yl hydrogen sulfate,
(2S,5R)-7-oxo-2-(N-((R)-piperidine-3-carbonyl)carbamimidoyl)-1,6-diazabicyclo[3.2.1]octan-6-yl hydrogen sulfate,
(2S,5R)-2-(N-((R)-1-methylpiperidine-3-carbonyl)carbamimidoyl)-7-oxo-1,6-diazabicyclo[3.2.1]octan-6-yl hydrogen sulfate,
(2S,5R)-2-(N-((R)-1-acetylpiperidine-3-carbonyl)carbamimidoyl)-7-oxo-1,6-diazabicyclo[3.2.1]octan-6-yl hydrogen sulfate,
(2S,5R)-7-oxo-2-(N-((R)-pyrrolidine-3-carbonyl)carbamimidoyl)-1,6-diazabicyclo[3.2.1]octan-6-yl hydrogen sulfate,
(2S,5R)-2-(N-((R)-1-ethylpyrrolidine-3-carbonyl)carbamimidoyl)-7-oxo-1,6-diazabicyclo[3.2.1]octan-6-yl hydrogen sulfate,
(2S,5R)-7-oxo-2-(N-((R)-pyrrolidine-3-carbonyl)carbamimidoyl)-1,6-diazabicyclo[3.2.1]octan-6-yl hydrogen sulfate,
(2S,5R)-2-(N-((R)-1-formylpyrrolidine-3-carbonyl)carbamimidoyl)-7-oxo-1,6-diazabicyclo[3.2.1]octan-6-yl hydrogen sulfate,
(2S,5R)-2-(N-((R)-1-acetylpyrrolidine-3-carbonyl)carbamimidoyl)-7-oxo-1,6-diazabicyclo[3.2.1]octan-6-yl hydrogen sulfate,
(2S,5R)-2-(N-(azetidine-3-carbonyl)carbamimidoyl)-7-oxo-1,6-diazabicyclo[3.2.1]octan-6-yl hydrogen sulfate,
tert-butyl 4-((imino((2S,5R)-7-oxo-6-(sulfooxy)-1,6-diazabicyclo[3.2.1]octan-2-yl)methyl)carbamoyl)piperidine-1-carboxylate,
(2S,5R)-2-(N-(1-carbamimidoylazetidine-3-carbonyl)carbamimidoyl)-7-oxo-1,6-diazabicyclo[3.2.1]octan-6-yl hydrogen sulfate,
(2S,5R)-7-oxo-2-(N-(tetrahydro-2H-thiopyran-4-carbonyl)carbamimidoyl)-1,6-diazabicyclo[3.2.1]octan-6-yl hydrogen sulfate,
(2S,5R)-7-oxo-2-(N-(tetrahydro-2H-pyran-4-carbonyl)carbamimidoyl)-1,6-diazabicyclo[3.2.1]octan-6-yl hydrogen sulfate,
(2S,5R)-2-(N-(azepane-3-carbonyl)carbamimidoyl)-7-oxo-1,6-diazabicyclo[3.2.1]octan-6-yl hydrogen sulfate,
(2S,5R)-2-(N-(1,1-dioxidotetrahydro-2H-thiopyran-4-carbonyl)carbamimidoyl)-7-oxo-1,6-diazabicyclo[3.2.1]octan-6-yl hydrogen sulfate,
(2S,5R)-2-(N-(1,4-oxazepane-6-carbonyl)carbamimidoyl)-7-oxo-1,6-diazabicyclo[3.2.1]octan-6-yl hydrogen sulfate,
(2S,5R)-2-(N-(1-acetylazepane-3-carbonyl)carbamimidoyl)-7-oxo-1,6-diazabicyclo[3.2.1]octan-6-yl hydrogen sulfate,
(2S,5R)-2-(N-((R)-1-methylpyrrolidine-3-carbonyl)carbamimidoyl)-7-oxo-1,6-diazabicyclo[3.2.1]octan-6-yl hydrogen sulfate,
(2S,5R)-2-(N-((R)-1-acetylpyrrolidine-3-carbonyl)carbamimidoyl)-7-oxo-1,6-diazabicyclo[3.2.1]octan-6-yl hydrogen sulfate,
(2S,5R)-2-(N-((R)-1-methylpyrrolidine-3-carbonyl)carbamimidoyl)-7-oxo-1,6-diazabicyclo[3.2.1]octan-6-yl hydrogen sulfate,
(2S,5R)-2-(N-((S)-1-acetylpiperidine-2-carbonyl)carbamimidoyl)-7-oxo-1,6-diazabicyclo[3.2.1]octan-6-yl hydrogen sulfate,
(2S,5R)-2-(N-((S)-1-methylpiperidine-2-carbonyl)carbamimidoyl)-7-oxo-1,6-diazabicyclo[3.2.1]octan-6-yl hydrogen sulfate,
tert-butyl (3R)-3-((imino((2S,5R)-7-oxo-6-(sulfooxy)-1,6-diazabicyclo[3.2.1]octan-2-yl)methyl)carbamoyl)pyrrolidine-1-carboxylate,
(2S,5R)-7-oxo-2-(N-(2-(pyrrolidin-3-yl)acetyl)carbamimidoyl)-1,6-diazabicyclo[3.2.1]octan-6-yl hydrogen sulfate,
(2S,5R)-7-oxo-2-(N-(2-(piperidin-3-yl)acetyl)carbamimidoyl)-1,6-diazabicyclo[3.2.1]octan-6-yl hydrogen sulfate,
(2S,5R)-7-oxo-2-(N-(2-(piperidin-4-yl)acetyl)carbamimidoyl)-1,6-diazabicyclo[3.2.1]octan-6-yl hydrogen sulfate,
(2S,5R)-7-oxo-2-(N-(2-(piperidin-2-yl)acetyl)carbamimidoyl)-1,6-diazabicyclo[3.2.1]octan-6-yl hydrogen sulfate,
(2S,5R)-2-(N-(2-(1,3-oxazinan-2-yl)acetyl)carbamimidoyl)-7-oxo-1,6-diazabicyclo[3.2.1]octan-6-yl hydrogen sulfate,
(2S,5R)-7-oxo-2-(N-(2-(piperazin-2-yl)acetyl)carbamimidoyl)-1,6-diazabicyclo[3.2.1]octan-6-yl hydrogen sulfate,
(2S,5R)-2-(N-(2-(1,3-thiazinan-2-yl)acetyl)carbamimidoyl)-7-oxo-1,6-diazabicyclo[3.2.1]octan-6-yl hydrogen sulfate,
(2S,5R)-7-oxo-2-(N-(2-(tetrahydrofuran-2-yl)acetyl)carbamimidoyl)-1,6-diazabicyclo[3.2.1]octan-6-yl hydrogen sulfate,
(2S,5R)-2-(N-(2-(4-methylpiperidin-4-yl)acetyl)carbamimidoyl)-7-oxo-1,6-diazabicyclo[3.2.1]octan-6-yl hydrogen sulfate,
(2S,5R)-7-oxo-2-(N-(2-(piperazin-1-yl)acetyl)carbamimidoyl)-1,6-diazabicyclo[3.2.1]octan-6-yl hydrogen sulfate,
(2S,5R)-2-(N-(2-cyclohexylacetyl)carbamimidoyl)-7-oxo-1,6-diazabicyclo[3.2.1]octan-6-yl hydrogen sulfate,
(2S,5R)-7-oxo-2-(N-(2-(piperidin-4-yl)acetyl)carbamimidoyl)-1,6-diazabicyclo[3.2.1]octan-6-yl hydrogen sulfate,
(2S,5R)-2-(N-(2-(4-methylpiperazin-1-yl)acetyl)carbamimidoyl)-7-oxo-1,6-diazabicyclo[3.2.1]octan-6-yl hydrogen sulfate,
(2S,5R)-2-(N-(2-(3-acetyltetrahydropyrimidin-1(2H)-yl)acetyl)carbamimidoyl)-7-oxo-1,6-diazabicyclo[3.2.1]octan-6-yl hydrogen sulfate,
(2S,5R)-2-(N-(2-(1-methylpiperidin-4-yl)acetyl)carbamimidoyl)-7-oxo-1,6-diazabicyclo[3.2.1]octan-6-yl hydrogen sulfate,
(2S,5R)-2-(N-(2-(1-acetylpiperidin-4-yl)acetyl)carbamimidoyl)-7-oxo-1,6-diazabicyclo[3.2.1]octan-6-yl hydrogen sulfate,
(2S,5R)-2-(N-(2-(1-methylpyrrolidin-3-yl)acetyl)carbamimidoyl)-7-oxo-1,6-diazabicyclo[3.2.1]octan-6-yl hydrogen sulfate,
(2S,5R)-2-(N-(2-(azetidin-3-yl)acetyl)carbamimidoyl)-7-oxo-1,6-diazabicyclo[3.2.1]octan-6-yl hydrogen sulfate,
(2S,5R)-7-oxo-2-(N-(2-(tetrahydro-2H-pyran-4-yl)acetyl)carbamimidoyl)-1,6-diazabicyclo[3.2.1]octan-6-yl hydrogen sulfate, (2S,5R)-7-oxo-2-(N-(2-(pyrrolidin-1-yl)acetyl)carbamimidoyl)-1,6-diazabicyclo[3.2.1]octan-6-yl hydrogen sulfate, (2S,5R)-2-(N-(2-(1,1-dioxidotetrahydro-2H-thiopyran-4-yl)acetyl)carbamimidoyl)-7-oxo-1,6-diazabicyclo[3.2.1]octan-6-yl hydrogen sulfate, (2S,5R)-7-oxo-2-(N-(2-(pyrrolidin-3-yloxy)acetyl)carbamimidoyl)-1,6-diazabicyclo[3.2.1]octan-6-yl hydrogen sulfate, (2S,5R)-7-oxo-2-(N-(2-(piperidin-4-yloxy)acetyl)carbamimidoyl)-1,6-diazabicyclo[3.2.1]octan-6-yl hydrogen sulfate, (2S,5R)-7-oxo-2-(N-(2-(piperidin-1-yl)acetyl)carbamimidoyl)-1,6-diazabicyclo[3.2.1]octan-6-yl hydrogen sulfate, (2S,5R)-2-(N-(2-(1-acetylpyrrolidin-3-yl)acetyl)carbamimidoyl)-7-oxo-1,6-diazabicyclo[3.2.1]octan-6-yl hydrogen sulfate, (2S,5R)-2-(N-(2-((1-methylpiperidin-4-yl)oxy)acetyl)carbamimidoyl)-7-oxo-1,6-diazabicyclo[3.2.1]octan-6-yl hydrogen sulfate, (2S,5R)-7-oxo-2-(N-(3-sulfamoylcyclobutane-1-carbonyl)carbamimidoyl)-1,6-diazabicyclo[3.2.1]octan-6-yl hydrogen sulfate, (2S,5R)-7-oxo-2-(N-(3-(pyridin-2-yl)propanoyl)carbamimidoyl)-1,6-diazabicyclo[3.2.1]octan-6-yl hydrogen sulfate, (2S,5R)-7-oxo-2-(N-(2-(pyridin-3-yl)acetyl)carbamimidoyl)-1,6-diazabicyclo[3.2.1]octan-6-yl hydrogen sulfate, (2S,5R)-7-oxo-2-(N-(2-(pyrimidin-5-yl)acetyl)carbamimidoyl)-1,6-diazabicyclo[3.2.1]octan-6-yl hydrogen sulfate, (2S,5R)-7-oxo-2-(N-(2-(pyridin-4-yl)acetyl)carbamimidoyl)-1,6-diazabicyclo[3.2.1]octan-6-yl hydrogen sulfate, (2S,5R)-2-(N-(2-(1H-imidazol-2-yl)acetyl)carbamimidoyl)-7-oxo-1,6-diazabicyclo[3.2.1]octan-6-yl hydrogen sulfate, (2S,5R)-2-(N-(2-(1H-imidazol-1-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-2-yl)acetyl)carbamimidoyl)-7-oxo-1,6-diazabicyclo[3.2.1]octan-6-yl hydrogen sulfate, (2S,5R)-2-(N-(2-(2-methyl-1H-imidazol-4-yl)acetyl)carbamimidoyl)-7-oxo-1,6-diazabicyclo[3.2.1]octan-6-yl hydrogen sulfate, (2S,5R)-2-(N-(2-(1-methyl-1H-pyrazol-3-yl)acetyl)carbamimidoyl)-7-oxo-1,6-diazabicyclo[3.2.1]octan-6-yl hydrogen sulfate, (2S,5R)-2-(N-(2-(1H-pyrazol-3-yl)acetyl)carbamimidoyl)-7-oxo-1,6-diazabicyclo[3.2.1]octan-6-yl hydrogen sulfate, (2S,5R)-2-(N-(2-(1-acetyl-1H-imidazol-2-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-5-yl)acetyl)carbamimidoyl)-7-oxo-1,6-diazabicyclo[3.2.1]octan-6-yl hydrogen sulfate, (2S,5R)-2-(N-(2-(2-aminothiazol-4-yl)acetyl)carbamimidoyl)-7-oxo-1,6-diazabicyclo[3.2.1]octan-6-yl hydrogen sulfate, (2S,5R)-2-(N-(2-(oxazol-4-yl)acetyl)carbamimidoyl)-7-oxo-1,6-diazabicyclo[3.2.1]octan-6-yl hydrogen sulfate, (2S,5R)-7-oxo-2-(N-(2-(thiazol-4-yl)acetyl)carbamimidoyl)-1,6-diazabicyclo[3.2.1]octan-6-yl hydrogen sulfate, (2S,5R)-2-(N-(2-(1H-imidazol-4-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-4-yl)acetyl)carbamimidoyl)-7-oxo-1,6-diazabicyclo[3.2.1]octan-6-yl hydrogen sulfate, (2S,5R)-2-(N-(2-(1H-1,2,4-triazol-3-yl)acetyl)carbamimidoyl)-7-oxo-1,6-diazabicyclo[3.2.1]octan-6-yl hydrogen sulfate, (2S,5R)-2-(N-(furan-2-carbonyl)carbamimidoyl)-7-oxo-1,6-diazabicyclo[3.2.1]octan-6-yl hydrogen sulfate, (2S,5R)-2-(N-benzoylcarbamimidoyl)-7-oxo-1,6-diazabicyclo[3.2.1]octan-6-yl hydrogen sulfate, (2S,5R)-2-(N-nicotinoylcarbamimidoyl)-7-oxo-1,6-diazabicyclo[3.2.1]octan-6-yl hydrogen sulfate, (2S,5R)-7-oxo-2-(N-(6-(trifluoromethyl)nicotinoyl)carbamimidoyl)-1,6-diazabicyclo[3.2.1]octan-6-yl hydrogen sulfate, (2S,5R)-2-(N-isonicotinoylcarbamimidoyl)-7-oxo-1,6-diazabicyclo[3.2.1]octan-6-yl hydrogen sulfate, (2S,5R)-7-oxo-2-(N-(pyridazine-3-carbonyl)carbamimidoyl)-1,6-diazabicyclo[3.2.1]octan-6-yl hydrogen sulfate, (2S,5R)-2-(N-(6-fluoronicotinoyl)carbamimidoyl)-7-oxo-1,6-diazabicyclo[3.2.1]octan-6-yl hydrogen sulfate, (2S,5R)-2-(N-(oxazole-4-carbonyl)carbamimidoyl)-7-oxo-1,6-diazabicyclo[3.2.1]octan-6-yl hydrogen sulfate, (2S,5R)-2-(N-(oxazole-5-carbonyl)carbamimidoyl)-7-oxo-1,6-diazabicyclo[3.2.1]octan-6-yl hydrogen sulfate, (2S,5R)-7-oxo-2-(N-(2-(trifluoromethyl)thiazole-4-carbonyl)carbamimidoyl)-1,6-diazabicyclo[3.2.1]octan-6-yl hydrogen sulfate, (2S,5R)-2-(N-(2-aminothiazole-4-carbonyl)carbamimidoyl)-7-oxo-1,6-diazabicyclo[3.2.1]octan-6-yl hydrogen sulfate, (2S,5R)-7-oxo-2-(N-(thiazole-5-carbonyl)carbamimidoyl)-1,6-diazabicyclo[3.2.1]octan-6-yl hydrogen sulfate, (2S,5R)-2-(N-(4-cyanobenzoyl)carbamimidoyl)-7-oxo-1,6-diazabicyclo[3.2.1]octan-6-yl hydrogen sulfate, (2S,5R)-7-oxo-2-(N-(2-phenylthiazole-4-carbonyl)carbamimidoyl)-1,6-diazabicyclo[3.2.1]octan-6-yl hydrogen sulfate, (2S,5R)-7-oxo-2-(N-(thiazole-2-carbonyl)carbamimidoyl)-1,6-diazabicyclo[3.2.1]octan-6-yl hydrogen sulfate, (2S,5R)-2-(N-(4-fluorobenzoyl)carbamimidoyl)-7-oxo-1,6-diazabicyclo[3.2.1]octan-6-yl hydrogen sulfate, (2S,5R)-7-oxo-2-(N-(5-(trifluoromethyl)picolinoyl)carbamimidoyl)-1,6-diazabicyclo[3.2.1]octan-6-yl hydrogen sulfate, (2S,5R)-7-oxo-2-(N-(4-(trifluoromethyl)benzoyl)carbamimidoyl)-1,6-diazabicyclo[3.2.1]octan-6-yl hydrogen sulfate, (2S,5R)-7-oxo-2-(N-(thiazole-4-carbonyl)carbamimidoyl)-1,6-diazabicyclo[3.2.1]octan-6-yl hydrogen sulfate, (2S,5R)-7-oxo-2-(N-(pyrimidine-5-carbonyl)carbamimidoyl)-1,6-diazabicyclo[3.2.1]octan-6-yl hydrogen sulfate, (2S,5R)-7-oxo-2-(N-(pyrimidine-4-carbonyl)carbamimidoyl)-1,6-diazabicyclo[3.2.1]octan-6-yl hydrogen sulfate, (2S,5R)-2-(N-(5-fluoropyrimidine-2-carbonyl)carbamimidoyl)-7-oxo-1,6-diazabicyclo[3.2.1]octan-6-yl hydrogen sulfate, (2S,5R)-7-oxo-2-(N-(2-(trifluoromethyl)pyrimidine-5-carbonyl)carbamimidoyl)-1,6-diazabicyclo[3.2.1]octan-6-yl hydrogen sulfate, (2S,5R)-7-oxo-2-(N-(5-(trifluoromethyl)pyrimidine-2-carbonyl)carbamimidoyl)-1,6-diazabicyclo[3.2.1]octan-6-yl hydrogen sulfate, (2S,5R)-2-(N-(5-fluoropicolinoyl)carbamimidoyl)-7-oxo-1,6-diazabicyclo[3.2.1]octan-6-yl hydrogen sulfate (2S,5R)-2-(N-(3,5-difluoropicolinoyl)carbamimidoyl)-7-oxo-1,6-diazabicyclo[3.2.1]octan-6-yl hydrogen sulfate, (2S,5R)-2-(N-(5,6-difluoropicolinoyl)carbamimidoyl)-7-oxo-1,6-diazabicyclo[3.2.1]octan-6-yl hydrogen sulfate, (2S,5R)-2-(N-(3,4-difluorobenzoyl)carbamimidoyl)-7-oxo-1,6-diazabicyclo[3.2.1]octan-6-yl hydrogen sulfate, (2S,5R)-7-oxo-2-(N-(3,4,5-trifluorobenzoyl)carbamimidoyl)-1,6-diazabicyclo[3.2.1]octan-6-yl hydrogen sulfate, (2S,5R)-2-(N-(1-methyl-1H-1,2,4-triazole-3-carbonyl)carbamimidoyl)-7-oxo-1,6-diazabicyclo[3.2.1]octan-6-yl hydrogen sulfate, (2S,5R)-2-(N-(isoxazole-3-carbonyl)carbamimidoyl)-7-oxo-1,6-diazabicyclo[3.2.1]octan-6-yl hydrogen sulfate, (2S,5R)-2-(N-(isoxazole-4-carbonyl)carbamimidoyl)-7-oxo-1,6-diazabicyclo[3.2.1]octan-6-yl hydrogen sulfate, (2S,5R)-2-(N-(1,2,4-oxadiazole-3-carbonyl)carbamimidoyl)-7-oxo-1,6-diazabicyclo[3.2.1]octan-6-yl hydrogen sulfate, (2S,5R)-2-(N-(1,2,5-oxadiazole-3-carbonyl)carbamimidoyl)-7-oxo-1,6-diazabicyclo[3.2.1]octan-6-yl hydrogen sulfate, (2S,5R)-2-(N-(4-methyl-4H-1,2,4-triazole-3-carbonyl)carbamimidoyl)-7-oxo-1,6-diazabicyclo[3.2.1]octan-6-yl hydrogen sulfate, (2S,5R)-2-(N-(1-methyl-1H-1,2,3-triazole-4-carbonyl)carbamimidoyl)-7-oxo-1,6-diazabicyclo[3.2.1]octan-6-yl hydrogen sulfate, (2S,5R)-7-oxo-2-(N-((S)-piperidine-2-carbonyl)carbamimidoyl)-1,6-diazabicyclo[3.2.1]octan-6-yl hydrogen sulfate, (2S,5R)-2-(N-((S)-1-acetylpiperidine-2-carbonyl)carbamimidoyl)-7-oxo-1,6-diazabicyclo[3.2.1]octan-6-yl hydrogen sulfate, (2S,5R)-7-oxo-2-(N-(3,4,5,6-tetrahydropyridazine-3-carbonyl)carbamimidoyl)-1,6-diazabicyclo[3.2.1]octan-6-yl hydrogen sulfate, (2S,5R)-2-(N-(1-methylazetidine-3-carbonyl)carbamimidoyl)-7-oxo-1,6-diazabicyclo[3.2.1]octan-6-yl hydrogen sulfate, (2S,5R)-2-(N-(1-acetylazetidine-3-carbonyl)carbamimidoyl)-7-oxo-1,6-diazabicyclo[3.2.1]octan-6-yl hydrogen sulfate, (2S,5R)-2-(N-(azetidine-3-carbonyl)carbamimidoyl)-7-oxo-1,6-diazabicyclo[3.2.1]octan-6-yl hydrogen sulfate, (2S,5R)-2-(N-(1-methylaziridine-2-carbonyl)carbamimidoyl)-7-oxo-1,6-diazabicyclo[3.2.1]octan-6-yl hydrogen sulfate, (2S,5R)-2-(N-(1-acetylaziridine-2-carbonyl)carbamimidoyl)-7-oxo-1,6-diazabicyclo[3.2.1]octan-6-yl hydrogen sulfate, (2S,5R)-2-(N-(aziridine-2-carbonyl)carbamimidoyl)-7-oxo-1,6-diazabicyclo[3.2.1]octan-6-yl hydrogen sulfate.

The present invention also relates to methods for the preparation of compounds of formula (I). The compounds of the present invention of formula (I) can be readily prepared by the following reaction Scheme 1 and examples using readily available starting materials, reagents and conventional synthesis procedures known to those of ordinary skill in this art.

SCHEME 1

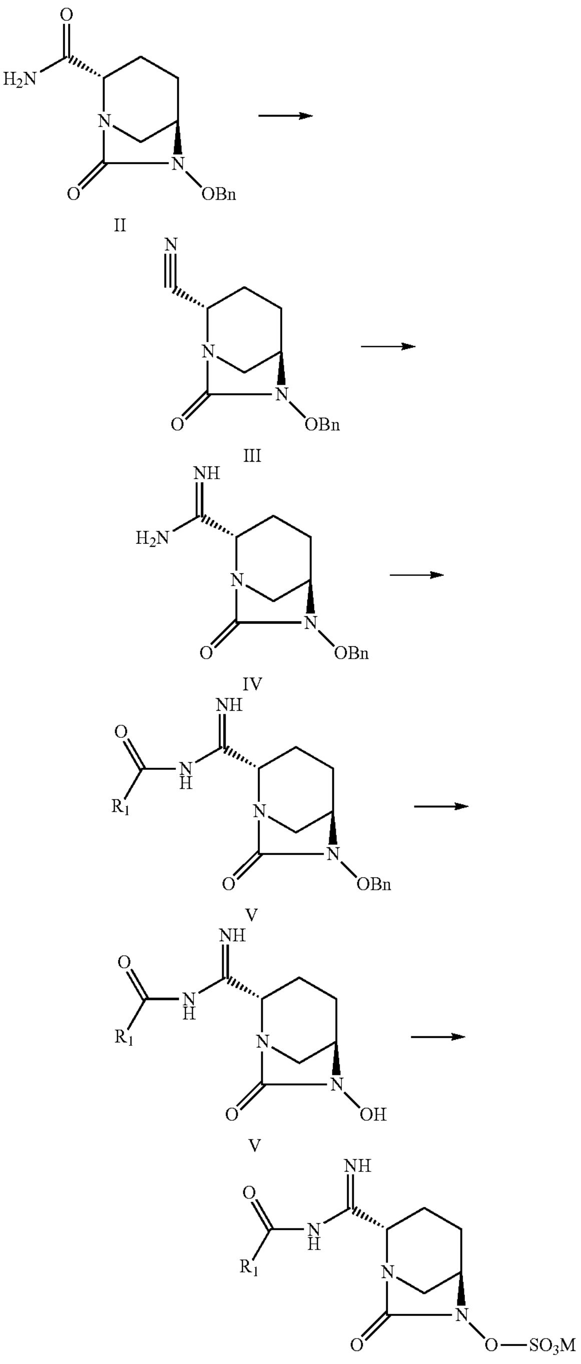

II

III

IV

V

V

I

The bicyclic intermediate amide (II) may be prepared following the literature (Org. Process Res. Dev. 2016, 20, 1799-1805).

Compounds of the general of formula (I) can be prepared by converting bicyclic amide (II) to the nitrile (Ill) in presence of a suitable reagents. The suitable reagents used for carrying out this step include, but are not limited to trifluoroacetic anhydride (TFAA) and triethylamine (TEA) or diisopropylethylamine (DIPEA), phosphoryl chloride ($POCl_3$) and TEA, and the like. The organic solvents useful in the reaction are not particularly limited and include any of those which do not adversely affect the reaction. Typical solvents include dichlomethane, chloroform, tetrahydrofuran and the like. The reaction is normally carried out at a temperature of from about 0° C. to 40° C., and preferably at room temperature under nitrogen. After completion of the reaction the desired product can be easily separated by conventional methods such as column chromatography, crystallization or similar methods.

The intermediate amidine (IV) can be prepared by substituting an ammonium ($NH_3$, or an appropriately ammonium salt form) to the nitrile (Ill) in presence of a suitable reagent. An appropriately ammonium salt such as ammonium chloride ($NH_4Cl$), ammonium bromide ($NH_4Br$), ammonium sulfate ($NH_4SO_4$) may be included. The suitable reagents useful for carrying out this step include, but are not limited to, trimethylaluminum, or triethylaluminum, or trifluoromethanesulfonate, or Lanthanum (Ill) and the like. The organic solvents useful in the reaction are not particularly limited and include any of those which do not adversely affect the reaction. Typical solvents include dichloromethane, chloroform, toluene, dimethylformamide, tetrahydrofuran, dimethylsulfoxide, and the like. The reaction is normally carried out at a temperature of from about 0° C. to about 100° C. After completion of the reaction, the desired product can be easily separated by conventional methods such as column chromatography, crystallization or similar methods.

The intermediate amide (V) may be prepared by coupling the amidine (IV) with an appropriate acid (Rr-$CO_2$H) in presence of a suitable reagent. The suitable coupling reagents useful for carrying out this step include, but are not limited to, N,N-dicyclohexylcarbodiimide (DCC) and 4-dimethylaminopyridine (DMAP), 1-[bis(dimethylamino) methylene]-1H-1,2,3-triazolo[4,5-b]pyridinium 3-oxo hexafluorophosphate (HATU) and base such as trimethylamine, triethylamine, N-methyl morpholine, or 2-chloro-4,6-dimethoxy-1,3,5-triazine (CDMT) and base such as N-methyl morpholine and the like. The organic solvents useful in the reaction are not particularly limited and include any of those which do not adversely affect the reaction. Typical solvents include dichloromethane, chloroform, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

In the following step, the intermediate amide (V) could be converted to the hydroxy compound (VI) under an atmosphere of hydrogen or hydrogen mixed with an inert diluent such as nitrogen or argon in the presence of a hydrogenation catalyst. The catalysts used in this hydrogenation reaction are the type of agents known in the art for this kind of deprotection and typical examples are the noble metals, such as nickel, palladium, platinum and rhodium. Examples of the catalysts are platinum, platinum oxide, palladium, palladium oxide and the like. The catalyst is usually present in the amount from about 1 to about 50 weight percent and preferably from about 5 to about 15 weight percent based on the compound of V. It is often convenient to suspend the catalyst on an inert support. A particularly convenient catalyst is palladium suspended on an inert support such as carbon, e.g., 5% or 10% by weight palladium on carbon.

This reaction may be conveniently effected at ambient temperature from 15 psi to 60 psi until reaction is complete (2 to 72 hours). Suitable solvents for this reaction are those which substantially dissolve the starting material of the formula (V), after reaction, the suitable solvents are sufficiently volatile to be removed by evaporation and do not themselves suffer hydrogenation. Examples of such solvents include methanol, ethanol, dioxane, ethyl acetate, tetrahydrofuran or a mixture of these solvents. Upon completion, the hydroxy intermediate (VI) can be purified by silica gel column chromatography or in many cases can be directly carried out to the next step without further purification.

Finally, the compound of formula (I) can be achieved by sulfation of the hydroxy intermediate (VI) using a sulfating reagent (e.g., pyridine-$SO_3$ complex, $NMe_3$-$SO_3$ complex, DMF-$SO_3$ complex and $ClSO_3H$) in an appropriate base (e.g., pyridine, triethylamine or 2-picoline) as described in the literature (WO2017155765A1, Org. Process Res. Dev. 2016, 20, 1799-1805). Thus, pyridine-$SO_3$ complex or $SO_3$—$NMe_3$ complex can be added to a solution of the hydroxy intermediate (VI) in a solvent in excess amount, if desired, to force the reaction to completion. The organic solvents useful for this transformation are not particularly limited and include those which do not adversely affect the reaction. Typical solvents include, but are not limited to, pyridine, tertrahydrofuran, isopropyl alcohol and water, dimethyl formamide, dimethylacetamide, acetonitrile, and the like. The transformation can be carried out at from 0° C. to 40° C., and more preferably at room temperature.

The compound of formula (I) also can be achieved by treating the sulfated intermediate with an acid to remove protecting group when the intermediate (VI) containing protection group, such as Boc., and the like. The treatment is suitably conducted at a temperature in a range from about −10° C. to about 100° C. and is typically conducted at a temperature in a range of from about 0° C. to about 35° C.

Suitable purification methods for the final compound of formula (I) are normal silica gel chromatograph, preparation HPLC, HP20 chromatograph, inon exchange resin and the like.

The compounds of the present invention of formula (I) also can be readily prepared by the following reaction Scheme 2 and examples using readily available starting materials, reagents and conventional synthesis procedures known to those of ordinary skill in this art.

SCHEME 2

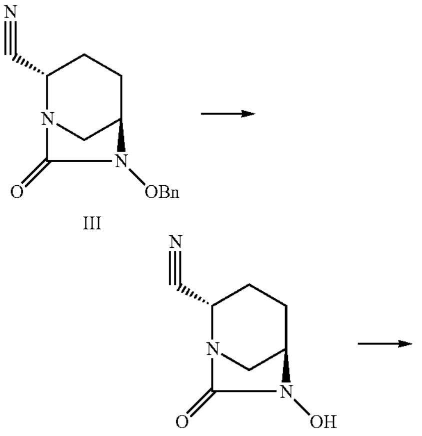

III

VII

-continued

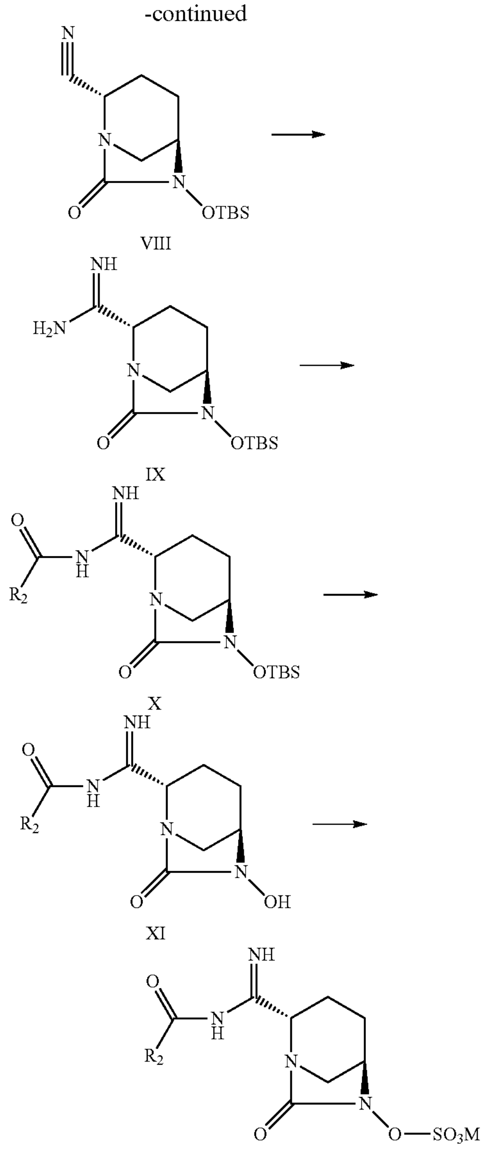

VIII

IX

X

XI

I

The intermediate nitrile (III) could be converted to the hydroxy compound (VII) under an atmosphere of hydrogen or hydrogen mixed with an inert diluent such as nitrogen or argon in the presence of a hydrogenation catalyst. The catalysts used in this hydrogenation reaction are the type of agents known in the art for this kind of deprotection and typical examples are the noble metals, such as nickel, palladium, platinum and rhodium. Examples of the catalysts are platinum, platinum oxide, palladium, palladium oxide and the like. The catalyst is usually present in the amount from about 1 to about 50 weight percent and preferably from about 5 to about 15 weight percent based on the compound (III). It is often convenient to suspend the catalyst on an inert support. A particularly convenient catalyst is palladium suspended on an inert support such as carbon, e.g., 5% or 10% by weight palladium on carbon. This reaction may be conveniently effected at ambient temperature from 15 psi to 60 psi until reaction is complete (2 to 72 hours). Suitable solvents for this reaction are those which substantially dissolve the starting material of the formula (III), after reaction, the suitable solvents are sufficiently volatile to be removed by evaporation and do not themselves suffer hydrogenation. Examples of such solvents include methanol, ethanol, dioxane, ethyl acetate, tetrahydrofuran or a mixture of these solvents. Upon completion, the hydroxy intermediate (VII) can be purified by silica gel column chromatography or in many cases can be directly carried out to the next step without further purification.

The intermediate silyl ether (VIII) can be prepared by protecting the hydroxy compound (VII) with proper silane group in presence of a suitable base reagent. A proper protecting silane reagent such as chlorotrimethylsilane (TMSCI), tert-butyldimethylchlorosilane (TBSCI), tert-butyldiphenylsilyl chloride (TBDPSCI) and the like. A suitable base reagent such as imidazole, triethylamine and the like?, The organic solvents useful in the reaction are not particularly limited and include any of those which do not adversely affect the reaction. Typical solvents include dichloromethane, chloroform, dimethylformamide, tetrahydrofuran and the like. The reaction is normally carried out at a temperature of from about 0° C. to about 100° C. After completion of the reaction the desired product can be easily separated by conventional methods such as column chromatography, crystallization or similar methods.

The intermediate amidine (IX) can be prepared by substituting an ammonium ($NH_3$, or an appropriately ammonium salt) to the nitrile (VIII) in presence of a suitable reagent. An appropriately ammonium salt such as ammonium chloride ($NH_4Cl$), ammonium bromide ($NH_4Br$), ammonium sulfate ($NH_4SO_4$) may be included. The suitable reagents useful for carrying out this step include, but are not limited to, trimethylaluminum, or triethylaluminum, or trifluoromethanesulfonate, or Lanthanum (III) and the like. The organic solvents useful in the reaction are not particularly limited and include any of those which do not adversely affect the reaction. Typical solvents include dichloromethane, chloroform, toluene, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

In the following step, the intermediate amide (X) may be prepared by coupling the amidine (IX) with an appropriate acid ($R_2$—$CO_2H$) in presence of a suitable reagent. The suitable coupling reagents useful for carrying out this step include, but are not limited to, N,N-dicyclohexylcarbodiimide (DCC) and 4-dimethylaminopyridine (DMAP), 1-[bis(dimethylamino)methylene]-1H-1,2,3-triazolo[4,5-b]pyridinium 3-oxo hexafluorophosphate (HATU) and base such as trimethylamine, triethylamine, N-methyl morpholine, or 2-chloro-4,6-dimethoxy-1,3,5-triazine (CDMT) and base such as N-methyl morpholine and the like. The organic solvents useful in the reaction are not particularly limited and include any of those which do not adversely affect the reaction. Typical solvents include dichloromethane, chloroform, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

The intermediate amide (X) could be converted to the hydroxy compound (XI) by deprotecting reaction in presence of a suitable reagent. The suitable reagents used for carrying out this step include, but are not limited to tetra-n-butylammonium fluoride (TBAF), acetic acid, hydrogen fluoride, trifluoroacetic acid and the like. The organic solvents useful in the reaction are not particularly limited and include any of those which do not adversely affect the reaction. Typical solvents include tetrahydrofuran, dichlomethane and the like. The reaction is normally carried out at a temperature of from about 0° C. to 40° C., and preferably at room temperature under nitrogen. After completion of the reaction the desired product can be easily separated by conventional methods such as column chromatography, crystallization or similar methods.

Finally, the compound of formula (I) can be achieved by sulfation of the hydroxy intermediate (XI) using a similar sulfating reagent above, the reaction condition and the purification methods described in Scheme 1.

EXAMPLES

Abbreviations

In the experiments the following abbreviations have been used:

δ: chemical shift in parts per million (ppm) by frequency
br s: broad single in NMR
d: doublet in NMR
dd: doublet of doublet in NMR
t: triplet in NMR
q: quartet in NMR
m: multiplet in NMR
J: coupling constant in NMR
Hz: hertz
MHz: megahertz
NMR: nuclear magnetic resonance
$ES^-$: negative ion mode in electrospray ionization mass spectrometry
$ES^+$: positive ion mode in electrospray ionization mass spectrometry
MS: mass spectrum
HPLC: high performance liquid chromatography
g: gram(s)
mg: milligram(s)
mmol: millimole(s)
mol: mole(s)
L: liter(s)
mL: milliliter(s)
M: molarity
h: hour(s)
min: minute(s)
Pd/C: palladium on carbon
DCC: N,N'-dicyclohexylcarbodiimide
DIAD: diisopropyl azodicarboxylate
DMAP: 4-dimethylaminopyridine
TEA: triethylamine
DIPEA: N,N-diisopropylethylamine
HATU: 0-(7-Aza-1H-benzotriazol-1-yl)-N,N,N',N'-tetramethyluronium hexafluorophosphate
TBAF: tetrabutylammonium fluoride
TFAA: trifluoroacetic anhydride
DCM: dichloromethane
DMF: dimethylformamide
DMSO: dimethyl sulfoxide
EtOAc: ethyl acetate
TFA: trifluoroacetic acid
THF: tertrahydrofuran
TLC: thin layer chromatography
TMS: tetramethylsilane
$CDCl_3$: deuterated chloroform
$CD_3OD$: deuterated methanol
$D_2O$: deuterium oxide
DMSO-$d_6$: deuterium dimethyl sulfoxide
pH: the negative logarithm of the hydrogen ion concentration
Boc: N-tert-butoxycarbonyl
Bn: benzyl
HPLC: high-performance liquid chromatography

Analytical Methods

All $^1H$ and $^{19}F$ NMR spectra were recorded on a Bruker AVANCE NEO 400 NMR operating at 400 MHz for $^1H$, and 376 MHz for $^{19}F$ respectively. NMR data was recorded in chemical shifts relative to tetramethylsilane (TMS) as internal standard. NMR spectra were run either in $CDCl_3$ containing 0.05% TMS, $CD_3OD$ containing 0.05% TMS, $D_2O$ or DMSO-$d_6$ containing 0.03% TMS.

Preparative HPLC was performed on an Agilent 1260 Infinity II System on Agilent 10 prep-C18 250×21.2 mm column, using an acetonitrile/aqueous 0.1% trifluoroacetic acid gradient, or an acetonitrile/aqueous 0.1% formic acid gradient at 22° C.

Mass spectra were performed on an Agilent 126011-6125 Separation Module using either $ES^-$ or $ES^+$ ionization modes.

Column Chromatography was performed with using Qingdao Inc. Silica Gel: CC Grade (230-400 Mesh).

Commercial solvents and reagents were generally used without further purification. All products were dried before characterisation and use in subsequent synthetic steps.

1. General Synthetic Methods

1.1 Synthesis of (2S,5R)-6-(benzyloxy)-7-oxo-1,6-diazabicyclo[3.2.1]octane-2-carboximidamide (BB-1)

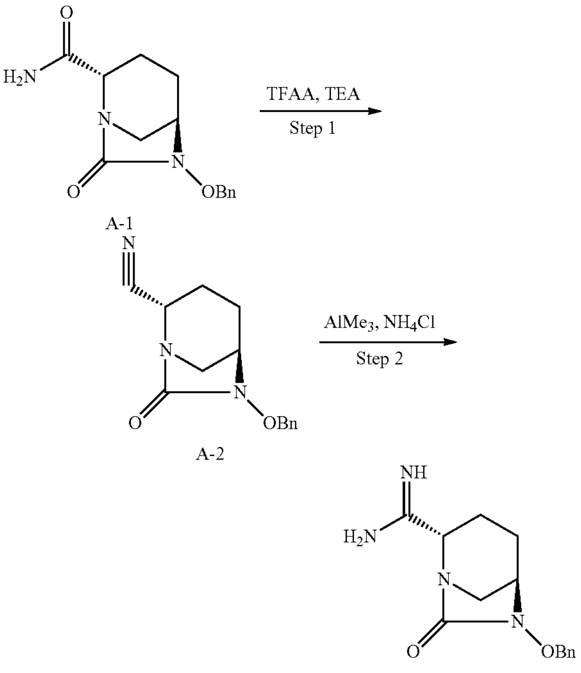

BB-1

Step 1: Synthesis of (2S,5R)-6-(benzyloxy)-7-oxo-1,6-diazabicyclo[3.2.1]octane-2-carbonitrile (A-2)

TFAA (0.3 g, 1.4 mmol) was added to a mixture of A-1 (0.2 g, 0.7 mmol) and TEA (0.7 g, 7.0 mmol) in DCM (5 mL) at 0° C. The resulting reaction mixture was heated at 35° C. for 3 hours, and then concentrated under reduced pressure. The residue was extracted with ethyl acetate, washed with water, brine, dried over $Na_2SO_4$ and filtrated. The filtrate was concentrated to give a residue, which was further purified by column chromatography eluting with 30% ethyl acetate in hexane to give the title compound A-2 (0.17 g, 64%) as a brown solid. $^1$H NMR (400 MHz, DMSO-$d_6$): δ 1.81-1.91 (m, 2H), 1.92-2.00 (m, 2H), 3.10 (d, J=11.7 Hz, 11H), 3.21 (d, J=12.3 Hz, 1H), 3.74 (s, 11H), 4.58 (d, J=6.6 Hz, 1H), 4.93 (d, J=11.6 Hz, 1H), 4.96 (d, J=11.6 Hz, 1H), 7.36-7.43 (m, 3H), 7.44-7.48 (m, 3H). LC-MS analysis: $[M+H]^+$=256.1.

Step 2: Synthesis of (2S,5R)-6-(benzyloxy)-7-oxo-1,6-diazabicyclo[3.2.1]octane-2-carboximidamide (BB-1)

$AlMe_3$ in n-hexane (2 N, 9.0 mL, 18.0 mmol) and $NH_4Cl$ (0.96 g, 18.0 mmol) were added to a solution of A-2 (3.08 g, 15.0 mmol) in anhydrous DCM (45 mL) at 0° C. The reaction mixture was stirred at room temperature overnight, cooled to 0° C., quenched by addition of silica gel (8 g) and methanol (8 mL). The resulting mixture was stirred at room temperature for 20 min, filtered off, rinsed with 10% methanol in DCM (2×30 mL). The filtrate was concentrated and purified by flash column chromatography using 2-5% MeOH in DCM to give the title compound BB-1 (1.45 g, 44%) as a white solid. $^1$H NMR (400 MHz, DMSO-$d_6$): δ1.61-1.79 (m, 2H), 1.80-1.92 (m, 2H), 2.77-2.95 (m, 2H), 3.12-3.21 (s, 1H), 3.80-3.92 (m, 1H), 4.09-4.15 (m, 1H), 4.74-4.84 (m, 2H), 6.52-6.66 (s, 2H), 7.33-7.42 (m, 3H), 7.45-7.54 (m, 2H). LC-MS analysis: $[M+Na]^+$=297.1.

1.2 Synthesis of (2S,5R)-6-((tert-butyldimethylsilyl)oxy)-7-oxo-1,6-diazabicyclo[3.2.1]octane-2-carboximidamide (BB-2)

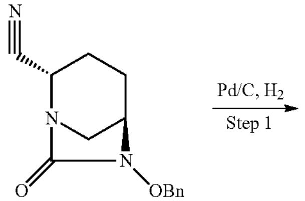

A-2

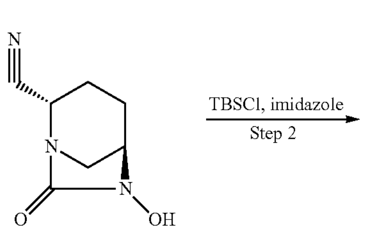

B-1

-continued

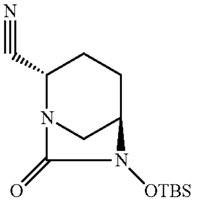

B-2

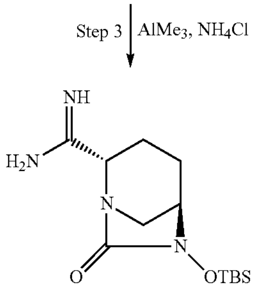

BB-2

Step 1: Synthesis of (2S,5R)-6-hydroxy-7-oxo-1,6-diazabicyclo[3.2.1]octane-2-carbonitrile (B-1)

Wet 5% Pd/C (720 mg) was added to a solution of compound A-2 (3.5 g, 13.6 mmol) in EtOAc and DCM (2:1, 15 mL), and then hydrogenated at room temperature under 45 psi pressure for 2 hours. After completion of reaction, the catalyst was removed by celite filtration and washed with EtOAc. The filtrate was concentrated to obtain the pale yellow compound B-1 (2.1 g, 95%) as a crude product which was used without purification for further reaction. $^1$H NMR (400 MHz, $CDCl_3$): δ 1.68-1.70 (m, 1H), 1.87-1.93 (m, 2H), 2.05-2.18 (m, 1H), 3.14-3.25 (m, 2H), 4.01-4.14 (m, 1H), 5.21 (br s, 1H).

Step 2: Synthesis of (2S,5R)-6-((tert-butyldimethylsilyl)oxy)-7-oxo-1,6-diazabicyclo[3.2.1]octane-2-carbonitrile (B-2)

Tert-butyldimethylsilyl chloride (2 g, 13.5 mmol) was added to a stirred solution of compound B-1 (1.5 g, 9 mmol) and imidazole (1.2 g, 18 mmol) in DCM (20 mL). The reaction mixture was stirred at room temperature overnight. The solids formed were filtered and the filtrate was washed with 0.1 N HCl followed by water and brine. The organic layer was dried over $MgSO_4$ and concentrated to furnish the crude product which was purified by column chromatography using DCM as a solvent to give the title compound B-2 (1.16 g, 46%) as a white solid. $^1$H NMR (400 MHz, $CDCl_3$): δ 0.00 (s, 3H), 0.06 (s, 3H), 0.78 (s, 9H), 1.69-1.76 (m, 2H), 2.00-2.13 (m, 2H), 3.00 (d, J=11.5 Hz, 1H), 3.19 (d, J=12.2 Hz, 1H), 3.46 (s, 1H), 4.17 (d, J=7.2 Hz, 1H).

Step 3: Synthesis of (2S,5R)-6-((tert-butyldimethylsilyl)oxy)-7-oxo-1,6-diazabicyclo[3.2.1]octane-2-carboximidamide (BB-2)

Trimethylaluminum (2 M in hexane, 2.9 mL, 5.8 mmol) was added dropwise to a suspension of ammonium chloride (358 mg, 5.87 mmol) in DCM (10 mL) at room temperature. The suspension was further stirred for 30 minutes followed by the dropwise addition of compound B-2 (1.1 g, 3.9 mmol) dissolved in DCM (10 mL). The reaction mixture was stirred overnight at room temperature while the progress of reaction was monitored by LCMS. Another portion of $NH_4Cl$ (358 mg, 5.87 mmol) and trimethylaluminum (2.9 mL, 5.8 mmol) was further added. The reaction mixture was further stirred at room temperature for 24 hours. Upon completion of reaction MeOH (50 mL) was added dropwise to quench the unreacted trimethylaluminum. Bulk of solid formed was filtered and the filter cake was washed with MeOH. The filtrate was concentrated to afford the white solid which was purified by column chromatography using DCM containing 2-4% MeOH to give the title product BB-2 (263 mg, 23%) as a white solid. $^1H$ NMR (400 MHz, $CDCl_3$): δ 0.00 (s, 6H), 0.77 (s, 9H), 1.62-1.66 (m, 2H), 1.73-1.78 (m, 1H), 1.83-1.87 (m, 1H), 2.80 (dd, J=11.2 Hz, 3.18 Hz, 1H), 2.95 (t, J=11.2 Hz, 1H), 3.64-3.72 (m, 1H), 3.80 (d, J=2.1 Hz, 1H), 5.76 (br s, 2H).

1.3 Synthesis of (E)-6-((tert-butoxycarbonyl)amino)-2,2-dimethyl-4-oxo-3,8-dioxa-5,7-diazaundec-5-en-11-oic acid (BB-3)

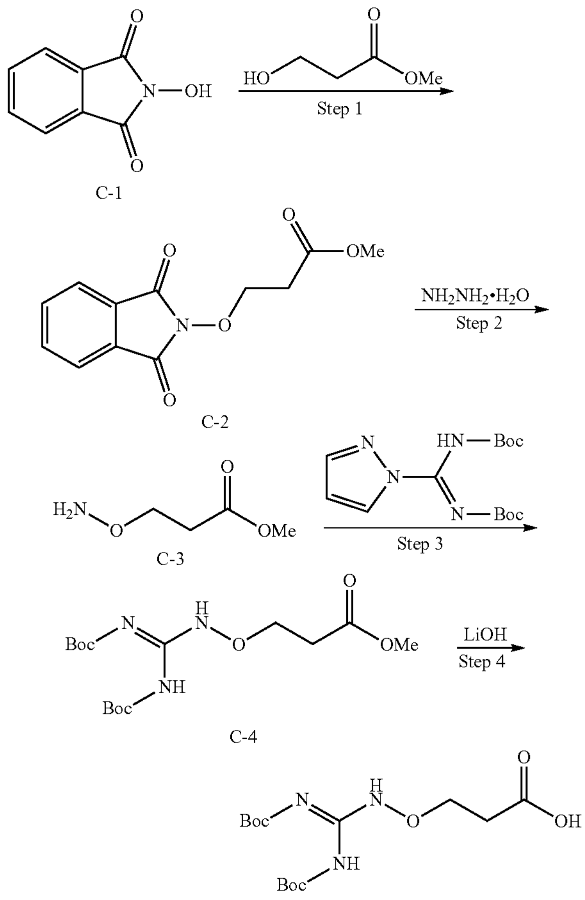

C-1, C-2, C-3, C-4, BB-3

Step 1: Synthesis of methyl 3-((1,3-dioxoisoindolin-2-yl)oxy)propanoate (C-2)

A solution of DIAD (2.40 g, 12.0 mmol) in THE (10 mL) was slowly added to a mixture of C-1 (1.96 g, 12.0 mmol), triphenylphosphine (TPP, 3.10 g, 12.0 mmol) and methyl 4-hydroxybutanoate (1.04 g, 10 mmol) in THE (30 mL) under ice water bath, then warmed up to room temperature and stirred overnight. The reaction mixture was concentrated, extracted with diethyl ether, washed with saturated $NaHCO_3$, brine, dried over $Na_2SO_4$ and filtrated. The filtrate was concentrated to give a residue, which was further purified by silica gel column chromatography eluting with 30% ethyl acetate in hexane to give the title compound C-2 (0.54 g, 21%) as an oil. $^1H$ NMR (400 MHz, $CDCl_3$): δ 2.86 (t, J=6.5 Hz, 2H), 3.72 (s, 3H), 4.52 (t, J=6.5 Hz, 2H), 7.75-7.79 (m, 2H), 7.82-7.87 (m, 2H).

Step 2: Synthesis of methyl 3-(aminooxy)propanoate (C-3)

Hydrazine hydrate (0.63 g, 12.6 mmol) was slowly added to a solution of C-2 (3.80 g, 14.0 mmol) in EtOH (30 mL) under cooled water bath, then warmed up to room temperature and stirred for 2 hours. The reaction mixture was filtrated to remove solid, the filtrate was concentrated to give the title compound C-3 (3.0 g) as an oil, which was directly used for next step without further purification. $^1H$ NMR (400 MHz, DMSO-$d_6$): δ 1.88 (t, J=6.3 Hz, 2H), 2.88 (s, 3H), 3.32 (t, J=6.3 Hz, 2H), 4.11 (br s, 2H).

Step 3: Synthesis of methyl (E)-6-((tert-butoxycarbonyl)amino)-2,2-dimethyl-4-oxo-3,8-dioxa-5,7-diazaundec-5-en-11-oate (C-4)

DIPEA (9.60 g, 75 mmol) was added to a solution of C-3 (3.0 g obtained above, 14.0 mmol) and N,N-bis-boc-1-guanylpyrazolen (9.0 g, 30 mmol) in MeOH (30 mL), and stirred at room temperature for 16 hours. The reaction mixture was concentrated to give a residue, which was purified by preparative HPLC on C18 column and lyophilized to give the title compound C-4 (3.2 g, 63% in two steps) as an oil. $^1H$ NMR (400 MHz, $CDCl_3$): δ 1.48 (s, 9H), 1.49 (s, 9H), 2.71 (t, J=5.8 Hz, 2H), 3.70 (s, 3H), 4.30 (t, J=5.8 Hz, 2H), 7.81 (s, 1H), 9.17 (s, 1H).

Step 4: Synthesis of (E)-6-((tert-butoxycarbonyl)amino)-2,2-dimethyl-4-oxo-3,8-dioxa-5,7-diazaundec-5-en-11-oic acid (BB-3)

1 N NaOH was added to a solution of C-4 (1.29 g, 3.57 mmol) in THE (8 mL) at 0° C., stirred at 0° C. for 2 hours. The reaction mixture was concentrated to give a residue, which was diluted with water (15 mL), washed with DCM (30 mL) to remove impurities. The aqueous layer was cooled 0° C., acidified pH-5 by 1 N HCl, lyophilized to give crude desired compound, which was dissolved with 5% MeOH in DCM (3×30 mL), filtrated to remove solid. The filtrate was concentrated to give the title compound BB-3 (1.22 g, 98%) as a white solid. $^1H$ NMR (400 MHz, DMSO-$d_6$): $^1H$ NMR (400 MHz, DMSO-$d_6$): δ 1.38 (s, 9H), 1.39 (s, 9H), 2.31 (t, J=6.2 Hz, 2H), 3.96 (t, J=6.2 Hz, 2H), 9.04 (s, 1H).

1.4 Synthesis of (R)-1-acetylpiperidine-3-carboxylic acid (BB-4)

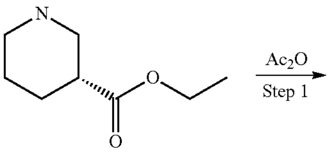

D-1

-continued

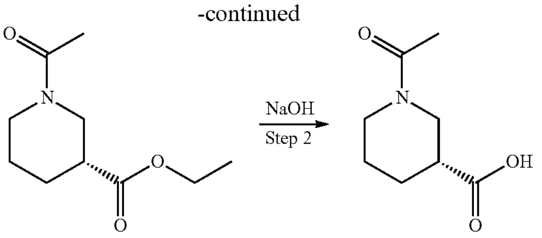

D-2 BB-4

Step 1: Synthesis of ethyl (R)-1-acetylpiperidine-3-carboxylate (D-2)

$Ac_2O$ (1.4 g, 14.3 mmol) was added to a solution of D-1 (2.0 g, 12.7 mmol) in DCM (20 mL), and stirred at room temperature for 24 hours. The reaction mixture was concentrated to give a residue, which was further purified by silica gel column chromatography eluting with 50% ethyl acetate in petroleum ether to give the title compound D-2 (2.41 g, 95%) as an oil. $^1H$ NMR (400 MHz, $CDCl_3$): δ 1.25 (t, J=7.1 Hz, 1.5H), 1.28 (t, J=7.1 Hz, 1.5H), 1.44-1.55 (m, 1H), 1.64-1.73 (m, 1H), 1.76-1.86 (m, 1H), 1.97-2.07 (m, 1H), 2.09 (s, 1.5H), 2.14 (s, 1.5H), 2.39-2.52 (m, 1H), 2.80-2.87 (m, 0.5H), 3.03-3.14 (m, 1H), 3.43-3.50 (m, 0.5H), 3.68-3.77 (m, 1H), 3.94-4.01 (m, 0.5H), 4.10-4.20 (m, 2H), 4.59-4.65 (m, 0.5H).

Step 2: Synthesis of (R)-1-acetylpiperidine-3-carboxylic acid (BB-4)

NaOH (2 N, 6 mL, 12 mmol) was added to a solution of D-2 (1.2 g, 6.0 mmol) in THE (8 mL) at 0° C., and stirred at 0° C. for 2 hours. The reaction mixture was concentrated to remove THE at 13° C. to give a residue, which was washed by DCM (10×2 mL), the aqueous layer was acidified to pH-4 by 3 N HCl at 0° C., and lyophilized to give a residue, which was extracted with DCM, the DCM layer was concentrated to give the title compound BB-4 (1.04 g, quantitative yield) as a solid. $^1H$ NMR (400 MHz, DMSO-$d_6$): δ 1.24-1.43 (m, 1H), 1.48-1.56 (m, 1H), 1.58-1.68 (m, 1H), 1.81-1.89 (m, 1H), 1.97 (s, 1.5H), 2.00 (s, 1.5H), 2.06-2.15 (m, 0.5H), 2.36-2.33 (m, 0.5H), 2.53-2.60 (m, 0.5H), 2.87-2.99 (m, 1H), 3.24-3.31 (m, 0.5H), 3.62-3.71 (m, 1H), 3.75-3.81 (m, 0.5H), 4.35-4.42 (m, 0.5H). 1.5 Synthesis of (S)-1-acetylpiperidine-3-carboxylic acid (BB-5)

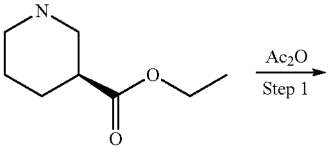

E-1

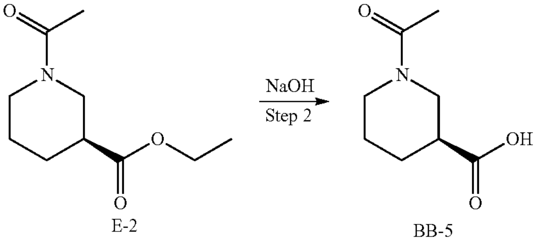

E-2 BB-5

Step 1: Synthesis of ethyl (S)-1-acetylpiperidine-3-carboxylate (E-2)

$Ac_2O$ (1.4 g, 14.3 mmol) was added to a solution of E-1 (2.0 g, 12.7 mmol) in DCM (20 mL), and stirred at room temperature for 24 hours. The reaction mixture was concentrated to give a residue, which was further purified by silica gel column chromatography eluting with 50% ethyl acetate in petroleum ether to give the title compound E-2 (2.51 g, 99%) as an oil. $^1H$ NMR (400 MHz, $CD_3Cl$): δ 1.25 (t, J=7.1 Hz, 1.5H), 1.28 (t, J=7.1 Hz, 1.5H), 1.41-1.55 (m, 1H), 1.64-1.73 (m, 1H), 1.76-1.86 (m, 1H), 1.97-2.07 (m, 1H), 2.09 (s, 1.5H), 2.14 (s, 1.5H), 2.39-2.52 (m, 1H), 2.80-2.87 (m, 0.5H), 3.03-3.14 (m, 1H), 3.43-3.50 (m, 0.5H), 3.68-3.77 (m, 1H), 3.94-4.01 (m, 0.5H), 4.10-4.20 (m, 2H), 4.59-4.65 (m, 0.5H).

Step 2: Synthesis of (R)-1-acetylpiperidine-3-carboxylic acid (BB-5)

NaOH (2 N, 6 mL, 12 mmol) was added to a solution of E-2 (1.2 g, 6.0 mmol) in THE (8 mL) at 0° C., and stirred at room temperature for 2 hours. The reaction mixture was concentrated to remove THF, water (5 mL) was added, washed by DCM (10×2 mL). The aqueous layer was acidified to pH-4 by 3 N HCl at 0° C., and lyophilized to give a residue, which was extracted with DCM, the DCM layer was concentrated to give the title compound BB-5 (0.88 g, 85%) as a solid. $^1H$ NMR (400 MHz, $CDCl_3$): δ 1.44-1.57 (m, 1H), 1.65-1.73 (m, 0.5H), 1.74-1.90 (m, 1.5H), 1.93-2.03 (m, 1H), 2.09 (s, 1.5H), 2.15 (s, 1.5H), 2.41-2.52 (m, 1H), 3.13-3.20 (m, 0.5H), 3.24-3.32 (m, 0.5H), 3.38-3.57 (m, 1.5H), 3.71-3.77 (m, 0.5H), 3.88-3.96 (m, 0.5H), 4.01-4.08 (m, 0.5H), 8.12 (br s, 1H).

1.6 Synthesis of (S)-1-acetylpyrrolidine-3-carboxylic acid (BB-6)

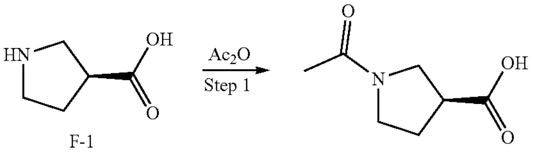

F-1 BB-6

(S)-pyrrolidine-3-carboxylic acid F-1 (0.23 g, 2 mmol) was added to a suspension of acetic anhydride (3 mL, 29.4 mmol) in water (0.5 mL), and stirred at room temperature for 3 hours. EtOH (100 mL) was added to the reaction mixture, and concentrated to give a residue, which was treated with EtOAc and petroleum ether (25/25 mL) to give a white solid. The solid was collected by filtration and dried over air to give the title compound BB-6 (0.29 g, 92%) as a solid. $^1H$ NMR (400 MHz, DMSO-$d_6$): δ 1.91 (s, 1.5H), 1.93 (s, 1.5H), 1.96-2.17 (m, 1.5H), 2.97-3.04 (m, 0.5H), 3.07-3.16 (m, 0.5H), 3.22-3.55 (m, 4H), 3.60-3.65 (m, 0.5H), 12.51 (br s, 1H).

1.7 Synthesis of (R)-1-acetylpyrrolidine-3-carboxylic acid (BB-7)

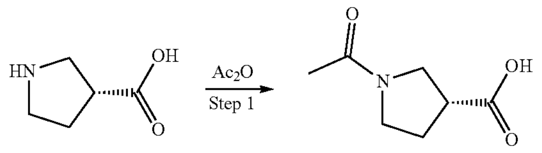

G-1 BB-7

(R)-pyrrolidine-3-carboxylic acid (G-1, 0.23 g, 2 mmol) was added to a suspension of acetic anhydride (3 mL, 29.4 mmol) in water (0.5 mL), and stirred at room temperature for 3 hours. EtOH (100 mL) was added to the reaction mixture, and concentrated to give a residue, which was treated with EtOAc and petroleum ether (25/25 mL) to give a white solid. The solid was collected by filtration and dried over air to give the title compound BB-7 (0.30 g, 95%) as a solid. $^1H$ NMR (400 MHz, DMSO-$d_6$): δ 1.91 (s, 1.5H), 1.93 (s, 1.5H), 1.96-2.17 (m, 1.5H), 2.97-3.04 (m, 0.5H), 3.07-3.16 (m, 0.5H), 3.22-3.55 (m, 4H), 3.60-3.65 (m, 0.5H), 12.51 (br s, 1H).

1.8 Synthesis of (S)-1-acetylpiperidine-2-carboxylic acid (BB-8)

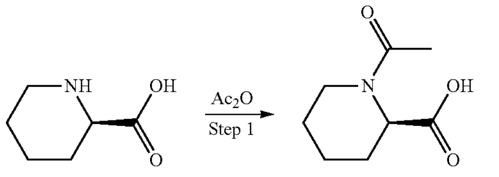

H-1 BB-8

(R)-piperidine-2-carboxylic acid (H-1, 1 g, 7.7 mmol) was added to a suspension of acetic anhydride (3 mL, 116 mmol) in water (2 mL), and stirred at room temperature for 3 hours. EtOH (100 mL) was added to the reaction mixture, and concentrated to give a residue, which was treated with EtOAc and petroleum ether (30/30 mL) to give a white solid. The solid was collected by filtration and dried over air to give the title compound BB-8 (0.9 g, 68%) as an solid. H NMR (400 MHz, DMSO-$d_6$): δ 1.24-1.55 (m, 5H), 1.88 (s, 2H), 1.94 (s, 1H), 2.19-2.31 (m, 1.2H), 2.64-2.73 (m, 0.8H), 3.34-3.44 (m, 0.6H), 4.06-4.10 (m, 0.6H), 4.16-4.22 (m, 0.4H), 4.76-4.80 (m, 0.4H).

1.9 Synthesis of (E)-6-((tert-butoxycarbonyl) amino)-2,2-dimethyl-4-oxo-3,8-dioxa-5,7-diazadodec-5-en-12-oic acid (BB-9)

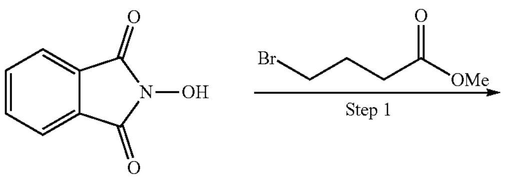

C-1

-continued

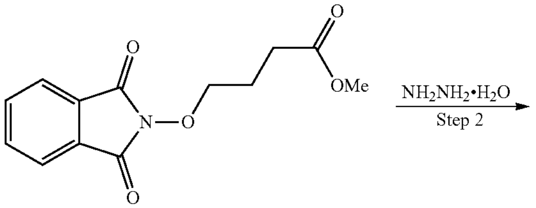

I-1

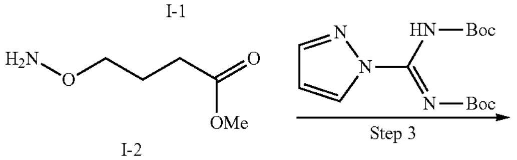

I-2

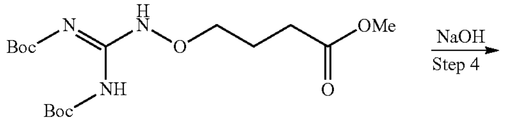

I-3

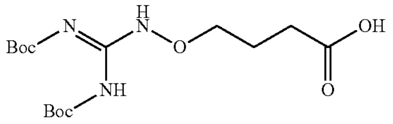

BB-9

Step 1: Synthesis of methyl 4-((1,3-dioxoisoindolin-2-yl)oxy)butanoate (1-1)

A mixture of methyl 4-bromobutanoate (14.7 g, 81.5 mmol), N-hydroxyphthalimide (C-1, 13.3 g, 81.5 mmol), and triethylamine (22.7 mL, 0.16 mol) in acetonitrile (110 mL) was refluxed for 3 hours. The insoluble solid was removed by filtration, and the filtrate was concentrated to give a residue. The residue was diluted with ethyl acetate (100 mL), washed successively with water and brine (100 mL), dried over anhydrous magnesium sulfate. The organic phase was concentrated, followed by recrystallization with hot ethanol to give the title compound 1-1 (16.8 g 78%) as a solid. $^1H$ NMR (400 MHz, $CDCl_3$): δ 2.09 (q, J=6.7 Hz, 2H), 2.66 (t, J=7.3 Hz, 2H), 3.70 (s, 3H), 4.26 (t, J=6.1 Hz, 2H), 7.79 (m, 4H).

Step 2: Synthesis of methyl 4-(aminooxy)butanoate (1-2)

Hydrazine (0.83 mL, 15.7 mmol) was slowly added to a solution of 1-1 (2.75 g, 10.45 mmol) in DCM (50 mL) at −10° C., then stirred for 1.5 hours at −10 to 0° C. The reaction mixture was filtrated to remove solid, the filtrate was concentrated to give the title compound 1-2 (1.39 g, quantitative) as a yellow oil, which was directly used for next step without further purification. $^1H$ NMR (400 MHz, $CDCl_3$): δ 1.92 (q, J=6.7 Hz, 2H), 2.38 (t, J=7.3 Hz, 2H), 3.61 (s, 3H), 3.62 (t, J=6.2 Hz, 2H), 5.25 (br s, 2H).

Step 3: Synthesis of methyl (E)-6-((tert-butoxycarbonyl)amino)-2,2-dimethyl-4-oxo-3,8-dioxa-5,7-diazadodec-5-en-12-oate (1-3)

DIPEA (2.17 g, 16.83 mmol) was added to a solution of 1-2 (0.75 g, obtained above) and N,N-bis-boc-1-guanylpyrazolen (2.09 g, 6.73 mmol) in MeOH (100 mL), and stirred at room temperature for 16 hours. The reaction mixture was concentrated to give a residue, which was purified by silica gel column chromatography eluting with 20% ethyl acetate in petroleum ether to give the title compound 1-3 (1.12 g, 57.6% in two steps) as an colourless oil. $^1$H NMR (400 MHz, $CDCl_3$): δ 1.40 (s, 9H), 1.41 (s, 9H), 1.90-2.02 (m, 2H), 2.35 (t, J=7.2 Hz, 2H), 3.61 (s, 3H), 4.00-4.05 (m, 2H).

Step 4: Synthesis of (Z)-6-((tert-Butoxycarbonyl) amino)-2,2-dimethyl-4-oxo-3,8-dioxa-5,7-diazadodec-5-en-12-oic acid (BB-9)

NaOH (64 mg, 1.6 mmol) was added to a solution of 1-3 (300 mg, 0.8 mmol) in water/THF (each 4 mL) at 0° C., stirred at 0° C. for 2 hours. The reaction mixture was concentrated to remove THE to give a residue, which was diluted with water (15 mL), washed with DCM (30 mL) to remove impurities. The aqueous layer was cooled 0° C., acidified pH-5 by 1 N HCl, lyophilized to give crude desired compound, which was dissolved with 5% MeOH in DCM (3x30 mL), filtrated to remove solid. The filtrate was concentrated to give the title compound BB-9 (1.22 g, 98%) as a white solid. $^1$H NMR (400 MHz, $CDCl_3$) b 1.42 (d, J=9.3 Hz, 18H), 1.85-2.06 (m, 2H), 2.40 (t, J=7.3 Hz, 2H), 4.02 (t, J=6.2 Hz, 2H), 5.23 (s, 1H), 7.47-7.83 (m, 1H), 9.02 (s, 1H). LC-MS analysis: $[M+H]^+$=362.2.

1.10 Synthesis of (E)-3-(2,3-bis(tert-butoxycarbonyl)guanidino)propanoic acid (BB-10)

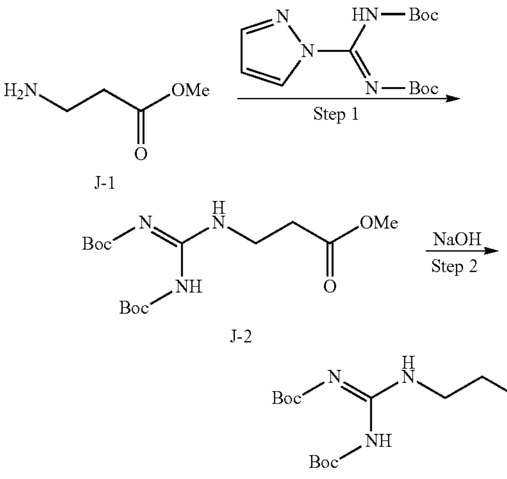

J-1

J-2

BB-10

Step 1: Synthesis of methyl (Z)-3-(2,3-bis(tert-butoxycarbonyl)guanidino)propanoate (J-2)

DIPEA (1.85 g, 14.33 mmol) was added to a solution of J-1 (0.50 g, HCl salt, 3.58 mmol) and N,N-bis-boc-1-guanylpyrazolen (1.67 g, 5.37 mmol) in acetonitrile (15 mL), and stirred at room temperature for 3 hours. The reaction mixture was concentrated to give a residue, which was diluted with EtOAc, washed with 1 N HCl solution, brine dried over $Na_2SO_4$. The organic layer was concentrated to give a residue, which was purified by silica gel column chromatography eluting with 10% ethyl acetate in petroleum ether to give the title compound J-2 (1.21 g, 97%) as a white solid. $^1$H NMR (400 MHz, $CDCl_3$): δ 1.39 (s, 9H), 1.47 (s, 9H), 2.58 (t, J=6.8 Hz, 2H), 3.51 (q, J=6.5 Hz, 2H), 3.61 (s, 3H), 8.48 (t, J=5.7 Hz, 1H), 11.47 (s, 1H).

Step 2: (Z)-3-(2,3-bis(tert-butoxycarbonyl)guanidino)propanoic acid (BB-10)

NaOH (0.12 g, 3 mmol) was added to a solution of J-2 (0.50 g, 1.5 mmol) in water/THF (each 5 mL) at 0° C., stirred at 0° C. for 2 hours. The reaction mixture was concentrated under reduced pressure to remove THF, the aqueous layer was cooled 0° C., acidified to pH-4 by 1 N HCl, extracted by DCM, dried over $Na_2SO_4$. The organic layer was concentrated to give the title compound BB-10 (0.5 g, quantitative) as a white solid. $^1$H NMR (400 MHz, $CDCl_3$) b 1.42 (s, 9H), 1.47 (s, 9H), 2.63 (t, J=5.9 Hz, 2H), 3.59 (t, J=5.9 Hz, 2H), 8.71 (s, 1H), 11.39 (br s, 1H).

2. Synthesis of the Final Compound

Example 1

(2S,5R)-2-(N-(furan-2-carbonyl)carbamimidoyl)-7-oxo-1,6-diazabicyclo[3.2.1]octan-6-yl hydrogen sulfate (compound 121 in table 1)

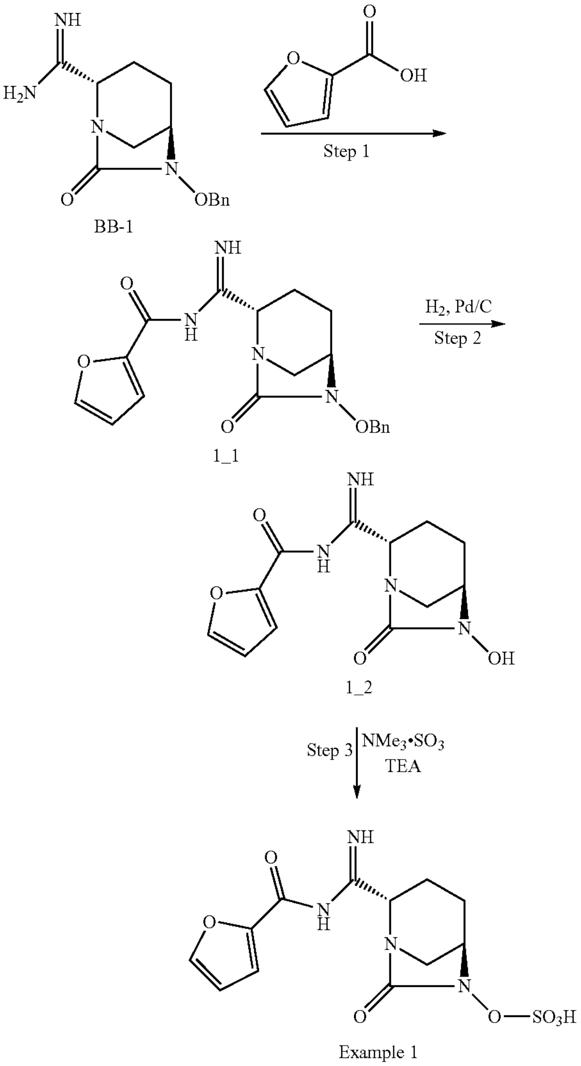

BB-1

1_1

1_2

Example 1

Step 1: Synthesis of N-(((2S,5R)-6-(benzyloxy)-7-oxo-1,6-diazabicyclo[3.2.1]octan-2-yl)(imino)methyl)furan-2-carboxamide (1_1)

Furan-2-carboxylic acid (122 mg, 1.09 mmol) was added to a mixture of (2S,5R)-6-(benzyloxy)-7-oxo-1,6-diazabicyclo[3.2.1]octane-2-carboximidamide (BB-1, 200 mg, 0.73 mmol), DAMP (89 mg, 0.73 mmol) and DCC (225 mg, 1.09 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 1_1 (202 mg, 75%) as an oil. $^1H$ NMR (400 MHz, $CDCl_3$): δ 1.88-1.98 (m, 1H), 2.03-2.11 (m, 1H), 2.14-2.20 (m, 1H), 2.24-2.35 (m, 1H), 3.45-3.54 (m, 1H), 4.20-4.29 (m, 1H), 4.60 (d, J=13.3 Hz, 1H), 4.87 (d, J=10.4 Hz, 1H), 4.92 (d, J=10.4 Hz, 1H), 5.36 (br s, 2H), 5.73 (d, J=4.8 Hz, 1H), 6.51 (dd, J=3.6, 1.7 Hz, 1H), 7.15 (d, J=3.6 Hz, 1H), 7.54 (d, J=1.7 Hz, 1H). LC-MS analysis: $[M+Na]^+$=391.2.

Step 2: Synthesis of N-(((2S,5R)-6-hydroxy-7-oxo-1,6-diazabicyclo[3.2.1]octan-2-yl)(imino)methyl)furan-2-carboxamide (1_2)

10% Pd/C (wet, 55% water w/w, 100 mg) was added to a solution of compound 11 (359 mg, 1 mmol) in EtOAc (15 mL). The mixture was stirred under $H_2$ (balloon) overnight, filtrated through a pad of celite, rinsed with EtOAc (3×10 mL). The filtrate was concentrated to give a residue, which was purified by flash chromatography on silica gel, eluting with 90% EtOAc in petroleum ether to give the title compound 1_2 (200 mg, 66%) as a white solid. $^1H$ NMR (400 MHz, $CD_3OD$): δ1.89-1.91 (m, 2H), 2.01-2.14 (m, 2H), 3.24-3.41 (m, 1H), 4.03-4.13 (m, 1H), 4.33-4.41 (m, 1H), 5.53-5.63 (m, 1H), 6.48-6.51 (m, 1H), 7.05-7.08 (m, 1H), 7.60-7.64 (m, 1H). LC-MS analysis: [M+Na]+=301.1.

Step 3: Synthesis of (2S,5R)-2-(N-(furan-2-carbonyl)carbamimidoyl)-7-oxo-1,6-diazabicyclo[3.2.1]octan-6-yl hydrogen sulfate (example 1)

A mixture of compound 12 (200 mg, 0.66 mmol), $SO_3 \cdot NMe_3$ (193 mg, 1.38 mmol) and TEA (1.0 mL, 7.0 mmol) in THE/water (5/5 mL) was stirred at room temperature overnight. The reaction mixture was concentrated to dryness under reduced pressure to give a residue, which was purified by prep. HPLC on an Agilent 10 prep-C18 250×21.2 mm column and lyophilized to give example 1 (25 mg, 11% in two steps) as a white solid. $^1H$ NMR (400 MHz, $D_2O$): $^1H$ NMR (400 MHz, $D_2O$): δ 1.81-1.90 (m, 1H), 1.92-2.00 (m, 1H), 2.04-2.12 (m, 2H), 3.39-3.50 (m, 1H), 3.98-4.06 (m, 1H), 4.49 (d, J=13.9 Hz, 1H), 5.60 (s, 1H), 6.50 (dd, J=3.6, 1.7 Hz, 1H), 7.05 (d, J=3.6 Hz, 1H), 7.58 (d, J=1.7 Hz, 1H). LC-MS analysis: [M−H]−=357.0.

Example 2

(2S,5R)-2-(N-benzoylcarbamimidoyl)-7-oxo-1,6-diazabicyclo[3.2.1]octan-6-yl hydrogen sulfate (compound 122 in table 1)

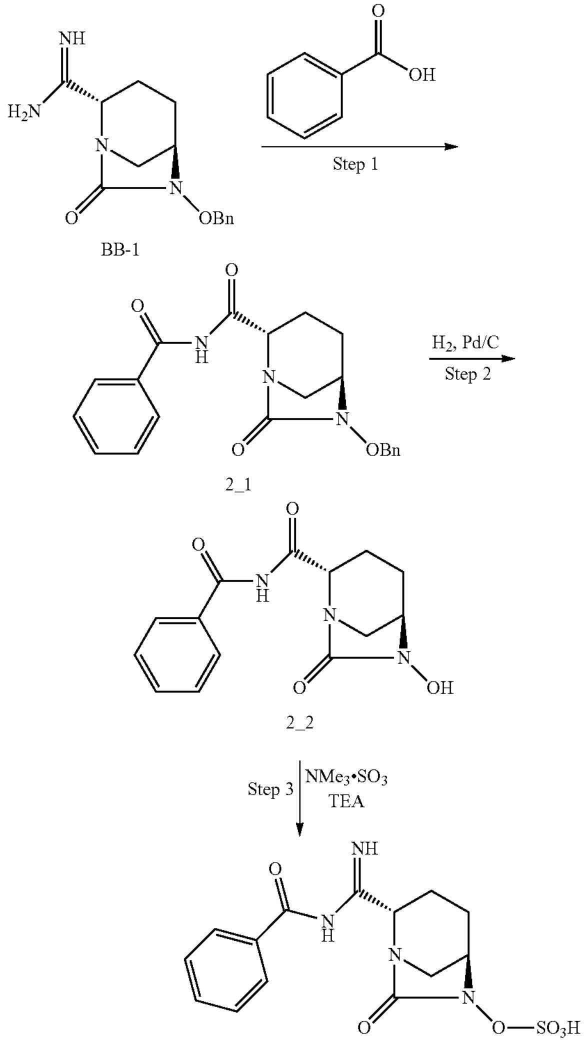

BB-1

2_1

2_2

Example 2

Step 1: Synthesis of N-(((2S,5R)-6-(benzyloxy)-7-oxo-1,6-diazabicyclo[3.2.1]octan-2-yl)(imino)methyl)benzamide (2_1)

Benzoic acid (67 mg, 0.55 mmol) was added to a solution of BB-1 (100 mg, 0.36 mmol), DAMP (67 mg, 0.55 mmol) and DCC (113 mg, 0.55 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 2_1 (140 mg, 67%) as an oil. $^1H$ NMR (400 MHz, $CDCl_3$): δ 1.77-1.93 (m, 2H), 2.05-2.36

(m, 2H), 3.24-3.35 (m, 1H), 4.07-4.25 (m, 2H), 4.66-4.83 (m, 2H), 5.39 (s, 2H), 7.27-7.42 (m, 10H). LC-MS analysis: $[M+Na]^+$=401.2.

Step 2: Synthesis of N-(((2S,5R)-6-hydroxy-7-oxo-1,6-diazabicyclo[3.2.1]octan-2-yl)(imino)methyl) benzamide(2_2)

10% Pd/C (wet, 55% water w/w, 50 mg) was added to a solution of compound 21 (140 mg, 0.37 mmol) in EtOAc (10 mL). The mixture was stirred under $H_2$ (balloon) at room temperature overnight, filtrated through a pad of celite, rinsed with EtOAc (3×10 mL). The filtrate was concentrated to give a residue, which was purified by flash chromatography on silica gel, eluting with 90% EtOAc in petroleum ether to give the title compound 2_2 (100 mg, 93%) as a white solid. $^1H$ NMR (400 MHz, $CD_3OD$): δ 1.57-1.63 (m, 1H), 1.70-1.77 (m, 1H), 2.01-2.10 (m, 2H), 3.28-3.40 (m, 1H), 3.89-4.12 (m, 2H), 5.59 (s, 1H), 7.36-7.43 (m, 5H). LC-MS analysis: $[M+Na]^+$=311.1.

Step 3: Synthesis of (2S,5R)-2-(N-benzoylcarbamimidoyl)-7-oxo-1,6-diazabicyclo[3.2.1]octan-6-yl hydrogen sulfate (example 2)

A mixture of compound 22 (100 mg, 0.33 mmol), $SO_3{\cdot}NMe_3$ (70 mg, 0.5 mmol) and TEA (0.5 mL, 3.3 mmol) in THF/water (5/5 mL) was stirred at room temperature overnight. The reaction mixture was concentrated to dryness under reduced pressure to give a residue, which was purified by prep. HPLC on an Agilent 10 prep-C18 250×21.2 mm column and lyophilized to give example 2 (30 mg, 24%) as a white solid. $^1H$ NMR (400 MHz, DMSO-$d_6$): δ51.82-2.08 (m, 4H), 3.17-3.31 (m, 1H), 3.71-3.85 (m, 1H), 3.98-4.07 (m, 1H), 5.57-5.69 (m, 1H), 6.54 (br s, 2H), 7.41-7.54 (m, 5H). LC-MS analysis: [M−H]−=367.1.

Example 3

Sodium (2S,5R)-7-oxo-2-(N-propionylcarbamimidoyl)-1,6-diazabicyclo[3.2.1]octan-6-yl sulfate (compound 4 in table 1)

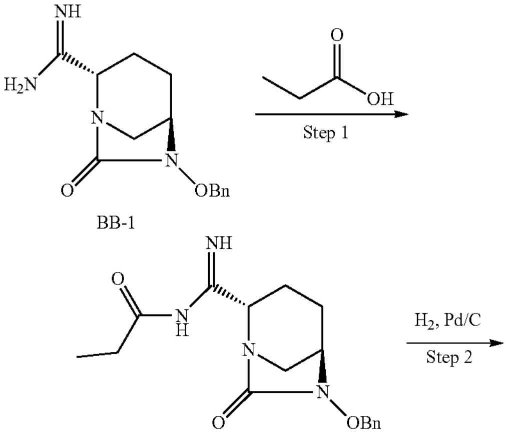

BB-1

3_1

-continued

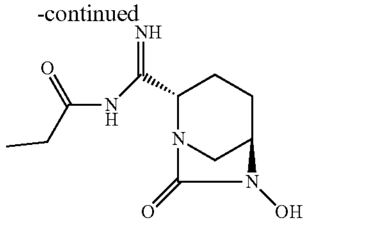

3_2

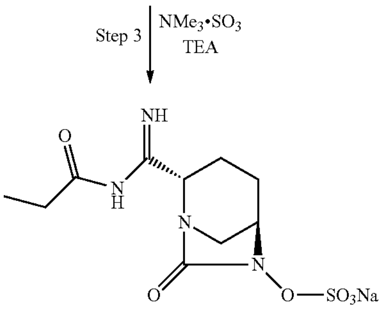

Example 3

Step 1: Synthesis of N-(((2S,5R)-6-(benzyloxy)-7-oxo-1,6-diazabicyclo[3.2.1]octan-2-yl)(imino)methyl)propionamide (3_1)

Propionic acid (27 mg, 0.36 mmol) was added to a solution of BB-1 (100 mg, 0.36 mmol), DAMP (67 mg, 0.55 mmol) and DCC (114 mg, 0.55 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 3_1 (100 mg, 84%) as an oil. $^1H$ NMR (400 MHz, $CDCl_3$): δ 1.36 (t, J=7.3 Hz, 3H), 1.65-1.83 (m, 2H), 1.87-1.96 (m, 1H), 2.01-2.13 (m, 1H), 2.36 (q, J=7.3 Hz, 2H), 3.37-3.47 (m, 1H), 3.77-3.84 (m, 1H), 4.02-4.09 (m, 1H), 4.85 (d, J=10.5 Hz, 1H), 4.93 (d, J=10.5 Hz, 1H), 5.22 (br s, 2H), 5.78-5.83 (m, 1H), 7.35-7.43 (3, 5H). LC-MS analysis: $[M+Na]^+$=353.2.

Step 2: Synthesis of N-(((2S,5R)-6-hydroxy-7-oxo-1,6-diazabicyclo[3.2.1]octan-2-yl)(imino)methyl) propionamide (3_2)

10% Pd/C (wet, 55% water w/w, 50 mg) was added to a solution of compound 31 (100 mg, 0.30 mmol) in EtOAc (5 mL). The mixture was stirred under $H_2$ (balloon) at room temperature overnight, filtered through a pad of celite, rinsed with EtOAc. The filtrate was concentrated to give a residue, which was purified by flash chromatography on silica gel, eluting with 90% EtOAc in petroleum ether to give the title compound 3_2 (105 mg, quantitative) as an oil. $^1H$ NMR (400 MHz, $CD_3OD$): δ1.13 (t, J=7.3 Hz, 3H), 1.82-1.93 (m, 2H), 2.08-2.18 (m, 2H), 2.39-2.57 (m, 2H), 3.37-3.45 (m, 1H), 3.87-3.94 (m, 1H), 4.02-4.14 (m, 1H), 5.75-5.79 (m, 1H). LC-MS analysis: $[M+Na]^+$=263.1.

Step 3: Synthesis of sodium (2S,5R)-7-oxo-2-(N-propionylcarbamimidoyl)-1,6-diazabicyclo[3.2.1] octan-6-yl sulfate (example 3)

A mixture of compound 32 (105 mg, 0.3 mmol), $SO_3{\cdot}NMe_3$ (90 mg, 0.65 mmol) and TEA (0.6 mL, 4.3 mmol) in THE/water (5/5 mL) was stirred at room temperature overnight. The reaction mixture was concentrated to dryness under reduced pressure to give a residue, which was purified by prep. HPLC on an Agilent 10 prep-C18 250×21.2 mm column and lyophilized, followed by Dowex-50wx $Na^+$ resin exchange using water as an eluent to give example 3 (30 mg, 31% in two steps) as a white solid. $^1H$ NMR (400 MHz, $D_2O$): δ 1.00 (t, J=7.2 Hz, 3H), 1.71-1.81 (m, 1H), 1.90-2.00 (m, 1H), 2.03-2.14 (m, 2H), 2.42 (q, J=7.2 Hz, 2H), 3.49 (t, J=11.7 Hz, 1H), 3.92-4.05 (m, 2H), 5.67 (d, J=3.9 Hz, 1H). LC-MS analysis: [M−Na]−=319.1.

Example 4

Sodium (2S,5R)-2-(N-(1-acetylpiperidine-4-carbonyl)carbamimidoyl)-7-oxo-1,6-diazabicyclo[3.2.1]octan-6-yl sulfate (compound 48 in table 1)

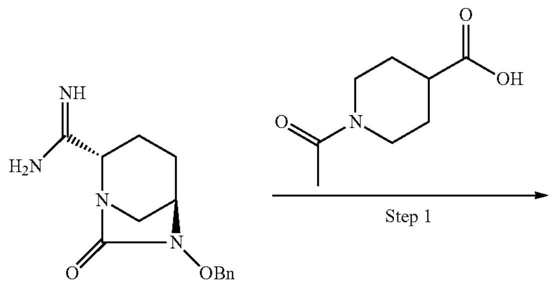

BB-1

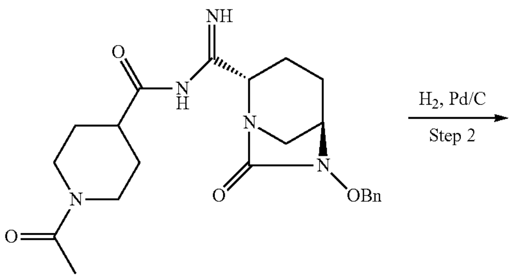

4_1

-continued

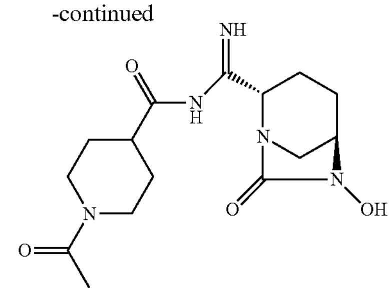

4_2

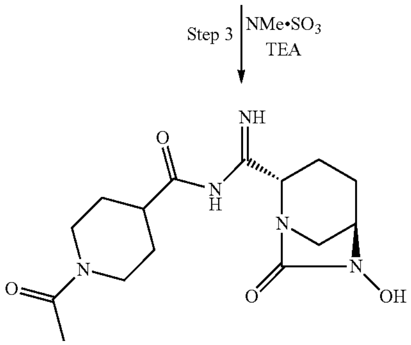

Example 4

Step 1: Synthesis of 1-acetyl-N-(((2S,5R)-6-(benzyloxy)-7-oxo-1,6-diazabicyclo[3.2.1]octan-2-yl)(imino)methyl)piperidine-4-carboxamide (4_1)

1-Acetylpiperidine-4-carboxylic acid (186 mg, 1.09 mmol) was added to a solution of BB-1 (200 mg, 0.73 mmol), DAMP (43 mg, 0.36 mmol) and DCC (225 mg, 1.09 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 41 (289 mg, 92%) as an oil. $^1H$ NMR (400 MHz, $CD_3OD$): δ 1.31-1.80 (m, 8H), 1.99 (s, 3H), 2.00-2.13 (m, 1H), 2.59-2.68 (m, 1H), 2.72-2.81 (m, 1H), 3.06-3.12 (m, 1H), 3.16-3.23 (m, 1H), 3.78-3.87 (m, 2H), 4.34-4.41 (m, 1H), 4.78-4.87 (m, 2H), 5.62 (s, 1H), 7.27-7.34 (m, 3H), 7.36-7.41 (m, 2H). LC-MS analysis: $[M+Na]^+$=450.2.

Step 2: Synthesis of 1-acetyl-N-(((2S,5R)-6-hydroxy-7-oxo-1,6-diazabicyclo[3.2.1]octan-2-yl)(imino)methyl)piperidine-4-carboxamide (4_2)

10% Pd/C (wet, 55% water w/w, 50 mg) was added to a solution of compound 41 (289 mg, 0.67 mmol) in EtOAc (30 mL). The mixture was stirred under $H_2$ (balloon) at room temperature overnight, filtered through a pad of celite, rinsed with EtOAc. The filtrate was concentrated to give a residue, which was purified by flash chromatography on silica gel, eluting with 90% EtOAc in petroleum ether to give the title compound 4_2 (250 mg, quantitative) as a white solid. $^1H$ NMR (400 MHz, $CD_3OD$): δ 1.37-1.70 (m, 8H), 1.99 (s, 3H), 2.01-2.11 (m, 1H), 2.52-2.75 (m, 2H), 2.83-2.96 (m, 2H), 3.07-3.16 (m, 1H), 3.26-3.42 (m, 2H), 4.35-4.46 (m, 2H), 5.65 (m, 1H). LC-MS analysis: [M+Na]+=360.2.

Step 3: Synthesis of sodium (2S,5R)-2-(N-(1-acetylpiperidine-4-carbonyl)carbamimidoyl)-7-oxo-1,6-diazabicyclo[3.2.1]octan-6-yl sulfate (example 4)

A mixture of compound 42 (250 mg, 0.67 mmol), $SO_3 \cdot NMe_3$ (160 mg, 1.11 mmol) and TEA (1 mL, 7.40 mmol) in THE/water (5/5 mL) was stirred at room temperature overnight. The reaction mixture was concentrated to dryness under reduced pressure to give a residue, which was purified by prep. HPLC on an Agilent 10 prep-C18 250×21.2 mm column and lyophilized, followed by Dowex-50wx $Na^+$ resin exchange eluting with water to give example 4 (38 mg, 14% in two steps) as a white solid. $^1H$ NMR (400 MHz, $D_2O$): δ 1.33-1.53 (m, 2H), 1.64-1.76 (m, 3H), 1.86-1.94 (m, 1H), 1.97 (s, 3H), 1.99-2.10 (m, 2H), 2.60-2.70 (m, 1H), 2.89-2.99 (m, 1H), 3.04-3.13 (m, 1H), 3.49 (t, J=12.4 Hz, 1H), 3.82 (d, J=13.1 Hz, 1H), 3.87-3.96 (m, 1H), 4.09 (d, J=13.3 Hz, 1H), 4.25 (d, J=13.3 Hz, 1H), 5.63 (d, J=3.0 Hz, 1H). LC-MS analysis: [M−Na]−=416.1.

Example 5

(2S,5R)-2-(N-nicotinoylcarbamimidoyl)-7-oxo-1,6-diazabicyclo[3.2.1]octan-6-yl hydrogen sulfate (compound 123 in table 1)

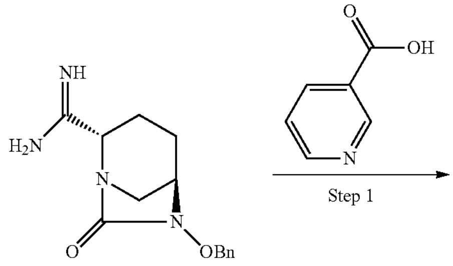

BB-1

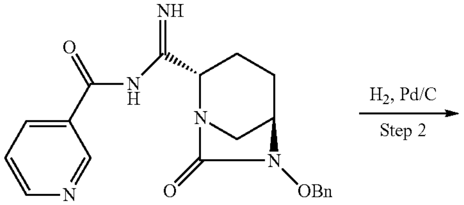

5_1

-continued

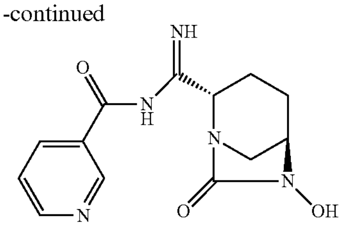

5_2

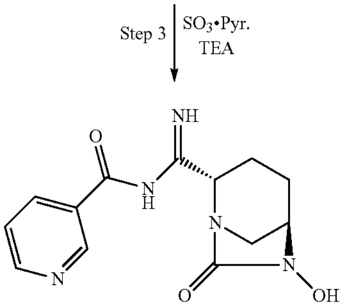

Example 5

Step 1: Synthesis of N-(((2S,5R)-6-(benzyloxy)-7-oxo-1,6-diazabicyclo[3.2.1]octan-2-yl)(imino)methyl)nicotinamide (5_1)

Nicotinic acid (337 mg, 2.73 mmol) was added to a solution of BB-1 (500 mg, 1.82 mmol), HATU (1.04 g, 2.73 mmol) and DIPEA (707 mg, 5.47 mmol) in DMF (5 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in hexane to give the title compound 51 (525 mg, 76%) as a white solid. LC-MS analysis: $[M+H]^+$=380.4.

Step 2: Synthesis of N-(((2S,5R)-6-hydroxy-7-oxo-1,6-diazabicyclo[3.2.1]octan-2-yl)(imino)methyl)nicotinamide (5_2)

10% Pd/C (wet, 55% water w/w, 100 mg) was added to a solution of compound 51 (200 mg, 0.52 mmol) in THE (3 mL). The mixture was stirred under $H_2$ (balloon) at room temperature overnight, filtered through a pad of celite, rinsed with EtOAc. The filtrate was concentrated in vacuum, and purified by flash silica gel chromatography using 10% MeOH in DCM to give the title compound 5_2 (67 mg, 44%) as a white solid. $^1H$ NMR (400 MHz, DMSO-$d_6$) 51.75-1.83 (m, 1H), 1.87-2.09 (m, 3H), 3.13-3.24 (m, 1H), 3.45-3.62 (m, 1H), 4.07-4.15 (m, 1H), 5.70 (s, 1H), 6.44 (s, 2H), 7.51 (dd, J=7.8, 4.8 Hz, 1H), 7.93 (dt, J=7.8, 1.7 Hz, 1H), 8.67-8.71 (m, 2H), 9.24 (s, 1H). LC-MS analysis: $[M+H]^+$=290.2.

Step 3: Synthesis of (2S,5R)-2-(N-nicotinoylcarbamimidoyl)-7-oxo-1,6-diazabicyclo[3.2.1]octan-6-yl hydrogen sulfate (example 5)

A mixture of compound 52 (406 mg, 1.45 mmol), $SO_3$-pyridine (569 mg, 7.27 mmol) in pyridine (20 mL) was stirred at room temperature overnight. The reaction mixture was concentrated to give a residue, which was purified by preparative HPLC on an Agilent 10 prep-C18 250×21.2 mm column and lyophilized to give example 5 (6 mg, 1%) as a white solid. $^1$H NMR (400 MHz, DMSO-$d_6$): δ51.85-2.08 (m, 4H), 3.23-3.38 (m, 1H), 4.01-4.13 (m, 2H), 5.62-5.75 (m, 1H), 6.52 (br s, 2H), 7.59 (dd, J=7.8, 4.6 Hz, 1H), 8.03 (d, J=7.8 Hz, 1H), 8.73-8.75 (m, 2H). LC-MS analysis: [M−H]−=368.1.

Example 6

Sodium (2S,5R)-7-oxo-2-(N-(6-(trifluoromethyl)nicotinoyl)carbamimidoyl)-1,6-diazabicyclo[3.2.1]octan-6-yl sulfate (compound 124 in table 1)

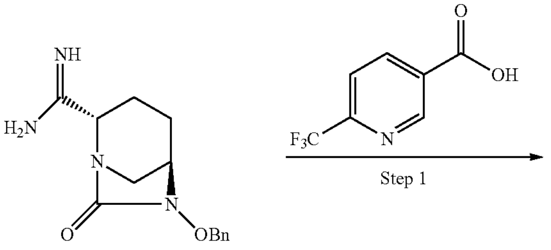

BB-1

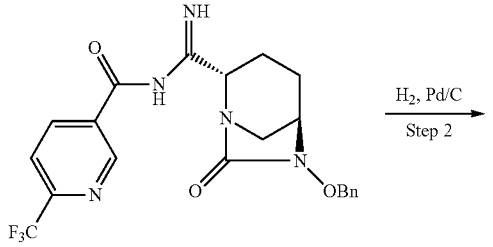

6_1

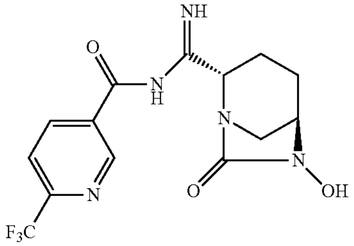

6_2

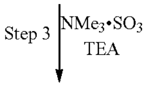

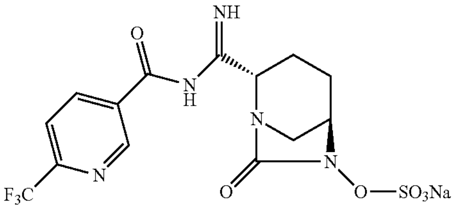

Example 6

Step 1: Synthesis of N-(((2S,5R)-6-(benzyloxy)-7-oxo-1,6-diazabicyclo[3.2.1]octan-2-yl)(imino)methyl)-6-(trifluoromethyl)nicotinamide (6_1)

6-(Trifluoromethyl)nicotinic acid (210 mg, 1.09 mmol) was added to a solution of BB-1 (200 mg, 0.73 mmol), DAMP (89 mg, 0.73 mmol) and DCC (309 mg, 1.50 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 6_1 (364 mg, 75%) as an oil. $^1$H NMR (400 MHz, $CDCl_3$): δ 1.90-1.99 (m, 1H), 2.06-2.14 (m, 1H), 2.17-2.31 (m, 2H), 3.31-3.67 (m, 2H), 4.76 (d, J=10.9 Hz, 1H), 4.85 (d, J=10.9 Hz, 1H), 5.68 (s, 1H), 5.76 (s, 1H), 7.32-7.36 (m, 5H), 7.77 (d, J=8.0 Hz, 2H), 7.95 (d, J=8.0 Hz, 1H), 8.75 (s, 1H). LC-MS analysis: $[M+Na]^+$=470.2.

Step 2: Synthesis of N-(((2S,5R)-6-hydroxy-7-oxo-1,6-diazabicyclo[3.2.1]octan-2-yl)(imino)methyl)-6-(trifluoromethyl)nicotinamide (6_2)

10% Pd/C (wet, 55% water w/w, 100 mg) was added to a solution of compound 61 (364 mg, 0.76 mmol) in EtOAc (20 mL). The mixture was stirred under $H_2$ (balloon) at room temperature overnight, filtered through a pad of celite, rinsed with EtOAc. The filtrate was concentrated to give a residue, which was purified by flash chromatography on silica gel, eluting with 90% EtOAc in petroleum ether to give the title compound 62 (200 mg, 73%) as a white solid. $^1$H NMR (400 MHz, $CD_3OD$): δ51.69-1.84 (m, 1H), 1.94-2.11 (m, 3H), 3.29-3.40 (m, 1H), 3.47-3.61 (m, 1H), 4.05-4.16 (m, 1H), 5.70 (s, 1H), 7.82 (d, J=8.1 Hz, 1H), 8.07 (d, J=8.1 Hz, 1H), 8.74 (s, 1H). LC-MS analysis: $[M+Na]^+$=380.1.

Step 3: Synthesis of sodium (2S,5R)-7-oxo-2-(N-(6-(trifluoromethyl)nicotinoyl)carbamimidoyl)-1,6-diazabicyclo[3.2.1]octan-6-yl sulfate Example 6

A mixture of compound 62 (224 mg, 0.62 mmol), $SO_3$·$NMe_3$ (218 mg, 1.57 mmol) and TEA (1 mL, 0.72 mmol) in THE/water (4/3 mL) was stirred at room temperature overnight. The reaction mixture was concentrated to dryness under reduced pressure to give a residue, which was purified by Dowex-50wx $Na^+$ resin, using water as an elution solvent, and lyophilized to give example 6 (265 mg, 98%) as a white solid. $^1$H NMR (400 MHz, $D_2O$): δ 1.88-2.02 (m, 2H), 2.03-2.18 (m, 2H), 3.47-3.56 (m, 1H), 3.63-3.71 (m, 1H), 3.98-4.06 (m, 1H), 5.70 (s, 1H), 7.87 (d, J=8.1 Hz, 1H), 8.08 (dd, J=8.1, 1.7 Hz, 1H), 8.66 (d, J=8.1 Hz, 1H). $^{19}$F NMR (376 MHz, DMSO-$d_6$)): δ −66.6 (s, 3F). LC-MS analysis: [M−Na]−=436.1.

Example 7

(2S,5R)-2-(N-isonicotinoylcarbamimidoyl)-7-oxo-1,6-diazabicyclo[3.2.1]octan-6-yl hydrogen sulfate (compound 125 in table 1)

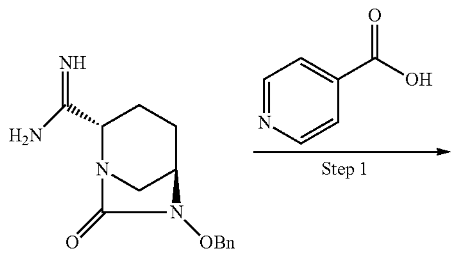

BB-1

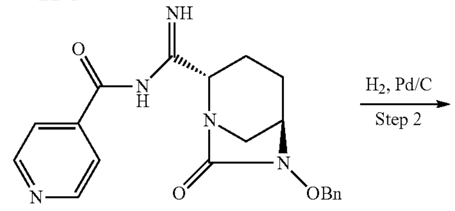

7_1

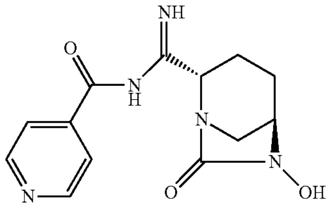

7_2

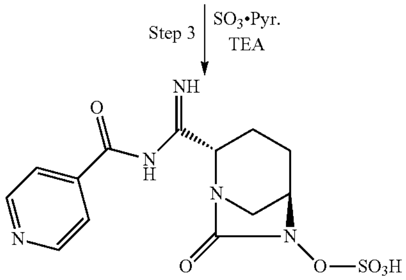

Example 7

Step 1: Synthesis of N-(((2S,5R)-6-(benzyloxy)-7-oxo-1,6-diazabicyclo[3.2.1]octan-2-yl)(imino)methyl)isonicotinamide (7_1)

Isonicotinic acid (337 mg, 2.73 mmol) was added to a solution of BB-1 (500 mg, 1.82 mmol), HATU (1.04 g, 2.73 mmol) and DIPEA (707 mg, 5.47 mmol) in DMF (5 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in hexane to give the title compound 71 (650 mg, 94%) as a white solid. LC-MS analysis: $[M+H]^+$=380.4.

Step 2: Synthesis of N-(((2S,5R)-6-hydroxy-7-oxo-1,6-diazabicyclo[3.2.1]octan-2-yl)(imino)methyl)isonicotinamide (7_2)

10% Pd/C (wet, 55% water w/w, 500 mg) was added to a solution of compound 71 (650 mg, 1.71 mmol) in THE (3 mL). The mixture was stirred under $H_2$ (balloon) at room temperature overnight, filtered through a pad of celite, rinsed with EtOAc. The filtrate was concentrated in vacuum, and purified by flash silica gel chromatography using 10% MeOH in DCM to give the title compound 72 (179 mg, 36%) as a white solid. $^{1}$H NMR (400 MHz, DMSO-$d_6$) δ 1.75-1.82 (m, 1H), 1.87-2.11 (m, 3H), 3.16-3.25 (m, 1H), 3.33-3.43 (m, 1H), 4.04-4.13 (m, 1H), 5.76 (s, 1H), 6.43 (s, 2H), 7.47 (d, J=4.9 Hz, 2H), 7.71 (d, J=4.9 Hz, 2H), 9.18 (s, 1H). LC-MS analysis: $[M+H]^+$=290.2.

Step 3: Synthesis of (2S,5R)-2-(N-isonicotinoylcarbamimidoyl)-7-oxo-1,6-diazabicyclo[3.2.1]octan-6-yl hydrogen sulfate (example 7)

A mixture of compound 72 (200 mg, 0.72 mmol), $SO_3$.pyridine (569 mg, 3.58 mmol) in pyridine (4 mL) was stirred at room temperature overnight. The reaction mixture was concentrated to give a residue, which was purified by prep. HPLC on an Agilent 10 prep-C18 250×21.2 mm column and lyophilized to give example 7 (5 mg, 2%) as a white solid. $^{1}$H NMR (400 MHz, DMSO-$d_6$): δ1.84-2.08 (m, 4H), 3.30-3.41 (m, 1H), 3.45-3.54 (m, 1H), 4.01-4.09 (m, 1H), 5.70-5.77 (m, 1H), 6.52 (br s, 2H), 7.74 (d, J=6.2 Hz, 2H), 8.83 (d, J=4.6 Hz, 2H). LC-MS analysis: $[M-H]^-$=368.1.

Example 8

Sodium (2S,5R)-7-oxo-2-(N-((R)-pyrrolidine-3-carbonyl)carbamimidoyl)-1,6-diazabicyclo[3.2.1]octan-6-yl sulfate (compound 56 in table 1)

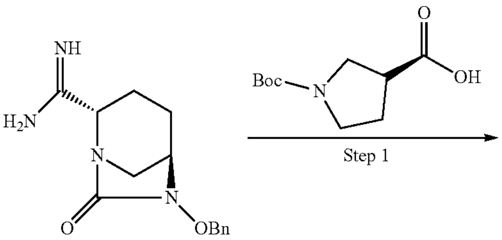

BB-1

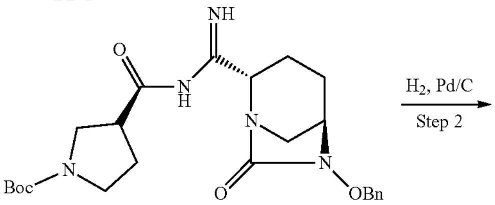

8_1

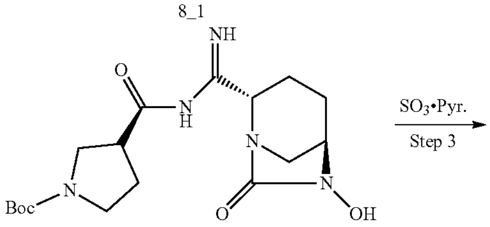

8_2

-continued

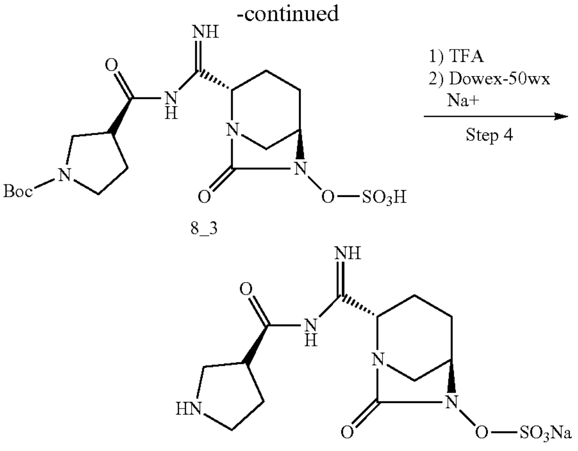

8_3

Example 8

Step 1: Synthesis of tert-butyl (3R)-3-((((2S,5R)-6-(benzyloxy)-7-oxo-1,6-diazabicyclo[3.2.1]octan-2-yl)(imino)methyl)carbamoyl)pyrrolidine-1-carboxylate (8_1)

(R)-1-(Tert-butoxycarbonyl)pyrrolidine-3-carboxylic acid (258 mg, 1.20 mmol) and DAMP (68 mg, 0.55 mmol) were added to a solution of DCC (248 mg, 1.20 mmol) in DCM (40 mL) at room temperature, after stirring for 20 minutes, BB-1 (216 mg, 0.78 mmol) was then added to the reaction mixture, and stirred overnight at room temperature. The reaction mixture was diluted with EtOAc, washed with saturated $NH_4Cl$, brine, dried over $Na_2SO_4$ and filtrated. The organic layer was concentrated to give a residue, which was purified by silica gel column chromatography eluting with 50% ethyl acetate in petroleum ether to give the title compound 81 (335 mg, 91%) as a white solid. $^1H$ NMR (400 MHz, DMSO-$d_6$): δ 1.39 (s, 9H), 1.68-1.76 (m, 1H), 1.82-2.03 (m, 5H), 3.19-3.41 (m, 5H), 3.44-3.53 (m, 1H), 3.85-3.96 (m, 2H), 4.81-4.88 (m, 2H), 5.68 (s, 1H), 6.74 (s, 2H), 7.34-7.42 (s, 3H), 7.47-7.54 (m, 2H). LC-MS analysis: $[M+Na]^+$=494.2.

Step 2: Synthesis of tert-butyl (3R)-3-((((2S,5R)-6-hydroxy-7-oxo-1,6-diazabicyclo[3.2.1]octan-2-yl)(imino)methyl)carbamoyl)pyrrolidine-1-carboxylate (8_2)

10% Pd/C (wet, 55% water w/w, 30 mg) was added to a solution of compound 81 (330 mg, 0.71 mmol) in THE (10 mL). The mixture was stirred under $H_2$ (balloon) at room temperature for two days, filtered through a pad of celite, rinsed with THF. The filtrate was concentrated to give the title compound 82 (270 mg, 99%) as an oil, which was directly used for next step without further purification. LC-MS analysis: $[M+Na]^+$=404.3.

Step 3: Synthesis of tert-butyl (3R)-3-((imino((2S,5R)-7-oxo-6-(sulfooxy)-1,6-diazabicyclo[3.2.1]octan-2-yl)methyl)carbamoyl)pyrrolidine-1-carboxylate (8_3)

A mixture of compound 82 (270 mg, 0.71 mmol), $SO_3$·pyridine (550 mg, 3.46 mmol) in pyridine (6 mL) was stirred at room overnight. The reaction mixture was concentrated to give a residue, which was suspensioned in DCM (15 mL), stirred at room temperature for 10 minutes, filtered off. The filtrate was concentrated to provide a residue, which was purified by silica gel column chromatography eluting with 5-15% MeOH in DCM, and followed by Dowex-50wx $Na^+$ resin purification, using water as elution solvent to give the title compound 83 (240 mg, 62%) as a oil. LC-MS analysis: [M–H]–=460.2.

Step 4: Synthesis of sodium (2S,5R)-7-oxo-2-(N-((R)-pyrrolidine-3-carbonyl)carbamimidoyl)-1,6-diazabicyclo[3.2.1]octan-6-yl sulfate (example 8)

TFA (1.2 mL) was added to a solution of compound 83 (240 mg 0.44 mmol) in anhydrous $CH_2Cl_2$ (5 mL) at 0° C. The mixture was stirred for 5 hours at 0° C., and then concentrated under reduced pressure to give a residue. The residue was dissolved with $CH_2Cl_2$ (15 mL) and extracted with water (2×10 mL). The aqueous layer was freeze-dried and purified by Dowex-50wx $Na^+$ resin, using water as an elution solvent to give example 8 (10 mg, 6%) as a white powder. $^1H$ NMR (400 MHz, $D_2O$): 51.96-2.17 (m, 4H), 2.27-2.42 (m, 2H), 3.26-3.42 (m, 3H), 3.50-3.68 (m, 3H), 3.94-4.03 (m, 1H), 4.06-4.12 (m, 1H), 5.64-5.68 (m, 1H). LC-MS analysis: [M–Na]–=360.1.

Example 9

(2S,5R)-2-(N-acetylcarbamimidoyl)-7-oxo-1,6-diazabicyclo[3.2.1]octan-6-yl hydrogen sulfate (compound 1 in table 1)

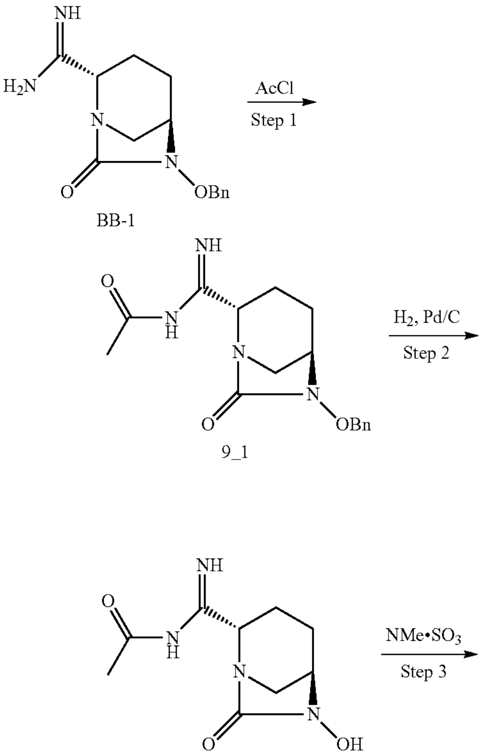

BB-1

9_1

9_2

-continued

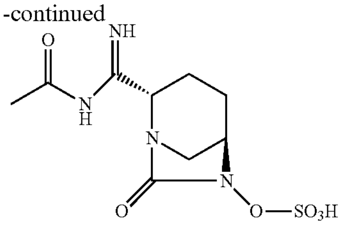

Example 9

Step 1: Synthesis of N-(((2S,5R)-6-(benzyloxy)-7-oxo-1,6-diazabicyclo[3.2.1]octan-2-yl)(imino)methyl)acetamide (9_1)

Acetyl chloride (0.05 mL, 0.70 mmol) was added to a solution of BB-1 (150 mg, 0.54 mmol) and TEA (0.17 mL, 1.21 mmol) in DCM (10 mL) at room temperature, and then stirred at room temperature under argon overnight. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 91 (167 mg, 97%) as an oil. $^1H$ NMR (400 MHz, $CDCl_3$): δ 1.73-1.83 (m, 1H), 2.01-2.08 (m, 1H), 2.10 (s, 3H), 2.14-2.32 (m, 2H), 3.38-3.50 (m, 1H), 3.70-3.82 (m, 1H), 4.02-4.09 (m, 1H), 4.85 (d, J=10.8 Hz, 1H), 4.92 (d, J=10.8 Hz, 1H), 5.48 (s, 2H), 5.75-5.80 (m, 1H), 7.39-7.44 (m, 5H). LC-MS analysis: $[M+Na]^+$=339.2.

Step 2: Synthesis of N-(((2S,5R)-6-hydroxy-7-oxo-1,6-diazabicyclo[3.2.1]octan-2-yl)(imino)methyl)acetamide (9_2)

10% Pd/C (wet, 55% water w/w, 20 mg) was added to a solution of compound 91 (100 mg, 0.32 mmol) in EtOAc (5 mL). The mixture was stirred under $H_2$ (balloon) at room temperature overnight, filtered through a pad of celite, rinsed with EtOAc. The filtrate was concentrated to give the title compound 92 (60 mg, 81%) as a white solid, directly used for next step without further purification. LC-MS analysis: $[M+Na]^+$=249.1.

Step 3: Synthesis of (2S,5R)-2-(N-acetylcarbamimidoyl)-7-oxo-1,6-diazabicyclo[3.2.1]octan-6-yl hydrogen sulfate (example 9)

A mixture of compound 92 (60 mg, 0.26 mmol), $SO_3 \cdot NMe_3$ complex (183 mg, 1.32 mmol) and TEA (1 mL, 7.22 mmol) in THE/Water (5/5 mL) was stirred at room temperature overnight. The reaction mixture was concentrated under reduced pressure to provide a residue, which was purified by preparative HPLC on an Agilent 10 prep-C18 250×21.2 mm column and lyophilized to give example 9 (10 mg, 12%) as a white solid. $^1H$ NMR (400 MHz, $CD_3OD$): δ 1.89-2.01 (m, 2H), 2.07 (s, 3H), 2.08-2.32 (m, 2H), 3.54 (dd, J=12.8, 11.2 Hz, 1H), 3.88-4.03 (m, 2H), 5.62 (d, J=4.3 Hz, 1H). LC-MS analysis: [M−H]−=305.1.

Example 10

Sodium (2S,5R)-7-oxo-2-(N-(pyrimidine-5-carbonyl)carbamimidoyl)-1,6-diazabicyclo[3.2.1]octan-6-yl sulfate (compound 140 in table 1)

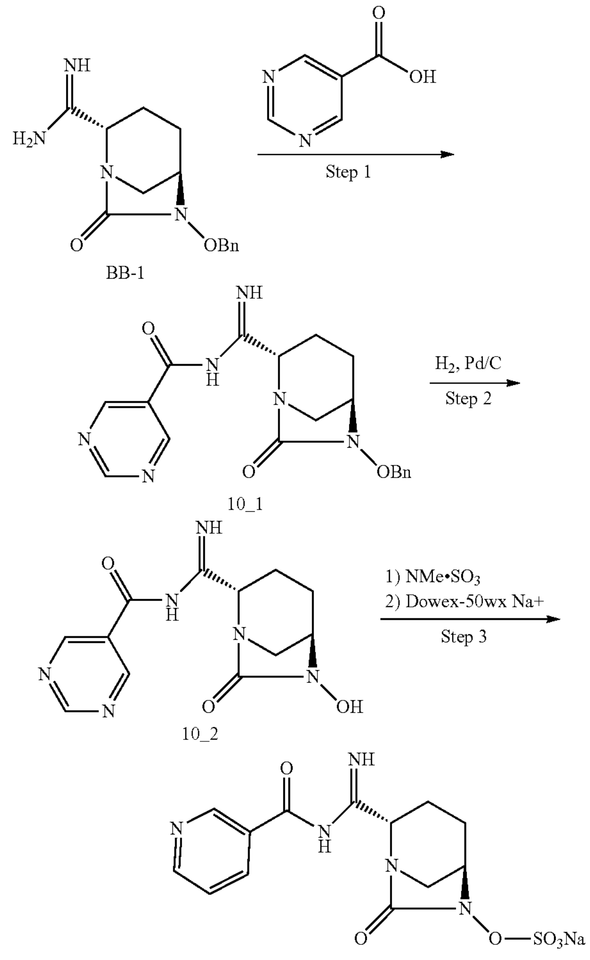

Example 10

Step 1: Synthesis of N-(((2S,5R)-6-(benzyloxy)-7-oxo-1,6-diazabicyclo[3.2.1]octan-2-yl)(imino)methyl)pyrimidine-5-carboxamide (10_1)

Pyrimidine-5-carboxylic acid (135 mg, 1.09 mmol) was added to a solution of BB-1 (200 mg, 0.73 mmol), DAMP (89 mg, 0.73 mmol) and DCC (309 mg, 1.5 mmol) in DCM (40 mL) at room temperature, and then stirred for 24 hours at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 10_1 (250 mg, 89%) as a white solid. $^1H$ NMR (400 MHz, DMSO-$d_6$): δ 1.86-2.09 (m, 4H), 3.22-3.30 (m, 1H), 4.10-4.20 (m, 1H), 4.32-4.39 (m, 1H), 4.79 (s, 2H), 5.70 (br s, 1H), 6.74 (s, 2H), 7.31-7.39 (m, 3H), 7.44-7.50 (m, 2H), 8.94 (s, 2H), 9.32 (s, 1H). LC-MS analysis: $[M+Na]^+$=403.2.

Step 2: Synthesis of N-(((2S,5R)-6-hydroxy-7-oxo-1,6-diazabicyclo[3.2.1]octan-2-yl)(imino)methyl) pyrimidine-5-carboxamide (10_2)

10% Pd/C (wet, 55% water w/w, 30 mg) was added to a solution of compound 101 (221 mg, 0.58 mmol) in EtOAc (20 mL). The mixture was stirred under $H_2$ (balloon) at room temperature overnight, filtered through a pad of celite, rinsed with EtOAc. The filtrate was concentrated to give the title compound 10_2 (160 mg, 95%) as a white solid, which was directly used for next step without further purification. $^1$H NMR (400 MHz, DMSO-$d_6$): δ1.76-1.83 (m, 1H), 1.90-2.09 (m, 3H), 3.11-3.18 (m, 1H), 3.38-3.61 (m, 1H), 4.06-4.18 (m, 1H), 5.62-5.81 (m, 1H), 6.44 (s, 2H), 8.96 (s, 2H), 9.26 (s, 1H), 9.30 (s, 1H). LC-MS analysis: $[M+Na]^+$=313.1.

Step 3: Synthesis of sodium (2S,5R)-7-oxo-2-(N-(pyrimidine-5-carbonyl)carbamimidoyl)-1,6-diazabicyclo[3.2.1]octan-6-yl sulfate (example 10)

A mixture of compound 102 (160 mg, 0.55 mmol), $SO_3$·$NMe_3$ (200 mg, 1.43 mmol) and TEA (2 mL, 14.45 mmol) in THE/water (10/10 mL) was stirred at room temperature overnight. The reaction mixture was concentrated under reduced pressure to provide a residue. The residue was dissolved with $CH_2Cl_2$ (20 mL) and extracted with water (2×10 mL). The aqueous layer was freeze-dried and purified by Dowex-50wx $Na^+$ resin, using water as an elution solvent to give example 10 (32 mg, 15%) as a white solid. $^1$H NMR (400 MHz, DMSO-$d_6$): δ 1.92-2.09 (m, 2H), 2.10-2.25 (m, 2H), 3.55-3.66 (m, 1H), 3.76-3.85 (m, 1H), 4.05-4.14 (m, 1H), 5.73 (s, 1H), 8.89 (s, 2H), 9.195 (s, 1H). LC-MS analysis: [M–Na]–=369.0.

Example 11

Sodium (2S,5R)-2-(N-(3-aminopropanoyl)carbamimidoyl)-7-oxo-1,6-diazabicyclo[3.2.1]octan-6-yl sulfate (compound 18 in table 1)

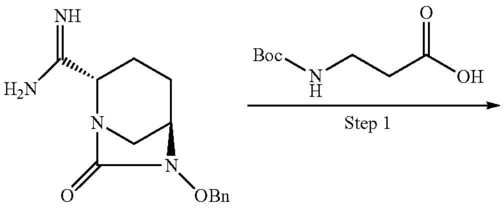

BB-1

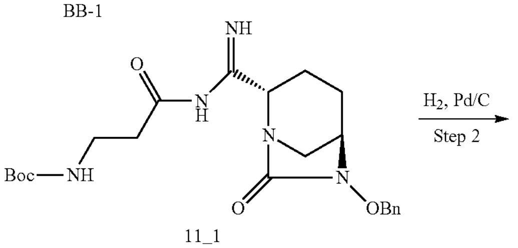

11_1

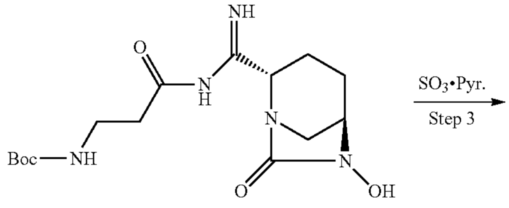

11_2

-continued

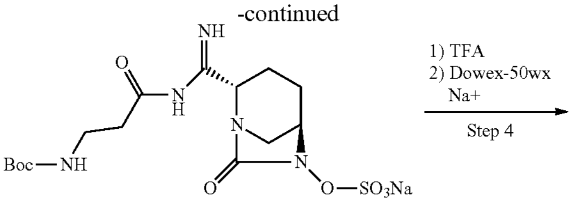

11_3

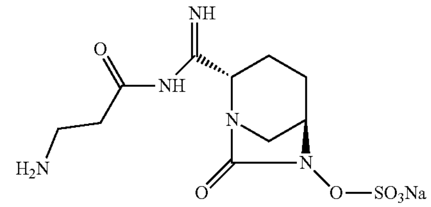

Example 11

Step 1: Synthesis of tert-butyl (3-((2S,5R)-6-(benzyloxy)-7-oxo-1,6-diazabicyclo[3.2.1]octane-2-carboximidamido)-3-oxopropyl)carbamate (11_1)

3-((tert-Butoxycarbonyl)amino)propanoic acid (335 mg, 1.77 mmol) was added to a solution of BB-1 (301 mg, 1.10 mmol), DAMP (70 mg, 0.57 mmol) and DCC (358 mg, 1.73 mmol) in THE (40 mL) at room temperature, and then stirred for 16 hours at room temperature under argon. The reaction mixture was concentrated to dryness, diluted with EtOAc, washed with saturated $NH_4Cl$, brine, dried over $Na_2SO_4$ and filtrated. The organic layer was concentrated to give a residue, which was purified by silica gel column chromatography eluting with 50-75% ethyl acetate in petroleum ether to give the title compound 11_1 (440 mg, 90%) as a white solid. $^1$H NMR (400 MHz, DMSO-$d_6$): δ 1.37 (s, 9H), 1.68-1.75 (m, 1H), 1.80-2.00 (m, 3H), 2.43-2.51 (m, 2H), 3.09-3.17 (m, 2H), 3.20-3.25 (m, 1H), 3.72-3.81 (m, 1H), 3.89-3.98 (m, 1H), 4.84 (s, 2H), 5.65 (s, 1H), 6.72 (s, 2H), 7.35-7.41 (m, 3H), 7.47-7.52 (m, 2H).

Step 2: Synthesis of tert-butyl (3-((2S,5R)-6-hydroxy-7-oxo-1,6-diazabicyclo[3.2.1]octane-2-carboximidamido)-3-oxopropyl)carbamate (11_2)

10% Pd/C (wet, 55% water w/w, 350 mg) was added to a solution of compound 111 (440 mg, 0.99 mmol) in EtOAc (20 mL) with a few drops of TEA. The mixture was hydrogenated under 45 psi at room temperature for 1 hour, filtered through a pad of celite, rinsed with EtOAc. The filtrate was concentrated to give a residue, which was purified by silica gel column chromatography eluting with 5% MeOH in DCM to give the title compound 11_2 (245 mg, 69%) as a yellow solid. $^1$H NMR (400 MHz, DMSO-$d_6$): δ 1.37 (s, 9H), 1.67-1.77 (m, 2H), 1.83-1.91 (m, 1H), 1.94-2.01 (m, 1H), 2.44-2.51 (m, 2H), 3.09-3.21 (m, 3H), 3.66-3.72 (m, 1H), 3.93-4.03 (m, 1H), 5.65 (s, 1H), 6.45 (s, 2H), 6.72 (t, J=5.1 Hz, 1H), 9.27 (s, 1H). LC-MS analysis: $[M+Na]^+$=378.2.

Step 3: Synthesis of (2S,5R)-2-(N-(3-((tert-butoxycarbonyl)amino)propanoyl)carbamimidoyl)-7-oxo-1,6-diazabicyclo[3.2.1]octan-6-yl hydrogen sulfate (11_3)

$SO_3$·Pyridine complex (550 mg, 3.45 mmol) was added to a solution of compound 112 (245 mg, 0.69 mmol) in anhydrous pyridine (7 mL). The mixture was stirred overnight, concentrated to dryness under reduced pressure. The residue was suspended with $CH_2Cl_2$ (10 mL), filtered off and rinsed with $CH_2Cl_2$ (2×3 mL). The filtrate was concentrated and purified by flash column chromatography using 5-15% MeOH in $CH_2CH_2$ to give the title compound 11_3 (332 mg, 94%) as a white foam. LC-MS analysis: $[M-H]^-$=434.1.

Step 4: Synthesis of sodium (2S,5R)-2-(N-(3-aminopropanoyl)carbamimidoyl)-7-oxo-1,6-diazabicyclo[3.2.1]octan-6-yl sulfate (example 11)

TFA (1.4 mL) was added to a solution of compound 113 (330 mg 0.64 mmol) in anhydrous $CH_2Cl_2$ (6 mL) at 0° C. The mixture was stirred for 3.5 hours at 0° C., and then concentrated under reduced pressure to give a residue. The residue was dissolved with $CH_2Cl_2$ (15 mL) and extracted with water (2×10 mL). The aqueous layer was freeze-dried and purified by Dowex-50wx $Na^+$ resin, using water as an elution solvent to give example 11 (22 mg, 10%) as a white powder. $^1H$ NMR (400 MHz, $D_2O$): δ 1.71-1.80 (m, 1H), 1.89-1.97 (m, 1H), 2.02-2.11 (m, 2H), 2.77-3.87 (m, 2H), 3.17 (t, J=6.0 Hz, 2H), 3.46-3.54 (m, 1H), 3.91-4.00 (m, 2H), 5.64 (d, J=4.6 Hz, 1H). LC-MS analysis: [M–Na]–=334.1.

Example 12

(2S,5R)-7-oxo-2-(N-(pyridazine-3-carbonyl)carbamimidoyl)-1,6-diazabicyclo[3.2.1]octan-6-yl hydrogen sulfate (compound 126 in table 1)

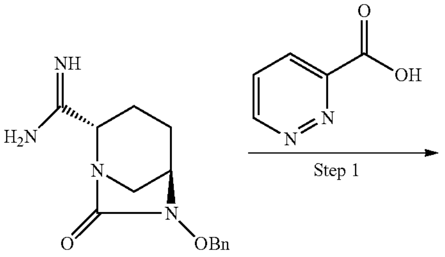

BB-1

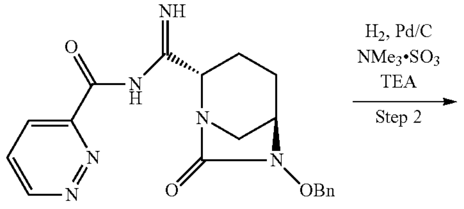

12_1

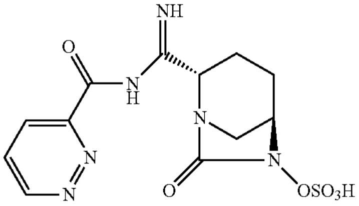

Example 12

Step 1: Synthesis of N-(((2S,5R)-6-(benzyloxy)-7-oxo-1,6-diazabicyclo[3.2.1]octan-2-yl)(imino)methyl)pyridazine-3-carboxamide (12_1)

Pyridazine-3-carboxylic acid (340 mg, 2.74 mmol) was added to a solution of BB-1 (500 mg, 1.82 mmol), HATU (1.04 g, 2.73 mmol) and DIPEA (707 mg, 5.47 mmol) in DCM/DMF (3/3 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in hexane to give the title compound 12_1 (354 mg, 51%) as a white solid. LC-MS analysis: $[M+H]^+$=381.4 and $[M+Na]^+$=403.4.

Step 2: Synthesis of (2S,5R)-7-oxo-2-(N-(pyridazine-3-carbonyl)carbamimidoyl)-1,6-diazabicyclo[3.2.1]octan-6-yl hydrogen sulfate (example 12)

A mixture of compound 12_1 (100 mg, 0.26 mmol), $SO_3 \cdot NMe_3$ (55 mg, 0.39 mmol), TEA (79 mg, 0.78 mmol) and 10% Pd/C (wet, 55% water w/w, 30 mg) in MeOH/water (2/2 mL) was stirred under $H_2$ (balloon) at room temperature overnight. The reaction was filtered through a pad of celite, rinsed with EtOAc. The filtrate was concentrated to give a residue, which was purified by preparative HPLC on an Agilent 10 prep-C18 250×21.2 mm column and lyophilized to give example 12 (4 mg, 4%) as a white solid. $^1H$ NMR (400 MHz, DMSO-$d_6$): δ 1.88-2.03 (m, 2H), 2.07-2.28 (m, 2H), 3.58-3.69 (m, 1H), 3.85-3.91 (m, 1H), 4.03-4.14 (m, 1H), 5.76-5.81 (m, 1H), 7.77-7.82 (m, 1H), 7.87-7.92 (m, 1H), 9.17-9.22 (m, 1H). LC-MS analysis: $[M-H]^-$=369.1.

Example 13

Sodium (2S,5R)-7-oxo-2-(N-(3-(pyridin-2-yl)propanoyl)carbamimidoyl)-1,6-diazabicyclo[3.2.1]octan-6-yl sulfate (compound 103 in table 1)

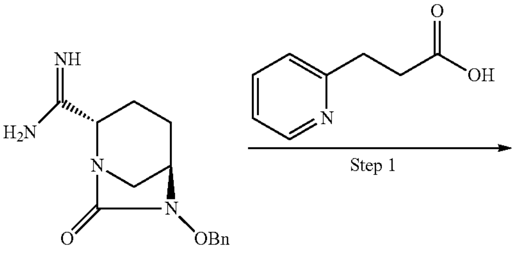

BB-1

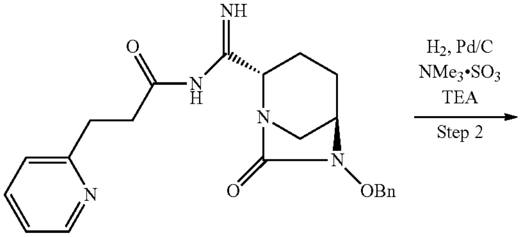

13-1

-continued

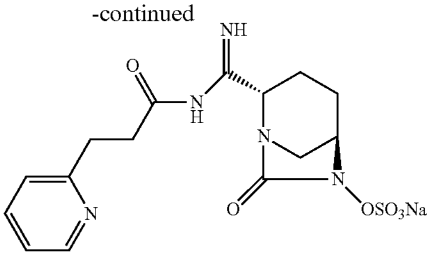

Example 13

Step 1: Synthesis of N-(((2S,5R)-6-(benzyloxy)-7-oxo-1,6-diazabicyclo[3.2.1]octan-2-yl)(imino)methyl)-3-(pyridin-2-yl)propanamide (13_1)

3-(Pyridin-2-yl)propanoic acid (82.7 mg, 0.54 mmol) was added to a solution of BB-1 (98 mg, 0.36 mmol), DCC (150 mg, 0.73 mmol) and DMAP (13 mg, 0.11 mmol) in DCM/DMF (5/5 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in hexane to give the title compound 13_1 (111 mg, 78%) as a white solid. LC-MS analysis: $[M+H]^+$=395.2.

Step 2: Synthesis of sodium (2S,5R)-7-oxo-2-(N-(3-(pyridin-2-yl)propanoyl)carbamimidoyl)-1,6-diazabicyclo[3.2.1]octan-6-yl sulfate (example 13)

A mixture of compound 13_1 (111 mg, 0.27 mmol), $SO_3 \cdot NMe_3$ (57 mg, 0.41 mmol), TEA (82 mg, 0.81 mmol) and 10% Pd/C (wet, 55% water w/w, 50 mg) in MeOH/water (2/2 mL) was stirred under $H_2$ (balloon) at room temperature overnight. The reaction was filtered through a pad of celite, rinsed with EtOAc. The filtrate was concentrated to give a residue, which was purified by Dowex-50wx $Na^+$ resin using water and lyophilized to give example 13 (30 mg, 28%) as a white solid. $^1H$ NMR (400 MHz, $D_2O$): δ 1.48-1.59 (m, 1H), 1.74-1.82 (m, 1H), 1.85-1.97 (m, 2H), 2.73-2.81 (m, 2H), 2.91-2.98 (m, 2H), 3.06-3.16 (m, 1H), 3.67-3.80 (m, 2H), 5.45-5.48 (m, 1H), 7.20-7.27 (m, 2H), 7.70-7.76 (m, 1H), 8.27 (d, J=4.7 Hz, 1H). LC-MS analysis: [M−Na]−=396.1.

Example 14

Sodium (2S,5R)-2-(N-(1-(tert-butoxycarbonyl)piperidine-4-carbonyl)carbamimidoyl)-7-oxo-1,6-diazabicyclo[3.2.1]octan-6-yl sulfate (compound 62 in table 1)

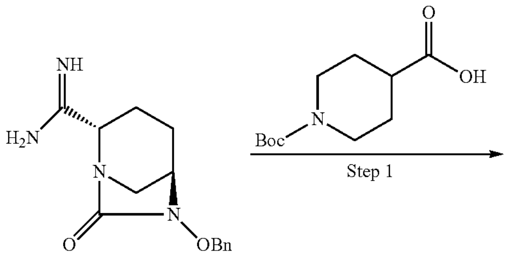

BB-1

-continued

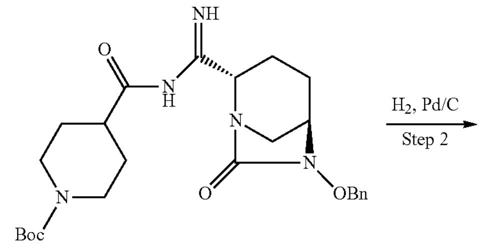

14_1

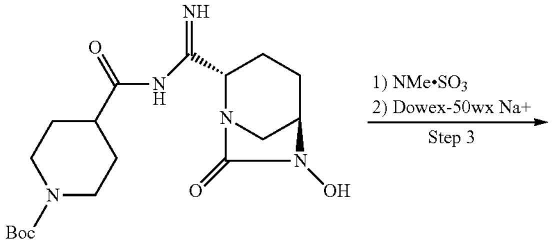

14_2

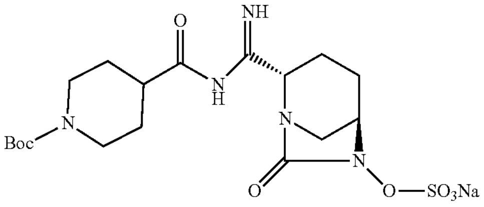

example 14

Step 1: Synthesis of tert-butyl 4-((((2S,5R)-6-(benzyloxy)-7-oxo-1,6-diazabicyclo[3.2.1]octan-2-yl)(imino)methyl)carbamoyl)piperidine-1-carboxylate (14_1)

1-(tert-Butoxycarbonyl)piperidine-4-carboxylic acid (250 mg, 1.09 mmol) was added to a solution of BB-1 (200 mg, 0.73 mmol), DAMP (89 mg, 0.73 mmol) and DCC (309 mg, 1.5 mmol) in DCM (10 mL) at room temperature, and then stirred for 4 hours at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 141 (230 mg, 65%) as an oil. LC-MS analysis: $[M+H]^+$=508.3.

Step 2: Synthesis of tert-butyl 4-((((2S,5R)-6-hydroxy-7-oxo-1,6-diazabicyclo[3.2.1]octan-2-yl)(imino)methyl)carbamoyl)piperidine-1-carboxylate (14_2)

10% Pd/C (wet, 55% water w/w, 200 mg) was added to a solution of compound 141 (230 mg, 0.47 mmol) in EtOAc (20 mL) and MeOH (1 mL). The mixture was stirred under $H_2$ (balloon) at room temperature overnight, filtered through a pad of celite, rinsed with EtOAc. The filtrate was concentrated to give the title compound 14_2 (180 mg, 96%) as a white solid, which was directly used for next step without further purification. LC-MS analysis: $[M+Na]^+$=418.2.

Step 3: Synthesis of sodium (2S,5R)-2-(N-(1-(tert-butoxycarbonyl)piperidine-4-carbonyl)carbamimidoyl)-7-oxo-1,6-diazabicyclo[3.2.1]octan-6-yl sulfate (example 14)

A mixture of compound 142 (180 mg, 0.45 mmol), $SO_3 \cdot NMe_3$ (300 mg, 2.15 mmol) and TEA (2 mL, 14.45 mmol) in THE/water (10/10 mL) was stirred at room temperature overnight. The reaction mixture was concentrated under reduced pressure to provide a residue, which was purified by preparative HPLC on an Agilent 10 prep-C18 250×21.2 mm column and lyophilized, followed by Dowex-50wx $Na^+$ resin using water as an eluting solvent to give example 14 (55 mg, 25% in two steps) as a white solid. $^1H$ NMR (400 MHz, $D_2O$): δ 1.33 (s, 9H), 1.35-1.47 (m, 2H), 1.62-1.76 (m, 3H), 1.90-1.98 (m, 1H), 2.02-2.13 (m, 2H), 2.72-2.83 (m, 2H), 2.84-2.92 (m, 1H), 3.51 (t, J=12.1 Hz, 1H), 3.90-4.01 (m, 3H), 4.09-4.15 (m, 1H), 5.66 (d, J=4.4 Hz, 1H). LC-MS analysis: [M−Na]−=475.1.

Example 15

Sodium (2S,5R)-2-(N-glycylcarbamimidoyl)-7-oxo-1,6-diazabicyclo[3.2.1]octan-6-yl sulfate (compound 8 in table 1)

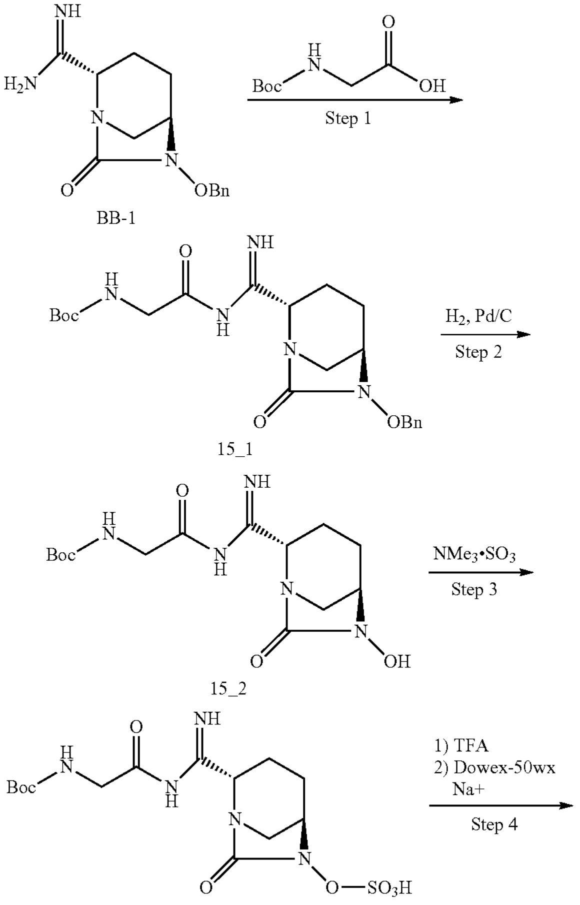

BB-1

15_1

15_2

15_3

-continued

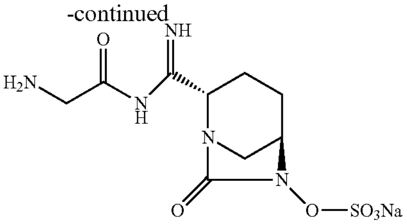

Example 15

Step 1: Synthesis of tert-butyl (2-((2S,5R)-6-(benzyloxy)-7-oxo-1,6-diazabicyclo[3.2.1]octane-2-carboximidamido)-2-oxoethyl)carbamate (15_1)

(tert-Butoxycarbonyl)glycine (200 mg, 1.09 mmol) was added to a solution of BB-1 (200 mg, 0.73 mmol), DAMP (89 mg, 0.73 mmol) and DCC (309 mg, 1.5 mmol) in DCM (30 mL) at room temperature, and then stirred at room temperature over night under argon. DAMP (89 mg, 0.73 mmol) and DCC (309 mg, 1.5 mmol) were added further to the reaction mixture, and stirred at room temperature for additional 6 hours. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 15_1 (301 mg, 71%) as an oil. LC-MS analysis: $[M+Na]^+$=454.2.

Step 2: Synthesis of tert-butyl (2-((2S,5R)-6-hydroxy-7-oxo-1,6-diazabicyclo[3.2.1]octane-2-carboximidamido)-2-oxoethyl)carbamate (15_2)

10% Pd/C (wet, 55% water w/w, 100 mg) was added to a solution of compound 151 (301 mg, 0.69 mmol) in EtOAc (30 mL) with a few drips of TEA. The mixture was stirred under $H_2$ (balloon) at room temperature overnight, filtered through a pad of celite, rinsed with EtOAc. The filtrate was concentrated to give the title compound 15_2 (212 mg, 71%) as a white solid, which was directly used for next step without further purification. LC-MS analysis: $[M+Na]^+$=364.2.

Step 3: Synthesis of (2S,5R)-2-(N-((tert-butoxycarbonyl)glycyl)carbamimidoyl)-7-oxo-1,6-diazabicyclo[3.2.1]octan-6-yl hydrogen sulfate (15_3)

A mixture of compound 152 (204 mg, 0.61 mmol), $SO_3 \cdot NMe_3$ (200 mg, 0.9 mmol) and TEA (2 mL, 6 mmol) in THE/water (10/10 mL) was stirred at room temperature overnight. The reaction mixture was concentrated under reduced pressure to provide the title compound 153 (450 mg, crude), which was directly used for next step without purification. $^1H$ NMR (400 MHz, $CD_3OD$): δ 1.34 (s, 9H), 1.92-2.04 (m, 4H), 3.08-3.13 (m, 1H), 3.46-3.55 (m, 2H), 3.86-3.93 (m, 2H), 5.59 (s, 1H). LC-MS analysis: $[M-H]^-$=420.2.

Step 4: Synthesis of sodium (2S,5R)-2-(N-glycylcarbamimidoyl)-7-oxo-1,6-diazabicyclo[3.2.1]octan-6-yl sulfate (example 15)

TFA (2 mL) was added to a solution of compound 15_3 (450 mg obtained above) in anhydrous $CH_2Cl_2$ (5 mL) at 0° C. The mixture was stirred for 4 hours at 0° C., and then concentrated under reduced pressure to give a residue. The residue was dissolved with $CH_2Cl_2$ (20 mL) and extracted with water (2×10 mL). The aqueous layer was freeze-dried and purified by Dowex-50wx $Na^+$ resin, using water as elution solvent to give example 15 (32 mg, 16% in two steps) as a white powder. $^1H$ NMR (400 MHz, $D_2O$): δ 1.74-1.84 (m, 1H), 1.89-1.97 (m, 1H), 2.01-2.14 (m, 2H), 3.53 (dd, J=13.6, 11.7 Hz, 1H), 3.75 (dd, J=13.6, 4.6 Hz, 1H), 3.91-4.04 (m, 3H), 5.60 (d, J=4.9 Hz, 1H). LC-MS analysis: [M−Na]−=320.1.

Example 16

Sodium (2S,5R)-7-oxo-2-(N-(thiazole-4-carbonyl)carbamimidoyl)-1,6-diazabicyclo[3.2.1]octan-6-yl sulfate (compound 139 in table 1)

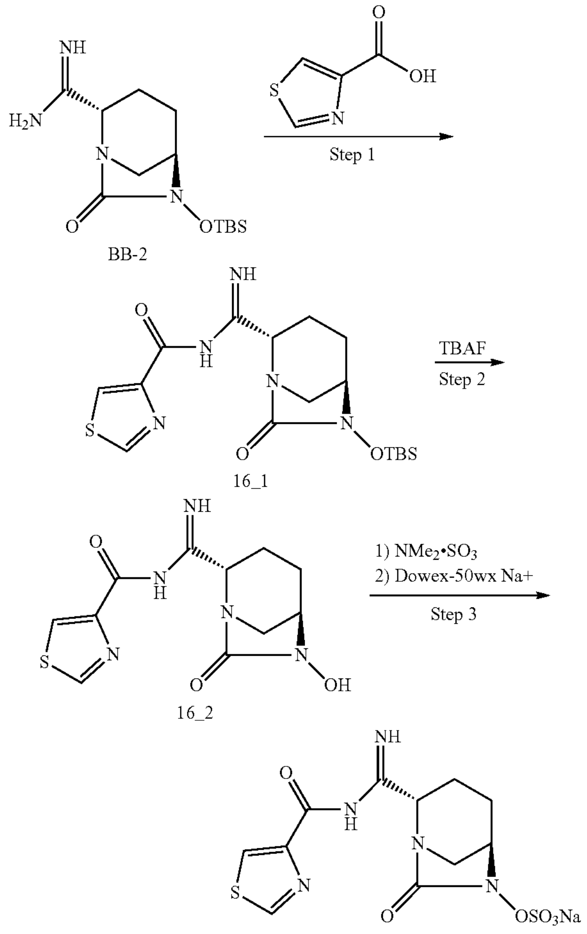

BB-2

16_1

16_2

Example 16

Step 1: Synthesis of N-(((2S,5R)-6-((tert-butyldimethylsilyl)oxy)-7-oxo-1,6-diazabicyclo[3.2.1]octan-2-yl)(imino)methyl)thiazole-4-carboxamide (16_1)

HATU (0.381 g, 1.00 mmol) and DIPEA (0.330 mL, 1.89 mmol) were added to a solution of thiazole-2-carboxylic acid (0.129 g, 1.00 mmol) and BB-2 (0.189 g, 0.630 mmol) in DCM (2 mL) and DMF (2 mL), and then stirred at room temperature for 24 hours. The reaction was quenched with saturated $NaHCO_3$ (2 mL) and water (6 mL), extracted with EtOAc. The organic layer was washed with water, then brine, dried over $Na_2SO_4$ and filtrated. The filtrate was concentrated to give a residue, which was purified by silica gel column chromatography eluting with 70% ethyl acetate in petroleum ether to give the title compound 161 (0.103 g, 40%) as a pale brown solid. $^1H$ NMR (400 MHz, DMSO-$d_6$): δ 0.15 (s, 6H), 0.94 (s, 9H), 1.82-1.93 (m, 2H), 1.99-2.13 (m, 2H), 3.28-3.35 (m, 1H), 3.58-3.70 (m, 1H), 4.44-4.54 (m, 1H), 5.72-5.92 (m, 1H), 6.58 (s, 2H), 8.38 (d, J=2.0 Hz, 1H), 9.22 (s, 1H). LC-MS analysis: $[M+Na]^+$=432.1.

Step 2: Synthesis of N-(((2S,5R)-6-hydroxy-7-oxo-1,6-diazabicyclo[3.2.1]octan-2-yl)(imino)methyl)thiazole-4-carboxamide (16_2)

TBAF (1 N in THF, 0.5 mL, 0.5 mmol) was added to a solution of compound 16_1 (100 mg, 0.244 mmol) in THE (3 mL) at 0° C. After stirring for 1 hour 0° C., the mixture was concentrated to dryness, diluted with EtOAc (30 mL), washed with water and brine. The organic layer was dried over $Na_2SO_4$ and filtrated. The filtrate was concentrated to give a residue, which was purified by silica gel column chromatography eluting with 2-5% MeOH in DCM to give the title compound 162 (48 mg, 67%) as a white solid. $^1H$ NMR (400 MHz, DMSO-$d_6$): δ 1.73-1.79 (m, 1H), 1.85-1.98 (m, 2H), 2.03-2.11 (m, 1H), 3.33-3.38 (m, 1H), 3.96-4.07 (m, 1H), 4.32-4.42 (m, 1H), 5.76-5.90 (m, 1H), 6.45 (s, 2H), 8.38 (d, J=2.0 Hz, 1H), 9.24 (d, J=2.0 Hz, 1H), 9.26 (s, 1H). LC-MS analysis: $[M+H]^+$=296.1.

Step 3: Synthesis of sodium (2S,5R)-7-oxo-2-(N-(thiazole-4-carbonyl)carbamimidoyl)-1,6-diazabicyclo[3.2.1]octan-6-yl sulfate (example 16)

A mixture of compound 162 (46.0 mg, 0.156 mmol), $SO_3 \cdot NMe_3$ (56.0 mg, 0.400 mmol) and TEA (0.110 mL, 0.790 mmol) in THE/water (3/2 mL) was stirred at room temperature overnight. The reaction mixture was concentrated under reduced pressure to provide a residue. The residue was purified by Dowex-50wx $Na^+$ resin, using water as an eluting solvent to give example 16 (35 mg, 56%) as a white solid. $^1H$ NMR (400 MHz, $D_2O$): δ 1.93-2.07 (m, 2H), 2.11-2.22 (m, 2H), 3.46-3.62 (m, 1H), 4.02-4.20 (m, 2H), 5.70 (s, 1H), 8.08 (s, 1H), 9.02 (d, J=2.0 Hz, 1H). LC-MS analysis: [M−Na]−=374.1.

Example 17

(2S,5R)-2-(N-(4-fluorobenzoyl)carbamimidoyl)-7-oxo-1,6-diazabicyclo[3.2.1]octan-6-yl hydrogen sulfate (compound 136 in table 1)

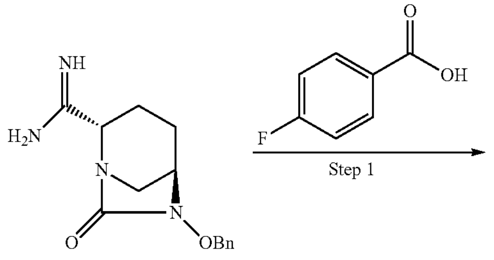

BB-1

-continued

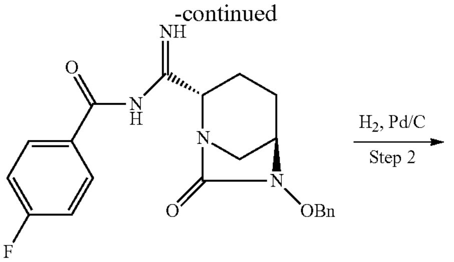

17_1

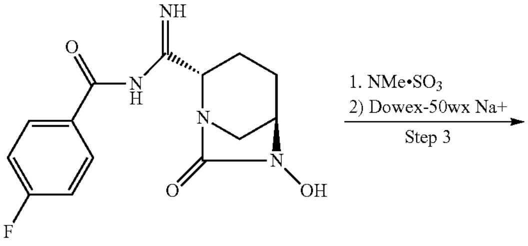

17_2

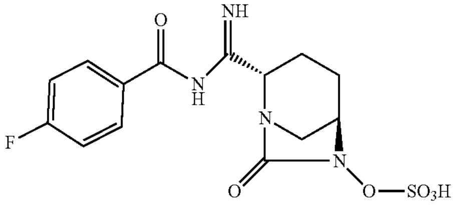

Example 17

Step 1: Synthesis of N-(((2S,5R)-6-(benzyloxy)-7-oxo-1,6-diazabicyclo[3.2.1]octan-2-yl)(imino)methyl)-4-fluorobenzamide (17_1)

4-Fluorobenzoic acid (155 mg, 1.09 mmol) was added to a solution of BB-1 (200 mg, 0.73 mmol), DAMP (89 mg, 0.73 mmol) and DCC (309 mg, 1.5 mmol) in DCM (10 mL) at room temperature, and then stirred for 4 hours at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 17_1 (287 mg, 66%) as a white solid. $^1$H NMR (400 MHz, $CD_3OD$): δ 1.80-1.92 (m, 2H), 1.98-2.15 (m, 2H), 3.01-3.18 (m, 1H), 3.30-3.55 (m, 1H), 3.91-3.98 (m, 1H), 4.78 (s, 2H), 5.41-5.56 (m, 1H), 7.09-7.14 (m, 2H), 7.21-7.26 (m, 2H). 7.27-7.34 (m, 3H), 7.36-7.41 (m, 2H). LC-MS analysis: [M+Na]+=419.2.

Step 2: Synthesis of 4-fluoro-N-(((2S,5R)-6-hydroxy-7-oxo-1,6-diazabicyclo[3.2.1]octan-2-yl)(imino)methyl)benzamide (17_2)

10% Pd/C (wet, 55% water w/w, 100 mg) was added to a solution of compound 171 (262 mg, 0.66 mmol) in THE (10 mL). The mixture was stirred under $H_2$ (balloon) at room temperature overnight, filtered through a pad of celite, rinsed with EtOAc. The filtrate was concentrated to give to give a residue, which was purified silica gel column chromatography eluting with 50% ethyl acetate in petroleum ether to give the title compound 172 (109 mg, 55%) as a white solid. $^1$H NMR (400 MHz, DMSO-$d_6$): δ 1.74-2.09 (m, 4H), 3.07-3.17 (m, 1H), 3.67-3.77 (m, 1H), 4.02-4.11 (m, 1H), 5.41-5.66 (m, 1H), 6.43 (s, 2H), 7.31 (t, J=8.9 Hz, 2H), 7.55 (dd, J=8.7, 5.4 Hz, 2H), 9.20 (s, 1H). $^{19}$F NMR (376 MHz, DMSO-$d_6$)): 6-109.6 (s, 1 F). LC-MS analysis: $[M+H]^+$=307.1.

Step 3: (2S,5R)-2-(N-(4-fluorobenzoyl)carbamimidoyl)-7-oxo-1,6-diazabicyclo[3.2.1]octan-6-yl hydrogen sulfate (example 17)

A mixture of compound 172 (200 mg, 0.66 mmol), $SO_3$·$NMe_3$ (150 mg, 1.07 mmol) and TEA (1 mL, 7.23 mmol) in THE/water (10/10 mL) was stirred at room temperature overnight. The reaction mixture was concentrated under reduced pressure to provide a residue, which was purified by preparative HPLC on an Agilent 10 prep-C18 250×21.2 mm column and lyophilized to give example 17 (20 mg, 8%) as a white solid. $^1$H NMR (400 MHz, $D_2O$): δ 1.91-2.15 (m, 2H), 2.08-2.20 (m, 2H), 3.39-3.53 (m, 1H), 3.80-3.91 (m, 1H), 3.97-4.09 (m, 1H), 5.68 (s, 1H), 7.17 (t, J=8.9 Hz, 2H), 7.46 (dd, J=8.9, 5.3 Hz, 2H). $^{19}$H NMR (376 MHz, $D_2O$): 5-108.9 (s, 1F). LC-MS analysis: $[M-H]^-$=385.1.

Example 18

Sodium (2S,5R)-7-oxo-2-(N-(piperidine-4-carbonyl)carbamimidoyl)-1,6-diazabicyclo[3.2.1]octan-6-yl sulfate (compound 46 in table 1)

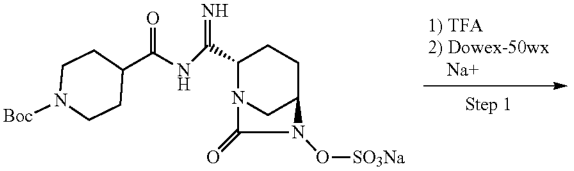

example 14

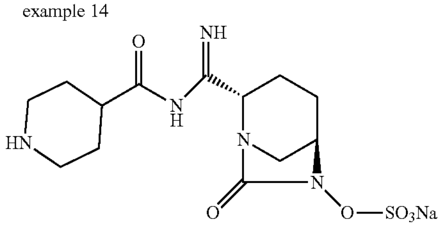

example 18

Step 1: Synthesis of sodium (2S,5R)-7-oxo-2-(N-(piperidine-4-carbonyl)carbamimidoyl)-1,6-diazabicyclo[3.2.1]octan-6-yl sulfate (example 18)

TFA (1.8 mL) was added to a solution of example 14 (350 mg, 0.63 mmol) DCM (6 mL) at 0° C. The reaction mixture was stirred for 3.5 hours at 0° C., and then concentrated under reduced pressure to dryness to give a residue. The residue was dissolved with $CH_2Cl_2$ (15 mL) and extracted with water (2×10 mL). The aqueous layer was freeze-dried and purified by Dowex-50wx $Na^+$ resin, using water as an elution solvent to give example 18 (15 mg, 6%) as a white powder. $^1$H NMR (400 MHz, $D_2O$): δ 1.62-1.74 (m, 3H), 1.80-1.92 (m, 3H), 1.94-2.07 (m, 2H), 2.85-3.05 (m, 3H), 3.31 (d, J=12.6 Hz, 2H), 4.47 (t, J=12.6 Hz, 1H), 3.83-3.91 (m, 1H), 4.02 (d, J=12.6 Hz, 1H), 5.59 (d, J=4.0 Hz, 1H). LC-MS analysis: [M-Na]-=374.1.

Example 19

Sodium (2S,5R)-2-(N-(3-acetamidopropanoyl)carbamimidoyl)-7-oxo-1,6-diazabicyclo[3.2.1]octan-6-yl sulfate (compound 22 in table 1)

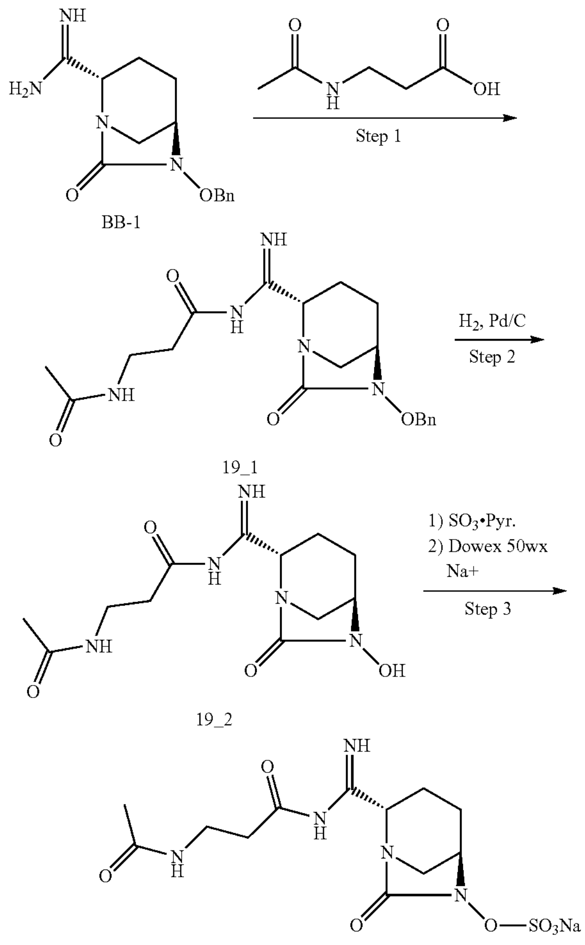

BB-1

19_1

19_2

Example 19

Step 1: Synthesis of 3-acetamido-N-(((2S,5R)-6-(benzyloxy)-7-oxo-1,6-diazabicyclo[3.2.1]octan-2-yl)(imino)methyl)propanamide (19_1)

3-Acetamidopropanoic acid (157 mg, 1.98 mmol) was added to a solution of BB-1 (220 mg, 0.80 mmol), HATU (457 mg, 1.34 mmol) and DIPEA (0.44 mL, 2.57 mmol) in DCM/DMF (each 3 mL) at room temperature, and then stirred at room temperature for 24 hours. The reaction mixture was diluted with EtOAc, washed with saturated $NaHCO_3$, water, Brine, dried over $Na_2SO_4$ and filtrated. The organic layer was concentrated to give a residue, which was purified by silica gel column chromatography eluting with 5% MeOH in DCM to give the title compound 19_1 (300 mg, 96%) as an oil. $^1H$ NMR (400 MHz, DMSO-d): 651.67-2.00 (m, 7H), 2.44-2.53 (m, 2H), 3.16-3.27 (m, 3H), 3.73-3.83 (m, 1H), 3.88-3.96 (m, 1H), 4.83 (s, 2H), 5.66 (s, 1H), 6.76 (s, 2H), 7.35-7.40 (m, 3H), 7.46-7.52 (m, 2H), 7.90 (s, 1H).

Step 2: Synthesis of 3-acetamido-N-(((2S,5R)-6-hydroxy-7-oxo-1,6-diazabicyclo[3.2.1]octan-2-yl)(imino)methyl)propanamide (19_2)

10% Pd/C (wet, 55% water w/w, 210 mg) was added to a solution of compound 191 (230 mg, 0.59 mmol) in EtOAc (20 mL) with a few drops of TEA. The mixture was stirred under $H_2$ (balloon) at room temperature for 24 hours, filtered through a pad of celite, rinsed with MeOH. The filtrate was concentrated to give a residue, which was purified by flash chromatography on silica gel, eluting with 5-10% MeOH in DCM to give the title compound 192 (124 mg, 70%) as a white solid. $^1H$ NMR (400 MHz, DMSO-$d_6$): δ 1.70-1.76 (m, 2H), 1.77 (s, 3H), 1.83-1.91 (m, 1H), 1.96-2.02 (m, 1H), 2.47-2.51 (m, 2H), 3.15-3.18 (m, 1H), 3.18-3.26 (m 2H), 3.65-3.71 (m, 1H), 3.92-4.00 (m, 1H), 5.67 (s, 1H), 6.50 (s, 2H), 7.90 (s, 1H), 9.30 (s, 1H). LC-MS analysis: [M+H]+=298.2.

Step 3: Synthesis of sodium (2S,5R)-2-(N-(3-acetamidopropanoyl)carbamimidoyl)-7-oxo-1,6-diazabicyclo[3.2.1]octan-6-yl sulfate (example 19)

A mixture of compound 192 (122 mg, 0.41 mmol), $SO_3$·Pyridine (330 mg, 2.08 mmol) in pyridine (5 mL) was stirred at room temperature overnight. $SO_3$·Pyridine (100 mg) was further added to the reaction mixture, and stirred at the room temperature for additional 3 days. The reaction mixture was concentrated to dryness under reduced pressure to give a residue, which was dissolved in water (20 mL) and lyophilized to give a solid. The solid was purified by preparative HPLC on an Agilent 10 prep-C18 250×21.2 mm column and lyophilized give the desired compound, which was further purified by Dowex-50wx $Na^+$ resin, using water as an elution solvent to give example 19 (23 mg, 15% in two steps) as a white solid. $^1H$ NMR (400 MHz, $D_2O$): δ 1.61-1.71 (m, 1H), 1.78 (s, 3H), 1.82-1.91 (m, 1H), 1.93-2.05 (m, 2H), 2.54 (t, J=6.3 Hz, 2H), 3.21-3.33 (m, 2H), 3.40 (t, J=13.4 Hz, 1H), 3.85-3.94 (m, 2H), 5.57 (d, J=3.5 Hz, 1H). LC-MS analysis: [M–Na]–=376.1.

Example 20

Sodium (2S,5R)-2-(N-(oxazole-4-carbonyl)carbamimidoyl)-7-oxo-1,6-diazabicyclo[3.2.1]octan-6-yl sulfate (compound 128 in table 1)

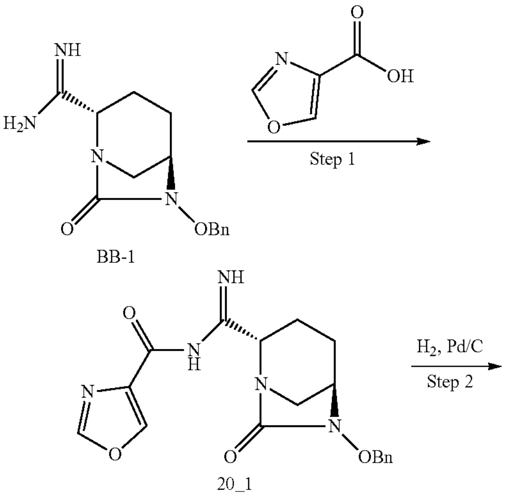

BB-1

20_1

-continued

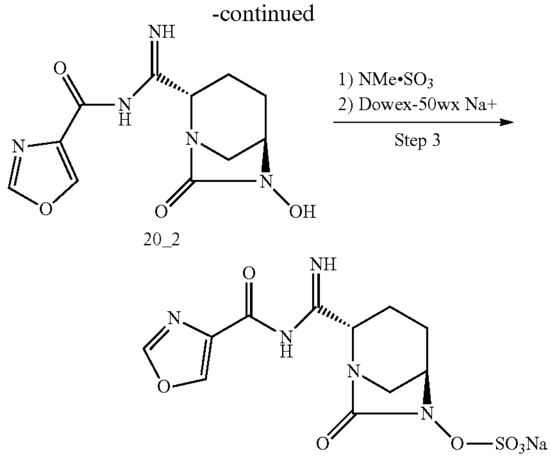

20_2

Example 20

Step 1: Synthesis of N-(((2S,5R)-6-(benzyloxy)-7-oxo-1,6-diazabicyclo[3.2.1]octan-2-yl)(imino)methyl)oxazole-4-carboxamide (20_1)

Oxazole-4-carboxylic acid (123 mg, 1.09 mmol) was added to a solution of BB-1 (200 mg, 0.73 mmol), DAMP (89 mg, 0.73 mmol) and DCC (309 mg, 1.5 mmol) in DCM (20 mL) at room temperature, and then stirred for 4 hours at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 20_1 (202 mg, 73%) as a white solid. LC-MS analysis: $[M+Na]^+=392.1$.

Step 2: Synthesis of N-(((2S,5R)-6-hydroxy-7-oxo-1,6-diazabicyclo[3.2.1]octan-2-yl)(imino)methyl)oxazole-4-carboxamide (20_2)

10% Pd/C (wet, 55% water w/w, 100 mg) was added to a solution of compound 201 (269 mg, 0.73 mmol) in EtOAc (30 mL) with a few drops of TEA. The mixture was stirred under $H_2$ (balloon) at room temperature overnight, filtered through a pad of celite, rinsed with EtOAc. The filtrate was concentrated to give the title compound 20_2 (203 mg, 72%) as a white solid, which was directly used for next step without further purification. LC-MS analysis: $[M+H]^+=280.1$.

Step 3: Synthesis of sodium (2S,5R)-2-(N-(oxazole-4-carbonyl)carbamimidoyl)-7-oxo-1,6-diazabicyclo[3.2.1]octan-6-yl sulfate (example 20)

A mixture of compound 202 (203 mg, 0.72 mmol), $SO_3 \cdot NMe_3$ (200 mg, 1.42 mmol) and TEA (2 mL, 14.46 mmol) in THE/water (10/10 mL) was stirred at room temperature overnight. The reaction mixture was concentrated under reduced pressure to provide a residue. The residue was purified by preparative HPLC on an Agilent 10 prep-C18 250×21.2 mm column and lyophilized to give the desired compound, which was further purified by Dowex-50wx $Na^+$ resin, using water as an elution solvent to give example 20 (20 mg, 8%) as a white solid. $^1H$ NMR (400 MHz, $D_2O$): δ 1.83-2.02 (m, 2H), 2.07-2.18 (m, 2H), 3.49-3.56 (m, 1H), 3.99-4.09 (m, 1H), 4.40-4.49 (m, 1H), 5.72 (br s, 1H), 8.16 (s, 1H), 8.30 (s, 1H). LC-MS analysis: [M–Na]-=358.1.

Example 21

Sodium (2S,5R)-2-(N-(oxazole-5-carbonyl)carbamimidoyl)-7-oxo-1,6-diazabicyclo[3.2.1]octan-6-yl sulfate (compound 129 in table 1)

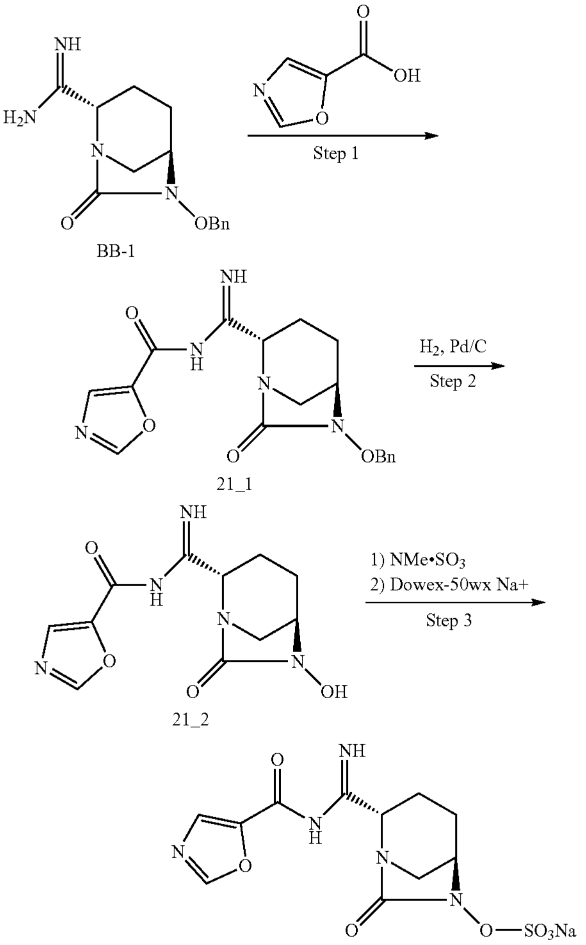

BB-1

21_1

21_2

Example 21

Step 1: Synthesis of N-(((2S,5R)-6-(benzyloxy)-7-oxo-1,6-diazabicyclo[3.2.1]octan-2-yl)(imino)methyl)oxazole-5-carboxamide (21_1)

Oxazole-5-carboxylic acid (123 mg, 1.09 mmol) was added to a solution of BB-1 (200 mg, 0.73 mmol), DAMP (89 mg, 0.73 mmol) and DCC (309 mg, 1.5 mmol) in DCM (20 mL) at room temperature, and then stirred for 4 hours at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 30% ethyl acetate in hexane to give the title compound 21_1 (204 mg, 75%) as a white solid. LC-MS analysis: $[M+Na]^+=392.3$.

Step 2: Synthesis of N-(((2S,5R)-6-hydroxy-7-oxo-1,6-diazabicyclo[3.2.1]octan-2-yl)(imino)methyl) oxazole-5-carboxamide (21_2)

10% Pd/C (wet, 55% water w/w, 200 mg) was added to a solution of compound 211 (204 mg, 0.55 mmol) in MeOH (20 mL) with a few drops of TEA. The mixture was stirred under $H_2$ (balloon) at room temperature overnight, filtered through a pad of celite, rinsed with EtOAc. The filtrate was concentrated to give the title compound 21_2 (160 mg) as a white solid, which was directly used for next step without further purification. $^1$H NMR (400 MHz, $CD_3OD$): δ1.71-2.01 (m, 4H), 3.43-3.49 (m, 1H), 4.17-4.23 (m, 1H), 4.32-4.43 (m, 1H), 5.74 (s, 1H), 7.67 (s, 1H), 7.84 (s, 1H), 8.41 (s, 1H). LC-MS analysis: $[M+H]^+$=280.1.

Step 3: Synthesis of sodium (2S,5R)-2-(N-(oxazole-5-carbonyl)carbamimidoyl)-7-oxo-1,6-diazabicyclo [3.2.1]octan-6-yl sulfate (example 21)

A mixture of compound 212 (160 mg obtained above), $SO_3{\cdot}NMe_3$ (300 mg, 2.13 mmol) and TEA (2 mL, 14.46 mmol) in THE/water (10/10 mL) was stirred at room temperature overnight. The reaction mixture was concentrated under reduced pressure to provide a residue. The residue was purified by prep. HPLC on an Agilent 10 prep-C18 250×21.2 mm column and lyophilized to give the desired compound, which was further purified by Dowex-50wx $Na^+$ resin, using water as an elution solvent to give example 21 (20 mg, 10% in two steps) as a white solid. $^1$H NMR (400 MHz, $D_2O$): δ 1.89-2.08 (m, 2H), 2.12-2.14 (m, 2H), 3.51-3.65 (m, 1H), 4.08-4.18 (m, 1H), 4.43-4.51 (m, 1H), 5.68 (d, J=4.6 Hz, 1H), 7.74 (s, 1H), 8.29 (s, 1H). LC-MS analysis: [M−Na]−=358.1.

Example 22

Sodium (2S,5R)-2-(N-(4-aminothiazole-2-carbonyl) carbamimidoyl)-7-oxo-1,6-diazabicyclo[3.2.1]octan-6-yl sulfate (compound 131 in table 1)

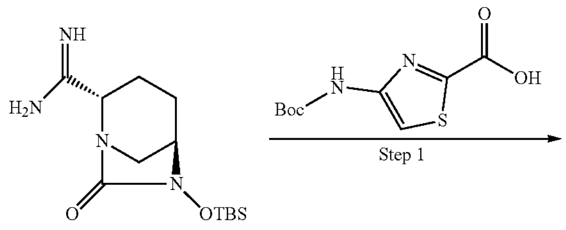

BB-2

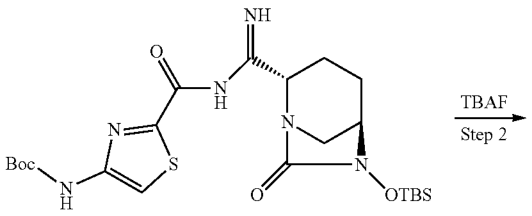

22_1

-continued

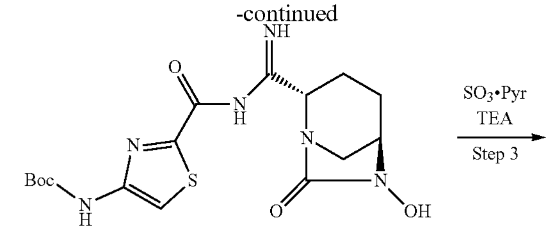

22_2

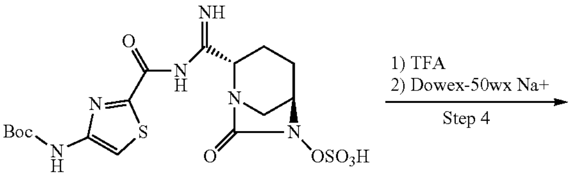

22_3

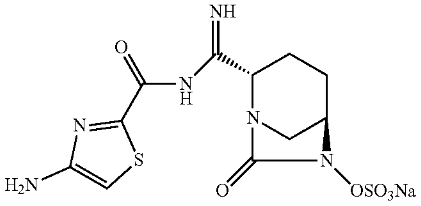

Example 22

Step 1: Synthesis of tert-butyl (2-((((2S,5R)-6-((tert-butyldimethylsilyl)oxy)-7-oxo-1,6-diazabicyclo[3.2.1]octan-2-yl)(imino)methyl)carbamoyl)thiazol-4-yl)carbamate (22_1)

4-((tert-Butoxycarbonyl)amino)thiazole-2-carboxylic acid (374 mg, 1.53 mmol) was added to a solution of BB-2 (305 mg, 1.02 mmol), HATU (581 mg, 1.53 mmol) and DIPEA (0.53 mL, 1.53 mmol) in DCM/DMF (each 3 mL) at room temperature, and then stirred at room temperature for 28 hours. The reaction mixture was diluted with EtOAc, washed with saturated $NaHCO_3$, water, brine, dried over $Na_2SO_4$ and filtrated. The organic layer was concentrated to give a residue, which was purified by silica gel column chromatography eluting with 50% EtOAc in petroleum ether to give the title compound 22_1 (440 mg, 80%) as a white foam. $^1$H NMR (400 MHz, DMSO-$d_6$): δ 0.12 (s, 6H), 0.92 (s, 9H), 1.49 (s, 9H), 1.79-1.90 (m, 2H), 2.00-2.77 (m, 2H), 3.16-3.27 (m, 1H), 3.53-3.63 (m, 1H), 4.33-4.41 (m, 1H), 6.59 (s, 2H), 7.72 (s, 1H), 11.66 (s, 1H). LC-MS analysis: $[M+H]^+$=525.1.

Step 2: Synthesis of tert-butyl (2-((((2S,5R)-6-hydroxy-7-oxo-1,6-diazabicyclo[3.2.1]octan-2-yl) (imino)methyl)carbamoyl)thiazol-4-yl)carbamate (22_2)

TBAF (1 N in THF, 1.07 mL, 1.07 mmol) was added to a solution of compound 221 (374 mg, 0.71 mmol) in THE (8 mL) at 0° C., warmed up to room temperature and stirred for 0.5 hour. The mixture was concentrated to dryness. It was diluted with EtOAc (30 mL), washed with water and brine. The organic layer was dried over $Na_2SO_4$ and filtrated. The filtrate was concentrated to give a residue, which was purified by silica gel column chromatography eluting with 5% MeOH in DCM to give the title compound 222 (235 mg, 80%) as a white solid. $^1$H NMR (400 MHz, DMSO-$d_6$): δ

1.48 (s, 9H), 1.72-1.78 (m, 1H), 1.82-1.95 (m, 2H), 2.00-2.06 (m, 1H), 3.02-3.12 (m, 1H), 3.91-3.99 (m, 1H), 4.17-4.27 (m, 1H), 5.83-6.04 (m, 1H), 6.45 (s, 2H), 7.71 (s, 1H), 9.24 (s, 1H), 11.68 (s, 1H). LC-MS analysis: $[M+H]^+=411.2$.

Step 3: Synthesis of (2S,5R)-2-(N-(4-((tert-butoxy-carbonyl)amino)thiazole-2-carbonyl)carbamimidoyl)-7-oxo-1,6-diazabicyclo[3.2.1]octan-6-yl hydrogen sulfate (22_3)

$SO_3$·Pyridine complex (600 mg, 3.77 mmol) was added to a solution of compound 222 (315 mg, 0.77 mmol) in anhydrous pyridine (7 mL). The mixture was stirred overnight, concentrated to dryness under reduced pressure. The residue was suspended with $CH_2Cl_2$ (10 mL), filtered off and rinsed with $CH_2Cl_2$ (2×3 mL). The filtrate was concentrated and purified by flash column chromatography using 5-10% MeOH in $CH_2CH_2$ to give the title compound 223 (560 mg, 90%) as a light yellow foam. LC-MS analysis: $[M-H]^-=489.1$.

Step 4: Synthesis of sodium (2S,5R)-2-(N-(4-aminothiazole-2-carbonyl)carbamimidoyl)-7-oxo-1,6-diazabicyclo[3.2.1]octan-6-yl sulfate (example 22)

TFA (2.1 mL) was added to a solution of compound 223 (560 mg, 0.73 mmol) in anhydrous $CH_2Cl_2$ (7 mL) at 0° C. and stirred for 3.5 hours at 0° C. TFA (1 mL) was further added to the reaction mixture, and stirred at 0° C. for additional 6.5 hours. The reaction mixture was concentrated under reduced pressure to give a residue. The residue was dissolved with $CH_2Cl_2$ (20 mL) and extracted with water (2×10 mL). The aqueous layer was freeze-dried to give a solid residue, which was purified by Dowex-50wx $Na^+$ resin, using water as an elution solvent to give example 22 (100 mg, 35%) as a white powder. $^1H$ NMR (400 MHz, $D_2O$): 51.90-2.01 (m, 2H), 2.06-2.16 (m, 2H), 3.31-3.45 (m, 1H), 3.93-4.16 (m, 1H), 4.18-4.41 (m, 1H), 5.58 (d, J=5.9 Hz, 1H), 7.10 (s, 1H). LC-MS analysis: [M–Na]–=389.0.

Example 23

Sodium (2S,5R)-7-oxo-2-(N-(thiazole-2-carbonyl)carbamimidoyl)-1,6-diazabicyclo[3.2.1]octan-6-yl sulfate (compound 135 in table 1)

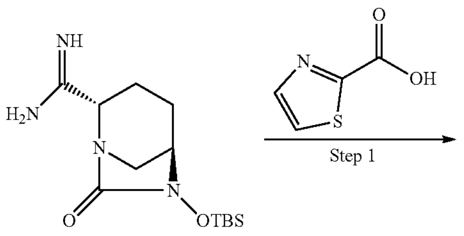

BB-2

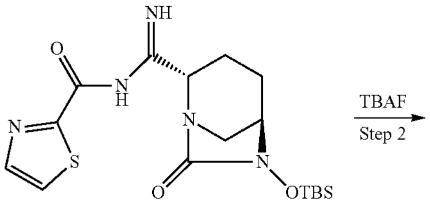

23_1

-continued

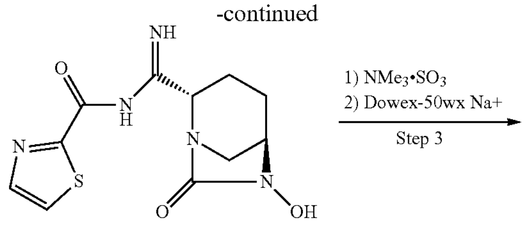

23_2

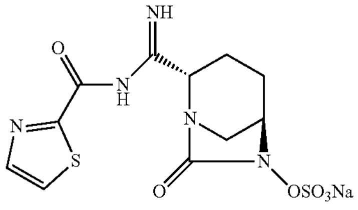

Example 23

Step 1: Synthesis of N-(((2S,5R)-6-((tert-butyldimethylsilyl)oxy)-7-oxo-1,6-diazabicyclo[3.2.1]octan-2-yl)(imino)methyl)thiazole-2-carboxamide (23_1)

TATU (43 mg, 1.13 mmol) and DIPEA (291 mg, 2.25 mmol) were added to a solution of thiazole-2-carboxylic acid (146 mg, 1.13 mmol) and BB-2 (224 mg, 0.75 mmol) in DCM (3 mL) and DMF (3 mL), and then stirred at room temperature for 30 hours. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 23_1 (176 mg, 82%) as an orange solid. $^1H$ NMR (400 MHz, $CDCl_3$): δ 1.88-2.06 (m, 2H), 2.14-2.21 (m, 1H), 2.27-2.37 (m, 1H), 3.20-3.30 (m, 1H), 3.31-3.41 (m, 1H), 3.65-3.76 (m, 1H), 4.17-4.23 (m, 1H), 4.72-4.79 (m, 1H), 5.45 (s, 1H), 5.80-5.92 (m, 1H), 7.60 (s, 1H), 7.91 (s, 1H). LC-MS analysis: $[M+H]^+=410.2$.

Step 2: Synthesis of N-(((2S,5R)-6-hydroxy-7-oxo-1,6-diazabicyclo[3.2.1]octan-2-yl)(imino)methyl) thiazole-2-carboxamide (23_2)

TBAF (1 N in THF, 1.11 mL, 1.11 mmol) was added to a solution of compound 231 (253 mg, 0.62 mmol) in THF (10 mL) at 0° C., warmed up to room temperature and stirred for 1 hour. The mixture was concentrated to dryness. It was diluted with EtOAc (50 mL), washed with water and brine. The organic layer was dried over $Na_2SO_4$ and filtrated. The filtrate was concentrated to give a residue, which was purified by silica gel column chromatography eluting with 50% ethyl acetate in petroleum to give the title compound 232 (136 mg, 74%) as an orange solid. LC-MS analysis: [M+Na]+=318.1.

Step 3: Synthesis of sodium (2S,5R)-7-oxo-2-(N-(thiazole-2-carbonyl)carbamimidoyl)-1,6-diazabicyclo[3.2.1]octan-6-yl sulfate (example 23)

A mixture of compound 232 (110 mg, 0.37 mmol), $SO_3$·$NMe_3$ (129 mg, 0.93 mmol) and TEA (45 mg, 0.44 mmol) in THF/water (4/3 mL) was stirred at room temperature overnight. The reaction mixture was concentrated under reduced pressure to provide a residue. The residue was purified by preparative HPLC on an Agilent 10 prep-C18 250×21.2 mm column and lyophilized to give the desired compound, which was further purified by Dowex-50wx $Na^+$ resin, using water as an elution solvent to give example 23 (50 mg, 36%) as a white solid. $^1H$ NMR (400 MHz, $D_2O$): δ 1.92-2.07 (m, 2H), 2.12-2.13 (m, 2H), 3.30-3.45 (m, 1H), 3.48-3.65 (m, 1H), 4.03-4.16 (m, 1H), 4.80-4.94 (m, 1H), 5.68-5.79 (m, 1H), 6.48-6.63 (m, 1H), 7.83 (d, J=3.1 Hz, 1H), 7.93 (d, J=3.1 Hz, 1H). LC-MS analysis: [M−Na]=374.0.

Example 24

Sodium (2S,5R)-7-oxo-2-(N-(2-(trifluoromethyl) thiazole-4-carbonyl)carbamimidoyl)-1,6-diazabicyclo[3.2.1]octan-6-yl sulfate (compound 130 in table 1)

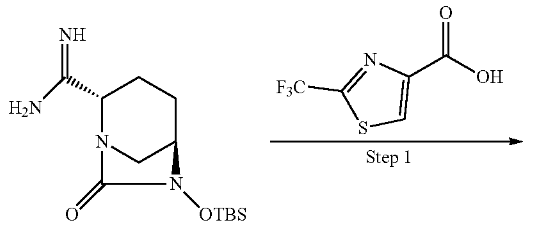

BB-2

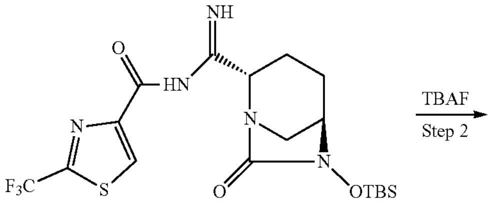

24_1

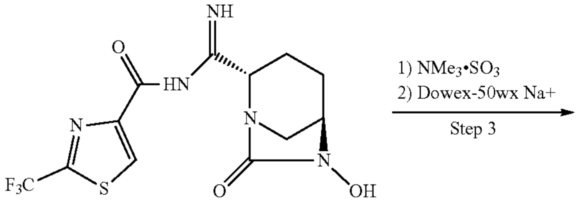

24_2

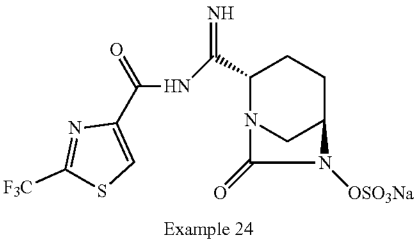

Example 24

Step 1: Synthesis of N-(((2S,5R)-6-((tert-butyldimethylsilyl)oxy)-7-oxo-1,6-diazabicyclo[3.2.1]octan-2-yl)(imino)methyl)-2-(trifluoromethyl)thiazole-4-carboxamide (24_1)

HATU (456 mg, 1.20 mmol) and DIPEA (0.40 mL, 2.25 mmol) were added to a solution of 2-(trifluoromethyl) thiazole-4-carboxylic acid (237 mg, 1.20 mmol) and BB-2 (224 mg, 0.75 mmol) in DCM (2.5 mL) and DMF (2.5 mL), and then stirred at room temperature for 24 hours. The reaction was quenched with saturated $NaHCO_3$ (3 mL) and water (6 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 24_1 (0.245 g, 68%) as a pale brown solid. $^1H$ NMR (400 MHz, DMSO-$d_6$): δ0.14 (s, 6H), 0.93 (s, 9H), 1.82-1.94 (m, 2H), 1.97-2.14 (m, 2H), 3.54-3.71 (m, 2H), 4.31-4.47 (m, 1H), 5.60-5.77 (m, 1H), 6.56 (s, 2H), 8.71 (s, 1H). $^{19}F$ NMR (400 MHz, DMSO-$d_6$): δ −59.9 (s, 3F). LC-MS analysis: $[M+H]^+$=478.2.

Step 2: Synthesis of N-(((2S,5R)-6-hydroxy-7-oxo-1,6-diazabicyclo[3.2.1]octan-2-yl)(imino)methyl)-2-(trifluoromethyl)thiazole-4-carboxamide (24_2)

TBAF (1 N in THF, 0.80 mL, 0.80 mmol) was added to a solution of compound 241 (243 mg, 0.51 mmol) in THF (5 mL) at 0° C. After stirring for 1 hour 0° C., the reaction mixture was concentrated to dryness. It was diluted with EtOAc (50 mL), washed with water and brine. The organic layer was dried over $Na_2SO_4$ and filtrated. The filtrate was concentrated to give a residue, which was purified by silica gel column chromatography eluting with 2-5% MeOH in DCM to give the title compound 24_2 (130 mg, 70%) as a white solid. $^1H$ NMR (400 MHz, DMSO-$d_6$): δ 1.73-81 (m, 1H), 1.86-1.99 (m, 2H), 2.01-2.11 (m, 1H), 2.92-3.14 (m, 1H), 3.97-4.11 (m, 2H), 5.53-5.76 (m, 1H), 6.44 (s, 2H), 5.80-5.92 (m, 1H), 8.69 (s, 1H), 9.25 (s, 1H). $^{19}F$ NMR (400 MHz, DMSO-$d_6$): δ −59.9 (s, 3F). LC-MS analysis: $[M+H]^+$=364.1.

Step 3: Synthesis of sodium (2S,5R)-7-oxo-2-(N-(2-(trifluoromethyl)thiazole-4-carbonyl)carbamimidoyl)-1,6-diazabicyclo[3.2.1]octan-6-yl sulfate (example 24)

A mixture of compound 242 (128 mg, 0.35 mmol), $SO_3{\cdot}NMe_3$ (110 mg, 0.79 mmol) and TEA (0.2 mL, 1.43 mmol) in THF/water (3/2 mL) was stirred at room temperature overnight. The reaction mixture was concentrated under reduced pressure to provide a residue. The residue was purified by Dowex-50wx $Na^+$ resin, using water as an elution solvent to give example 24 (156 mg, 96%) as a white solid. $^1H$ NMR (400 MHz, $D_2O$): δ 1.94-2.12 (m, 2H), 2.15-2.27 (m, 2H), 3.54-3.67 (m, 1H), 4.08-4.25 (m, 2H), 5.68-5.81 (m, 1H), 8.39 (s, 1H). $^{19}F$ NMR (376 MHz, $D_2O$): δ −61.2 (s, 3 F). LC-MS analysis: [M−Na]−=442.0.

Example 25

Sodium (2S,5R)-7-oxo-2-(N-(2-(pyrimidin-2-yl)acetyl)carbamimidoyl)-1,6-diazabicyclo[3.2.1]octan-6-yl sulfate (compound 105 in table 1)

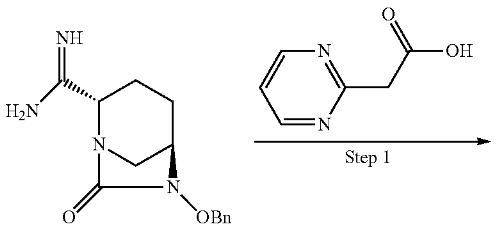

BB-1

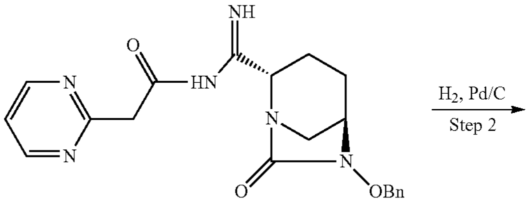

25_1

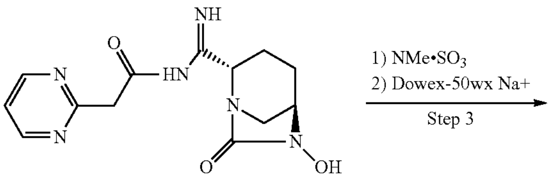

25_2

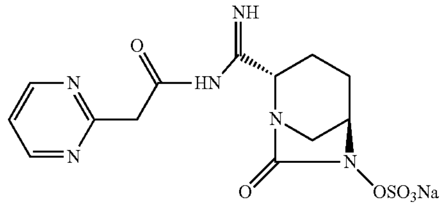

Example 25

Step 1: Synthesis of N-(((2S,5R)-6-(benzyloxy)-7-oxo-1,6-diazabicyclo[3.2.1]octan-2-yl)(imino)methyl)-2-(pyrimidin-2-yl)acetamide (25_1)

2-(Pyrimidin-2-yl)acetic acid (0.76 g, 5.74 mmol) was added to a solution of BB-1 (1.0 g, 3.65 mmol), HATU (2.18 g, 5.74 mmol) and DIPEA (0.94 g, 7.30 mmol) in DCM/DMF (5/5 mL) at room temperature, and then stirred overnight at room temperature under $N_2$. The reaction mixture was diluted with DCM, washed with brine, dried over $Na_2SO_4$ and filtrated. The organic layer was concentrated to give a residue, which was purified by silica gel column chromatography eluting with 50% ethyl acetate in petroleum ether to give the title compound 251 (621 mg, 43%) as a yellow solid. LC-MS analysis: $[M+H]^+$=395.4 and $[M+Na]^+$=417.4.

Step 2: Synthesis of N-(((2S,5R)-6-hydroxy-7-oxo-1,6-diazabicyclo[3.2.1]octan-2-yl)(imino)methyl)-2-(pyrimidin-2-yl)acetamide (25_2)

10% Pd/C (wet, 55% water w/w, 250 mg) was added to a solution of compound 251 (500 mg, 1.27 mmol) in MeOH (6 mL). The mixture was stirred under $H_2$ (balloon) at room temperature overnight, filtered through a pad of celite, rinsed with MeOH. The filtrate was concentrated in vacuum, and purified by flash silica gel chromatography using 10% MeOH in DCM to give the title compound 252 (126 mg, 33%) as a white solid. $^1$H NMR (400 MHz, DMSO-$d_6$) δ 1.68-1.78 (m, 1H), 1.84-2.05 (m, 3H), 3.20-3.26 (m, 1H), 3.77-3.96 (m, 2H), 4.06-4.12 (m, 2H), 5.70 (s, 1H), 6.40 (s, 2H), 7.39 (t, J=4.3 Hz, 1H), 8.75 (d, J=4.7 Hz, 2H), 9.28 (s, 1H). LC-MS analysis: $[M+H]^+$=305.1.

Step 3: Synthesis of sodium (2S,5R)-7-oxo-2-(N-(2-(pyrimidin-2-yl)acetyl)carbamimidoyl)-1,6-diazabicyclo[3.2.1]octan-6-yl sulfate (example 25)

A mixture of compound 25_2 (126 mg, 0.41 mmol), $SO_3 \cdot NMe_3$ (138 mg, 1.01 mmol) and TEA (0.22 mL, 1.58 mmol) in THF/water (3/3 mL) was stirred at room temperature overnight. The reaction mixture was concentrated under reduced pressure to provide a residue. The residue was purified by Dowex-50wx $Na^+$ resin, using water as an elution solvent to give example 25 (158 mg, 94%) as a white solid. $^1$H NMR (400 MHz, $D_2O$): δ 1.80-1.92 (m, 1H), 1.94-2.05 (m, 1H), 2.08-2.20 (m, 2H), 3.56 (t, J=12.8 Hz, 1H), 3.83-3.92 (m, 1H), 3.95-4.02 (m, 1H), 4.13-4.28 (m, 2H), 5.75 (d, J=4.7 Hz, 1H), 7.46 (t, J=5.1 Hz, 1H), 8.73 (d, J=5.1 Hz, 2H). LC-MS analysis: [M−Na]−=383.1.

Example 26

Sodium (2S,5R)-2-(N-((S)-1-acetylpiperidine-3-carbonyl)carbamimidoyl)-7-oxo-1,6-diazabicyclo[3.2.1]octan-6-yl sulfate (compound 55 in table 1)

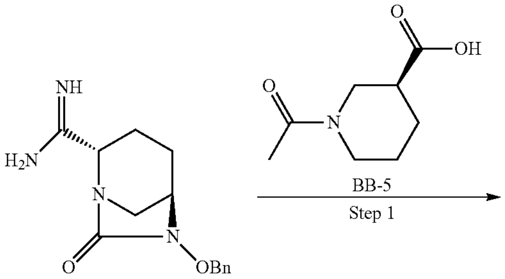

BB-1

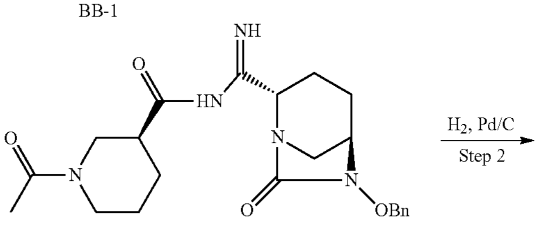

26_1

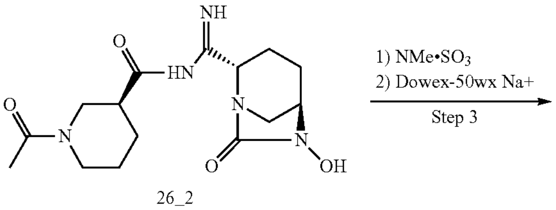

26_2

-continued

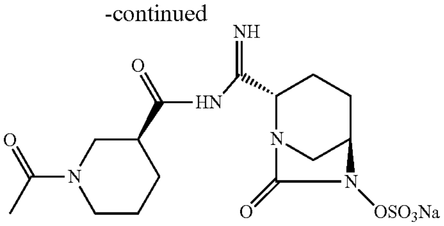

Example 26

Step 1: Synthesis of (3S)-1-acetyl-N-(((2S,5R)-6-(benzyloxy)-7-oxo-1,6-diazabicyclo[3.2.1]octan-2-yl)(imino)methyl)piperidine-3-carboxamide (26_1)

DIPEA (0.420 mL, 2.40 mmol), followed by BB-1 (220 mg, 0.800 mmol) were added to a mixture of (S)-1-acetylpiperidine-3-carboxylic acid BB-5 (215 mg, 1.26 mmol) and HATU (475 mg, 1.26 mmol) in DCM/DMF (2.5/2.5 mL) at room temperature, and then stirred for 22 hours. The reaction mixture was quenched with saturated $NaHCO_3$, water, extracted with EtOAc. The organic layer was washed with water, brine, dried over $Na_2SO_4$ and filtrated. The organic layer was concentrated to give a residue, which was purified by silica gel column chromatography eluting with 2-5% MeOH in $CH_2Cl_2$ to give the title compound 261 (278 mg, 81%) as a pale yellow solid. $^1H$ NMR (400 MHz, DMSO-$d_6$): δ 1.38-1.55 (m, 2H), 1.57-1.77 (m, 3H), 1.79-1.99 (m, 3H), 2.01 (s, 3H), 2.50-2.61 (m, 1H), 2.71-2.89 (m, 1H), 2.96-3.26 (m, 2H), 3.67-4.03 (m, 3H), 4.16-4.32 (m, 1H), 4.74-4.92 (m, 2H), 5.57-5.71 (m, 1H), 6.64-6.86 (m, 2H), 7.31-7.42 (m, 3H), 7.44-7.56 (m, 2H). LC-MS analysis: $[M+H]^+$=428.3.

Step 2: Synthesis of (3S)-1-acetyl-N-(((2S,5R)-6-hydroxy-7-oxo-1,6-diazabicyclo[3.2.1]octan-2-yl)(imino)methyl)piperidine-3-carboxamide (26_2)

10% Pd/C (180 mg) was added to a solution of compound 26_1 (276 mg, 0.64 mmol) in THE (10 mL) with 3 drops of TEA. The mixture was stirred under $H_2$ (balloon) at room temperature overnight, filtered through a pad of celite, rinsed with MeOH. The filtrate was concentrated and purified by silica gel column chromatography eluting with 5-10% MeOH in $CH_2Cl_2$ to give the title compound 262 (136 mg, 63%) as a white solid, $^1H$ NMR (400 MHz, DMSO-$d_6$): δ1.43-1.55 (m, 2H), 1.57-1.65 (m, 1H), 1.67-1.93 (m, 4H), 1.94-2.02 (m, 1H), 2.02 (s, 3H), 2.57-2.73 (m, 1H), 2.80-2.90 (m, 1H), 2.99-3.23 (m, 2H), 3.66-3.90 (m, 2H), 4.00-4.12 (m, 1H), 4.18-4.32 (m, 1H), 5.61-5.70 (m, 1H), 6.42-6.48 (m, 2H), 9.26 (s, 1H). LC-MS analysis: $[M+H]^+$=338.2.

Step 3: Synthesis of sodium (2S,5R)-2-(N-((S)-1-acetylpiperidine-3-carbonyl)carbamimidoyl)-7-oxo-1,6-diazabicyclo[3.2.1]octan-6-yl sulfate (example 26)

A mixture of compound 262 (133 mg, 0.395 mmol), $SO_3 \cdot NMe_3$ (139 mg, 1.0 mmol) and TEA (0.21 mL, 1.51 mmol) in THE/water (4/3 mL) was stirred at room temperature overnight. The reaction mixture was concentrated under reduced pressure to provide a residue, added water (10 mL), and lyophilized to give a solid. The solid was purified by Dowex-50wx $Na^+$ resin, using water as an elution solvent to give example 26 (160 mg, 97%) as a white solid. $^1H$ NMR (400 MHz, $D_2O$): δ 1.45-1.64 (m, 2H), 1.75-1.87 (m, 2H), 1.91-2.03 (m, 1H), 2.08 (s, 1.5H), 2.09 (s, 1.5H), 2.09-2.21 (m, 2H), 2.81-3.10 (m, 3H), 3.29-3.39 (m, 1H), 3.53-3.64 (m, 1H), 3.72-3.84 (m, 1H), 4.04-4.15 (m, 2H), 5.68-5.73 (m, 1H). LC-MS analysis: [M−Na]−=416.2.

Example 27

Sodium (2S,5R)-2-(N-((R)-1-acetylpiperidine-3-carbonyl)carbamimidoyl)-7-oxo-1,6-diazabicyclo[3.2.1]octan-6-yl sulfate (compound 52 in table 1)

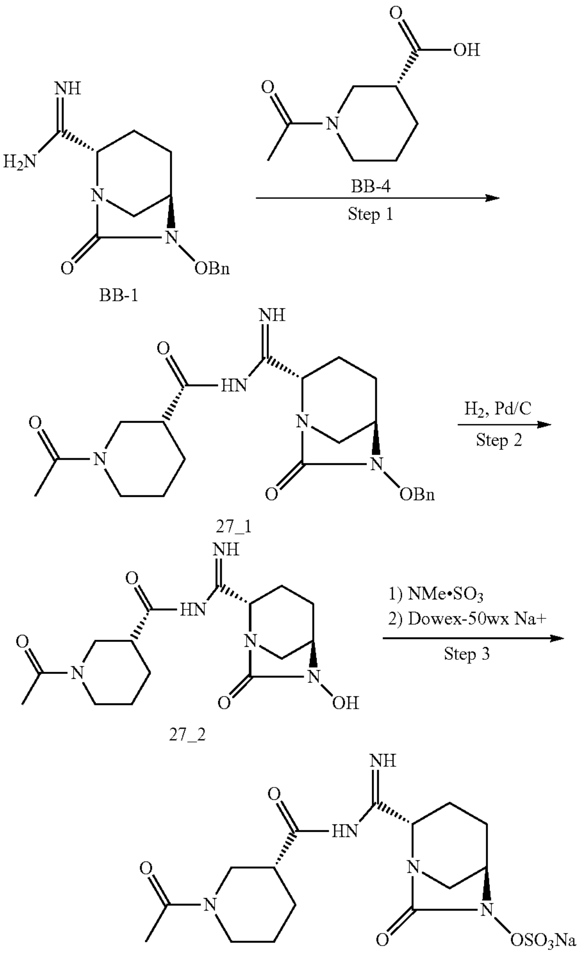

BB-1

27_1

27_2

Example 27

Step 1: Synthesis of (3R)-1-acetyl-N-(((2S,5R)-6-(benzyloxy)-7-oxo-1,6-diazabicyclo[3.2.1]octan-2-yl)(imino)methyl)piperidine-3-carboxamide (27_1)

DIPEA (0.420 mL, 2.40 mmol), followed by BB-1 (220 mg, 0.80 mmol) was added to a mixture of (R)-1-acetylpiperidine-3-carboxylic acid BB-4 (215 mg, 1.26 mmol) and HATU (475 mg, 1.26 mmol) in DCM/DMF (2.5/2.5 mL) at room temperature, and then stirred for 40 hours. The reaction mixture was quenched with saturated $NaHCO_3$, water, extracted with EtOAc. The organic layer was washed with water, brine, dried over $Na_2SO_4$ and filtrated. The organic layer was concentrated to give a residue, which was purified by silica gel column chromatography eluting with 2-5% MeOH in $CH_2Cl_2$ to give the title compound 271 (320 mg, 93%) as a pale brown solid. $^1$H NMR (400 MHz, DMSO-$d_6$): δ 1.39-1.54 (m, 2H), 1.56-1.74 (m, 2H), 1.80-1.93 (m, 2H), 1.93-2.05 (m, 5H), 2.51-2.62 (m, 1H), 2.71-2.88 (m, 1H), 2.94-3.28 (m, 2H), 3.68-3.95 (m, 3H), 4.17-4.38 (m, 1H), 4.78-4.92 (m, 2H), 5.57-5.70 (m, 1H), 6.65-6.86 (m, 2H), 7.32-7.42 (m, 3H), 7.46-7.55 (m, 2H). LC-MS analysis: $[M+H]^+$=428.3.

Step 2: Synthesis of (3R)-1-acetyl-N-(((2S,5R)-6-hydroxy-7-oxo-1,6-diazabicyclo[3.2.1]octan-2-yl)(imino)methyl)piperidine-3-carboxamide (27_2)

10% Pd/C (250 mg) was added to a solution of compound 27_1 (320 mg, 0.75 mmol) in THE (10 mL) with 3 drops of TEA. The mixture was stirred under $H_2$ (balloon) at room temperature for 30 hours, filtered through a pad of celite, rinsed with MeOH. The filtrate was concentrated and purified by silica gel column chromatography eluting with 2-6% MeOH in $CH_2Cl_2$ to give the title compound 27_2 (170 mg, 67%) as a white solid, $^1$H NMR (400 MHz, DMSO-$d_6$): δ1.38-1.54 (m, 2H), 1.56-1.80 (m, 3H), 1.83-2.05 (m, 6H), 2.52-2.63 (m, 1H), 2.65-2.86 (m, 1H), 2.93-3.24 (m, 2H), 3.67-3.96 (m, 3H), 4.24-4.36 (m, 1H), 5.58-5.70 (m, 1H), 6.40-6.54 (m, 2H), 9.31 (s, 1H). LC-MS analysis: $[M+H]^+$=338.2.

Step 3: Synthesis of sodium (2S,5R)-2-(N-((R)-1-acetylpiperidine-3-carbonyl)carbamimidoyl)-7-oxo-1,6-diazabicyclo[3.2.1]octan-6-yl sulfate (example 27)

A mixture of compound 272 (170 mg, 0.50 mmol), $SO_3 \cdot NMe_3$ (139 mg, 1.0 mmol) and TEA (0.24 mL, 1.72 mmol) in THE/water (4/3 mL) was stirred at room temperature overnight. The reaction mixture was concentrated under reduced pressure to provide a residue, added water (10 mL), and lyophilized to give a solid. The solid was purified by Dowex-50wx $Na^+$ resin, using water as an elution solvent to give example 27 (215 mg, 98%) as a white solid. $^1$H NMR (400 MHz, $D_2O$): δ 1.47-1.66 (m, 2H), 1.68-1.87 (m, 2H), 1.96-2.06 (m, 1H), 2.09 (s, 3H), 2.11-2.21 (m, 2H), 2.81-3.03 (m, 2H), 3.11-3.19 (m, 0.5H), 3.30-3.38 (m, 0.5H), 3.55-3.64 (m, 1H), 3.74-3.84 (m, 1H), 3.96-4.14 (m, 2.5H), 4.20-4.26 (m, 0.5H), 5.96-5.74 (m, 1H). LC-MS analysis: $[M-Na]^-$=416.2.

Example 28

Sodium (2S,5R)-2-(N-((S)-1-methylpiperidine-3-carbonyl)carbamimidoyl)-7-oxo-1,6-diazabicyclo[3.2.1]octan-6-yl sulfate (compound 54 in table 1)

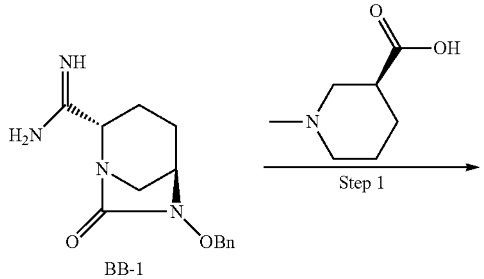

BB-1

-continued

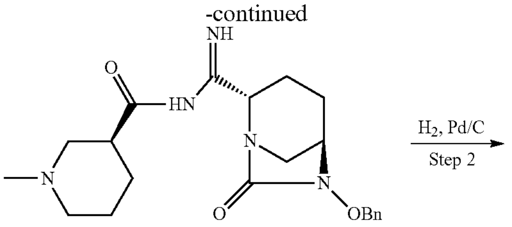

28_1

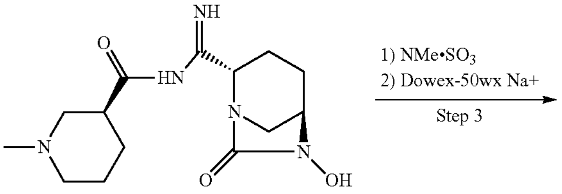

28_2

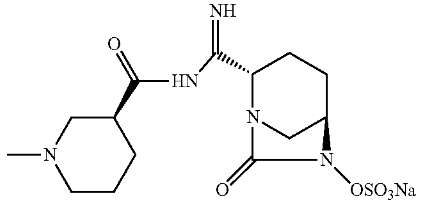

Example 28

Step 1: Synthesis of (3S)-N-(((2S,5R)-6-(benzyloxy)-7-oxo-1,6-diazabicyclo[3.2.1]octan-2-yl)(imino)methyl)-1-methylpiperidine-3-carboxamide (28_1)

DIPEA (0.39 mL, 2.25 mmol), followed by BB-1 (215 mg, 0.75 mmol) was added to a mixture of (S)-1-methylpiperidine-3-carboxylic acid (215 mg, 1.50 mmol) and HATU (475 mg, 1.26 mmol) in DCM/DMF (3/2 mL) at room temperature, and then stirred for 30 hours. The reaction mixture was quenched with saturated $NaHCO_3$, extracted with DCM. The organic layer was washed with water, brine, dried over $Na_2SO_4$ and filtrated. The organic layer was concentrated to give a residue, which was purified by silica gel column chromatography eluting with 2-5% MeOH in $CH_2Cl_2$ to give the title compound 28_1 (195 mg, 65%) as a pale brown solid. $^1$H NMR (400 MHz, DMSO-$d_6$): δ 1.48-1.78 (m, 4H), 1.82-2.04 (m, 4H), 2.29 (s, 3H), 2.74-2.96 (m, 3H), 3.00-3.06 (m, 1H), 3.14-3.24 (m, 1H), 3.31-3.38 (m, 1H), 3.73-3.96 (m, 2H), 4.85 (s, 2H), 5.66 (s, 1H), 6.75 (s, 2H), 7.34-7.41 (m, 3H), 7.46-7.53 (m, 2H). LC-MS analysis: $[M+H]^+$=400.2.

Step 2: Synthesis of (3S)-N-(((2S,5R)-6-hydroxy-7-oxo-1,6-diazabicyclo[3.2.1]octan-2-yl)(imino)methyl)-1-methylpiperidine-3-carboxamide (28_2)

10% Pd/C (wet, 55% water w/w, 220 mg) was added to a solution of compound 281 (195 mg, 0.49 mmol) in THE (10 mL) with a few drops of TEA. The mixture was stirred under $H_2$ (balloon) at room temperature for 22 hours, filtered through a pad of celite, rinsed with EtOAc. The filtrate was concentrated to give the title compound 28_2 (155 mg, quantitative) as a white solid, which was directly used for next step without further purification. $^1$H NMR (400 MHz, DMSO-$d_6$): δ 1.46-1.79 (m, 4H), 1.83-2.04 (m, 4H), 2.21 (s, 3H), 2.70-2.97 (m, 5H), 3.16-3.26 (m 1H), 3.73-3.82 (m, 1H), 3.87-3.98 (m, 1H), 5.65 (s, 1H), 6.46 (s, 2H), 9.28 (s, 1H). LC-MS analysis: $[M+H]^+$=310.2.

Step 3: Synthesis of sodium (2S,5R)-2-(N-((S)-1-methylpiperidine-3-carbonyl)carbamimidoyl)-7-oxo-1,6-diazabicyclo[3.2.1]octan-6-yl sulfate (example 28)

A mixture of compound 282 (155 mg obtained above), $SO_3 \cdot NMe_3$ (150 mg, 1.08 mmol) and TEA (0.21 mL, 1.50 mmol) in THE/water (3/3 mL) was stirred at room temperature for 23 hours. The reaction mixture was concentrated under reduced pressure to provide a residue. The residue was purified by further purified by Dowex-50wx $Na^+$ resin, using water as an elution solvent to give example 28 (134 mg, 70% in two steps) as a white solid. $^1H$ NMR (400 MHz, $D_2O$): 51.44-1.71 (m, 1H), 1.75-2.03 (m, 5H), 2.08-2.18 (m, 2H), 2.82 (s, 3H), 2.86-2.95 (m, 1H), 3.02-3.11 (m, 1H), 3.33-3.67 (m, 4H), 3.95-4.08 (m, 2H), 5.70 (s, 1H). LC-MS analysis: $[M-Na]^-$=388.2.

Example 29

Sodium (2S,5R)-2-(N-((R)-1-methylpiperidine-3-carbonyl)carbamimidoyl)-7-oxo-1,6-diazabicyclo[3.2.1]octan-6-yl sulfate (compound 51 in table 1)

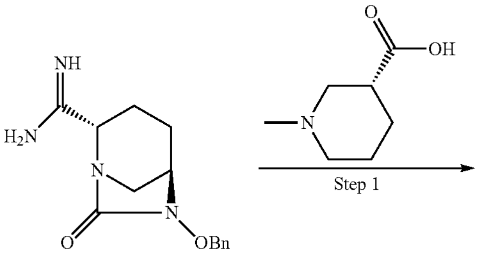

BB-1

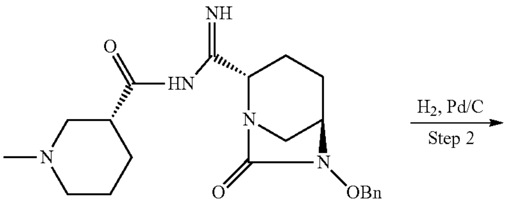

29_1

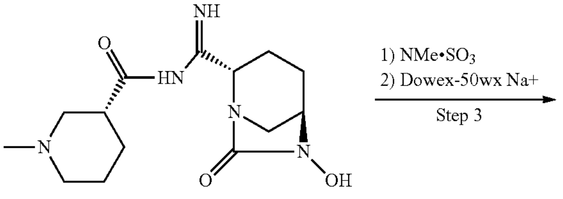

29_2

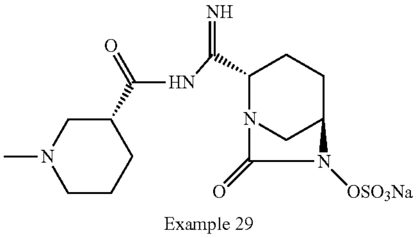

Example 29

Step 1: Synthesis of (3R)-N-(((2S,5R)-6-(benzyloxy)-7-oxo-1,6-diazabicyclo[3.2.1]octan-2-yl)(imino)methyl)-1-methylpiperidine-3-carboxamide (27_1)

DIPEA (0.39 mL, 2.25 mmol), followed by BB-1 (215 mg, 0.75 mmol) were added to a mixture of (R)-1-methylpiperidine-3-carboxylic acid (220 mg, 1.23 mmol) and HATU (470 mg, 1.25 mmol) in DCM/DMF (3/2 mL) at room temperature, and then stirred for 40 hours. The reaction mixture was quenched with saturated $NaHCO_3$, extracted with DCM. The organic layer was washed with water, brine, dried over $Na_2SO_4$ and filtrated. The organic layer was concentrated to give a residue, which was purified by silica gel column chromatography eluting with 2-5% MeOH in $CH_2Cl_2$ to give the title compound 29_1 (230 mg, 76%) as a pale brown solid. $^1H$ NMR (400 MHz, DMSO-$d_6$): δ 1.53-1.80 (m, 4H), 1.82-2.04 (m, 4H), 2.28 (s, 3H), 2.79-2.89 (m, 3H), 2.97-3.04 (m, 3H), 3.78-3.93 (m, 2H), 4.84 (s, 2H), 5.65 (s, 1H), 6.76 (s, 2H), 7.35-7.41 (m, 3H), 7.48-7.52 (m, 2H). LC-MS analysis: $[M+H]^+$=400.2.

Step 2: Synthesis of (3R)-N-(((2S,5R)-6-hydroxy-7-oxo-1,6-diazabicyclo[3.2.1]octan-2-yl)(imino)methyl)-1-methylpiperidine-3-carboxamide (29_2)

10% Pd/C (wet, 55% water w/w, 230 mg) was added to a solution of compound 291 (230 mg, 0.58 mmol) in THE (10 mL) with a few drops of TEA. The mixture was stirred under $H_2$ (balloon) at room temperature for 16 hours, filtered through a pad of celite, rinsed with EtOAc. The filtrate was concentrated to give the title compound 29_2 (170 mg, 94%) as a white solid, which was directly used for next step without further purification. $^1H$ NMR (400 MHz, DMSO-$d_6$): δ 1.46-1.79 (m, 4H), 1.83-2.04 (m, 4H), 2.22 (s, 3H), 2.71-2.83 (m, 3H), 2.90-2.99 (m, 2H), 3.17-3.24 (m 1H), 3.73-3.82 (m, 1H), 3.85-3.97 (m, 1H), 5.65 (s, 1H), 6.48 (s, 2H), 9.28 (s, 1H). LC-MS analysis: $[M+H]^+$=310.2.

Step 3: Synthesis of sodium (2S,5R)-2-(N-((R)-1-methylpiperidine-3-carbonyl)carbamimidoyl)-7-oxo-1,6-diazabicyclo[3.2.1]octan-6-yl sulfate (example 29)

A mixture of compound 292 (170 mg, 0.55 mmol), $SO_3 \cdot NMe_3$ (216 mg, 1.15 mmol) and TEA (0.29 mL, 2.08 mmol) in THE/water (6/3 mL) was stirred at room temperature for 22 hours. The reaction mixture was concentrated under reduced pressure to provide a residue. The residue was purified by further purified by Dowex-50wx $Na^+$ resin, using water as an elution solvent to give example 29 (136 mg, 63%) as a white solid. $^1H$ NMR (400 MHz, $D_2O$): 651.73-1.91 (m, 4H), 1.93-2.04 (m, 2H), 2.05-2.17 (m, 2H), 2.81 (s, 3H), 2.83-2.94 (m, 1H), 3.00-3.10 (m, 1H), 3.32-3.61 (m, 4H), 3.93-4.04 (m, 2H), 5.65 (d, J=4.8 Hz, 1H). LC-MS analysis: $[M-Na]^-$=388.2.

Example 30

Sodium (2S,5R)-2-(N-((S)-1-acetylpyrrolidine-3-carbonyl)carbamimidoyl)-7-oxo-1,6-diazabicyclo[3.2.1]octan-6-yl sulfate (compound 71 in table 1)

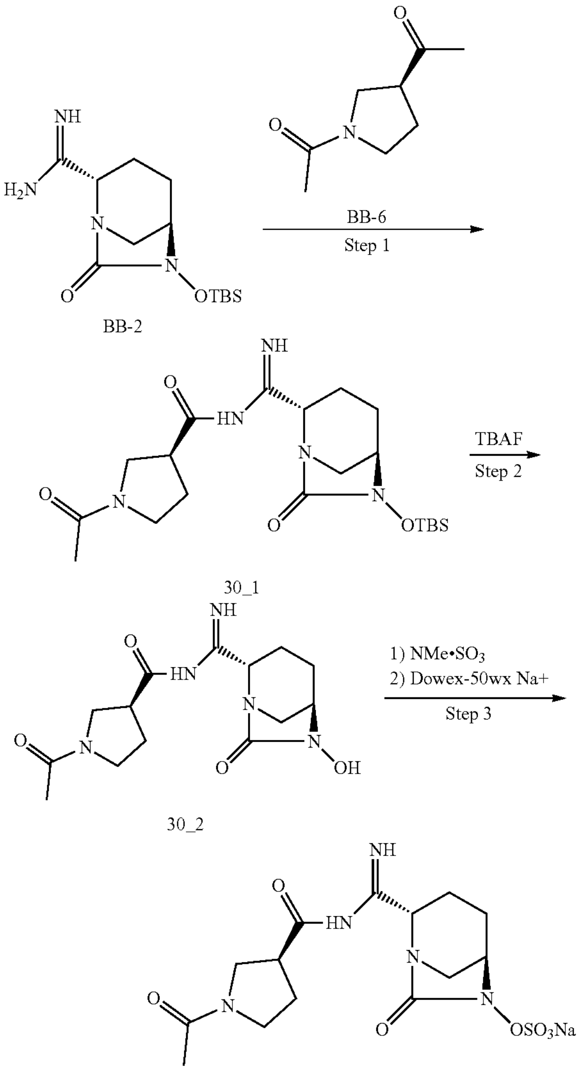

BB-2
30_1
30_2
Example 30

Step 1: Synthesis of (3S)-1-acetyl-N-(((2S,5R)-6-((tert-butyldimethylsilyl)oxy)-7-oxo-1,6-diazabicyclo[3.2.1]octan-2-yl)(imino)methyl)pyrrolidine-3-carboxamide (30_1)

(S)-1-Acetylpyrrolidine-3-carboxylic acid (190 mg, 1.26 mmol) was added to a solution of BB-2 (342 mg, 1.14 mmol), DAMP (85 mg, 0.69 mmol) and DCC (352 mg, 1.71 mmol) in DCM (5 mL) at room temperature, and then stirred overnight at room temperature to give a suspension. The solid was filtrated, the filtrate was concentrated to give a residue, which was purified by silica gel column chromatography eluting with 5% MeOH in DCM to give the title compound 30_1 (263 mg, 52%) as an oil. $^1$H NMR (400 MHz, $CDCl_3$): δ 0.26 (s, 3H), 0.27 (s, 3H), 1.00 (s, 4.5H), 1.02 (s, 4.5H), 1.70-1.81 (m, 1H), 1.99-2.31 (m, 9H), 3.20-3.34 (m, 1H), 3.43-3.53 (m, 1H), 3.55-3.69 (m, 3H), 3.73-3.83 (m, 1H), 3.87-3.98 (m, 1), 5.73-5.79 (m, 2H), 5.85 (s, 1H). LC-MS analysis: $[M+H]^+$=438.2.

Step 2: Synthesis of (3S)-1-acetyl-N-(((2S,5R)-6-hydroxy-7-oxo-1,6-diazabicyclo[3.2.1]octan-2-yl)(imino)methyl)pyrrolidine-3-carboxamide (30_2)

TBAF (1 N in THF, 0.6 mL, 0.6 mmol) was added to a solution of compound 30_1 (240 mg, 0.55 mmol) in THF (5 mL) at 0° C., warmed up to room temperature and stirred for 3 hours. The mixture was concentrated to dryness, added water, washed with EtOAc. The water phase was added EtOH (100 mL), and concentrated to give a solid residue, which was purified by silica gel column chromatography eluting with 8% MeOH in DCM to give the title compound 30_2 (170 mg, 96%) as a white solid. $^1$H NMR (400 MHz, $CD_3OD$): δ 1.81-1.91 (m, 2H), 1.98-2.19 (m, 7H), 2.21-2.31 (m, 1H), 3.38-3.47 (m, 1H), 3.50-3.70 (m, 4H), 3.95-4.02 (m, 1H), 4.05-4.12 (m, 1H), 5.71-5.77 (m, 1H). LC-MS analysis: $[M+H]^+$=324.1.

Step 3: Synthesis of sodium (2S,5R)-2-(N-((S)-1-acetylpyrrolidine-3-carbonyl)carbamimidoyl)-7-oxo-1,6-diazabicyclo[3.2.1]octan-6-yl sulfate (example 30)

A mixture of compound 302 (90 mg, 0.27 mmol), $SO_3{\cdot}NMe_3$ (97 mg, 0.69 mmol) and TEA (0.15 mL, 1.08 mmol) in THF/water (2/2 mL) was stirred at room temperature overnight. The reaction mixture was concentrated under reduced pressure to provide a residue. The residue was purified by Dowex-50wx $Na^+$ resin, using water as an elution solvent to give example 30 (102 mg, 94%) as a white solid. $^1$H NMR (400 MHz, $D_2O$): δ 1.81-1.91 (m, 1H), 2.01-2.11 (m, 5H), 2.13-2.35 (m, 3H), 4.36 (t, J=7.0 Hz, 1H), 3.54-3.81 (m, 5H), 4.02-4.13 (m, 1H), 4.20 (d, J=13.2 Hz, 1H), 5.73-5.78 (m, 1H). LC-MS analysis: $[M-Na]^-$=402.2.

Example 31

Sodium (2S,5R)-2-(N-((R)-1-acetylpyrrolidine-3-carbonyl)carbamimidoyl)-7-oxo-1,6-diazabicyclo[3.2.1]octan-6-yl sulfate (compound 60 in table 1)

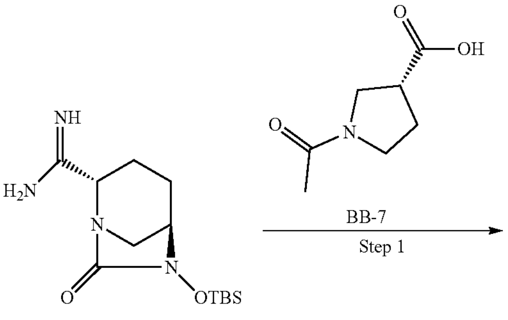

BB-2

-continued

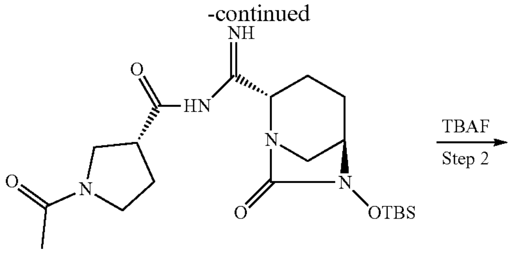

31_1

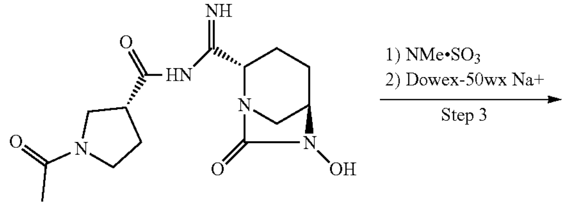

31_2

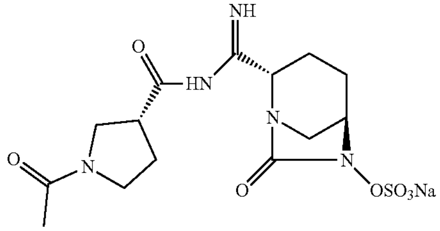

Example 31

Step 1: Synthesis of (3R)-1-acetyl-N-(((2S,5R)-6-((tert-butyldimethylsilyl)oxy)-7-oxo-1,6-diazabicyclo[3.2.1]octan-2-yl)(imino)methyl)pyrrolidine-3-carboxamide (31_1)

(R)-1-Acetylpyrrolidine-3-carboxylic acid (204 mg, 1.29 mmol) was added to a solution of BB-2 (298 mg, 1.0 mmol), DAMP (85 mg, 0.69 mmol) and DCC (412 mg, 2.0 mmol) in DCM (5 mL) at room temperature, and then stirred overnight at room temperature to give a suspension. The solid was filtrated, the filtrate was concentrated to give a residue, which was purified by silica gel column chromatography eluting with 5% MeOH in DCM to give the title compound 31_1 (110 mg, 25%) as an oil. $^1$H NMR (400 MHz, DMSO-$d_6$): δ 0.26 (s, 6H), 1.00 (s, 4.5H), 1.01 (s, 4.5H), 1.70-1.81 (m, 1H), 1.96-2.31 (m, 9H), 3.15-3.31 (m, 1H), 3.43-3.96 (m, 6H), 5.38 (br s, 2H), 5.76 (s, 1H). LC-MS analysis: $[M+H]^+$=438.2.

Step 2: Synthesis of (3R)-1-acetyl-N-(((2S,5R)-6-hydroxy-7-oxo-1,6-diazabicyclo[3.2.1]octan-2-yl)(imino)methyl)pyrrolidine-3-carboxamide (31_2)

TBAF (1 N in THF, 0.5 mL, 0.5 mmol) was added to a solution of compound 31_1 (200 mg, 0.45 mmol) in THE (5 mL) at 0° C., warmed up to room temperature and stirred for 3 hours. The mixture was concentrated to dryness, added water, washed with EtOAc. The water phase was added EtOH (100 mL), and concentrated to give a solid residue, which was purified by silica gel column chromatography eluting with 8% MeOH in DCM to give the title compound 31_2 (140 mg, 96%) as a white solid. $^1$H NMR (400 MHz, DMSO-$d_6$): δ1.59-1.70 (m, 3H), 1.73-1.87 (m, 1H), 1.94-2.02 (m, 4H), 2.15-2.32 (m, 2H), 3.17-3.25 (m, 2H), 3.43-3.53 (m, 1H), 3.55-3.69 (m, 1H), 3.71-3.80 (m, 1H), 3.89-4.03 (m, 1H), 4.05-4.16 (m, 1H), 5.70-5.75 (m, 1H). LC-MS analysis: $[M+H]^+$=324.1.

Step 3: Synthesis of sodium (2S,5R)-2-(N-((R)-1-acetylpyrrolidine-3-carbonyl)carbamimidoyl)-7-oxo-1,6-diazabicyclo[3.2.1]octan-6-yl sulfate (example 31)

A mixture of compound 312 (150 mg, 0.46 mmol), $SO_3 \cdot NMe_3$ (139 mg, 1.0 mmol) and TEA (0.22 mL, 1.58 mmol) in THF/water (3/3 mL) was stirred at room temperature overnight. The reaction mixture was concentrated under reduced pressure to provide a residue, which was purified by Dowex-50wx $Na^+$ resin, using water as an elution solvent to give example 31 (168 mg, 85%) as a white solid. $^1$H NMR (400 MHz, $D_2O$): 51.72-1.84 (m, 1H), 1.92-2.03 (m, 5H), 2.05-2.31 (m, 3H), 3.39 (t, J=6.9 Hz, 1H), 3.46-3.60 (m, 4H), 3.63-3.68 (m, 1H), 3.94-4.04 (m, 1H), 4.12 (d, J=13.3 Hz, 1H), 5.68 (s, 1H). LC-MS analysis: $[M-Na]^-$=402.1.

Example 32

Sodium (2S,5R)-2-(N-((S)-1-methylpyrrolidine-3-carbonyl)carbamimidoyl)-7-oxo-1,6-diazabicyclo[3.2.1]octan-6-yl sulfate (compound 72 in table 1)

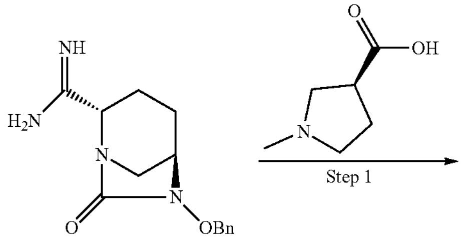

BB-1

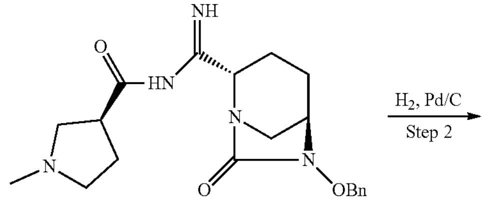

32_1

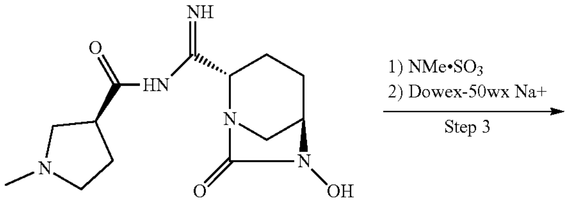

32_2

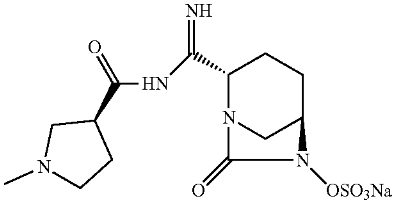

Example 32

Step 1: Synthesis of (3S)-N-(((2S,5R)-6-(benzyloxy)-7-oxo-1,6-diazabicyclo[3.2.1]octan-2-yl)(imino)methyl)-1-methylpyrrolidine-3-carboxamide (32_1)

DIPEA (0.41 mL, 2.41 mmol), followed by BB-1 (220 mg, 0.80 mmol) were added to a mixture of (S)-1-methylpyrrolidine-3-carboxylic acid (210 mg, 1.62 mmol) and HATU (480 mg, 1.26 mmol) in DCM/DMF (3/2 mL) at room temperature, and then stirred for 40 hours. The reaction mixture was quenched with saturated $NaHCO_3$, extracted with DCM. The organic layer was washed with water, brine, dried over $Na_2SO_4$ and filtrated. The organic layer was concentrated to give a residue, which was purified by silica gel column chromatography eluting with 2-5% MeOH in $CH_2Cl2$ to give the title compound 32_1 (157 mg, 51%) as a brown solid. $^1H$ NMR (400 MHz, DMSO-$d_6$): δ 1.69-1.78 (m, 1H), 1.82-2.06 (m, 5H), 2.14-2.24 (m, 1H), 2.70 (s, 3H), 3.21-3.35 (m, 4H), 3.50-3.57 (m, 1H), 3.80-3.87 (m, 1H), 3.93-3.99 (m, 1H), 4.86 (s, 2H), 5.69 (s, 1H), 6.75 (s, 2H), 7.35-7.41 (m, 3H), 7.46-7.53 (m, 2H). LC-MS analysis: $[M+H]^+$=386.1.

Step 2: Synthesis of (3S)-N-(((2S,5R)-6-hydroxy-7-oxo-1,6-diazabicyclo[3.2.1]octan-2-yl)(imino)methyl)-1-methylpyrrolidine-3-carboxamide (32_2)

10% Pd/C (wet, 55% water w/w, 200 mg) was added to a solution of compound 321 (155 mg, 0.58 mmol) in THE (8 mL) with a few drops of TEA. The mixture was stirred under $H_2$ (balloon) at room temperature for 16 hours, filtered through a pad of celite, rinsed with EtOAc. The filtrate was concentrated to give the title compound 32_2 (125 mg, quantitative) as a white solid, which was directly used for next step without further purification. LC-MS analysis: $[M+H]^+$=296.2.

Step 3: Synthesis of sodium (2S,5R)-2-(N-((S)-1-methylpyrrolidine-3-carbonyl)carbamimidoyl)-7-oxo-1,6-diazabicyclo[3.2.1]octan-6-yl sulfate (example 32)

A mixture of compound 322 (125 mg, obtained above), $SO_3 \cdot NMe_3$ (139 mg, 1.0 mmol) and TEA (0.21 mL, 1.50 mmol) in THE/water (3/3 mL) was stirred at room temperature for 21 hours. The reaction mixture was concentrated under reduced pressure to provide a residue. The residue was purified by further purified by Dowex-50wx $Na^+$ resin, using water as an elution solvent to give example 32 (74 mg, 49% in two steps) as a white solid. $^1H$ NMR (400 MHz, $D_2O$): δ 1.76-1.86 (m, 1.5H), 1.95-2.03 (m, 1.5H), 2.07-2.19 (m, 3H), 2.44-2.56 (m, 1H), 2.91 (s, 3H), 3.54-3.64 (m, 2H), 3.71-3.82 (m, 2H), 3.97-4.09 (m, 3H), 5.67 (s, 1H). LC-MS analysis: $[M-Na]^-$=374.1.

Example 33

Sodium (2S,5R)-2-(N-((R)-1-methylpyrrolidine-3-carbonyl)carbamimidoyl)-7-oxo-1,6-diazabicyclo[3.2.1]octan-6-yl sulfate (compound 70 in table 1)

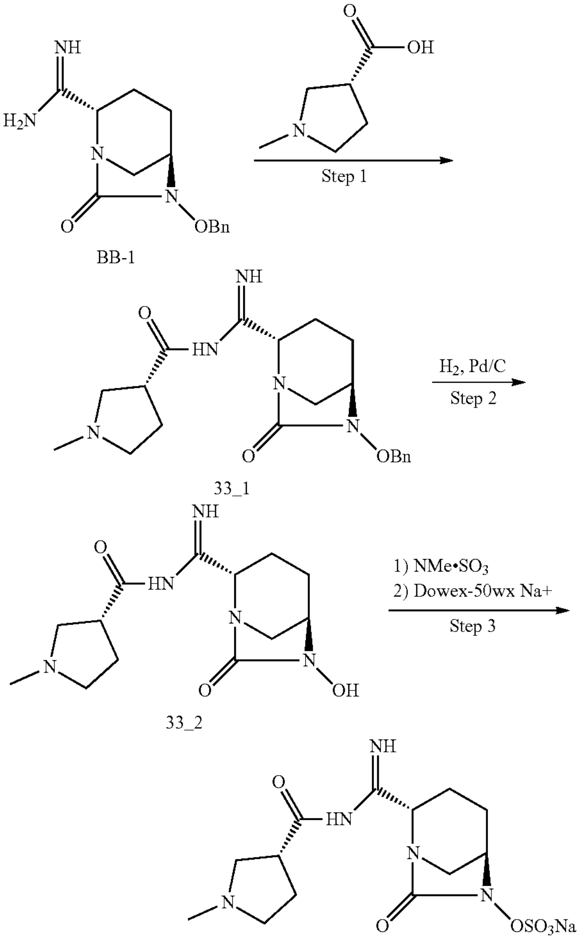

Step 1: Synthesis of (3R)-N-(((2S,5R)-6-(benzyloxy)-7-oxo-1,6-diazabicyclo[3.2.1]octan-2-yl)(imino)methyl)-1-methylpyrrolidine-3-carboxamide (33_1)

DIPEA (0.62 mL, 3.56 mmol), followed by BB-1 (330 mg, 1.20 mmol) were added to a mixture of (R)-1-methylpyrrolidine-3-carboxylic acid (300 mg, 2.33 mmol) and HATU (718 mg, 1.89 mmol) in DCM/DMF (3/3 mL) at room temperature, and then stirred for 48 hours. The reaction mixture was quenched with saturated $NaHCO_3$, extracted with DCM. The organic layer was washed with water, brine, dried over $Na_2SO_4$ and filtrated. The organic layer was concentrated to give a residue, which was purified by silica gel column chromatography eluting with 2-5% MeOH in $CH_2Cl2$ to give the title compound 33_1 (204 mg, 44%) as a brown solid. $^1H$ NMR (400 MHz, DMSO-$d_6$): δ 1.69-1.81 (m, 1H), 1.83-2.05 (m, 5H), 2.20-2.30 (m, 1H), 2.60 (s, 3H), 2.93-2.99 (m, 1H), 3.16-3.27 (m, 3H), 3.44-3.52 (m, 1H), 3.81-3.87 (m, 1H), 3.90-3.97 (m, 1H), 4.85 (s, 2H), 5.68 (s, 1H), 6.74 (s, 2H), 7.35-7.41 (m, 3H), 7.47-7.53 (m, 2H). LC-MS analysis: $[M+H]^+$=386.2.

Step 2: Synthesis of (3R)-N-(((2S,5R)-6-hydroxy-7-oxo-1,6-diazabicyclo[3.2.1]octan-2-yl)(imino) methyl)-1-methylpyrrolidine-3-carboxamide (33_2)

10% Pd/C (wet, 55% water w/w, 200 mg) was added to a solution of compound 331 (200 mg, 0.52 mmol) in THE (10 mL) with a few drops of TEA. The mixture was stirred under $H_2$ (balloon) at room temperature for 20 hours, filtered through a pad of celite, rinsed with EtOAc. The filtrate was concentrated to give the title compound 33_2 (160 mg, quantitative) as a white solid, which was directly used for next step without further purification. LC-MS analysis: $[M+H]^+$=296.2.

Step 3: Synthesis of sodium (2S,5R)-2-(N-((R)-1-methylpyrrolidine-3-carbonyl)carbamimidoyl)-7-oxo-1,6-diazabicyclo[3.2.1]octan-6-yl sulfate (example 33)

A mixture of compound 332 (160 mg, obtained above), $SO_3{\cdot}NMe_3$ (147 mg, 1.04 mmol) and TEA (0.22 mL, 1.55 mmol) in THE/water (3/3 mL) was stirred at room temperature for 21 hours. The reaction mixture was concentrated under reduced pressure to provide a residue. The residue was further purified by Dowex-50wx $Na^+$ resin, using water as an elution solvent to give example 33 (75 mg, 38% in two steps) as a white solid. $^1H$ NMR (400 MHz, $D_2O$): δ 1.75-1.85 (m, 1H), 1.96-2.06 (m, 2H), 2.07-2.23 (m, 3H), 2.58-2.68 (m, 1H), 2.90 (s, 3H), 3.54-3.62 (m, 1H), 3.64-3.71 (m, 2H), 3.75-3.83 (m, 1H), 3.87-4.08 (m, 3H), 5.66 (s, 1H). LC-MS analysis: $[M-Na]^-$=374.1.

Example 34

Sodium (2S,5R)-7-oxo-2-(N-(2-(pyridin-3-yl)acetyl) carbamimidoyl)-1,6-diazabicyclo[3.2.1]octan-6-yl sulfate (compound 104 in table 1)

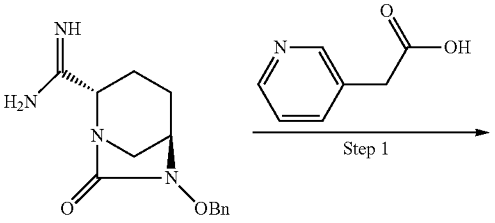

BB-1

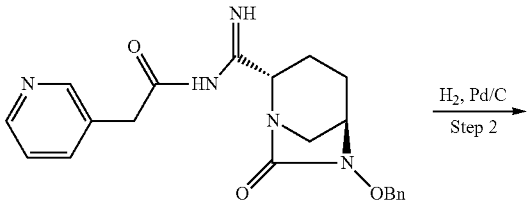

34_1

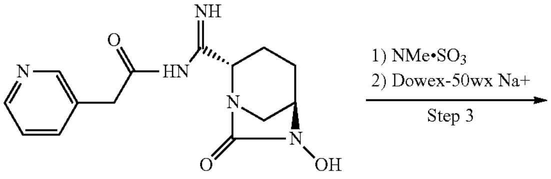

34_2

-continued

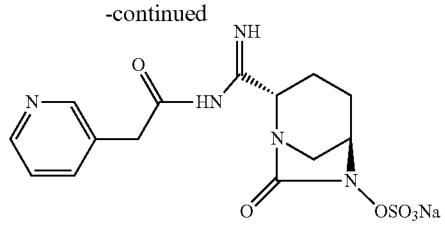

Example 34

Step 1: Synthesis of N-(((2S,5R)-6-(benzyloxy)-7-oxo-1,6-diazabicyclo[3.2.1]octan-2-yl)(imino) methyl)-2-(pyridin-3-yl)acetamide (34_1)

2-(Pyridin-3-yl)acetic acid (0.78 g, 5.74 mmol) was added to a solution of BB-1 (1.01 g, 3.65 mmol), HATU (2.18 g, 5.74 mmol) and DIPEA (0.94 g, 7.30 mmol) in DCM/DMF (5/5 mL) at room temperature, and then stirred over night at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in petroleum ether to give the title compound 341 (0.66 g, 46%) as a white solid. LC-MS analysis: $[M+H]^+$=394.2.

Step 2: Synthesis of N-(((2S,5R)-6-hydroxy-7-oxo-1,6-diazabicyclo[3.2.1]octan-2-yl)(imino)methyl)-2-(pyridin-3-yl)acetamide (34_2)

10% Pd/C (wet, 55% water w/w, 250 mg) was added to a solution of compound 341 (500 mg, 1.27 mmol) in MeOH (5 mL). The mixture was stirred under $H_2$ (balloon) at room temperature overnight, filtered through a pad of celite, rinsed with MeOH. The filtrate was concentrated under vacuum, and purified by flash silica gel chromatography using 10% MeOH in DCM to give the title compound 342 (85 mg, 22%) as a white solid. $^1H$ NMR (400 MHz, DMSO-$d_6$) δ 1.70-2.06 (m, 4H), 3.78-3.94 (m, 3H), 5.67 (s, 1H), 6.48 (s, 2H), 7.33 (dd, J=7.7, 5.0 Hz, 1H), 7.62 (d, J=7.1 Hz, 1H), 8.39-8.46 (m, 2H), 9.34 (s, 1H). LC-MS analysis: $[M+H]^+$=304.3 Step 3: Synthesis of sodium (2S,5R)-7-oxo-2-(N-(2-(pyridin-3-yl)acetyl)carbamimidoyl)-1,6-diazabicyclo[3.2.1]octan-6-yl sulfate (example 34)

A mixture of compound 342 (85 mg, 0.28 mmol), $SO_3{\cdot}NMe_3$ (97 mg, 0.70 mmol) and TEA (0.15 mL, 1.08 mmol) in THE/water (3/2 mL) was stirred at room temperature overnight. The reaction mixture was concentrated under reduced pressure to provide a residue. The residue was purified by Dowex-50wx $Na^+$ resin, using water as an elution solvent to give example 34 (76 mg, 67%) as a white solid. $^1H$ NMR (400 MHz, $D_2O$): δ 1.77-1.89 (m, 1H), 1.97-2.05 (m, 1H), 2.09-2.21 (m, 2H), 2.57-3.64 (m, 1H), 3.92-4.03 (m, 3H), 4.13-4.20 (m, 1H), 5.71 (d, J=4.6 Hz, 1H), 7.54 (dd, J=7.9, 5.2 Hz, 1H), 7.85 (d, J=7.9 Hz, 1H), 8.41 (s, 1H), 8.47 (d, J=5.2 Hz, 1H). LC-MS analysis: $[M-Na]^-$=382.1.

Example 35

Sodium (2S,5R)-7-oxo-2-(N-(2-(piperidin-1-yl) acetyl)carbamimidoyl)-1,6-diazabicyclo[3.2.1]octan-6-yl sulfate (compound 99 in table 1)

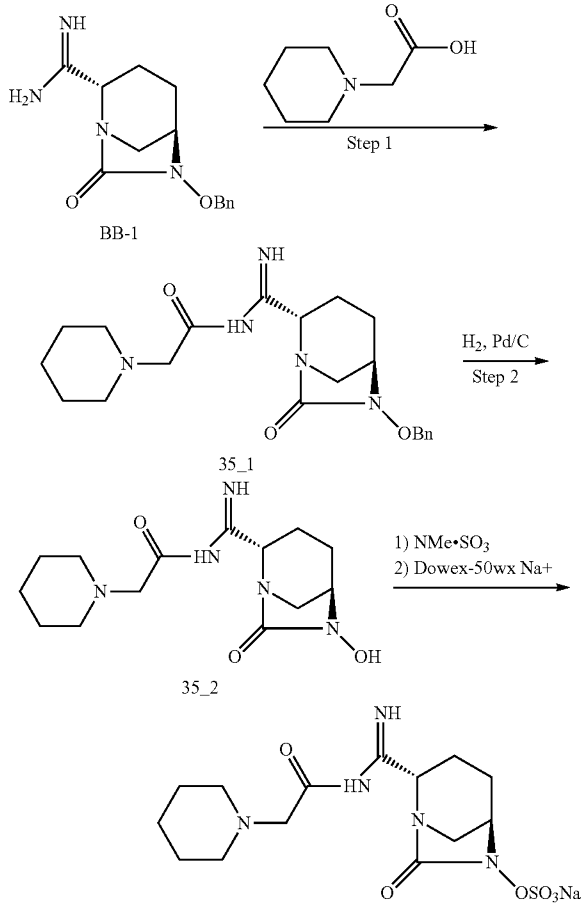

BB-1

35_1

35_2

Example 35

Step 1: Synthesis of N-(((2S,5R)-6-(benzyloxy)-7-oxo-1,6-diazabicyclo[3.2.1]octan-2-yl)(imino) methyl)-2-(piperidin-1-yl)acetamide (35_1)

2-(Piperidin-1-yl)acetic acid (260 mg, 1.45 mmol) was added to a solution of BB-1 (230 mg, 0.84 mmol), HATU (550 mg, 1.45 mmol) and DIPEA (0.73 mL, 4.20 mmol) in DCM/DMF (3/3 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in petroleum ether to give the title compound 35_1 (245 mg, 73%) as a yellow solid. LC-MS analysis $[M+H]^+$=400.2.

Step 2: Synthesis of N-(((2S,5R)-6-hydroxy-7-oxo-1,6-diazabicyclo[3.2.1]octan-2-yl)(imino)methyl)-2-(piperidin-1-yl)acetamide (35_2)

10% Pd/C (wet, 55% water w/w, 240 mg) was added to a solution of compound 351 (240 mg, 0.60 mmol) in THE (10 mL) with a few drops of TEA. The mixture was stirred under $H_2$ (balloon) at room temperature overnight, filtered through a pad of celite, rinsed with EtOAc. The filtrate was concentrated to give the title compound 35_2 (190 mg, quantitative) as a white solid, directly used for next step without further purification. LC-MS analysis: $[M+H]^+$=310.2.

Step 3: Synthesis of sodium (2S,5R)-7-oxo-2-(N-(2-(piperidin-1-yl)acetyl)carbamimidoyl)-1,6-diazabicyclo[3.2.1]octan-6-yl sulfate (example 35)

A mixture of compound 352 (190 mg obtained above), $SO_3$·$NMe_3$ (167 mg, 1.20 mmol) and TEA (0.25 mL, 1.79 mmol) in THE/water (3/3 mL) was stirred at room temperature overnight. The reaction mixture was concentrated under reduced pressure to provide a residue. The residue was purified by Dowex-50wx $Na^+$ resin, using water as an elution solvent to give example 35 (65 mg, 65% in two steps) as a white solid. $^1H$ NMR (400 MHz, $D_2O$): δ 1.67-1.87 (m, 6H), 1.90-2.01 (m, 1H), 2.04-2.23 (m, 3H), 3.25-3.38 (m, 2H), 3.48-3.60 (m, 2H), 3.71-3.78 (m, 1H), 3.97-4.05 (m, 1H), 4.13-4.25 (m, 2H), 4.35 (t, J=7.1 Hz, 1H), 5.63 (s, 1H). LC-MS analysis: [M–Na]-=388.1.

Example 36

Sodium (2S,5R)-2-(N-(2-cyclohexylacetyl)carbamimidoyl)-7-oxo-1,6-diazabicyclo[3.2.1]octan-6-yl sulfate (compound 86 in table 1)

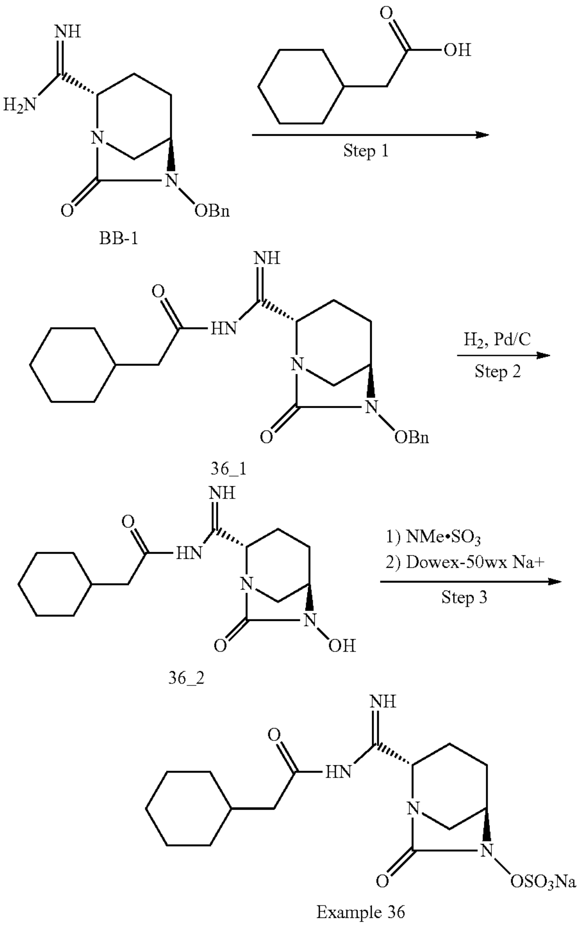

BB-1

36_1

36_2

Example 36

Step 1: Synthesis of N-(((2S,5R)-6-(benzyloxy)-7-oxo-1,6-diazabicyclo[3.2.1]octan-2-yl)(imino)methyl)-2-cyclohexylacetamide (36_1)

2-Cyclohexylacetic acid (465 mg, 3.28 mmol) was added to a solution of BB-1 (600 mg, 2.19 mmol), HATU (1.25 g, 3.28 mmol) and DIPEA (847 mg, 6.57 mmol) in DMF (4 mL) at room temperature, and then stirred overnight at room temperature under $N_2$. The reaction mixture was diluted with DCM, washed with brine, saturated $NH_4Cl$, dried over $Na_2SO_4$ and filtrated. The organic layer was concentrated to give a residue, which was purified by silica gel column chromatography eluting with 50% ethyl acetate in hexane to give the title compound 36_1 (520 mg, 59%) as a white solid. LC-MS analysis: $[M+H]^+$=399.3.

Step 2: Synthesis of 2-cyclohexyl-N-(((2S,5R)-6-hydroxy-7-oxo-1,6-diazabicyclo[3.2.1]octan-2-yl)(imino)methyl)acetamide (36_2)

10% Pd/C (wet, 55% water w/w, 500 mg) was added to a solution of compound 361 (500 mg, 1.25 mmol) in THE (10 mL). The mixture was stirred under $H_2$ (balloon) at room temperature overnight, filtered through a pad of celite, rinsed with EtOAc. The filtrate was concentrated in vacuum, and purified by flash silica gel chromatography using 10% MeOH in DCM to give the title compound 362 (160 mg, 41%) as an oil. $^1$H NMR (400 MHz, DMSO-$d_6$) δ 0.87-0.98 (m, 2H), 1.07-1.27 (m, 3H), 1.57-1.76 (m, 8H), 1.82-1.91 (m, 1H), 1.97-2.04 (m, 1H), 2.21-2.29 (m, 2H), 3.14-3.20 (m, 1H), 3.73-3.80 (m, 1H), 3.87-3.95 (m, 1H), 5.67 (s, 1H), 6.47 (s, 2H), 9.26 (s, 1H), LC-MS analysis: $[M+H]^+$=309.3.

Step 3: Synthesis of sodium (2S,5R)-2-(N-(2-cyclohexylacetyl)carbamimidoyl)-7-oxo-1,6-diazabicyclo[3.2.1]octan-6-yl sulfate (example 36)

A mixture of compound 362 (159 mg, 0.52 mmol), $SO_3$·$NMe_3$ (147 mg, 1.04 mmol) and TEA (0.22 mL, 1.53 mmol) in THE/water (3/3 mL) was stirred at room temperature overnight. The reaction mixture was concentrated under reduced pressure to provide a residue. The residue was purified by Dowex-50wx $Na^+$ resin, using water as an elution solvent to give example 36 (210 mg, 98%) as a white solid. $^1$H NMR (400 MHz, $D_2O$): δ 0.86-0.97 (m, 2H), 1.00-1.23 (m, 3H), 1.50-1.64 (m, 6H), 1.69-1.79 (m, 1H), 1.93-2.01 (m, 1H), 2.04-2.16 (m, 2H), 2.22-2.38 (m, 2H), 3.51 (t, J=12.3 Hz, 1H), 3.90-3.99 (m, 1H), 4.07 (d, J=13.1 Hz, 1H), 5.68 (d, J=4.3 Hz, 1H). LC-MS analysis: $[M-Na]^-$=387.2.

Example 37

Sodium (2S,5R)-2-(N-(cyclohexanecarbonyl)carbamimidoyl)-7-oxo-1,6-diazabicyclo[3.2.1]octan-6-yl sulfate (compound 25 in table 1)

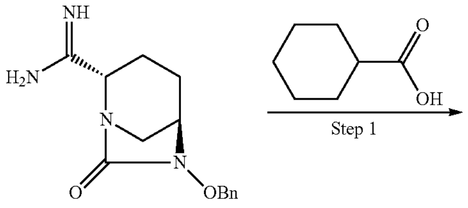

BB-1

-continued

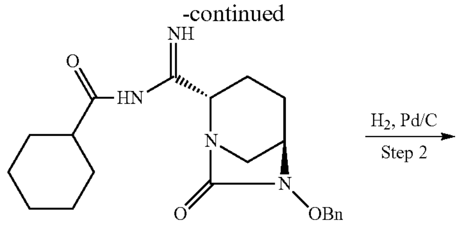

37_1

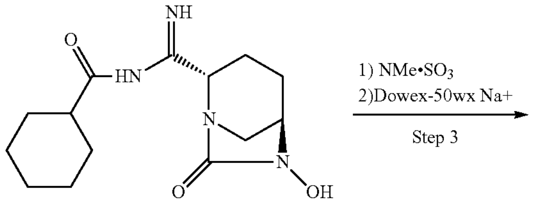

37_2

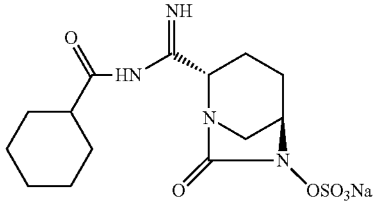

Example 37

Step 1: Synthesis of N-(((2S,5R)-6-(benzyloxy)-7-oxo-1,6-diazabicyclo[3.2.1]octan-2-yl)(imino)methyl)cyclohexanecarboxamide (37_1)

Cyclohexanecarboxylic acid (561 mg, 4.38 mmol) was added to a solution of BB-1 (800 mg, 2.92 mmol), HATU (1.66 g, 4.38 mmol) and DIPEA (1.13 g, 8.75 mmol) in DMF (5 mL) at room temperature, and then stirred overnight at room temperature under $N_2$. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 50% ethyl acetate in hexane to give the title compound 37_1 (960 mg, 85%) as a white solid. LC-MS analysis: $[M+H]^+$=385.2.

Step 2: Synthesis of N-(((2S,5R)-6-hydroxy-7-oxo-1,6-diazabicyclo[3.2.1]octan-2-yl)(imino)methyl)cyclohexanecarboxamide (37_2)

10% Pd/C (wet, 55% water w/w, 500 mg) was added to a solution of compound 371 (800 mg, 2.08 mmol) in THE (6 mL). The mixture was stirred under $H_2$ (balloon) at room temperature overnight, filtered through a pad of celite, rinsed with EtOAc. The filtrate was concentrated in vacuum, and purified by flash silica gel chromatography using 10% MeOH in DCM to give the title compound 372 (137 mg, 22%) as a white solid. $^1$H NMR (400 MHz, DMSO-$d_6$) 51.10-1.19 (m, 1H), 1.23-1.35 (m, 4H), 1.58-1.76 (m, 7H), 1.83-1.94 (m, 1H), 1.97-2.04 (m, 1H), 2.53-2.60 (m, 1H), 3.18 (t, J=11.4 Hz, 1H), 3.76-3.86 (m, 1H), 3.87-3.97 (m, 1H), 5.66 (s, 1H), 6.48 (s, 2H), 9.28 (s, 1H). LC-MS analysis: $[M+H]^+$=295.1.

Step 3: Synthesis of sodium (2S,5R)-2-(N-(cyclohexanecarbonyl)carbamimidoyl)-7-oxo-1,6-diazabicyclo[3.2.1]octan-6-yl sulfate (example 37)

A mixture of compound 372 (124 mg, 0.42 mmol), $SO_3$·$NMe_3$ (120 mg, 0.86 mmol) and TEA (0.21 mL, 1.50 mmol) in THE/water (3/3 mL) was stirred at room temperature overnight. The reaction mixture was concentrated under reduced pressure to provide a residue. The residue was purified by Dowex-50wx $Na^+$ resin, using water as an elution solvent to give example 37 (170 mg, 99%) as a white solid. $^1H$ NMR (400 MHz, $D_2O$): δ 1.06-1.29 (m, 5H), 1.55-1.76 (m, 6H), 1.93-2.00 (m, 1H), 2.04-2.15 (m, 2H), 2.59-2.68 (m, 1H), 3.50 (t, J=12.4 Hz, 1H), 3.90-3.97 (m, 1H), 4.13 (d, J=13.1 Hz, 1H), 5.69 (d, J=4.6 Hz, 1H). LC-MS analysis: $[M-Na]^-$=373.1.

Example 38

Sodium (2S,5R)-7-oxo-2-(N-(2-(tetrahydro-2H-pyran-4-yl)acetyl)carbamimidoyl)-1,6-diazabicyclo [3.2.1]octan-6-yl sulfate (compound 94 in table 1)

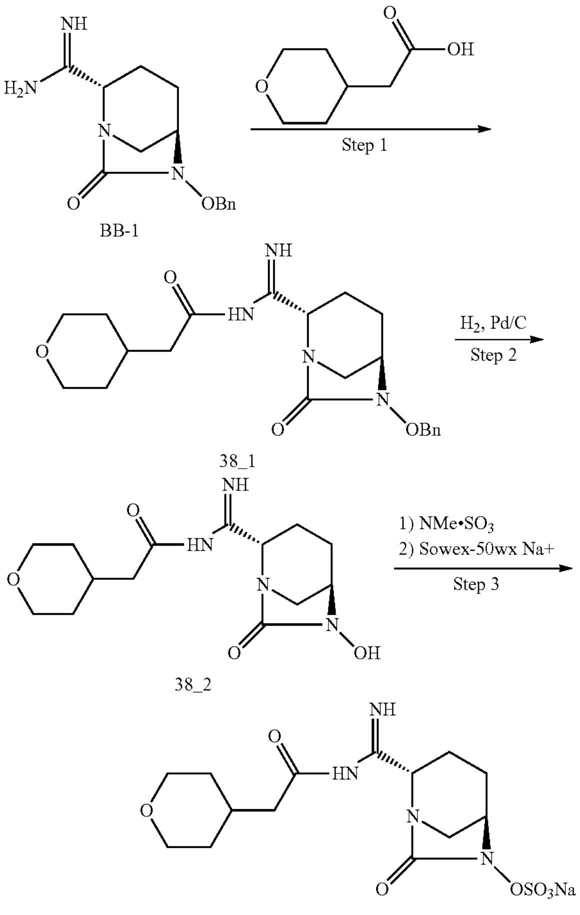

BB-1
38_1
38_2
Example 38

Step 1: Synthesis of N-(((2S,5R)-6-(benzyloxy)-7-oxo-1,6-diazabicyclo[3.2.1]octan-2-yl)(imino) methyl)-2-(tetrahydro-2H-pyran-4-yl)acetamide (38_1)

TATU (418 mg, 1.10 mmol) and DIPEA (490 mg, 3.79 mmol) were added to a solution of 2-(Tetrahydro-2H-pyran-4-yl)acetic acid (158 mg, 1.09 mmol) and BB-1 (200 mg, 0.73 mmol) in DMF (3 mL), and then stirred at room temperature for 30 hours. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 38_1 (250 mg, 86%) as an oil. $^1H$ NMR (400 MHz, DMSO-$d_6$): δ 1.13-1.24 (m, 2H), 1.50-1.59 (m, 2H), 1.62-1.73 (m, 1H), 1.80-2.03 (m, 4H), 2.24-2.34 (m, 2H), 3.14-3.22 (m, 1H), 3.23-3.31 (m, 2H). 3.76-3.90 (m, 4H), 4.84 (s, 2H), 5.64-5.69 (m, 1H), 6.75 (s, 2H), 7.34-7.42 (m, 3H), 7.46-7.53 (m, 2H). LC-MS analysis: $[M+H]^+$=401.2.

Step 2: Synthesis of N-(((2S,5R)-6-hydroxy-7-oxo-1,6-diazabicyclo[3.2.1]octan-2-yl)(imino)methyl)-2-(tetrahydro-2H-pyran-4-yl)acetamide (38_2)

10% Pd/C (wet, 55% water w/w, 200 mg) was added to a solution of compound 381 (250 mg, 0.63 mmol) in MeOH (10 mL). The mixture was stirred under $H_2$ (balloon) at room temperature for 40 minutes, filtered through a pad of celite, rinsed with EtOAc. The filtrate was concentrated to give the title compound 382 (140 mg, quantitative) as a white solid, which was directly used for next step without further purification. $^1H$ NMR (400 MHz, DMSO-$d_6$): δ 1.13-1.24 (m, 2H), 1.47-1.58 (m, 2H), 1.63-1.73 (m, 2H), 1.81-2.02 (m, 3H), 2.25-2.34 (m, 2H), 3.13-3.31 (m, 3H), 3.73-3.81 (m, 3H), 3.87-3.98 (m, 1H), 5.61-5.69 (m, 1H), 6.46 (s, 2H), 9.26 (s, 1H). LC-MS analysis: $[M+H]^+$=311.1.

Step 3: Synthesis of sodium (2S,5R)-7-oxo-2-(N-(2-(tetrahydro-2H-pyran-4-yl)acetyl)carbamimidoyl)-1,6-diazabicyclo[3.2.1]octan-6-yl sulfate (example 38)

A mixture of compound 382 (130 mg, 0.42 mmol), $SO_3{\cdot}NMe_3$ (139 mg, 1.0 mmol) and TEA (0.21 mL, 1.51 mmol) in THE/water (3/3 mL) was stirred at room temperature overnight. The reaction mixture was concentrated under reduced pressure to provide a residue. The residue was diluted with water (10 mL), and lyophilized to give a solid. The solid was purified by Dowex-50wx $Na^+$ resin, using water as an elution solvent and lyophilized to give example 38 (162 mg, 99%) as a white solid. $^1H$ NMR (400 MHz, $D_2O$): δ 1.22-1.34 (m, 2H), 1.53-1.61 (m, 2H), 1.71-1.81 (m, 1H), 1.87-2.01 (m, 2H), 2.04-2.17 (m, 2H), 2.33-2.46 (m, 2H), 3.37-3.45 (m, 2H), 3.53 (t, J=11.9 Hz, 1H), 3.55-3.91 (m, 2H), 3.92-4.01 (m, 1H), 4.07 (d, J=13.7 Hz, 1H), 5.68 (d, J=4.6 Hz, 1H). LC-MS analysis: $[M-Na]^-$=389.2.

Example 39

Sodium (2S,5R)-2-(N-(2-(1H-imidazol-1-yl)acetyl) carbamimidoyl)-7-oxo-1,6-diazabicyclo[3.2.1]octan-6-yl sulfate (compound 108 in table 1)

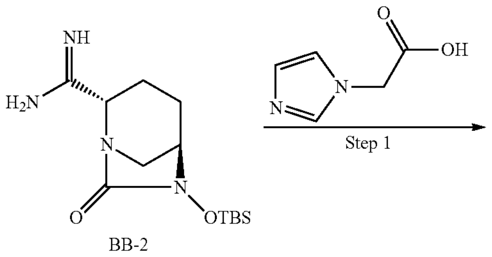

BB-2

-continued

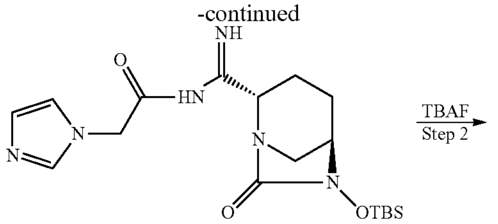

39_1

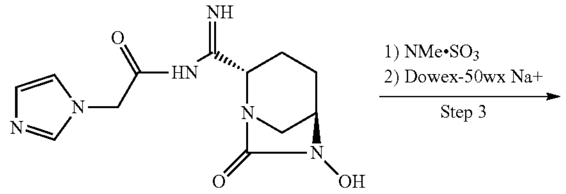

39_2

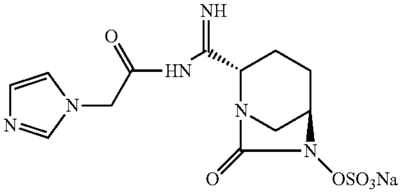

Example 39

Step 1: Synthesis of N-(((2S,5R)-6-(benzyloxy)-7-oxo-1,6-diazabicyclo[3.2.1]octan-2-yl)(imino)methyl)-2-(1H-imidazol-1-yl)acetamide (39_1)

HATU (704 mg, 1.85 mmol) and DIPEA (0.82 mL, 4.08 mmol) were added to a solution of 2-(1H-imidazol-1-yl) acetic acid (490 mg, 1.87 mmol) and BB-2 (279 mg, 0.94 mmol) in DMF/DCM (each 3.5 mL), and then stirred at room temperature for 24 hours. The reaction was quenched with saturated $NaHCO_3$, extracted with EtOAc. The organic layer was washed with water, then brine, dried over $Na_2SO_4$ and filtrated. The filtrate was concentrated to give a residue, which was purified by silica gel column chromatography eluting with 5% MeOH in DCM containing 0.2% TEA to give the title compound 39_1 (220 mg, 57%) as a yellow solid. LC-MS analysis: $[M+H]^+$=407.2 Step 2: Synthesis of N-(((2S,5R)-6-hydroxy-7-oxo-1,6-diazabicyclo[3.2.1]octan-2-yl)(imino)methyl)-2-(1H-imidazol-1-yl)acetamide (39_2)

TBAF (1 N in THF, 0.65 mL, 0.65 mmol) was added to a solution of compound 391 (220 mg, 0.54 mmol) in THF (5 mL) at 0° C., and stirred at 0° C. for 1.5 hours. The mixture was concentrated to dryness, added 5 mL of water, extracted with EtOAc and DCM. The organic layer was dried over $Na_2SO_4$, and filtrated. The filtrate was concentrated to give the title compound 392 (188 mg, 98%) as a brown solid. LC-MS analysis: $[M+H]^+$=293.1.

Step 3: Synthesis of sodium (2S,5R)-2-(N-(2-(1H-imidazol-1-yl)acetyl)carbamimidoyl)-7-oxo-1,6-diazabicyclo[3.2.1]octan-6-yl sulfate (example 39)

A mixture of compound 392 (188 mg obtained above), $SO_3 \cdot NMe_3$ (177 mg, 1.27 mmol) and TEA (0.25 mL, 1.79 mmol) in THF/water (3/3 mL) was stirred at room temperature overnight. The reaction mixture was concentrated under reduced pressure to provide a residue. The residue was purified Dowex-50wx $Na^+$ resin, using water as an elution solvent to give example 39 (95 mg, 44% in two steps) as a white solid. $^1H$ NMR (400 MHz, $D_2O$): δ 1.77-1.89 (m, 1H), 1.95-2.03 (m, 1H), 2.07-2.17 (m, 2H), 3.60-3.67 (m, 1H), 3.92-3.98 (m, 1H), 4.05-4.14 (m, 1H), 5.22 (d, J=17.4 Hz, 1H), 5.29 (d, J=17.4 Hz, 1H), 5.63 (d, J=5.3 Hz, 1H), 7.20-7.23 (m 2H), 8.17 (s, 1H). LC-MS analysis: $[M-Na]^-$=371.1.

Example 40

Sodium (2S,5R)-2-(N-(4-acetamidocyclohexane-1-carbonyl)carbamimidoyl)-7-oxo-1,6-diazabicyclo[3.2.1]octan-6-yl sulfate (compound 40 in table 1)

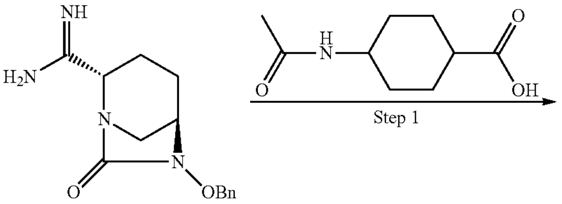

BB-1

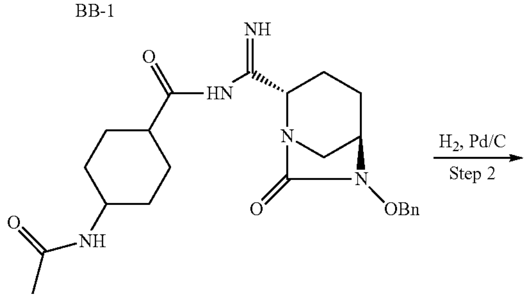

40_1

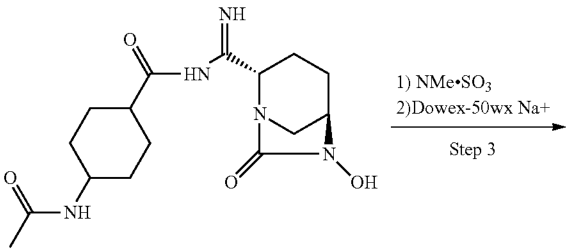

40_2

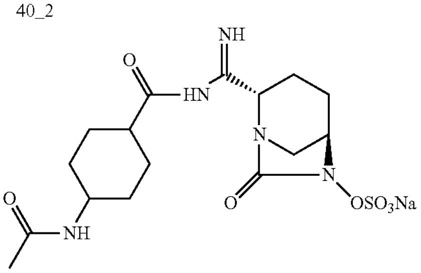

Example 40

Step 1: Synthesis of 4-acetamido-N-(((2S,5R)-6-(benzyloxy)-7-oxo-1,6-diazabicyclo[3.2.1]octan-2-yl)(imino)methyl)cyclohexane-1-carboxamide (40_1)

4-Acetamidocyclohexane-1-carboxylic acid (150 mg, 0.81 mmol) was added to a solution of BB-1 (200 mg, 0.73 mmol), DAMP (100 mg, 0.76 mmol) and DCC (309 mg, 1.5 mmol) in DCM (30 mL) at room temperature, and then stirred overnight at room temperature under argon. The reaction mixture concentrated, extracted with EtOAc, washed with water, brine, dried over $Na_2SO_4$ and filtrated. The filtrate was concentrated to give a residue, which was purified by silica gel column chromatography eluting with 5% MeOH in ethyl acetate to give the title compound 40_1 (180 mg, 55%) as an oil. $^1H$ NMR (400 MHz, $CDCl_3$): δ 1.54-1.86 (m, 8H), 1.94 (s, 3H), 2.04-2.12 (m, 4H), 2.31-2.38 (m, 1H), 3.32-3.42 (m, 1H), 3.69-3.83 (m, 2H), 3.99-4.08 (m, 1H), 4.84 (d, J=10.7 Hz, 1H), 4.93 (d, J=10.7 Hz, 1H), 5.29-5.39 (m 2H), 5.79 (s, 1H), 7.37-7.44 (m, 5H). LC-MS analysis: $[M+H]^+$=442.2.

Step 2: Synthesis of 4-acetamido-N-(((2S,5R)-6-hydroxy-7-oxo-1,6-diazabicyclo[3.2.1]octan-2-yl)(imino)methyl)cyclohexane-1-carboxamide (40_2)

10% Pd/C (wet, 55% water w/w, 100 mg) was added to a solution of compound 401 (180 mg, 0.41 mmol) in THE (3 mL). The mixture was stirred under $H_2$ (balloon) at room temperature overnight, filtered through a pad of celite, rinsed with EtOAc. The filtrate was concentrated to give the title compound 402 (150 mg) as a white solid, which was directly used for next step without further purification. LC-MS analysis: $[M+H]^+$=352.2.

Step 3: Synthesis of sodium (2S,5R)-2-(N-(4-acetamidocyclohexane-1-carbonyl)carbamimidoyl)-7-oxo-1,6-diazabicyclo[3.2.1]octan-6-yl sulfate (example 40)

A mixture of compound 402 (150 mg obtained above), $SO_3 \cdot NMe_3$ (100 mg, 2.64 mmol) and TEA (0.5 mL, 7.07 mmol) in THE/water (10/10 mL) was stirred at room temperature overnight. The reaction mixture was concentrated under reduced pressure to provide a residue. The residue was diluted with water (10 mL), and lyophilized to give a solid. The solid was purified by Dowex-50wx $Na^+$ resin, using water as an elution solvent and lyophilized to give example 40 (150 mg, 85% in two steps) as a white solid. $^1H$ NMR (400 MHz, $D_2O$): δ 1.17-1.29 (m, 2H), 1.32-1.45 (m, 2H), 1.65-1.80 (m, 3H), 1.81-1.98 (m, 6H), 2.03-2.17 (m, 2H), 2.57-2.67 (m, 1H), 3.44-3.55 (m, 2H), 3.90-4.01 (m, 1H), 4.12 (d, J=13.7 Hz, 1H), 5.68 (d, J=4.3 Hz, 1H). LC-MS analysis: $[M-Na]^-$=430.1.

Example 41

Sodium (2S,5R)-2-(N-(1-methylpiperidine-4-carbonyl)carbamimidoyl)-7-oxo-1,6-diazabicyclo[3.2.1]octan-6-yl sulfate (compound 47 in table 1)

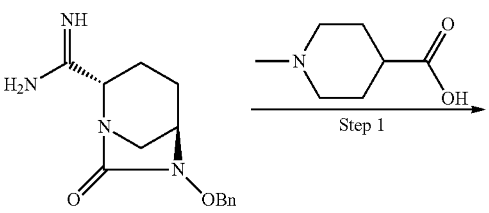

BB-1

-continued

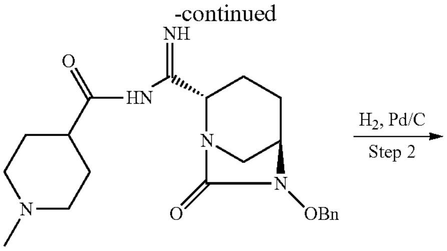

41_1

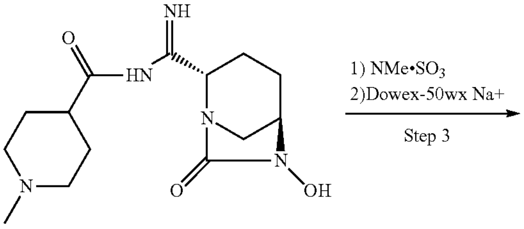

41_2

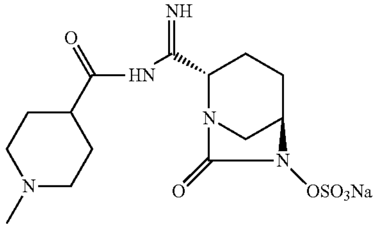

41_2

Step 1: Synthesis of N-(((2S,5R)-6-(benzyloxy)-7-oxo-1,6-diazabicyclo[3.2.1]octan-2-yl)(imino)methyl)-1-methylpiperidine-4-carboxamide (41_1)

1-Methylpiperidine-4-carboxylic acid (160 mg, 1.09 mmol) was added to a solution of BB-1 (200 mg, 0.73 mmol), DAMP (89 mg, 0.73 mmol) and DCC (309 mg, 1.5 mmol) in DCM (20 mL) at room temperature, and then stirred overnight at room temperature under argon. The reaction mixture was diluted with DCM, washed with water, saturated $NH_4Cl$, dried over $Na_2SO_4$ and filtrated. The organic layer was concentrated to give a residue, which was purified by silica gel column chromatography eluting with 8% ethyl acetate in MeOH to give the title compound 41_1 (200 mg, 68%) as a white solid. LC-MS analysis: $[M+H]^+$=400.1.

Step 2: Synthesis of N-(((2S,5R)-6-hydroxy-7-oxo-1,6-diazabicyclo[3.2.1]octan-2-yl)(imino)methyl)-1-methylpiperidine-4-carboxamide (41_2)

10% Pd/C (wet, 55% water w/w, 100 mg) was added to a solution of compound 411 (200 mg, 0.50 mmol) in THE (10 mL), and stirred under $H_2$ (balloon) at room temperature overnight, filtered through a pad of celite, rinsed with EtOAc. The filtrate was concentrated to give the title compound 412 (100 mg) as a white solid, which was directly used for next step without further purification. LC-MS analysis: $[M+H]^+$=310.3.

Step 3: Synthesis of sodium (2S,5R)-2-(N-(1-methylpiperidine-4-carbonyl)carbamimidoyl)-7-oxo-1,6-diazabicyclo[3.2.1]octan-6-yl sulfate (example 41)

A mixture of compound 412 (100 mg obtained above), $SO_3 \cdot NMe_3$ (100 mg, 0.64 mmol) and TEA (1 mL, 7.23 mmol) in THF/water (5/5 mL) was stirred at room temperature overnight. The reaction mixture was concentrated under reduced pressure to provide a residue. The residue was purified by preparative HPLC on an Agilent 10 prep-C18 250×21.2 mm column and lyophilized to give the desired compound, which was further purified by Dowex-50wx $Na^+$ resin, using water as an elution solvent to give example 41 (20 mg, 10% in two steps) as a white solid. $^1H$ NMR (400 MHz, $D_2O$): δ 1.73-1.86 (m, 3H), 1.92-2.04 (m, 3H), 2.05-2.16 (m, 2H), 2.78 (s, 3H), 2.95-3.07 (m, 3H), 3.47-3.61 (m, 3H), 3.97 (d, J=11.17 Hz, 1H), 4.11 (d, J=14.1 Hz, 1H), 5.68 (s, 1H). LC-MS analysis: $[M-Na]^-$=388.1.

Example 42

Sodium (2S,5R)-2-(N-(2-(4-methylpiperazin-1-yl)acetyl)carbamimidoyl)-7-oxo-1,6-diazabicyclo[3.2.1]octan-6-yl sulfate (compound 88 in table 1)

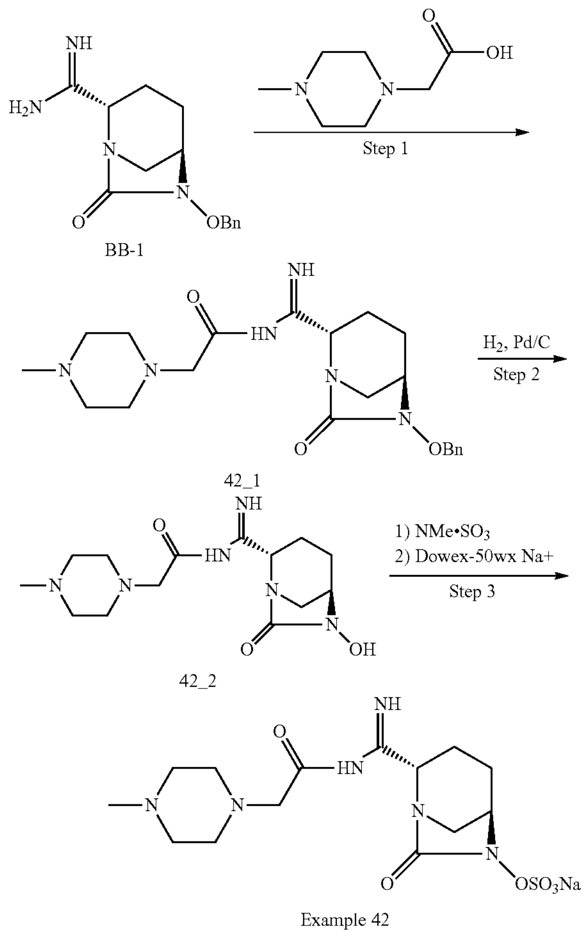

BB-1
42_1
42_2
Example 42

Step 1: Synthesis of N-(((2S,5R)-6-(benzyloxy)-7-oxo-1,6-diazabicyclo[3.2.1]octan-2-yl)(imino)methyl)-2-(4-methylpiperazin-1-yl)acetamide (42_1)

HATU (400 mg, 1.05 mmol) and DIPEA (0.40 mL, 2.25 mmol) were added to a solution of 2-(4-methylpiperazin-1-yl)acetic acid (167 mg, 1.05 mmol) and BB-1 (205 mg, 0.75 mmol) in DMF/DCM (2/3 mL), and then stirred at room temperature for 23 hours. The reaction was quenched with saturated $NaHCO_3$, extracted with DCM. The organic layer was washed brine, dried over $Na_2SO_4$ and filtrated. The filtrate was concentrated to give a residue, which was purified by silica gel column chromatography eluting with 4% MeOH in DCM containing 0.2% TEA to give the title compound 42_1 (310 mg, 99%) as a white solid. $^1H$ NMR (400 MHz, DMSO-$d_6$): δ 1.64-1.75 (m, 1H), 1.77-2.06 (m, 3H), 2.21 (s, 1.5H), 2.23 (s, 1.5H), 2.31-2.47 (m, 4H), 2.72-2.83 (m, 1H), 3.07-3.14 (m, 1H), 3.18-3.28 (m, 1H), 3.29-3.42 (m, 2H), 3.71-3.83 (m, 1H), 3.91-4.01 (m, 1H), 4.07-4.15 (m, 1H), 4.29-4.38 (m, 1H), 4.77-4.89 (m, 2H), 5.58 (s, 1H), 6.72 (s, 2H), 7.33-7.41 (m, 3H), 7.46-7.53 (m, 2H). LC-MS analysis: $[M+H]^+$=415.2.

Step 2: Synthesis of N-(((2S,5R)-6-hydroxy-7-oxo-1,6-diazabicyclo[3.2.1]octan-2-yl)(imino)methyl)-2-(4-methylpiperazin-1-yl)acetamide (42_2)

10% Pd/C (wet, 55% water w/w, 300 mg) was added to a solution of compound 421 (310 mg, 0.74 mmol) in THF (15 mL) with a few drops of TEA. The mixture was stirred under $H_2$ (balloon) at room temperature overnight, filtered through a pad of celite, rinsed with EtOAc. The filtrate was concentrated to give the title compound 42_2 (245 mg, quantitative) as a yellow solid, directly used for next step without further purification. LC-MS analysis: $[M+H]^+$=325.2.

Step 3: Synthesis of sodium (2S,5R)-2-(N-(2-(4-methylpiperazin-1-yl)acetyl)carbamimidoyl)-7-oxo-1,6-diazabicyclo[3.2.1]octan-6-yl sulfate (example 42)

A mixture of compound 422 (245 mg obtained above), $SO_3$·$NMe_3$ (139 mg, 1.0 mmol) and TEA (0.21 mL, 1.50 mmol) in THF/water (3/3 mL) was stirred at room temperature overnight. The reaction mixture was concentrated under reduced pressure to provide a residue. The residue was purified Dowex-50wx $Na^+$ resin, using water as an elution solvent to give example 42 (93 mg, 26% in two steps) as a white solid. $^1H$ NMR (400 MHz, $D_2O$): δ 1.75-1.82 (m, 1H), 1.93-2.00 (m, 1H), 2.06-2.20 (m, 2H), 2.44-2.55 (m, 1H), 2.79 (s, 1.5H), 2.80 (s, 1.5H), 2.94-3.11 (m, 3H), 3.27-3.43 (m, 3H), 3.44-3.57 (m, 3H), 3.61-3.68 (m, 1H), 3.92-4.01 (m, 1H), 4.03-4.10 (m, 1H), 5.61 (d, J=4.5 Hz, 1H). LC-MS analysis: $[M-Na]^-$=443.1.

Example 43

(2S,5R)-2-(N-(3-(Guanidinooxy)propanoyl)carbamimidoyl)-7-oxo-1,6-diazabicyclo[3.2.1]octan-6-yl hydrogen sulfate (compound 19 in table 1)

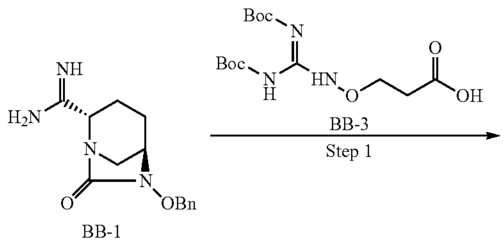

BB-3
BB-1

-continued

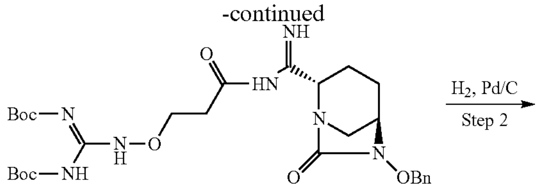

43_1

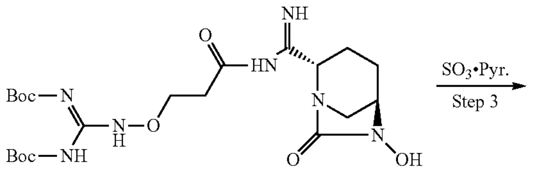

43_2

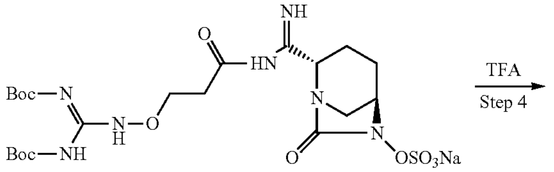

43_3

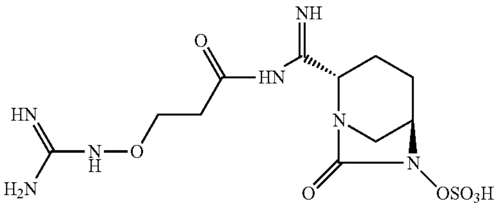

Example 43

Step 1: Synthesis of N-(((2S,5R)-6-(benzyloxy)-7-oxo-1,6-diazabicyclo[3.2.1]octan-2-yl)(imino)methyl)-3-(guanidinooxy)propanamide with diboc compound (43_1)

TATU (602 mg, 1.58 mmol) and DIPEA (0.58 mL, 3.30 mmol) were added to a solution of (E)-6-((tert-butoxycarbonyl)amino)-2,2-dimethyl-4-oxo-3,8-dioxa-5,7-diazaundec-5-en-11-oic acid (BB-3, 558 mg, 1.61 mmol) in DCM/DMF (3/6 mL), and then added BB-1 (301 mg, 1.10 mmol), stirred at room temperature for 3 hours. The reaction mixture was concentrated, and then quenched with saturated $NaHCO_3$ (3 mL) and water (7 mL), extracted with EtOAc. The organic layer was washed with water, brine, dried over $Na_2SO_4$ and filtrated. The filtrate was concentrated to give a residue, which was purified by silica gel column chromatography eluting with 50% ethyl acetate in petroleum ether to give the title compound 43_1 (589 mg, 88%) as a white solid. $^1$H NMR (400 MHz, DMSO-$d_6$): δ 1.38 (s, 9H), 1.39 (s, 9H), 1.63-1.73 (m, 1H), 1.79-2.03 (m, 3H), 2.66-2.73 (m, 2H), 3.16-3.25 (m, 1H), 3.75-3.83 (m, 1H), 3.86-3.95 (m, 1H), 4.00-4.07 (m, 2H), 4.80-4.87 (m, 2H), 5.65 (s, 1H), 6.74 (br s, 2H), 7.34-7.41 (m, 3H), 7.45-7.52 (m, 2H), 8.67 (s, 1H), 9.04 (s, 1H).

Step 2: Synthesis of 3-(guanidinooxy)-N-(((2S,5R)-6-hydroxy-7-oxo-1,6-diazabicyclo[3.2.1]octan-2-yl)(imino)methyl)propanamide with diboc compound (43_2)

10% Pd/C (wet, 55% water w/w, 310 mg) was added to a solution of compound 431 (580 mg, 0.98 mmol) in EtOAc (10 mL) with a few drops of TEA, and stirred under $H_2$ (balloon) at room for 7 hours. The reaction mixture was filtered through a pad of celite, rinsed with EtOAc (2×10 mL), and MeOH (3×10 mL). The filtrate was concentrated to give a residue, which was purified by silica gel column chromatography eluting with 3-5% MeOH in DCM to give the title compound 432 (420 mg, 85%) as a white solid. $^1$H NMR (400 MHz, DMSO-$d_6$): δ 1.38 (s, 9H), 1.39 (s, 9H), 1.67-1.77 (m, 2H), 1.82-1.91 (m, 1H), 1.95-2.04 (m, 1H), 2.66-2.77 (m, 2H), 3.15-3.23 (m, 1H), 3.72-3.79 (m, 1H), 3.91-3.97 (m, 1H), 4.05 (t, J=4.0 Hz, 2H), 5.65 (s, 1H), 6.43 (s, 1H), 6.47 (s, 1H), 8.68 (s, 1H), 9.02 (s, 1H), 9.36 (s, 1H).

Step 3: Synthesis of sodium (2S,5R)-2-(N—((E)-6-((tert-butoxycarbonyl)amino)-2,2-dimethyl-4-oxo-3,8-dioxa-5,7-diazaundec-5-en-11-oyl)carbamimidoyl)-7-oxo-1,6-diazabicyclo[3.2.1]octan-6-yl sulfate (43_3)

A mixture of compound 432 (415 mg, 0.81 mmol), $SO_3$.pyridine (625 mg, 3.93 mmol) in pyridine (8 mL) was stirred at room temperature for 40 hours. The reaction mixture was concentrated to give a residue, which was suspensioned in DCM (15 mL), stirred at room temperature for 10 minutes, filtered off. The filtrate was concentrated to provide a residue, which was purified by silica gel column chromatography eluting with 5-15% MeOH in DCM, and followed by Dowex-50wx $Na^+$ resin purification, using water as an elution solvent to give the title compound 43_3 (620 mg, 85%) as a white foam. $^1$H NMR (400 MHz, $D_2O$): δ 1.37 (s, 9H), 1.38 (s, 9H), 1.70-1.81 (m, 1H), 1.92-2.00 (m, 1H), 2.04-2.14 (m, 2H), 2.75-2.80 (m, 2H), 3.45-3.52 (m, 1H), 3.93-3.99 (m, 1H), 4.05-4.11 (m, 1H), 4.16-4.22 (m, 2H), 5.70 (s, 1H). LC-MS analysis: $[M-Na]^-$=592.2.

Step 4: Synthesis of (2S,5R)-2-(N-(3-(guanidinooxy)propanoyl)carbamimidoyl)-7-oxo-1,6-diazabicyclo[3.2.1]octan-6-yl hydrogen sulfate (example 43)

TFA (0.5 mL) was added to a solution of compound 433 (51 mg, 0.09 mmol) and $Et_3SiH$ (0.05 mL, 0.30 mmol) in anhydrous $CH_2Cl_2$ (0.5 mL) at 0° C. and stirred for 7.5 hours at 0° C. The reaction mixture was concentrated under reduced pressure to give a residue, which was purified by preparation HPLC on an Agilent 10 prep-C18 250×21.2 mm column and lyophilized to give example 43 (6 mg, 25%) as a white powder. $^1$H NMR (400 MHz, $D_2O$): δ 1.71-1.81 (m, 1H), 1.92-2.01 (m, 1H), 2.04-2.14 (m, 2H), 2.73-2.78 (m, 2H), 3.45-3.52 (m, 1H), 3.93-3.99 (m, 1H), 4.05-4.11 (m, 1H), 4.10-4.16 (m, 2H), 5.71 (s, 1H). LC-MS analysis: $[M-H]^-$=392.1.

Example 44

Sodium (2S,5R)-7-oxo-2-(N-(4-phenylthiazole-2-carbonyl)carbamimidoyl)-1,6-diazabicyclo[3.2.1] octan-6-yl sulfate (compound 134 in table 1)

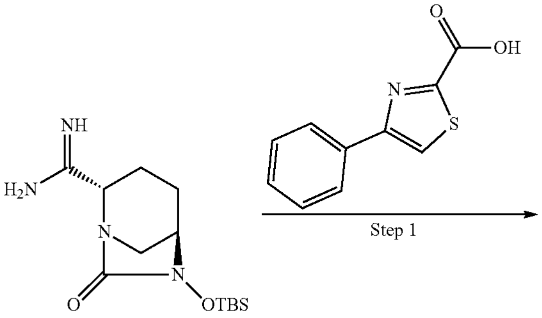

BB-2

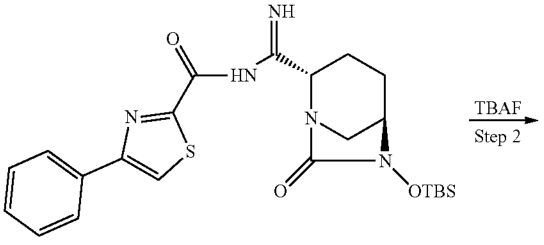

44_1

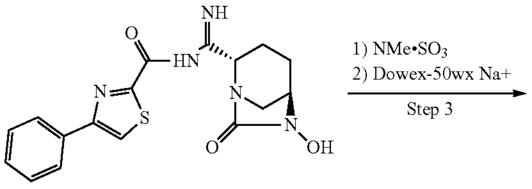

44_2

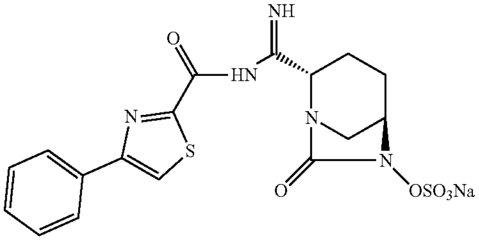

Example 44

Step 1: Synthesis of N-(((2S,5R)-6-((tert-butyldimethylsilyl)oxy)-7-oxo-1,6-diazabicyclo[3.2.1]octan-2-yl)(imino)methyl)-4-phenylthiazole-2-carboxamide (44_1)

TATU (399 mg, 1.05 mmol) and DIPEA (268 mg, 2.1 mmol) were added to a solution of thiazole-2-carboxylic acid (215 mg, 1.05 mmol) and BB-2 (209 mg, 0.7 mmol) in DCM/DMF (each 3 mL), and then stirred at room temperature for 30 hours. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 44_1 (267 mg, 78%) as an oil. $^1$H NMR (400 MHz, DMSO-$d_6$): δ 0.00 (s, 6H), 0.78 (s, 9H), 1.73-1.80 (m, 2H), 1.86-2.00 (m, 2H), 3.20-3.22 (m, 1H), 3.54-3.64 (m, 1H), 4.41-4.68 (m, 1H), 5.64-5.81 (m, 1H), 6.42 (br s, 1H), 7.37-7.42 (m, 3H), 7.85-7.90 (m, 2H), 8.22 (s, 1H). LC-MS analysis: $[M+H]^+$=486.2.

Step 2: Synthesis of N-(((2S,5R)-6-hydroxy-7-oxo-1,6-diazabicyclo[3.2.1]octan-2-yl)(imino)methyl)-4-phenylthiazole-2-carboxamide (44_2)

TBAF (1 N in THF, 0.9 mL, 0.9 mmol) was added to a solution of compound 44_1 (242 mg, 0.5 mmol) in THE (7 mL) at 0° C., warmed up to room temperature and stirred for 1 hour. The mixture was concentrated to dryness. It was diluted with EtOAc (50 mL), washed with water and brine. The organic layer was dried over $Na_2SO_4$ and filtrated. The filtrate was concentrated to give a residue, which was purified by silica gel column chromatography eluting with 50% ethyl acetate in petroleum to give the title compound 442 (77 mg, 42%) as a white solid. LC-MS analysis: $[M+H]^+$=372.1.

Step 3: Synthesis of sodium (2S,5R)-7-oxo-2-(N-(4-phenylthiazole-2-carbonyl)carbamimidoyl)-1,6-diazabicyclo[3.2.1]octan-6-yl sulfate (example 44)

A mixture of compound 442 (100 mg, 0.27 mmol), $SO_3 \cdot NMe_3$ (94 mg, 0.67 mmol) and TEA (32 mg, 1.2 mmol) in THE/water (4/3 mL) was stirred at room temperature overnight. The reaction mixture was concentrated under reduced pressure to provide a residue, which was purified by Dowex-50wx $Na^+$ resin using water as an elution solvent, followed by lyophilization to give example 44 (10 mg, 8%) as a white solid. $^1$H NMR (400 MHz, $D_2O$): δ 1.85-2.02 (m, 2H), 2.04-2.18 (m, 2H), 3.44-3.55 (m, 1H), 3.99-4.14 (m, 1H), 4.30-4.44 (m, 1H), 5.63 (s, 1H), 7.38-7.44 (m, 3H), 7.82-7.87 (m, 2H), 7.97 (s, 1H). LC-MS analysis: $[M-Na]^-$=450.1.

Example 45

Sodium (2S,5R)-2-(N-(4-cyanobenzoyl)carbamimidoyl)-7-oxo-1,6-diazabicyclo[3.2.1]octan-6-yl sulfate (compound 133 in table 1)

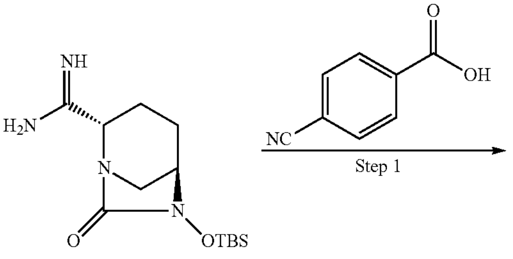

BB-2

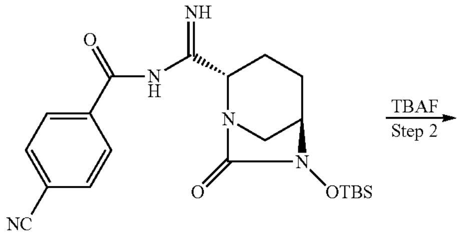

45_1

-continued

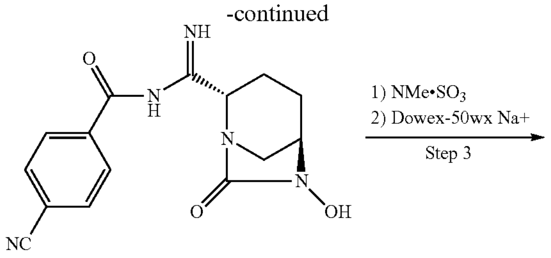

45_2

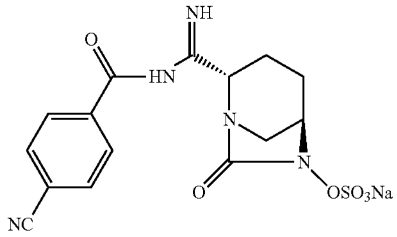

Example 45

Step 1: Synthesis of N-(((2S,5R)-6-((tert-butyldimethylsilyl)oxy)-7-oxo-1,6-diazabicyclo[3.2.1]octan-2-yl)(imino)methyl)-4-cyanobenzamide (45_1)

TATU (526 mg, 1.58 mmol) and DIPEA (434 mg, 2.76 mmol) were added to a solution of 4-cyanobenzoic acid (204 mg, 1.558 mmol) and BB-2 (275 mg, 0.92 mmol) in DCM/DMF (each 3 mL), and then stirred at room temperature overnight. The reaction was quenched with saturated $NaHCO_3$ (5 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum to give the title compound 45_1 (194 mg, 49%) as an oil. $^1$H NMR (400 MHz, $CDCl_3$): δ −0.02 (s, 3H), 0.00 (s, 3H), 0.78 (s, 9H), 1.67-1.77 (m, 1H), 1.83-1.90 (m, 1H), 1.97-2.09 (m, 2H), 3.31-3.41 (m, 1H), 3.47-3.57 (m, 1H), 3.66-3.75 (m, 1H), 5.56 (s, 1H), 7.37 (d, J=8.2 Hz, 2H), 7.56 (d, J=8.2 Hz, 2H). LC-MS analysis: $[M+H]^+$=428.2.

Step 2: Synthesis of 4-cyano-N-(((2S,5R)-6-hydroxy-7-oxo-1,6-diazabicyclo[3.2.1]octan-2-yl)(imino)methyl)benzamide (45_2)

TBAF (1 N in THF, 0.72 mL, 0.72 mmol) was added to a solution of compound 451 (170 mg, 0.4 mmol) in THF (5 mL) at 0° C., warmed up to room temperature and stirred for 1 hour. The mixture was concentrated to dryness. It was diluted with EtOAc (50 mL), washed with water and brine. The organic layer was dried over $Na_2SO_4$ and filtrated. The filtrate was concentrated to give a residue, which was purified by silica gel column chromatography eluting with 3% MeOH in DCM to give the title compound 452 (120 mg, 95%) as an orange solid. LC-MS analysis: $[M+H]^+$=314.1.

Step 3: Synthesis of sodium (2S,5R)-2-(N-(4-cyanobenzoyl)carbamimidoyl)-7-oxo-1,6-diazabicyclo[3.2.1]octan-6-yl sulfate (example 45)

A mixture of compound 452 (105 mg, 0.34 mmol), $SO_3 \cdot NMe_3$ (118 mg, 0.84 mmol) and TEA (39 mg, 0.4 mmol) in THF/water (4/3 mL) was stirred at room temperature overnight. The reaction mixture was concentrated under reduced pressure to provide a residue, which was purified by Dowex-50wx $Na^+$ resin using water as an elution solvent, followed by lyophilization to give example 45 (9 mg, 7%) as a white solid. $^1$H NMR (400 MHz, $D_2O$): δ 1.95-2.06 (m, 2H), 2.08-2.22 (m, 2H), 3.46-3.54 (m, 1H), 3.68-3.75 (m, 1H), 3.98-4.07 (m, 1H), 5.73 (s, 1H), 7.56 (d, J=7.8 Hz, 2H), 7.82 (d, J=7.8 Hz, 2H). LC-MS analysis: $[M-Na]^-$=392.1.

Example 46

Sodium (2S,5R)-2-(N-((R)-1-acetylpiperidine-2-carbonyl)carbamimidoyl)-7-oxo-1,6-diazabicyclo[3.2.1]octan-6-yl sulfate (compound 73 in table 1)

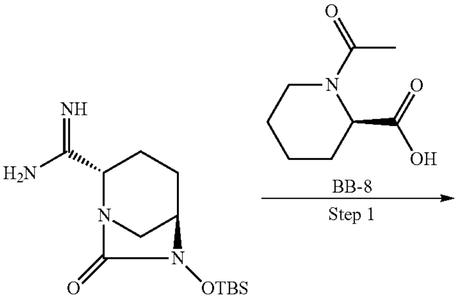

BB-2

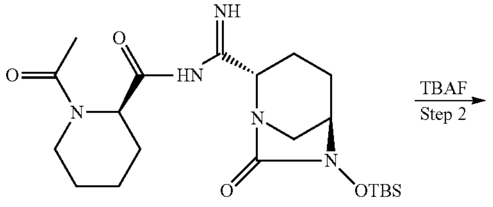

46_1

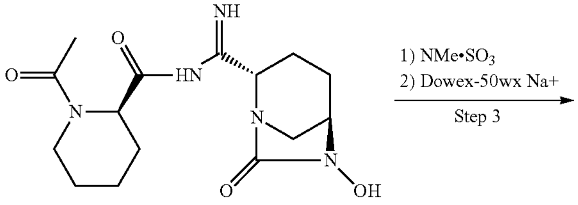

46_2

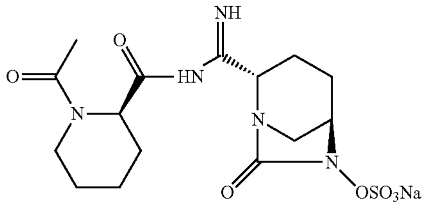

Example 46

Step 1: Synthesis of (2R)-1-acetyl-N-(((2S,5R)-6-((tert-butyldimethylsilyl)oxy)-7-oxo-1,6-diazabicyclo[3.2.1]octan-2-yl)(imino)methyl)piperidine-2-carboxamide (46_1)

A mixture of BB-2 (400 mg, 1.34 mmol) and (R)-1-acetylpiperidine-2-carboxylic acid (BB-8, 380 mg, 1.94 mmol) in DCM (20 mL) was added DAMP (98 mg, 0.80 mmol) and DCC (552 mg, 2.7 mmol) at room temperature. The reaction mixture was refluxed for 16 hours. After the completion of reaction the reaction mixture was cooled and solids were filtrated. The filtrate was evaporated to dryness to get a residue, which was purified silica gel column chromatography eluting with 2% MeOH in DCM to obtain the title compound 46_1 (292 mg, 62%) as a white solid. $^1$H NMR (400 MHz, $CDCl_3$): δ 0.17 (s, 6H), 0.92 (s, 9H), 1.21-1.43 (m, 2H), 1.59-1.73 (m, 4H), 1.87-1.90 (m, 3H), 2.11 (s, 3H), 3.18-3.25 (m, 1H), 3.40-3.47 (m, 1H), 3.62-3.65 (m, 2H), 3.75-3.87 (m, 2H), 5.32 (s, 1H), 5.41-5.44 (m, 2H), 5.63 (s, 1H). LCMS analysis $[M+Na]^+$=474.3.

Step 2: Synthesis of (2R)-1-acetyl-N-(((2S,5R)-6-hydroxy-7-oxo-1,6-diazabicyclo[3.2.1]octan-2-yl)(imino)methyl)piperidine-2-carboxamide (46_2)

TBAF (1M solution in THF, 0.7 mL, 0.7 mmol) was added to a solution of Compound 46_1 (292 mg, 0.64 mmol) in THE (5 mL) dropwise at 0° C. The reaction mixture was stirred at this temperature for 3 hours. The solvent was removed to obtain a thick slurry, which was subjected to silica gel column eluted by 6-8% MeOH in DCM, and subsequent recrystallization from EtOAc and petroleum ether to afford the title compound 462 (187 mg, 92%) as a white solid. $^1$H NMR (400 MHz, DMSO-$d_6$): δ 1.59-1.74 (m, 4H), 1.82-1.93 (m, 2H), 1.98-2.03 (m, 2H), 2.04 (s, 3H), 3.2 (t, J=12.3 Hz, 1H), 3.42-3.45 (m, 1H), 3.68-3.72 (m, 1H), 3.92-3.99 (m, 1H), 5.64 (s, 1H), 6.44 (s, 2H), 9.25 (s, 1H). LC-MS analysis: $[M+Na]^+$=360.2.

Step 3: Synthesis of sodium (2S,5R)-2-(N-((R)-1-acetylpiperidine-2-carbonyl)carbamimidoyl)-7-oxo-1,6-diazabicyclo[3.2.1]octan-6-yl sulfate (example 46)

A mixture of compound 462 (150 mg, 0.44 mmol), $SO_3{\cdot}NMe_3$ (139 mg, 1.0 mmol) and TEA (0.21 mL, 1.50 mmol) in THE/water (3/3 mL) was stirred at room temperature overnight. The reaction mixture was concentrated under reduced pressure to provide a residue. The residue was purified by Dowex-50wx $Na^+$ resin, using water as an elution solvent to give example 46 (170 mg, 83%) as a white solid. $^1$H NMR (400 MHz, $D_2O$): δ 1.47-1.83 (m, 6H), 1.93-2.44 (m, 7H), 3.31-3.45 (m, 1H), 3.47-3.55 (m 1H), 3.60-3.68 (m, 1H), 3.90-4.04 (m, 2H), 4.95-5.03 (m, m, 1H), 5.60 (s, 1H). LC-MS analysis: $[M-Na]^-$=416.1.

Example 47

(2S,5R)-2-(N-(4-(Guanidinooxy)butanoyl)carbamimidoyl)-7-oxo-1,6-diazabicyclo[3.2.1]octan-6-yl hydrogen sulfate (compound 20 in table 1)

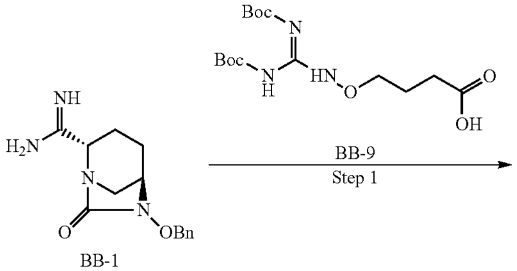

BB-1

-continued

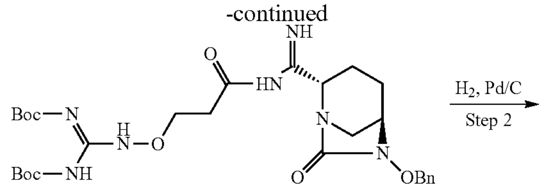

47_1

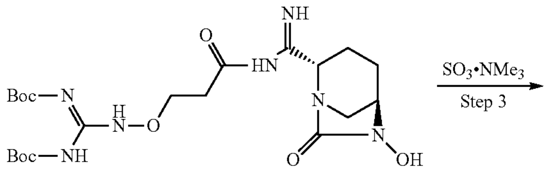

47_2

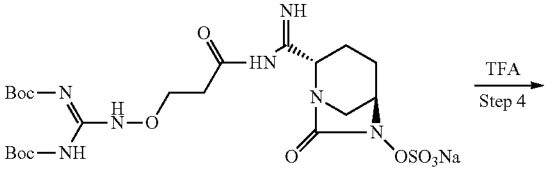

47_3

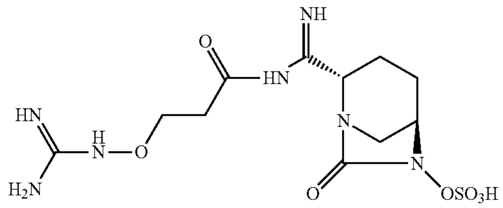

Example 47

Step 1: Synthesis of N-(((2S,5R)-6-(benzyloxy)-7-oxo-1,6-diazabicyclo[3.2.1]octan-2-yl)(imino)methyl)-4-(guanidinooxy)butanamide with diboc compound (47_1)

TATU (209 mg, 0.55 mmol)) and DIPEA (100 uL, 0.55 mmol) were added to a solution of BB-9 (200 mg, 0.55 mmol) in DMF (3 mL), and then BB-1 (100 mg, 0.37 mmol) was added to the reaction mixture, stirred at room temperature overnight. The reaction mixture was diluted with EtOAc, washed with saturated $NH_4Cl$, brine, dried by $Na_2SO_4$. The organic layer was concentrated to give a residue, which was purified by silica gel column chromatography eluting with 50% ethyl acetate in petroleum ether to give the title compound 471 (100 mg, 46%) as an oil. $^1$H NMR (400 MHz, $CDCl_3$) b 1.44 (s, 9H), 1.49 (s, 9H), 1.64-1.70 (m, 1H), 1.70-1.80 (m, 1H), 1.89-2.07 (m, 4H), 2.38-2.54 (m, 2H), 3.34-3.48 (m, 1H), 3.80-3.86 (m, 1H), 4.03-4.10 (m, 2H), 4.16-4.21 (m, 1H). 4.84 (d, J=10.6 Hz, 1H), 4.91 (d, J=10.6 Hz, 1H), 5.41 (s, 1H), 5.80 (d, J=4.9 Hz, 1H), 7.37-7.42 (m, 5H), 7.80 (s, 1H), 9.04 (s, 1H). LC-MS analysis: $[M+Na]^+$=618.3.

Step 2: Synthesis of 4-(guanidinooxy)-N-(((2S,5R)-6-hydroxy-7-oxo-1,6-diazabicyclo[3.2.1]octan-2-yl)(imino)methyl)butanamide with diboc compound (47_2)

10% Pd/C (wet, 55% water w/w, 50 mg) was added to a solution of compound 471 (100 mg, 0.17 mmol) in THE (20 mL), and stirred under $H_2$ (balloon) at room overnight. The reaction mixture was filtered through a pad of celite, rinsed with EtOAc (2×10 mL), and MeOH (3×10 mL). The filtrate was concentrated to give the title compound 472 (80 mg, 88%) as a white solid. LC-MS analysis: $[M+H]^+$=528.2.

Step 3: Synthesis of sodium (2S,5R)-2-(N—((E)-6-((tert-butoxycarbonyl)amino)-2,2-dimethyl-4-oxo-3,8-dioxa-5,7-diazadodec-5-en-12-oyl)carbamimidoyl)-7-oxo-1,6-diazabicyclo[3.2.1]octan-6-yl sulfate (47_3)

A mixture of compound 472 (80 mg, 0.15 mmol), $SO_3 \cdot NMe_3$ (32 mg, 0.22 mmol) and TEA (0.2 mL) in THE/Water (each 2.5 mL) was stirred at room temperature overnight. The reaction mixture was concentrated to give a residue, which was purified by Dowex-50wx $Na^+$ resin, using water as an elution solvent to give the title compound 473 (51 mg, 56%) as a white solid. $^1H$ NMR (400 MHz, $D_2O$): δ 1.30 (s, 9H), 1.32 (s, 9H), 1.62-1.72 (m, 1H), 1.76-1.92 (m, 3H), 1.98-2.08 (m, 2H), 2.41-2.50 (m, 2H), 3.40-3.47 (m, 1H), 3.71-3.76 (m, 1H), 3.86-3.91 (m, 2H), 3.94-4.00 (m, 1H), 5.61 (s, 1H). LC-MS analysis: $[M-Na]^-$=606.2.

Step 4: Synthesis of (2S,5R)-2-(N-(4-(guanidinooxy)butanoyl)carbamimidoyl)-7-oxo-1,6-diazabicyclo[3.2.1]octan-6-yl hydrogen sulfate (example 47)

TFA (0.5 mL) was added to a solution of compound 473 (51 mg, 0.08 mmol) and $Et_3SiH$ (0.05 mL, 0.30 mmol) in anhydrous $CH_2Cl_2$ (0.5 mL) at 0° C. and stirred for 7.5 hours at 0° C. The reaction mixture was concentrated under reduced pressure to give a residue, which was purified by preparative HPLC on an Agilent 10 prep-C18 250×21.2 mm column and lyophilized to give example 47 (6 mg, 25%) as a white powder. $^1H$ NMR (400 MHz, $D_2O$): δ 1.62-1.72 (m, 1H), 1.76-1.92 (m, 3H), 1.98-2.10 (m, 2H), 2.41-2.48 (m, 2H), 3.40-3.457 (m, 1H), 3.71-3.76 (m, 1H), 3.86-3.93 (m, 2H), 3.94-4.00 (m, 1H), 5.63 (s, 1H). LC-MS analysis: $[M-H]^-$=407.1.

Example 48

Sodium (2S,5R)-7-oxo-2-(N-(pyrimidine-4-carbonyl)carbamimidoyl)-1,6-diazabicyclo[3.2.1]octan-6-yl sulfate (compound 141 in table 1)

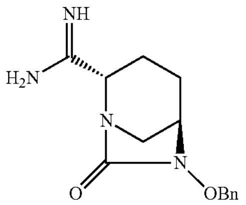

BB-1

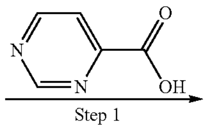

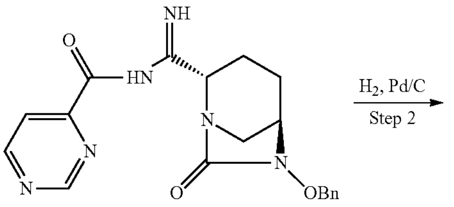

48_1

-continued

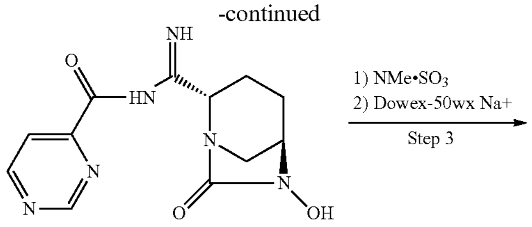

48_2

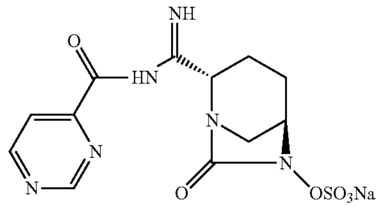

Example 48

Step 1: Synthesis of N-(((2S,5R)-6-(benzyloxy)-7-oxo-1,6-diazabicyclo[3.2.1]octan-2-yl)(imino)methyl)acetamide (48_1)

Pyrimidine-4-carboxylic acid (181 mg, 1.46 mmol) was added to a solution of BB-1 (200 mg, 0.73 mmol), HATU (581 mg, 1.53 mmol) and DIPEA (283 mg, 2.19 mmol) in DMF (3 mL) at room temperature, and then stirred for 24 hours at room temperature. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 481 (222 mg, 80%) as a yellow oil. LC-MS analysis: $[M+H]^+$=381.1.

Step 2: Synthesis of N-(((2S,5R)-6-hydroxy-7-oxo-1,6-diazabicyclo[3.2.1]octan-2-yl)(imino)methyl) pyrimidine-4-carboxamide (48_2)

10% Pd/C (wet, 55% water w/w, 100 mg) was added to a solution of compound 481 (222 mg, 0.58 mmol) in MeOH (10 mL). The mixture was stirred under $H_2$ (balloon) at room temperature overnight, filtered through a pad of celite, rinsed with EtOAc. The filtrate was concentrated to give a residue, which was purified silica gel column chromatography eluting with 50% ethyl acetate in petroleum ether to give the title compound 482 (60 mg, 36%) as a solid. $^1H$ NMR (400 MHz, DMSO-$d_6$): δ 1.87-1.99 (m, 3H), 2.08-2.14 (m, 1H), 3.23-3.31 (m, 1H), 3.31-3.51 (m, 1H), 3.98-4.09 (m, 1H), 5.81 (s, 1H), 7.79 (t, J=5.0 Hz, 1H), 9.03 (d, J=5.0 Hz, 1H), 9.19 (s, 1H), 9.29 (d, J=3.9 Hz, 1H), 9.33 (s, 1H). LC-MS analysis: $[M+H]^+$=291.2.

Step 3: Synthesis of sodium (2S,5R)-7-oxo-2-(N-(pyrimidine-4-carbonyl)carbamimidoyl)-1,6-diazabicyclo[3.2.1]octan-6-yl sulfate (example 48)

A mixture of compound 482 (60 mg, 0.21 mmol), $SO_3 \cdot NMe_3$ (74 mg, 0.53 mmol) and TEA (0.11 mL, 0.78 mmol) in THE/water (2/2 mL) was stirred at room temperature overnight. The reaction mixture was concentrated under reduced pressure to provide a residue, which was purified by Dowex-50wx $Na^+$ resin, using water as an elution solvent to give example 48 (80 mg, 97%) as a white solid. $^1H$ NMR (400 MHz, $D_2O$): δ 1.93-2.06 (m, 2H), 2.09-2.25 (m, 2H), 3.52-3.61 (m, 1H), 3.70-3.76 (m, 1H), 4.02-4.13 (m, 1H), 5.77 (s, 1H), 7.70 (d, J=5.3 Hz, 1H), 8.93 (d, J=5.3 Hz, 1H), 9.17 (s, 1H). LC-MS analysis: $[M-Na]^-$=369.0.

Example 49

Sodium (2S,5R)-7-oxo-2-(N-(4-(trifluoromethyl)benzoyl)carbamimidoyl)-1,6-diazabicyclo[3.2.1]octan-6-yl sulfate (compound 138 in table 1)

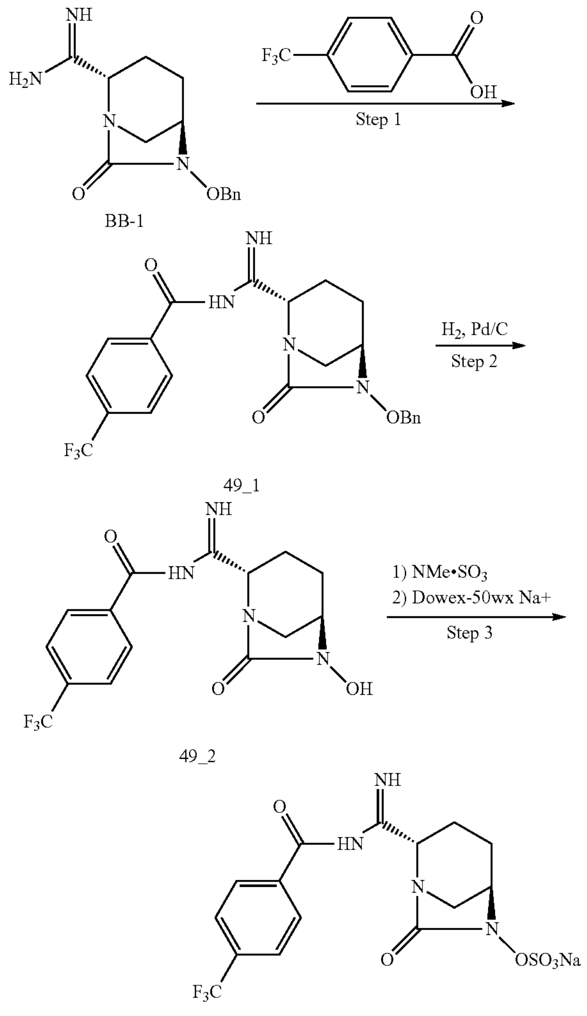

BB-1

49_1

49_2

Example 49

Step 1: Synthesis of N-(((2S,5R)-6-(benzyloxy)-7-oxo-1,6-diazabicyclo[3.2.1]octan-2-yl)(imino)methyl)-4-(trifluoromethyl)benzamide (49_1)

4-(Trifluoromethyl)benzoic acid (277 mg, 1.46 mmol) was added to a solution of BB-1 (200 mg, 0.73 mmol), HATU (581 mg, 1.53 mmol) and DIPEA (283 mg, 2.19 mmol) in DMF (3 mL) at room temperature, and then stirred for 24 hours at room temperature. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 49_1 (270 mg, 80%) as a brown solid. $^1H$ NMR (400 MHz, DMSO-$d_6$): δ1.87-2.09 (m, 4H), 3.06-3.19 (m, 1H), 3.35-3.42 (m, 1H), 4.01-4.11 (m, 1H), 4.78 (s, 2H), 5.65-5.77 (m, 1H), 6.72 (s, 2H), 7.30-7.37 (m, 3H), 7.41-7.48 (m, 2H), 7.67 (d, J=7.9 Hz, 2H), 7.84 (d, J=7.9 Hz, 2H). $^{19}F$ NMR (376 MHz, DMSO-$d_6$)): δ −61.1 (s, F). LC-MS analysis: $[M+H]^+$=447.1.

Step 2: Synthesis of N-(((2S,5R)-6-hydroxy-7-oxo-1,6-diazabicyclo[3.2.1]octan-2-yl)(imino)methyl)-4-(trifluoromethyl)benzamide (49_2)

10% Pd/C (wet, 55% water w/w, 100 mg) was added to a solution of compound 491 (270 mg, 0.58 mmol) in THE (10 mL). The mixture was stirred under $H_2$ (balloon) at room temperature overnight, filtered through a pad of celite, rinsed with EtOAc. The filtrate was concentrated to give a residue, which was purified silica gel column chromatography eluting with 50% ethyl acetate in petroleum ether to give the title compound 492 (99 mg, 47%) as a solid. $^1H$ NMR (400 MHz, DMSO-$d_6$): δ 1.74-1.82 (m, 1H), 1.87-2.09 (m, 2H), 3.06-3.24 (m, 1H), 3.35-3.52 (m, 1H), 4.04-4.13 (m, 1H), 5.74 (br s, 1H), 6.43 (s, 2H), 7.71 (d, J=8.0 Hz, 2H), 7.85 (d, J=8.0 Hz, 2H), 9.20 (s, 1H). $^{19}F$ NMR (376 MHz, DMSO-$d_6$)): δ −61.3 (s, F). LC-MS analysis: $[M+H]^+$=357.1.

Step 3: Synthesis of sodium (2S,5R)-7-oxo-2-(N-(4-(trifluoromethyl)benzoyl)carbamimidoyl)-1,6-diazabicyclo[3.2.1]octan-6-yl sulfate Example 49

A mixture of compound 492 (99 mg, 0.27 mmol), $SO_3 \cdot NMe_3$ (98 mg, 0.70 mmol) and TEA (0.15 mL, 1.08 mmol) in THE/water (3/2.5 mL) was stirred at room temperature overnight. The reaction mixture was concentrated under reduced pressure to provide a residue. The residue was purified by Dowex-50wx $Na^+$ resin, using water as an elution solvent to give example 49 (115 mg, 97%) as a white solid. $^1H$ NMR (400 MHz, $D_2O$): δ 1.94-2.06 (m, 2H), 2.08-2.24 (m, 2H), 3.45-3.56 (m, 1H), 3.71-3.80 (m, 1H), 4.01-4.09 (m, 1H), 5.75 (s, 1H), 7.58 (d, J=7.8 Hz, 2H), 7.77 (d, J=7.8 Hz, 2H). $^{19}H$ NMR (376 MHz, $D_2O$): 6-62.8 (s, 3F). LC-MS analysis: $[M-Na]^-$=435.1.

Example 50

Sodium (2S,5R)-7-oxo-2-(N-(5-(trifluoromethyl)picolinoyl)carbamimidoyl)-1,6-diazabicyclo[3.2.1]octan-6-yl sulfate (compound 137 in table 1)

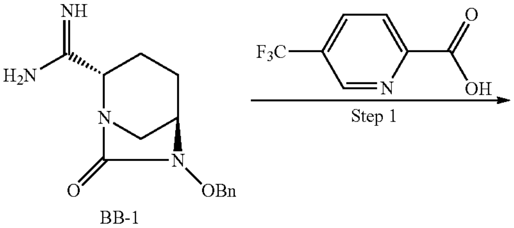

BB-1

-continued

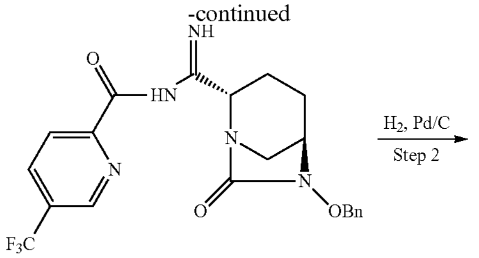

50_1

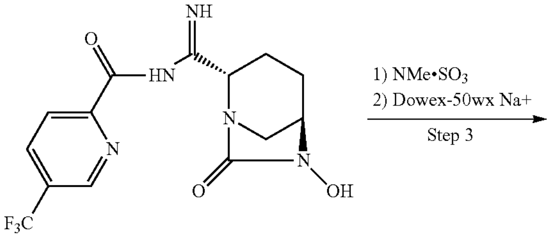

50_2

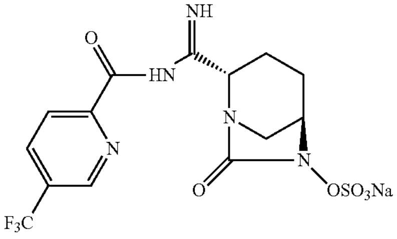

Example 50

Step 1: Synthesis of N-(((2S,5R)-6-(benzyloxy)-7-oxo-1,6-diazabicyclo[3.2.1]octan-2-yl)(imino)methyl)-5-(trifluoromethyl)picolinamide (50_1)

5-(Trifluoromethyl)picolinic acid (345 mg, 1.81 mmol) was added to a solution of BB-1 (329 mg, 1.20 mmol), HATU (684 mg, 1.80 mmol) and DIPEA (0.62 mL, 3.61 mmol) in DMF/DCM (3/3 mL) at room temperature, and then stirred for 24 hours at room temperature. The reaction was quenched with saturated $NaHCO_3$ (3 mL) and water (7 mL), extracted with EtOAc. The organic layer was washed with water, then brine, dried over $Na_2SO_4$ and filtrated. The filtrate was concentrated to give a residue, which was purified by silica gel column chromatography eluting with 50% ethyl acetate in petroleum ether to give the title compound 50_1 (530 mg, 98%). $^1H$ NMR (400 MHz, $CDCl_3$): δ 2.02-2.11 (m, 2H), 2.17-2.35 (m, 2H), 3.50-3.60 (m, 1H), 4.14-4.19 (m, 1H), 4.25-4.36 (m, 1H), 4.80 (d, J=10.4 Hz, 1H), 4.86 (d, J=10.4 Hz, 1H), 5.85 (s, 1H), 7.36-7.39 (m, 3H), 7.40-7.44 (m, 2H), 7.85 (d, J=8.2 Hz, 1H), 8.08 (d, J=8.2 Hz, 1H), 8.88 (s, 1H). LC-MS analysis: $[M+Na]^+$=470.2.

Step 2: Synthesis of N-(((2S,5R)-6-hydroxy-7-oxo-1,6-diazabicyclo[3.2.1]octan-2-yl)(imino)methyl)-5-(trifluoromethyl)picolinamide (50_2)

10% Pd/C (wet, 55% water w/w, 100 mg) was added to a solution of compound 501 (530 mg, 1.18 mmol) in THE (10 mL). The mixture was stirred under $H_2$ (balloon) at room temperature overnight, filtered through a pad of celite, rinsed with EtOAc. The filtrate was concentrated to give a residue, which was purified by flash chromatography on silica gel, eluting with 90% EtOAc in petroleum ether to give the title compound 502 (187 mg, 44%) as a white solid. $^1H$ NMR (400 MHz, $CD_3OD$): δ1.78-1.98 (m, 2H), 2.04-2.16 (m, 2H), 3.33-3.42 (m, 1H), 3.72-3.79 (m, 1H), 4.10-4.20 (m, 1H), 5.77 (s, 1H), 7.79 (d, J=8.2 Hz, 1H), 8.19 (d, J=8.2 Hz, 1H), 8.86 (s, 1H). LC-MS analysis: $[M+Na]^+$=380.1.

Step 3: Synthesis of sodium (2S,5R)-7-oxo-2-(N-(5-(trifluoromethyl)picolinoyl)carbamimidoyl)-1,6-diazabicyclo[3.2.1]octan-6-yl sulfate Example 50

A mixture of compound 502 (187 mg, 0.52 mmol), $SO_3{\cdot}NMe_3$ (109 mg, 0.78 mmol) and TEA (0.08 mL, 0.63 mmol) in THE/water (4/3 mL) was stirred at room temperature overnight. The reaction mixture was concentrated to dryness under reduced pressure to give a residue, which was purified by Dowex-50wx $Na^+$ resin, using water as an elution solvent, and lyophilized to give example 50 (223 mg, 98%) as a white solid. $^1H$ NMR (400 MHz, $D_2O$): δ 1.95-2.05 (m, 2H), 2.09-2.23 (m, 2H), 3.50-3.58 (m, 1H), 3.65-3.71 (m, 1H), 4.02-4.11 (m, 1H), 5.78 (s, 1H), 7.77 (d, J=7.7 Hz, 1H), 8.28 (d, J=7.7 Hz, 1H), 8.69 (s, 1H). $^{19}F$ NMR (376 MHz, $D_2O$): δ −62.8 (s, 3F). LC-MS analysis: $[M-Na]^-$=436.1.

Example 51

(2S,5R)-2-(N-(3-guanidinopropanoyl)carbamimidoyl)-7-oxo-1,6-diazabicyclo[3.2.1]octan-6-yl hydrogen sulfate (compound 21 in table 1)

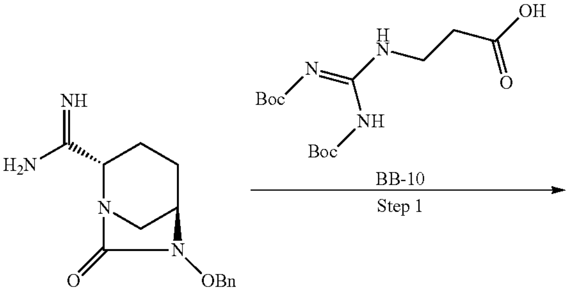

BB-1

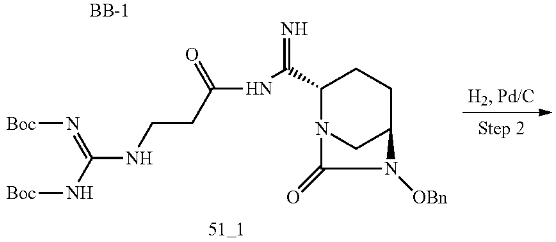

51_1

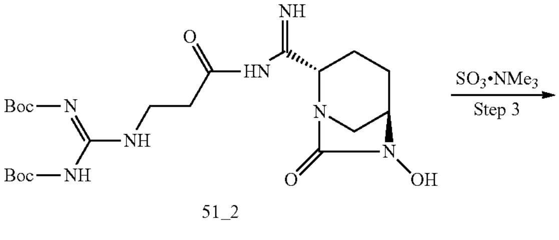

51_2

-continued

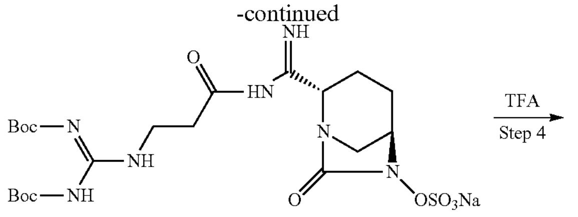

51_3

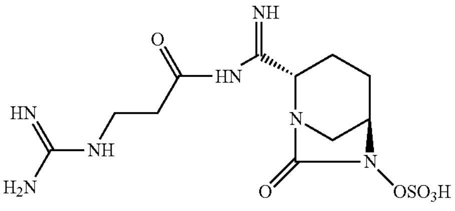

Example 51

Step 1: Synthesis of N-(((2S,5R)-6-(benzyloxy)-7-oxo-1,6-diazabicyclo[3.2.1]octan-2-yl)(imino)methyl)-3-guanidinopropanamide with diboc compound(51_1)

TATU (570 mg, 1.50 mmol) and DIPEA (260 uL, 1.5 mmol) were added to a solution of BB-10 (500 mg, 1.5 mmol) in DMF (3 mL), and then BB-1 (274 mg, 1.0 mmol) was added to the reaction mixture, stirred at room temperature overnight. The reaction mixture was diluted with EtOAc, washed with saturated $NH_4Cl$, brine, dried by $Na_2SO_4$. The organic layer was concentrated to give a residue, which was purified by silica gel column chromatography eluting with 50% ethyl acetate in petroleum ether to give the title compound 51_1 (200 mg, 35%) as an oil. $^1H$ NMR (400 MHz, $CDCl_3$) b 1.48 (s, 9H), 1.49 (s, 9H), 1.73-1.83 (m, 1H), 1.97-2.26 (m, 3H), 2.52-2.57 (m, 2H), 3.34-3.42 (m, 1H), 3.69-3.77 (m, 2H), 4.01-4.09 (m, 2H), 4.83 (d, J=10.7 Hz, 1H), 4.91 (d, J=10.7 Hz, 1H), 5.37 (s, 1H), 5.80 (d, J=4.2 Hz, 1H), 7.36-7.43 (m, 5H), 8.67 (t, J=5.8 Hz, 1H), 11.44 (s, 1H). LC-MS analysis: $[M+H]^+$=588.3.

Step 2: Synthesis of 3-guanidino-N-(((2S,5R)-6-hydroxy-7-oxo-1,6-diazabicyclo[3.2.1]octan-2-yl)(imino)methyl)propanamide with diboc compound (51_2)

10% Pd/C (wet, 55% water w/w, 100 mg) was added to a solution of compound 511 (200 mg, 0.34 mmol) in THE (10 mL), and stirred under $H_2$ (balloon) at room overnight. The reaction mixture was filtered through a pad of celite, rinsed with EtOAc (2×10 mL), and MeOH (3×10 mL). The filtrate was concentrated to give the title compound 512 (150 mg, 88%) as a white solid, which was directly used for next step without further purification LC-MS analysis: $[M+H]^+$=498.3.

Step 3: Synthesis of sodium (2S,5R)-2-(N-(3-((Z)-2,3-bis(tert-butoxycarbonyl)guanidino)propanoyl)carbamimidoyl)-7-oxo-1,6-diazabicyclo[3.2.1]octan-6-yl sulfate (51_3)

A mixture of compound 512 (150 mg, 0.3 mmol), $SO_3 \cdot NMe_3$ (632 mg, 0.45 mmol) and TEA (0.5 mL) in THE/Water (each 10 mL) was stirred at room temperature overnight. The reaction mixture was concentrated to give a residue, which was purified by Dowex-50wx $Na^+$ resin, using water as an elution solvent to give the title compound 513 (25 mg, 14%) as a white solid. LC-MS analysis: $[M-Na]^-$=576.3.

Step 4: Synthesis of (2S,5R)-2-(N-(3-guanidinopropanoyl)carbamimidoyl)-7-oxo-1,6-diazabicyclo[3.2.1]octan-6-yl hydrogen sulfate (example 51)

TFA (0.2 mL) was added to a solution of compound 513 (25 mg, 0.04 mmol) and $Et_3SiH$ (0.05 mL, 0.30 mmol) in anhydrous $CH_2Cl_2$ (0.5 mL) at 0° C. and stirred for 7.5 hours at 0° C. The reaction mixture was concentrated under reduced pressure to give a residue, which was purified by preparative HPLC on an Agilent 10 prep-C18 250×21.2 mm column and lyophilized to give example 51 (5 mg, 33%) as a white powder. LC-MS analysis: $[M-H]^-$=376.1.

Example 52

Sodium (2S,5R)-7-oxo-2-(N-(3,4,5,6-tetrahydropyridazine-3-carbonyl)carbamimidoyl)-1,6-diazabicyclo[3.2.1]octan-6-yl sulfate (compound 159 in table 1)

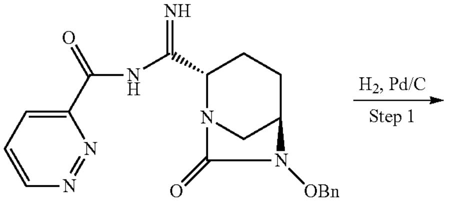

12_1

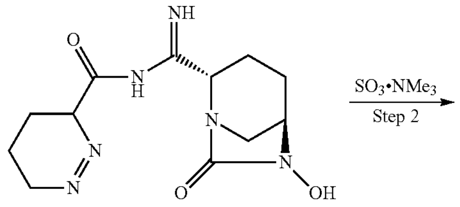

52_1

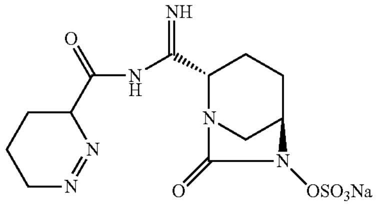

Example 52

Step 1: Synthesis of N-(((2S,5R)-6-hydroxy-7-oxo-1,6-diazabicyclo[3.2.1]octan-2-yl)(imino)methyl)-3,4,5,6-tetrahydropyridazine-3-carboxamide (52_1)

10% Pd/C (wet, 55% water w/w, 89 mg) was added to a solution of compound 121 (89 mg, 0.23 mmol) in THE (20 mL). The mixture was stirred under $H_2$ (balloon) at room temperature for 24 hours, filtered through a pad of celite, rinsed with EtOAc. The filtrate was concentrated to give a residue, which was purified silica gel column chromatography eluting with 50% ethyl acetate in petroleum ether to give the title compound 52_1 (33 mg, 43%) as a oil. $^1H$ NMR (400 MHz, DMSO-$d_6$): δ 1.68-1.80 (m, 4H), 1.82-1.91 (m, 1H), 1.95-2.03 (m, 1H), 2.18-2.36 (m, 2H), 2.91-3.01 (m, 1H), 3.05-3.12 (m, 3H), 3.84-3.93 (m, 1H), 4.33-4.41 (m, 1H), 5.71-5.77 (m, 1H), 6.42 (s, 2H), 9.21 (s, 1H). LC-MS analysis: $[M+H]^+$=295.1.

Step 2: Synthesis of sodium (2S,5R)-7-oxo-2-(N-(3,4,5,6-tetrahydropyridazine-3-carbonyl)carbamimidoyl)-1,6-diazabicyclo[3.2.1]octan-6-yl sulfate (example 52)

A mixture of compound 52_1 (30 mg, 0.10 mmol), $SO_3 \cdot NMe_3$ (28 mg, 0.20 mmol) and TEA (0.05 mL, 0.33 mmol) in THE/water (2/2 mL) was stirred at room temperature overnight. The reaction mixture was concentrated under reduced pressure to provide a residue. The residue was purified by Dowex-50wx $Na^+$ resin, using water as an elution solvent to give example 52 (22 mg, 55%) as a white solid. LC-MS analysis: $[M-Na]^-$=373.1.

Pharmacological Methods

Antibacterial activity and synergistic activity:

Compounds of the present invention alone, meropenam (MER) alone, and as a combination with test antibiotic (meropenam) were tested for antimicrobial activity by determining minimum inhibitory concentration (MIC, mg/L) using the broth microdilution method according to the guidelines of the Clinical Laboratories and Standards Institute ("Methods for Dilution Antimicrobial Susceptibility Tests for Bacterial that Grow Aerobically", Approved standard, 7th ed., Clinical and Laboratories Standards Institute (CLSI) Document M7-A8, Wayne, Pa., USA, 2009). Meropenam as a test antibiotic compound was dissolved in DMSO. Meropenam was then diluted in microbial growth medium (Mueller-Hinton Broth II, cation adjusted) resulting in a final concention range of 0.125-64 mg/L in serial two-fold dilution. In all cases the final DMSO concentration was less than 0.5%. Bacteria were added to 96-well microtitre plates containing the serial two-fold dilutions of the compounds; the final cell density was approximately $5\times10^5$ colony forming units/mL (CFU/mL). Plates were incubated at 37° C. for 18-24 hours and read visually. The MIC, i.e. the lowest concentration of the test compound that inhibited visible growth of the bacteria, was recorded. The same assay conditions were used when the compounds of present invention alone, and as a combination with test meropenam antibiotic compound was tested for minimum inhibitory concentration (MIC, mg/L). Whilst meropenam was serially diluted as described above, a constant concentration of the present invention of 4 gg/mL was used.

The antimicrobial activity by deterring minimum inhibitory concentration (MIC, mg/L) against bacteria listed in Table 2 and Table 3.

Bacterial strains that were used to evaluate the antimicrobial activity using the MIC determination included but were not limited to *E. coli* clinical isolate (strain 1), *E. coli* 8739 (strain 2), *K. pneumoniae* clinical isolate (strain 3), *K. pneumoniae* 700603 (strain 4), *E. cloacae* clinical isolate (strain 5), *E. cloacae* 700323 (strain 6), *A. baumannii* clinical isolate (strain 7), *A. baumannii* 19606 (strain 8), *P. aeruginosa* clinical isolate (strain 9), *P. aeruginosa* 9027 (strain 10).

TABLE 2

Synergy of the inhibitor example 1 to example 52 (4 mg/L) in combination with meropenam (MER, Ex. 1 to Ex. 7, MIC, mg/L)

| Organism | MER Alone | MER + Ex. 1 | MER + Ex. 2 | MER + Ex. 3 | MER + Ex. 4 | MER + Ex. 5 | MER + Ex. 6 | MER + Ex. 7 |
|---|---|---|---|---|---|---|---|---|
| strain 1 | 2.0 | 0.5 | 2 | 0.5 | <0.125 | <0.125 | 0.5 | <0.125 |
| strain 2 | 2.0 | <0.125 | 0.25 | <0.125 | <0.125 | <0.125 | <0.125 | <0.125 |
| strain 3 | 2.0 | 2.0 | 1 | 2.0 | <0.125 | <0.125 | 2.0 | <0.125 |
| strain 4 | 1.0 | 0.25 | 0.25 | 1.0 | <0.125 | <0.125 | 0.5 | <0.125 |
| strain 5 | 2.0 | 2.0 | 2 | 2.0 | 1.0 | 0.25 | 2.0 | 0.25 |
| strain 6 | 2.0 | 1.0 | 0.25 | 2.0 | 0.250 | 0.25 | 2.0 | 0.25 |
| strain 7 | 2.0 | 2.0 | 2 | 2.0 | 2.0 | 1.0 | 2.0 | 1.0 |
| strain 8 | 1.0 | 0.5 | 0.5 | 0.5 | 1.0 | 0.5 | 0.5 | 0.25 |
| strain 9 | 2.0 | 0.5 | 2 | 0.5 | 1.0 | 0.5 | 0.5 | 1.0 |
| strain 10 | 2.0 | 1.0 | 1 | 0.5 | 0.5 | 0.5 | 1.0 | 0.25 |

Synergy of the inhibitor example 1 to example 52 (4 mg/L) in combination with meropenam (Ex. 8 to Ex. 13, MIC, mg/L)

| Organism | MER Alone | MER + Ex. 8 | MER + Ex. 9 | MER + Ex. 10 | MER + Ex. 11 | MER + Ex. 12 | MER + Ex. 13 |
|---|---|---|---|---|---|---|---|
| strain 1 | 2.0 | <0.125 | 0.5 | 0.5 | <0.125 | <0.125 | <0.125 |
| strain 2 | 2.0 | <0.125 | <0.125 | 0.5 | <0.125 | <0.125 | <0.125 |
| strain 3 | 2.0 | <0.125 | 2.0 | 2.0 | <0.125 | <0.125 | <0.125 |
| strain 4 | 1.0 | <0.125 | 0.5 | 1.0 | <0.125 | <0.125 | <0.125 |
| strain 5 | 2.0 | 0.5 | 2.0 | 2.0 | 0.5 | 1.0 | 0.5 |
| strain 6 | 2.0 | 0.5 | 1.0 | 2.0 | 0.25 | 0.5 | 0.5 |
| strain 7 | 2.0 | 2.0 | 2.0 | 2.0 | 1.0 | 2.0 | 2.0 |
| strain 8 | 1.0 | 0.5 | 0.5 | 1.0 | 0.5 | 0.5 | 1.0 |
| strain 9 | 2.0 | 0.25 | 0.5 | 1.0 | 0.25 | 0.5 | 0.25 |
| strain 10 | 2.0 | 0.5 | 1.0 | 2.0 | 0.5 | 0.5 | 0.5 |

TABLE 2-continued

Synergy of the inhibitor example 1 to example 52 (4 mg/L) in combination with meropenam (Ex. 14 to Ex. 19, MIC, mg/L)

| Organism | MER Alone | MER + Ex. 14 | MER + Ex. 15 | MER + Ex. 16 | MER + Ex. 17 | MER + Ex. 18 | MER + Ex. 19 |
|---|---|---|---|---|---|---|---|
| strain 1 | 2.0 | <0.125 | <0.125 | 0.25 | 1.0 | 0.25 | <0.125 |
| strain 2 | 2.0 | <0.125 | <0.125 | 0.5 | 0.25 | 0.5 | 0.25 |
| strain 3 | 2.0 | <0.125 | <0.125 | 0.25 | 2.0 | 0.25 | 1.0 |
| strain 4 | 1.0 | <0.125 | <0.125 | 0.25 | 0.25 | 0.25 | 0.25 |
| strain 5 | 2.0 | 0.5 | 1.0 | 0.5 | 2.0 | 2.0 | 1.0 |
| strain 6 | 2.0 | 0.5 | 0.5 | 0.5 | 1.0 | 1.0 | 1.0 |
| strain 7 | 2.0 | 2.0 | 2.0 | 0.5 | 2.0 | 2.0 | 2.0 |
| strain 8 | 1.0 | 0.5 | 0.5 | 0.5 | 1.0 | 2.0 | 0.5 |
| strain 9 | 2.0 | 0.25 | 0.25 | 0.25 | 1.0 | 1.0 | 0.5 |
| strain 10 | 2.0 | 0.5 | 0.25 | 0.5 | 1.0 | 0.25 | 1.0 |

Synergy of the inhibitor example 1 to example 52 (4 mg/L) in combination with meropenam (Ex. 20 to Ex. 26, MIC, mg/L)

| Organism | MER Alone | MER + Ex. 20 | MER + Ex. 21 | MER + Ex. 22 | MER + Ex. 23 | MER + Ex. 24 | MER + Ex. 25 | MER + Ex. 26 |
|---|---|---|---|---|---|---|---|---|
| strain 1 | 2.0 | 0.25 | 0.25 | 0.25 | 0.25 | 0.25 | 0.25 | 0.25 |
| strain 2 | 2.0 | 0.25 | 0.25 | 0.25 | 0.5 | 0.25 | 0.25 | 0.25 |
| strain 3 | 2.0 | 0.25 | 0.25 | 1.0 | 0.25 | 0.25 | 0.25 | 1.0 |
| strain 4 | 1.0 | 0.25 | 0.25 | 0.25 | 0.25 | 0.25 | 0.25 | 0.25 |
| strain 5 | 2.0 | 2.0 | 2.0 | 0.5 | 0.5 | 0.5 | 0.5 | 2.0 |
| strain 6 | 2.0 | 1.0 | 0.25 | 1.0 | 1.0 | 0.5 | 1.0 | 0.5 |
| strain 7 | 2.0 | 2.0 | 2.0 | 2.0 | 1.0 | 2.0 | 2.0 | 2.0 |
| strain 8 | 1.0 | 1.0 | 0.5 | 0.5 | 0.5 | 0.5 | 0.5 | 0.5 |
| strain 9 | 2.0 | 0.25 | 0.25 | 0.25 | 0.25 | 0.25 | 0.25 | 1.0 |
| strain 10 | 2.0 | 1.0 | 1.0 | 0.5 | 0.5 | 1.0 | 1.0 | 0.5 |

Synergy of the inhibitor example 1 to example 52 (4 mg/L) in combination with meropenam (Ex. 27 to Ex. 32, MIC, mg/L)

| Organism | MER Alone | MER + Ex. 27 | MER + Ex. 28 | MER + Ex. 29 | MER + Ex. 30 | MER + Ex. 31 | MER + Ex. 32 |
|---|---|---|---|---|---|---|---|
| strain 1 | 2.0 | 0.25 | <0.125 | <0.125 | 0.25 | 0.25 | <0.125 |
| strain 2 | 2.0 | 0.25 | <0.125 | <0.125 | 0.25 | 0.25 | <0.125 |
| strain 3 | 2.0 | 2.0 | <0.125 | <0.125 | 0.25 | 0.25 | <0.125 |
| strain 4 | 1.0 | 0.25 | <0.125 | <0.125 | 0.25 | 0.25 | <0.125 |
| strain 5 | 2.0 | 1.0 | 0.25 | 0.25 | 0.5 | 0.5 | 0.25 |
| strain 6 | 2.0 | 0.5 | 0.25 | 1.0 | 0.5 | 1.0 | 0.5 |
| strain 7 | 2.0 | 2.0 | 1.0 | 1.0 | 1.0 | 1.0 | 1.0 |
| strain 8 | 1.0 | 1.0 | 0.25 | 1.0 | 0.5 | 0.5 | 1.0 |
| strain 9 | 2.0 | 1.0 | 0.5 | 0.25 | 0.25 | 0.25 | 0.5 |
| strain 10 | 2.0 | 0.5 | 0.25 | 0.25 | 0.5 | 0.5 | 0.5 |

Synergy of the inhibitor example 1 to example 52 (4 mg/L) in combination with meropenam (Ex. 33 to Ex. 38, MIC, mg/L)

| Organism | MER Alone | MER + Ex. 33 | MER + Ex. 34 | MER + Ex. 35 | MER + Ex. 36 | MER + Ex. 37 | MER + Ex. 38 |
|---|---|---|---|---|---|---|---|
| strain 1 | 2.0 | <0.125 | 0.25 | <0.125 | <0.125 | 1.0 | 0.25 |
| strain 2 | 2.0 | <0.125 | 0.25 | <0.125 | <0.125 | <0.125 | 0.25 |
| strain 3 | 2.0 | <0.125 | 0.5 | <0.125 | <0.125 | 2.0 | 0.25 |
| strain 4 | 1.0 | <0.125 | 0.25 | <0.125 | <0.125 | 0.25 | 0.25 |
| strain 5 | 2.0 | 0.25 | 0.5 | 0.25 | 0.25 | 2.0 | 0.5 |
| strain 6 | 2.0 | 0.5 | 1.0 | 0.5 | <0.125 | 0.5 | 0.5 |
| strain 7 | 2.0 | 1.0 | 2.0 | 1.0 | 2.0 | 2.0 | 2.0 |
| strain 8 | 1.0 | 0.5 | 0.5 | 0.5 | 1.0 | 0.5 | 0.5 |
| strain 9 | 2.0 | 0.25 | 0.25 | 0.25 | 0.5 | 0.5 | 0.25 |
| strain 10 | 2.0 | 0.25 | 0.5 | 0.25 | 0.25 | 0.5 | 0.25 |

Synergy of the inhibitor example 1 to example 52 (4 mg/L) in combination with meropenam (Ex. 39 to Ex. 45, MIC, mg/L)

| Organism | MER Alone | MER + Ex. 39 | MER + Ex. 40 | MER + Ex. 41 | MER + Ex. 42 | MER + Ex. 43 | MER + Ex. 44 | MER + Ex. 45 |
|---|---|---|---|---|---|---|---|---|
| strain 1 | 2.0 | <0.125 | 0.25 | 0.5 | <0.125 | 1.0 | 0.25 | 0.25 |
| strain 2 | 2.0 | <0.125 | 0.25 | 0.5 | <0.125 | 0.5 | 0.25 | 0.25 |
| strain 3 | 2.0 | <0.125 | 0.25 | 2.0 | <0.125 | 2.0 | 0.25 | 0.25 |
| strain 4 | 1.0 | <0.125 | 0.25 | 0.5 | <0.125 | 0.5 | 0.25 | 0.25 |
| strain 5 | 2.0 | 0.25 | 1.0 | 2.0 | 0.25 | 2.0 | 1.0 | 0.5 |
| strain 6 | 2.0 | <0.125 | 1.0 | 0.5 | <0.125 | 0.5 | 0.5 | 0.5 |

TABLE 2-continued

| | | | | | | | | |
|---|---|---|---|---|---|---|---|---|
| strain 7 | 2.0 | 1.0 | 2.0 | 2.0 | 2.0 | 2.0 | 2.0 | 2.0 |
| strain 8 | 1.0 | 0.5 | 0.5 | 0.5 | 0.5 | 0.5 | 0.5 | 0.5 |
| strain 9 | 2.0 | 0.25 | 0.25 | 0.25 | 0.25 | 0.5 | 0.5 | 0.5 |
| strain 10 | 2.0 | 0.5 | 0.5 | 1.0 | <0.125 | 0.5 | 0.5 | 0.5 |

Synergy of the inhibitor example 1 to example 52 (4 mg/L) in combination with meropenam (Ex. 46 to Ex. 52, MIC, mg/L)

| Organism | MER Alone | MER + Ex. 46 | MER + Ex. 47 | MER + Ex. 48 | MER + Ex. 49 | MER + Ex. 50 | MER + Ex. 51 | MER + Ex. 52 |
|---|---|---|---|---|---|---|---|---|
| strain 1 | 2.0 | 1.0 | 0.5 | 1.0 | 0.5 | 1.0 | <0.125 | <0.125 |
| strain 2 | 2.0 | 0.5 | <0.125 | 0.5 | 0.25 | 0.25 | <0.125 | <0.125 |
| strain 3 | 2.0 | 2.0 | <0.125 | 2.0 | 2.0 | 2.0 | <0.125 | <0.125 |
| strain 4 | 1.0 | 0.25 | <0.125 | 0.5 | 0.5 | 0.5 | <0.125 | <0.125 |
| strain 5 | 2.0 | 1.0 | 0.25 | 2.0 | 2.0 | 2.0 | 0.25 | 0.25 |
| strain 6 | 2.0 | 0.5 | 0.5 | 1.0 | 2.0 | 1.0 | 1.0 | 0.5 |
| strain 7 | 2.0 | 2.0 | 2.0 | 2.0 | 2.0 | 2.0 | 1.0 | 1.0 |
| strain 8 | 1.0 | 0.5 | 0.5 | 0.5 | 0.5 | 0.5 | 0.5 | 1.0 |
| strain 9 | 2.0 | 0.25 | 0.5 | 0.5 | 1.0 | 0.5 | 0.25 | 0.25 |
| strain 10 | 2.0 | 0.5 | <0.125 | 1.0 | 0.5 | 1.0 | <0.125 | 0.25 |

TABLE 3

Antibacterial activity of example 1 to example 52 (Ex. 1 to 9, MIC, mg/L)

| Organism | Ex. 1 Alone | Ex. 2 Alone | Ex. 3 Alone | Ex. 4 Alone | Ex. 5 Alone | Ex. 6 Alone | Ex. 7 Alone | Ex. 8 Alone | Ex. 9 Alone |
|---|---|---|---|---|---|---|---|---|---|
| strain 1 | >64 | >64 | >64 | >64 | >64 | >64 | >64 | >64 | >64 |
| strain 2 | >64 | >64 | >64 | >64 | >64 | >64 | >64 | >64 | >64 |
| strain 3 | >64 | >64 | >64 | >64 | >64 | >64 | >64 | >64 | >64 |
| strain 4 | >64 | >64 | >64 | >64 | >64 | >64 | >64 | >64 | >64 |
| strain 5 | >64 | >64 | >64 | >64 | >64 | >64 | >64 | >64 | >64 |
| strain 6 | >64 | >64 | >64 | >64 | >64 | >64 | >64 | >64 | >64 |
| strain 7 | >64 | >64 | >64 | >64 | >64 | >64 | >64 | >64 | >64 |
| strain 8 | >64 | >64 | >64 | >64 | >64 | >64 | >64 | >64 | >64 |
| strain 9 | >64 | >64 | >64 | >64 | >64 | >64 | >64 | >64 | >64 |
| strain 10 | >64 | >64 | >64 | >64 | >64 | >64 | >64 | >64 | >64 |

Antibacterial activity of example 1 to example 52 (Ex. 10 to 18, MIC, mg/L)

| Organism | Ex. 10 Alone | Ex. 11 Alone | Ex. 12 Alone | Ex. 13 Alone | Ex. 14 Alone | Ex. 15 Alone | Ex. 16 Alone | Ex. 17 Alone | Ex. 18 Alone |
|---|---|---|---|---|---|---|---|---|---|
| strain 1 | >64 | >64 | >64 | >64 | >64 | >64 | >64 | >64 | >64 |
| strain 2 | >64 | >64 | >64 | >64 | >64 | >64 | >64 | >64 | >64 |
| strain 3 | >64 | >64 | >64 | >64 | >64 | >64 | >64 | >64 | >64 |
| strain 4 | >64 | >64 | >64 | >64 | >64 | >64 | >64 | >64 | >64 |
| strain 5 | >64 | >64 | >64 | >64 | >64 | >64 | >64 | >64 | >64 |
| strain 6 | >64 | >64 | >64 | >64 | >64 | >64 | >64 | >64 | >64 |
| strain 7 | >64 | >64 | >64 | >64 | >64 | >64 | >64 | >64 | >64 |
| strain 8 | >64 | >64 | >64 | >64 | >64 | >64 | >64 | >64 | >64 |
| strain 9 | >64 | >64 | >64 | >64 | >64 | >64 | >64 | >64 | >64 |
| strain 10 | >64 | >64 | >64 | >64 | >64 | >64 | >64 | >64 | >64 |

Antibacterial activity of example 1 to example 52 (Ex. 19 to 27, MIC, mg/L)

| Organism | Ex. 19 Alone | Ex. 20 Alone | Ex. 21 Alone | Ex. 22 Alone | Ex. 23 Alone | Ex. 24 Alone | Ex. 25 Alone | Ex. 26 Alone | Ex. 27 Alone |
|---|---|---|---|---|---|---|---|---|---|
| strain 1 | >64 | >64 | >64 | >64 | >64 | >64 | >64 | >64 | >64 |
| strain 2 | >64 | >64 | >64 | >64 | >64 | >64 | >64 | >64 | >64 |
| strain 3 | >64 | >64 | >64 | >64 | >64 | >64 | >64 | >64 | >64 |
| strain 4 | >64 | >64 | >64 | >64 | >64 | >64 | >64 | >64 | >64 |
| strain 5 | >64 | >64 | >64 | >64 | >64 | >64 | >64 | >64 | >64 |
| strain 6 | >64 | >64 | >64 | >64 | >64 | >64 | >64 | >64 | >64 |
| strain 7 | >64 | >64 | >64 | >64 | >64 | >64 | >64 | >64 | >64 |
| strain 8 | >64 | >64 | >64 | >64 | >64 | >64 | >64 | >64 | >64 |
| strain 9 | >64 | >64 | >64 | >64 | >64 | >64 | >64 | >64 | >64 |
| strain 10 | >64 | >64 | >64 | >64 | >64 | >64 | >64 | >64 | >64 |

TABLE 3-continued

Antibacterial activity of example 1 to example 52 (Ex. 28 to 36, MIC, mg/L)

| Organism | Ex. 28 Alone | Ex. 29 Alone | Ex. 30 Alone | Ex. 31 Alone | Ex. 32 Alone | Ex. 33 Alone | Ex. 34 Alone | Ex. 35 Alone | Ex. 36 Alone |
|---|---|---|---|---|---|---|---|---|---|
| strain 1 | >64 | >64 | >64 | >64 | >64 | >64 | >64 | >64 | >64 |
| strain 2 | >64 | >64 | >64 | >64 | >64 | >64 | >64 | >64 | >64 |
| strain 3 | >64 | >64 | >64 | >64 | >64 | >64 | >64 | >64 | >64 |
| strain 4 | >64 | >64 | >64 | >64 | >64 | >64 | >64 | >64 | >64 |
| strain 5 | >64 | >64 | >64 | >64 | >64 | >64 | >64 | >64 | >64 |
| strain 6 | >64 | >64 | >64 | >64 | >64 | >64 | >64 | >64 | >64 |
| strain 7 | >64 | >64 | >64 | >64 | >64 | >64 | >64 | >64 | >64 |
| strain 8 | >64 | >64 | >64 | >64 | >64 | >64 | >64 | >64 | >64 |
| strain 9 | >64 | >64 | >64 | >64 | >64 | >64 | >64 | >64 | >64 |
| strain 10 | >64 | >64 | >64 | >64 | >64 | >64 | >64 | >64 | >64 |

Antibacterial activity of example 1 to example 52 (Ex. 37 to 44, MIC, mg/L)

| Organism | Ex. 37 Alone | Ex. 38 Alone | Ex. 39 Alone | Ex. 40 Alone | Ex. 41 Alone | Ex. 42 Alone | Ex. 43 Alone | Ex. 44 Alone |
|---|---|---|---|---|---|---|---|---|
| strain 1 | >64 | >64 | >64 | >64 | >64 | >64 | >64 | >64 |
| strain 2 | >64 | >64 | >64 | >64 | >64 | >64 | >64 | >64 |
| strain 3 | >64 | >64 | >64 | >64 | >64 | >64 | >64 | >64 |
| strain 4 | >64 | >64 | >64 | >64 | >64 | >64 | >64 | >64 |
| strain 5 | >64 | >64 | >64 | >64 | >64 | >64 | >64 | >64 |
| strain 6 | >64 | >64 | >64 | >64 | >64 | >64 | >64 | >64 |
| strain 7 | >64 | >64 | >64 | >64 | >64 | >64 | >64 | >64 |
| strain 8 | >64 | >64 | >64 | >64 | >64 | >64 | >64 | >64 |
| strain 9 | >64 | >64 | >64 | >64 | >64 | >64 | >64 | >64 |
| strain 10 | >64 | >64 | >64 | >64 | >64 | >64 | >64 | >64 |

Antibacterial activity of example 1 to example 52 (Ex. 45 to 52, MIC, mg/L)

| Organism | Ex. 45 Alone | Ex. 46 Alone | Ex. 47 Alone | Ex. 48 Alone | Ex. 49 Alone | Ex. 50 Alone | Ex. 51 Alone | Ex. 52 Alone |
|---|---|---|---|---|---|---|---|---|
| strain 1 | >64 | >64 | >64 | >64 | >64 | >64 | >64 | >64 |
| strain 2 | >64 | >64 | >64 | >64 | >64 | >64 | >64 | >64 |
| strain 3 | >64 | >64 | >64 | >64 | >64 | >64 | >64 | >64 |
| strain 4 | >64 | >64 | >64 | >64 | >64 | >64 | >64 | >64 |
| strain 5 | >64 | >64 | >64 | >64 | >64 | >64 | >64 | >64 |
| strain 6 | >64 | >64 | >64 | >64 | >64 | >64 | >64 | >64 |
| strain 7 | >64 | >64 | >64 | >64 | >64 | >64 | >64 | >64 |
| strain 8 | >64 | >64 | >64 | >64 | >64 | >64 | >64 | >64 |
| strain 9 | >64 | >64 | >64 | >64 | >64 | >64 | >64 | >64 |
| strain 10 | >64 | >64 | >64 | >64 | >64 | >64 | >64 | >64 |

Test for lactamase Inhibitory activity:

The inhibitory activities of present compounds against various enzymes are measured by spectrophotometric assay using 490 nM and using nitrocefin as a substrate [J. Antimicrob. Chemother., 28, pp 775-776 (1991)]. The concentration of inhibitor ($IC_{50}$) which inhibits by 50% the reaction of hydrolysis of nitrocefin by the enzyme is determined.

In light of the data described herein, persons of skill in the art would expect that all of the compounds within the scope of formula (I), salts of such compounds, solvates of such compounds, and salts thereof, and deuterated compounds of all such compounds, salts and solvates (i.e., compounds of formula (I) modified in that they have been deuterated, salts of compounds of formula (I) modified in that they have been deuterated, and solvates of compounds of formula (I) modified in that they have been deuterated) would be effective on their own as antibacterial compounds, and in combination with 3-lactam antibiotics.

Efficacy of the 3-lactamase inhibitors can be evaluated in combination with ceftazidime aztreonam, meropenem and other class of carbapenems and cephalosporins in murine infection models such as septicemia, pneumonia and thigh infection models (Ref: Andrea Endimiani et. al. Antimicrobial Agents and Chemotherapy, January 2011, page 82-85). For murine acute lethal septicemia model, mice were infected by the intraperitoneal injection of the clinical strains resulting in death of the untreated controls within 24-48 hours. In particular, a fresh predetermined bacterial inoculum of approximately $3.3\times10^5$ to $3.6\times10^5$ CFU in 5% hog gastric mucin grown overnight. Thirty minutes post infection, a single subcutaneous dose of meropenam with and without 3-lactamase inhibitor was initiated and the survival ratio monitored for 5 days twice daily. For each strain tested, the dosing regimen used are meropenam alone (doses of 512, 1024 & 2048 mg/kg of body weight) and meropenam plus β-lactamase inhibitor at ratio of 2:1, 4:1, 8:1, 16:1 & 32:1 (meropenam doses were 4, 8, 16, 32 & 64 mg/kg for each ratio). The median effective dose for 50% protective dose ($ED_{50}$) of animals was determined by a computerized program of Probit analysis. Survival rates stratified for different dosing regimen were also obtained. For experimental *pneumoniae* model, immunocompromised mice were used and intratracheally infected with *Klebsiella pneumoniae* strains. Mice in this model developed bacteraemia *pneumoniae* and fatal disease within 2 to 4 days with lung bacterial burden at 16-18 hours post infection of $10^{11}$ to $10^{13}$ cfu/gm lung. Treatment with meropenam and inhibitor at a ratio of 2/1 & 4/1 demonstrated efficacy with significant 3 to 6 log reduction in lung counts compared to meropenam alone and was relevant to the clinical situation. Human testing of the β-lactamase inhibitor can be conducted in combination with partner antibiotic at a set ratio utilizing standard clinical development practice.

What we claim is:

1. A compound selected from the group consisting of:

(2S,5R)-2-(N-acetylcarbamimidoyl)-7-oxo-1,6-diazabicyclo[3.2.1]octan-6-yl hydrogen sulfate, (2S,5R)-7-oxo-2-(N-pivaloylcarbamimidoyl)-1,6-diazabicyclo[3.2.1]octan-6-yl hydrogen sulfate, (2S,5R)-7-oxo-2-(N-(3,3,3-trifluoropropanoyl)carbamimidoyl)-1,6-diazabicyclo[3.2.1]octan-6-yl hydrogen sulfate, (2S,5R)-7-oxo-2-(N-propionylcarbamimidoyl)-1,6-diazabicyclo[3.2.1]octan-6-yl hydrogen sulfate, (2S,5R)-2-(N-butyrylcarbamimidoyl)-7-oxo-1,6-diazabicyclo[3.2.1]octan-6-yl hydrogen sulfate, (2S,5R)-2-(N-isobutyrylcarbamimidoyl)-7-oxo-1,6-diazabicyclo[3.2.1]octan-6-yl hydrogen sulfate, (2S,5R)-2-(N-(acetylglycyl)carbamimidoyl)-7-oxo-1,6-diazabicyclo[3.2.1]octan-6-yl hydrogen sulfate, (2S,5R)-2-(N-glycylcarbamimidoyl)-7-oxo-1,6-diazabicyclo[3.2.1]octan-6-yl hydrogen sulfate, (2S,5R)-2-(N-(2-hydroxyacetyl)carbamimidoyl)-7-oxo-1,6-diazabicyclo[3.2.1]octan-6-yl hydrogen sulfate, (2S,5R)-2-(N-(carbamoylglycyl)carbamimidoyl)-7-oxo-1,6-diazabicyclo[3.2.1]octan-6-yl hydrogen sulfate, 3-oxo-3-((2S,5R)-7-oxo-6-(sulfooxy)-1,6-diazabicyclo[3.2.1]octane-2-carboximidamido)propanoic acid, (2S,5R)-2-(N-(2-methoxyacetyl)carbamimidoyl)-7-oxo-1,6-diazabicyclo[3.2.1]octan-6-yl hydrogen sulfate, (2S,5R)-2-(N-alanylcarbamimidoyl)-7-oxo-1,6-diazabicyclo[3.2.1]octan-6-yl hydrogen sulfate, (2S,5R)-2-(N-(3-amino-3-oxopropanoyl)carbamimidoyl)-7-oxo-1,6-diazabicyclo[3.2.1]octan-6-yl hydrogen sulfate, (2S,5R)-2-(N-(3-morpholinopropanoyl)carbamimidoyl)-7-oxo-1,6-diazabicyclo[3.2.1]octan-6-yl hydrogen sulfate, (2S,5R)-2-(N-(carbamimidoylglycyl)carbamimidoyl)-7-oxo-1,6-diazabicyclo[3.2.1]octan-6-yl hydrogen sulfate, (2S,5R)-2-(N-(2-(guanidinooxy)acetyl)carbamimidoyl)-7-oxo-1,6-diazabicyclo[3.2.1]octan-6-yl hydrogen sulfate, (2S,5R)-2-(N-(3-aminopropanoyl)carbamimidoyl)-7-oxo-1,6-diazabicyclo[3.2.1]octan-6-yl hydrogen sulfate, (2S,5R)-2-(N-(3-(guanidinooxy)propanoyl)carbamimidoyl)-7-oxo-1,6-diazabicyclo[3.2.1]octan-6-yl hydrogen sulfate, (2S,5R)-2-(N-(4-(guanidinooxy)butanoyl)carbamimidoyl)-7-oxo-1,6-diazabicyclo[3.2.1]octan-6-yl hydrogen sulfate, (2S,5R)-2-(N-(3-guanidinopropanoyl)carbamimidoyl)-7-oxo-1,6-diazabicyclo[3.2.1]octan-6-yl hydrogen sulfate, (2S,5R)-2-(N-(3-acetamidopropanoyl)carbamimidoyl)-7-oxo-1,6-diazabicyclo[3.2.1]octan-6-yl hydrogen sulfate, (2S,5R)-7-oxo-2-(N-(3-(piperidin-1-yl)propanoyl)carbamimidoyl)-1,6-diazabicyclo[3.2.1]octan-6-yl hydrogen sulfate, (2S,5R)-7-oxo-2-(N-(3-(piperazin-1-yl)propanoyl)carbamimidoyl)-1,6-diazabicyclo[3.2.1]octan-6-yl hydrogen sulfate, (2S,5R)-2-(N-(cyclohexanecarbonyl)carbamimidoyl)-7-oxo-1,6-diazabicyclo[3.2.1]octan-6-yl hydrogen sulfate, (2S,5R)-2-(N-(cyclobutanecarbonyl)carbamimidoyl)-7-oxo-1,6-diazabicyclo[3.2.1]octan-6-yl hydrogen sulfate, (2S,5R)-2-(N-(cyclopentanecarbonyl)carbamimidoyl)-7-oxo-1,6-diazabicyclo[3.2.1]octan-6-yl hydrogen sulfate, (2S,5R)-2-(N-(3-aminocyclopentane-1-carbonyl)carbamimidoyl)-7-oxo-1,6-diazabicyclo[3.2.1]octan-6-yl hydrogen sulfate, (2S,5R)-2-(N-(3-(dimethylamino)cyclopentane-1-carbonyl)carbamimidoyl)-7-oxo-1,6-diazabicyclo[3.2.1]octan-6-yl hydrogen sulfate, (2S,5R)-2-(N-(3-(methylamino)cyclopentane-1-carbonyl)carbamimidoyl)-7-oxo-1,6-diazabicyclo[3.2.1]octan-6-yl hydrogen sulfate, (2S,5R)-2-(N-(3-acetamidocyclopentane-1-carbonyl)carbamimidoyl)-7-oxo-1,6-diazabicyclo[3.2.1]octan-6-yl hydrogen sulfate, (2S,5R)-2-(N-(2-aminocyclopentane-1-carbonyl)carbamimidoyl)-7-oxo-1,6-diazabicyclo[3.2.1]octan-6-yl hydrogen sulfate, (2S,5R)-2-(N-(2-(dimethylamino)cyclopentane-1-carbonyl)carbamimidoyl)-7-oxo-1,6-diazabicyclo[3.2.1]octan-6-yl hydrogen sulfate, (2S,5R)-2-(N-(2-acetamidocyclopentane-1-carbonyl)carbamimidoyl)-7-oxo-1,6-diazabicyclo[3.2.1]octan-6-yl hydrogen sulfate, (2S,5R)-2-(N-(2-acetamidocyclopropane-1-carbonyl)carbamimidoyl)-7-oxo-1,6-diazabicyclo[3.2.1]octan-6-yl hydrogen sulfate, (2S,5R)-2-(N-(2-(methylamino)cyclopropane-1-carbonyl)carbamimidoyl)-7-oxo-1,6-diazabicyclo[3.2.1]octan-6-yl hydrogen sulfate, (2S,5R)-2-(N-(4-aminocyclohexane-1-carbonyl)carbamimidoyl)-7-oxo-1,6-diazabicyclo[3.2.1]octan-6-yl hydrogen sulfate, (2S,5R)-2-(N-(4-(dimethylamino)cyclohexane-1-carbonyl)carbamimidoyl)-7-oxo-1,6-diazabicyclo[3.2.1]octan-6-yl hydrogen sulfate, (2S,5R)-2-(N-(cycloheptanecarbonyl)carbamimidoyl)-7-oxo-1,6-diazabicyclo[3.2.1]octan-6-yl hydrogen sulfate, (2S,5R)-2-(N-(4-acetamidocyclohexane-1-carbonyl)carbamimidoyl)-7-oxo-1,6-diazabicyclo[3.2.1]octan-6-yl hydrogen sulfate, (2S,5R)-2-(N-(3-aminocyclohexane-1-carbonyl)carbamimidoyl)-7-oxo-1,6-diazabicyclo[3.2.1]octan-6-yl hydrogen sulfate, (2S,5R)-2-(N-(3-(dimethylamino)cyclohexane-1-carbonyl)carbamimidoyl)-7-oxo-1,6-diazabicyclo[3.2.1]octan-6-yl hydrogen sulfate, (2S,5R)-2-(N-(3-(methylamino)cyclohexane-1-carbonyl)carbamimidoyl)-7-oxo-1,6-diazabicyclo[3.2.1]octan-6-yl hydrogen sulfate, (2S,5R)-2-(N-(3-acetamidocyclohexane-1-carbonyl)carbamimidoyl)-7-oxo-1,6-diazabicyclo[3.2.1]octan-6-yl hydrogen sulfate, (2S,5R)-2-(N-(2-aminocyclopropane-1-carbonyl)carbamimidoyl)-7-oxo-1,6-diazabicyclo[3.2.1]octan-6-yl hydrogen sulfate, (2S,5R)-7-oxo-2-(N-(piperidine-4-carbonyl)carbamimidoyl)-1,6-diazabicyclo[3.2.1]octan-6-yl hydrogen sulfate, (2S,5R)-2-(N-(1-methylpiperidine-4-carbonyl)carbamimidoyl)-7-oxo-1,6-diazabicyclo[3.2.1]octan-6-yl hydrogen sulfate, (2S,5R)-2-(N-(1-acetylpiperidine-4-carbonyl)carbamimidoyl)-7-oxo-1,6-diazabicyclo[3.2.1]octan-6-yl hydrogen sulfate, ethyl 4-((imino((2S,5R)-7-oxo-6-(sulfooxy)-1,6-diazabicyclo[3.2.1]octan-2-yl)methyl)carbamoyl)piperidine-1-carboxylate, (2S,5R)-7-oxo-2-(N-((R)-piperidine-3-carbonyl)carbamimidoyl)-1,6-diazabicyclo[3.2.1]octan-6-yl hydrogen sulfate, (2S,5R)-2-(N-((R)-1-methylpiperidine-3-carbonyl)carbamimidoyl)-7-oxo-1,6-diazabicyclo[3.2.1]octan-6-yl hydrogen sulfate, (2S,5R)-2-(N-((R)-1-acetylpiperidine-3-carbonyl)carbamimidoyl)-7-oxo-1,6-diazabicyclo[3.2.1]octan-6-yl hydrogen sulfate, (2S,5R)-7-oxo-2-(N-((R)-piperidine-3-carbonyl)carbamimidoyl)-1,6-diazabicyclo[3.2.1]octan-6-yl hydrogen sulfate, (2S,5R)-2-(N-((R)-1-methylpiperidine-3-carbonyl)carbamimidoyl)-7-oxo-1,6-diazabicyclo[3.2.1]octan-6-yl hydrogen sulfate, (2S,5R)-2-(N-((R)-1-acetylpiperidine-3-carbonyl)carbamimidoyl)-7-oxo-1,6-diazabicyclo[3.2.1]octan-6-yl hydrogen sulfate, (2S,5R)-7-oxo-2-(N-((R)-pyrrolidine-3-carbonyl)carbamimidoyl)-1,6-diazabicyclo[3.2.1]octan-6-yl hydrogen sulfate, (2S,5R)-2-(N-((R)-1-ethylpyrrolidine-3-carbonyl)carbamimidoyl)-7-oxo-1,6-diazabicyclo[3.2.1]octan-6-yl hydrogen sulfate, (2S,5R)-7-oxo-2-(N-((R)-pyrrolidine-3-carbonyl)carbamimidoyl)-1,6-diazabicyclo[3.2.1]octan-6-yl hydrogen sulfate, (2S,5R)-2-(N-((R)-1-formylpyrrolidine-3-carbonyl)carbamimidoyl)-7-oxo-1,6-diazabicyclo[3.2.1]octan-6-yl hydrogen sulfate, (2S,5R)-2-(N-((R)-1-acetylpyrrolidine-3-carbonyl)carbamimidoyl)-7-oxo-1,6-diazabicyclo[3.2.1]octan-6-yl hydrogen sulfate, (2S,5R)-2-(N-(azetidine-3-carbonyl)carbamimidoyl)-7-oxo-1,6-diazabicyclo[3.2.1]octan-6-yl hydrogen sulfate, tert-butyl 4-((imino((2S,5R)-7-oxo-6-(sulfooxy)-1,6-diazabicyclo[3.2.1]octan-2-yl)methyl)carbamoyl)piperidine-1-carboxylate, (2S,5R)-2-(N-(1-carbamimidoylazetidine-3-carbonyl)carbamimidoyl)-7-oxo-1,6-diazabicyclo[3.2.1]octan-6-yl hydrogen sulfate, (2S,5R)-7-oxo-2-(N-(tetrahydro-2H-thiopyran-4-carbonyl)carbamimidoyl)-1,6-diazabicyclo[3.2.1]octan-6-yl hydrogen sulfate, (2S,5R)-7-oxo-2-(N-(tetrahydro-2H-pyran-4-carbonyl)carbamimidoyl)-1,6-diazabicyclo[3.2.1]octan-6-yl hydrogen sulfate, (2S,5R)-2-(N-(azepane-3-carbonyl)carbamimidoyl)-7-oxo-1,6-diazabicyclo[3.2.1]octan-6-yl hydrogen sulfate, (2S,5R)-2-(N-(1,1-dioxidotetrahydro-2H-thiopyran-4-carbonyl)carbamimidoyl)-7-oxo-1,6-diazabicyclo[3.2.1]octan-6-yl hydrogen sulfate, (2S,5R)-2-(N-(1,4-oxazepane-6-carbonyl)carbamimidoyl)-7-oxo-1,6-diazabicyclo[3.2.1]octan-6-yl hydrogen sulfate, (2S,5R)-2-(N-(1-acetylazepane-3-carbonyl)carbamimidoyl)-7-oxo-1,6-diazabicyclo[3.2.1]octan-6-yl hydrogen sulfate, (2S,5R)-2-(N-((R)-1-methylpyrrolidine-3-carbonyl)carbamimidoyl)-7-oxo-1,6-diazabicyclo[3.2.1]octan-6-yl hydrogen sulfate, (2S,5R)-2-(N-((R)-1-acetylpyrrolidine-3-carbonyl)carbamimidoyl)-7-oxo-1,6-diazabicyclo[3.2.1]octan-6-yl hydrogen sulfate, (2S,5R)-2-(N-((R)-1-methylpyrrolidine-3-carbonyl)carbamimidoyl)-7-oxo-1,6-diazabicyclo[3.2.1]octan-6-yl hydrogen sulfate, (2S,5R)-2-(N-((S)-1-acetylpiperidine-2-carbonyl)carbamimidoyl)-7-oxo-1,6-diazabicyclo[3.2.1]octan-6-yl hydrogen sulfate, (2S,5R)-2-(N-((S)-1-methylpiperidine-2-carbonyl)carbamimidoyl)-7-oxo-1,6-diazabicyclo[3.2.1]octan-6-yl hydrogen sulfate, tert-butyl (3R)-3-((imino((2S,5R)-7-oxo-6-(sulfooxy)-1,6-diazabicyclo[3.2.1]octan-2-yl)methyl)carbamoyl)pyrrolidine-1-carboxylate, (2S,5R)-7-oxo-2-(N-(2-(pyrrolidin-3-yl)acetyl)carbamimidoyl)-1,6-diazabicyclo[3.2.1]octan-6-yl hydrogen sulfate, (2S,5R)-7-oxo-2-(N-(2-(piperidin-3-yl)acetyl)carbamimidoyl)-1,6-diazabicyclo[3.2.1]octan-6-yl hydrogen sulfate, (2S,5R)-7-oxo-2-(N-(2-(piperidin-4-yl)acetyl)carbamimidoyl)-1,6-diazabicyclo[3.2.1]octan-6-yl hydrogen sulfate, (2S,5R)-7-oxo-2-(N-(2-(piperidin-2-yl)acetyl)carbamimidoyl)-1,6-diazabicyclo[3.2.1]octan-6-yl hydrogen sulfate, (2S,5R)-2-(N-(2-(1,3-oxazinan-2-yl)acetyl)carbamimidoyl)-7-oxo-1,6-diazabicyclo[3.2.1]octan-6-yl hydrogen sulfate, (2S,5R)-7-oxo-2-(N-(2-(piperazin-2-yl)acetyl)carbamimidoyl)-1,6-diazabicyclo[3.2.1]octan-6-yl hydrogen sulfate, (2S,5R)-2-(N-(2-(1,3-thiazinan-2-yl)acetyl)carbamimidoyl)-7-oxo-1,6-diazabicyclo[3.2.1]octan-6-yl hydrogen sulfate, (2S,5R)-7-oxo-2-(N-(2-(tetrahydrofuran-2-yl)acetyl)carbamimidoyl)-1,6-diazabicyclo[3.2.1]octan-6-yl hydrogen sulfate, (2S,5R)-2-(N-(2-(4-methylpiperidin-4-yl)acetyl)carbamimidoyl)-7-oxo-1,6-diazabicyclo[3.2.1]octan-6-yl hydrogen sulfate, (2S,5R)-7-oxo-2-(N-(2-(piperazin-1-yl)acetyl)carbamimidoyl)-1,6-diazabicyclo[3.2.1]octan-6-yl hydrogen sulfate, (2S,5R)-2-(N-(2-cyclohexylacetyl)carbamimidoyl)-7-oxo-1,6-diazabicyclo[3.2.1]octan-6-yl hydrogen sulfate, (2S,5R)-7-oxo-2-(N-(2-(piperidin-4-yl)acetyl)carbamimidoyl)-1,6-diazabicyclo[3.2.1]octan-6-yl hydrogen sulfate, (2S,5R)-2-(N-(2-(4-methylpiperazin-1-yl)acetyl)carbamimidoyl)-7-oxo-1,6-diazabicyclo[3.2.1]octan-6-yl hydrogen sulfate, (2S,5R)-2-(N-(2-(3-acetyltetrahydropyrimidin-1(2H)-yl)acetyl)carbamimidoyl)-7-oxo-1,6-diazabicyclo[3.2.1]octan-6-yl hydrogen sulfate, (2S,5R)-2-(N-(2-(1-methylpiperidin-4-yl)acetyl)carbamimidoyl)-7-oxo-1,6-diazabicyclo[3.2.1]octan-6-yl hydrogen sulfate, (2S,5R)-2-(N-(2-(1-acetylpiperidin-4-yl)acetyl)carbamimidoyl)-7-oxo-1,6-diazabicyclo[3.2.1]octan-6-yl hydrogen sulfate, (2S,5R)-2-(N-(2-(1-methylpyrrolidin-3-yl)acetyl)carbamimidoyl)-7-oxo-1,6-diazabicyclo[3.2.1]octan-6-yl hydrogen sulfate, (2S,5R)-2-(N-(2-(azetidin-3-yl)acetyl)carbamimidoyl)-7-oxo-1,6-diazabicyclo[3.2.1]octan-6-yl hydrogen sulfate, (2S,5R)-7-oxo-2-(N-(2-(tetrahydro-2H-pyran-4-yl)acetyl)carbamimidoyl)-1,6-diazabicyclo[3.2.1]octan-6-yl hydrogen sulfate, (2S,5R)-7-oxo-2-(N-(2-(pyrrolidin-1-yl)acetyl)carbamimidoyl)-1,6-diazabicyclo[3.2.1]octan-6-yl hydrogen sulfate, (2S,5R)-2-(N-(2-(1,1-dioxidotetrahydro-2H-thiopyran-4-yl)acetyl)carbamimidoyl)-7-oxo-1,6-diazabicyclo[3.2.1]octan-6-yl hydrogen sulfate, (2S,5R)-7-oxo-2-(N-(2-(pyrrolidin-3-yloxy)acetyl)carbamimidoyl)-1,6-diazabicyclo[3.2.1]octan-6-yl hydrogen sulfate, (2S,5R)-7-oxo-2-(N-(2-(piperidin-4-yloxy)acetyl)carbamimidoyl)-1,6-diazabicyclo[3.2.1]octan-6-yl hydrogen sulfate, (2S,5R)-7-oxo-2-(N-(2-(piperidin-1-yl)acetyl)carbamimidoyl)-1,6-diazabicyclo[3.2.1]octan-6-yl hydrogen sulfate, (2S,5R)-2-(N-(2-(1-acetylpyrrolidin-3-yl)acetyl)carbamimidoyl)-7-oxo-1,6-diazabicyclo[3.2.1]octan-6-yl hydrogen sulfate, (2S,5R)-2-(N-(2-((1-methylpiperidin-4-yl)oxy)acetyl)carbamimidoyl)-7-oxo-1,6-diazabicyclo[3.2.1]octan-6-yl hydrogen sulfate, (2S,5R)-7-oxo-2-(N-(3-sulfamoylcyclobutane-1-carbonyl)carbamimidoyl)-1,6-diazabicyclo[3.2.1]octan-6-yl hydrogen sulfate, (2S,5R)-7-oxo-2-(N-(3-(pyridin-2-yl)propanoyl)carbamimidoyl)-1,6-diazabicyclo[3.2.1]octan-6-yl hydrogen sulfate, (2S,5R)-7-oxo-2-(N-(2-(pyridin-3-yl)acetyl)carbamimidoyl)-1,6-diazabicyclo[3.2.1]octan-6-yl hydrogen sulfate, (2S,5R)-7-oxo-2-(N-(2-(pyrimidin-5-yl)acetyl)carbamimidoyl)-1,6-diazabicyclo[3.2.1]octan-6-yl hydrogen sulfate, (2S,5R)-7-oxo-2-(N-(2-(pyridin-4-yl)acetyl)carbamimidoyl)-1,6-diazabicyclo[3.2.1]octan-6-yl hydrogen sulfate, (2S,5R)-2-(N-(2-(1H-imidazol-2-yl)acetyl)carbamimidoyl)-7-oxo-1,6-diazabicyclo[3.2.1]octan-6-yl hydrogen sulfate, (2S,5R)-2-(N-(2-(1H-imidazol-1-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-2-yl)acetyl)carbamimidoyl)-7-oxo-1,6-diazabicyclo[3.2.1]octan-6-yl hydrogen sulfate, (2S,5R)-2-(N-(2-(2-methyl-1H-imidazol-4-yl)acetyl)carbamimidoyl)-7-oxo-1,6-diazabicyclo[3.2.1]octan-6-yl hydrogen sulfate, (2S,5R)-2-(N-(2-(1-methyl-1H-pyrazol-3-yl)acetyl)carbamimidoyl)-7-oxo-1,6-diazabicyclo[3.2.1]octan-6-yl hydrogen sulfate, (2S,5R)-2-(N-(2-(1H-pyrazol-3-yl)acetyl)carbamimidoyl)-7-oxo-1,6-diazabicyclo[3.2.1]octan-6-yl hydrogen sulfate, (2S,5R)-2-(N-(2-(1-acetyl-1H-imidazol-2-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-5-yl)acetyl)carbamimidoyl)-7-oxo-1,6-diazabicyclo[3.2.1]octan-6-yl hydrogen sulfate, (2S,5R)-2-(N-(2-(2-aminothiazol-4-yl)acetyl)carbamimidoyl)-7-oxo-1,6-diazabicyclo[3.2.1]octan-6-yl hydrogen sulfate, (2S,5R)-2-(N-(2-(oxazol-4-yl)acetyl)carbamimidoyl)-7-oxo-1,6-diazabicyclo[3.2.1]octan-6-yl hydrogen sulfate, (2S,5R)-7-oxo-2-(N-(2-(thiazol-4-yl)acetyl)carbamimidoyl)-1,6-diazabicyclo[3.2.1]octan-6-yl hydrogen sulfate, (2S,5R)-2-(N-(2-(1H-imidazol-4-yl)acetyl)carbamimidoyl)-7-oxo-1,6-diazabicyclo[3.2.1]octan-6-yl hydrogen sulfate, (2S,5R)-2-(N-(2-(1-methyl-1H-imidazol-4-yl)acetyl)carbamimidoyl)-7-oxo-1,6-diazabicyclo[3.2.1]octan-6-yl hydrogen sulfate, (2S,5R)-2-(N-(2-(1H-1,2,4-triazol-3-yl)acetyl)carbamimidoyl)-7-oxo-1,6-diazabicyclo[3.2.1]octan-6-yl hydrogen sulfate, (2S,5R)-2-(N-(furan-2-carbonyl)carbamimidoyl)-7-oxo-1,6-diazabicyclo[3.2.1]octan-6-yl hydrogen sulfate, (2S,5R)-2-(N-benzoylcarbamimidoyl)-7-oxo-1,6-diazabicyclo[3.2.1]octan-6-yl hydrogen sulfate, (2S,5R)-2-(N-nicotinoylcarbamimidoyl)-7-oxo-1,6-diazabicyclo[3.2.1]octan-6-yl hydrogen sulfate, (2S,5R)-7-oxo-2-(N-(6-(trifluoromethyl)nicotinoyl)carbamimidoyl)-1,6-diazabicyclo[3.2.1]octan-6-yl hydrogen sulfate, (2S,5R)-2-(N-isonicotinoylcarbamimidoyl)-7-oxo-1,6-diazabicyclo[3.2.1]octan-6-yl hydrogen sulfate, (2S,5R)-7-oxo-2-(N-(pyridazine-3-carbonyl)carbamimidoyl)-1,6-diazabicyclo[3.2.1]octan-6-yl hydrogen sulfate, (2S,5R)-2-(N-(6-fluoronicotinoyl)carbamimidoyl)-7-oxo-1,6-diazabicyclo[3.2.1]octan-6-yl hydrogen sulfate, (2S,5R)-2-(N-(oxazole-4-carbonyl)carbamimidoyl)-7-oxo-1,6-diazabicyclo[3.2.1]octan-6-yl hydrogen sulfate, (2S,5R)-2-(N-(oxazole-5-carbonyl)carbamimidoyl)-7-oxo-1,6-diazabicyclo[3.2.1]octan-6-yl hydrogen sulfate, (2S,5R)-7-oxo-2-(N-(2-(trifluoromethyl)thiazole-4-carbonyl)carbamimidoyl)-1,6-diazabicyclo[3.2.1]octan-6-yl hydrogen sulfate, (2S,5R)-2-(N-(2-aminothiazole-4-carbonyl)carbamimidoyl)-7-oxo-1,6-diazabicyclo[3.2.1]octan-6-yl hydrogen sulfate, (2S,5R)-7-oxo-2-(N-(thiazole-5-carbonyl)carbamimidoyl)-1,6-diazabicyclo[3.2.1]octan-6-yl hydrogen sulfate, (2S,5R)-2-(N-(4-cyanobenzoyl)carbamimidoyl)-7-oxo-1,6-diazabicyclo[3.2.1]octan-6-yl hydrogen sulfate, (2S,5R)-7-oxo-2-(N-(2-phenylthiazole-4-carbonyl)carbamimidoyl)-1,6-diazabicyclo[3.2.1]octan-6-yl hydrogen sulfate, (2S,5R)-7-oxo-2-(N-(thiazole-2-carbonyl)carbamimidoyl)-1,6-diazabicyclo[3.2.1]octan-6-yl hydrogen sulfate, (2S,5R)-2-(N-(4-fluorobenzoyl)carbamimidoyl)-7-oxo-1,6-diazabicyclo[3.2.1]octan-6-yl hydrogen sulfate, (2S,5R)-7-oxo-2-(N-(5-(trifluoromethyl)picolinoyl)carbamimidoyl)-1,6-diazabicyclo[3.2.1]octan-6-yl hydrogen sulfate, (2S,5R)-7-oxo-2-(N-(4-(trifluoromethyl)benzoyl)carbamimidoyl)-1,6-diazabicyclo[3.2.1]octan-6-yl hydrogen sulfate, (2S,5R)-7-oxo-2-(N-(thiazole-4-carbonyl)carbamimidoyl)-1,6-diazabicyclo[3.2.1]octan-6-yl hydrogen sulfate, (2S,5R)-7-oxo-2-(N-(pyrimidine-5-carbonyl)carbamimidoyl)-1,6-diazabicyclo[3.2.1]octan-6-yl hydrogen sulfate, (2S,5R)-7-oxo-2-(N-(pyrimidine-4-carbonyl)carbamimidoyl)-1,6-diazabicyclo[3.2.1]octan-6-yl hydrogen sulfate, (2S,5R)-2-(N-(5-fluoropyrimidine-2-carbonyl)carbamimidoyl)-7-oxo-1,6-diazabicyclo[3.2.1]octan-6-yl hydrogen sulfate, (2S,5R)-7-oxo-2-(N-(2-(trifluoromethyl)pyrimidine-5-carbonyl)carbamimidoyl)-1,6-diazabicyclo[3.2.1]octan-6-yl hydrogen sulfate, (2S,5R)-7-oxo-2-(N-(5-(trifluoromethyl)pyrimidine-2-carbonyl)carbamimidoyl)-1,6-diazabicyclo[3.2.1]octan-6-yl hydrogen sulfate, (2S,5R)-2-(N-(5-fluoropicolinoyl)carbamimidoyl)-7-oxo-1,6-diazabicyclo[3.2.1]octan-6-yl hydrogen sulfate, (2S,5R)-2-(N-(3,5-difluoropicolinoyl)carbamimidoyl)-7-oxo-1,6-diazabicyclo[3.2.1]octan-6-yl hydrogen sulfate, (2S,5R)-2-(N-(5,6-difluoropicolinoyl)carbamimidoyl)-7-oxo-1,6-diazabicyclo[3.2.1]octan-6-yl hydrogen sulfate, (2S,5R)-2-(N-(3,4-difluorobenzoyl)carbamimidoyl)-7-oxo-1,6-diazabicyclo[3.2.1]octan-6-yl hydrogen sulfate, (2S,5R)-7-oxo-2-(N-(3,4,5-trifluorobenzoyl)carbamimidoyl)-1,6-diazabicyclo[3.2.1]octan-6-yl hydrogen sulfate, (2S,5R)-2-(N-(1-methyl-1H-1,2,4-triazole-3-carbonyl)carbamimidoyl)-7-oxo-1,6-diazabicyclo[3.2.1]octan-6-yl hydrogen sulfate, (2S,5R)-2-(N-(isoxazole-3-carbonyl)carbamimidoyl)-7-oxo-1,6-diazabicyclo[3.2.1]octan-6-yl hydrogen sulfate, (2S,5R)-2-(N-(isoxazole-4-carbonyl)carbamimidoyl)-7-oxo-1,6-diazabicyclo[3.2.1]octan-6-yl hydrogen sulfate, (2S,5R)-2-(N-(1,2,4-oxadiazole-3-carbonyl)carbamimidoyl)-7-oxo-1,6-diazabicyclo[3.2.1]octan-6-yl hydrogen sulfate, (2S,5R)-2-(N-(1,2,5-oxadiazole-3-carbonyl)carbamimidoyl)-7-oxo-1,6-diazabicyclo[3.2.1]octan-6-yl hydrogen sulfate, (2S,5R)-2-(N-(4-methyl-4H-1,2,4-triazole-3-carbonyl)carbamimidoyl)-7-oxo-1,6-diazabicyclo[3.2.1]octan-6-yl hydrogen sulfate, (2S,5R)-2-(N-(1-methyl-1H-1,2,3-triazole-4-carbonyl)carbamimidoyl)-7-oxo-1,6-diazabicyclo[3.2.1]octan-6-yl hydrogen sulfate, (2S,5R)-7-oxo-2-(N-((S)-piperidine-2-carbonyl)carbamimidoyl)-1,6-diazabicyclo[3.2.1]octan-6-yl hydrogen sulfate, (2S,5R)-2-(N-((S)-1-acetylpiperidine-2-carbonyl)carbamimidoyl)-7-oxo-1,6-diazabicyclo[3.2.1]octan-6-yl hydrogen sulfate, (2S,5R)-7-oxo-2-(N-(3,4,5,6-tetrahydropyridazine-3-carbonyl)carbamimidoyl)-1,6-diazabicyclo[3.2.1]octan-6-yl hydrogen sulfate, (2S,5R)-2-(N-(1-methylazetidine-3-carbonyl)carbamimidoyl)-7-oxo-1,6-diazabicyclo[3.2.1]octan-6-yl hydrogen sulfate, (2S,5R)-2-(N-(1-acetylazetidine-3-carbonyl)carbamimidoyl)-7-oxo-1,6-diazabicyclo[3.2.1]octan-6-yl hydrogen sulfate, (2S,5R)-2-(N-(azetidine-3-carbonyl)carbamimidoyl)-7-oxo-1,6-diazabicyclo[3.2.1]octan-6-yl hydrogen sulfate, (2S,5R)-2-(N-(1-methylaziridine-2-carbonyl)carbamimidoyl)-7-oxo-1,6-diazabicyclo[3.2.1]octan-6-yl hydrogen sulfate, (2S,5R)-2-(N-(1-acetylaziridine-2-carbonyl)carbamimidoyl)-7-oxo-1,6-diazabicyclo[3.2.1]octan-6-yl hydrogen sulfate, (2S,5R)-2-(N-(aziridine-2-carbonyl)carbamimidoyl)-7-oxo-1,6-diazabicyclo[3.2.1]octan-6-yl hydrogen sulfate, or pharmaceutically acceptable salts of such compounds, or deuterated compounds of such compounds and salts.

2. The compound as recited in claim 1, which is selected from the following group of compounds:

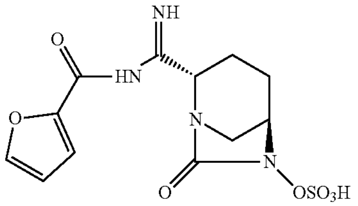

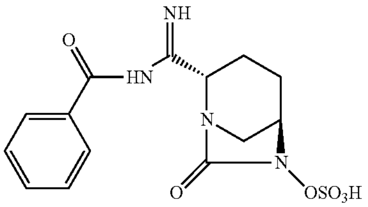

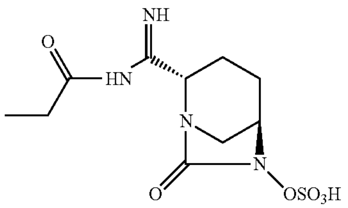

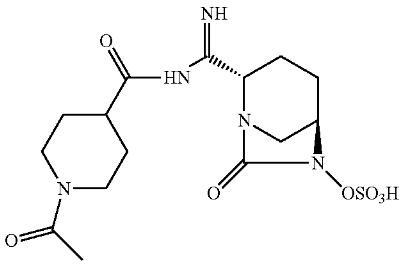

-continued
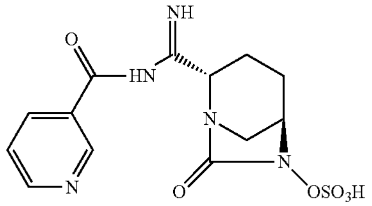
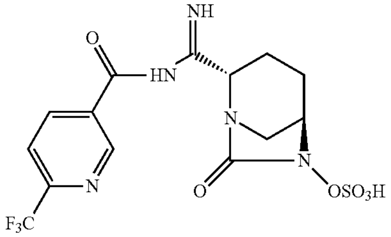
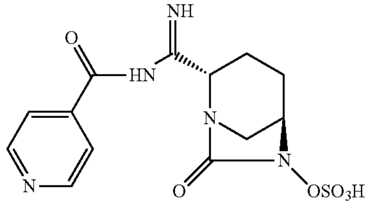
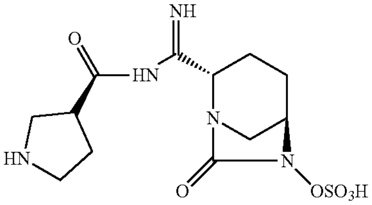
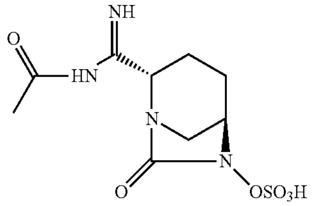
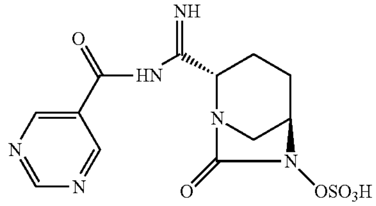
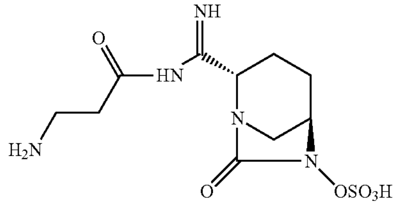
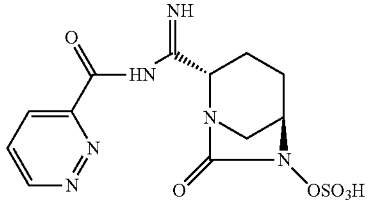
-continued
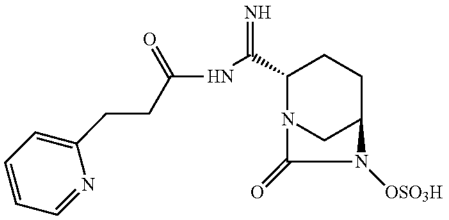
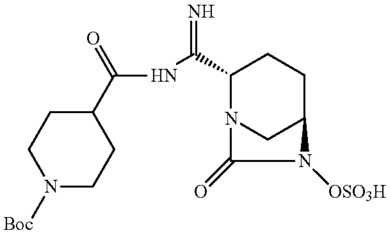
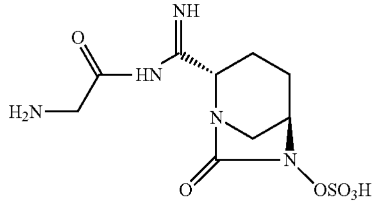
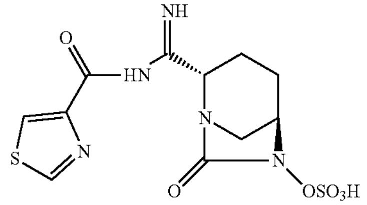
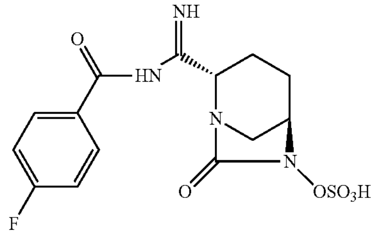
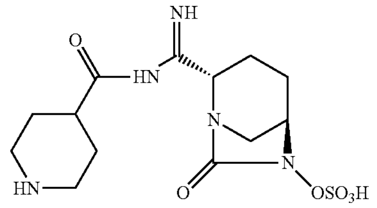
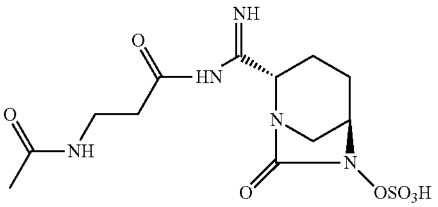
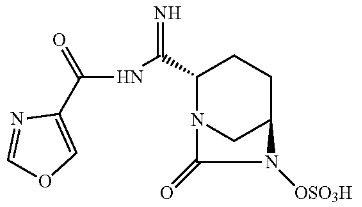

-continued
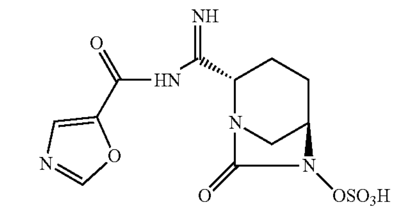
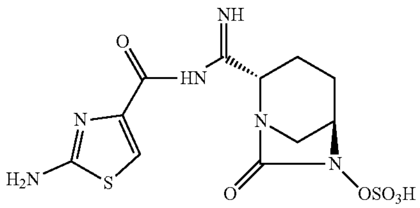
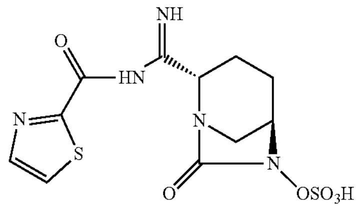
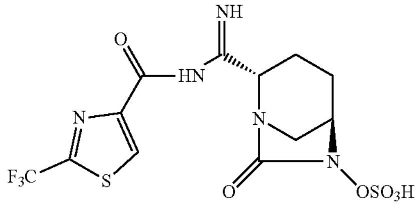
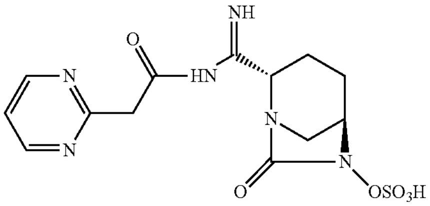
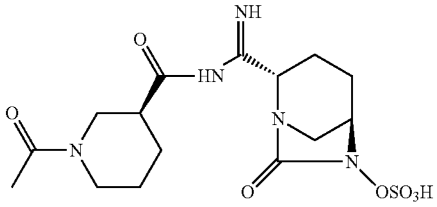
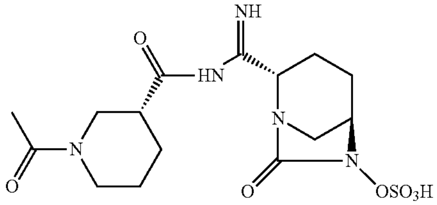
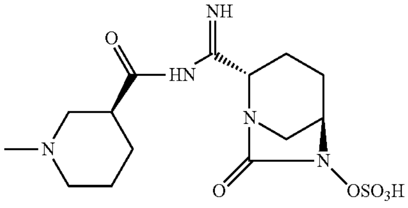
-continued
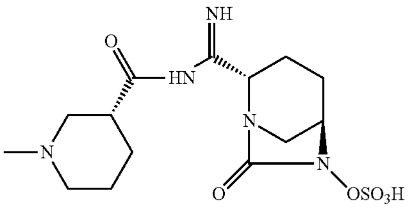
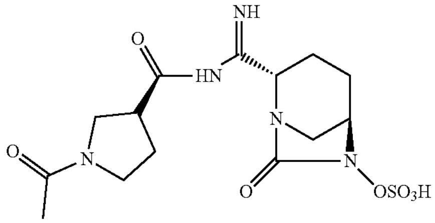
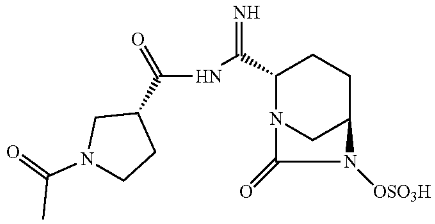
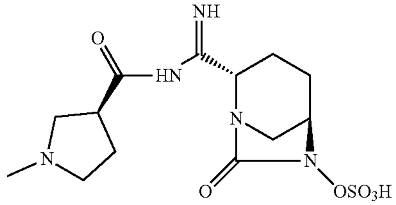
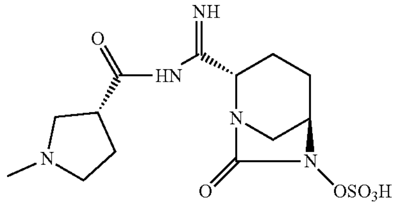
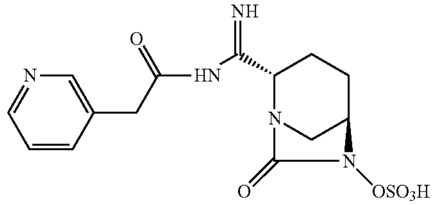
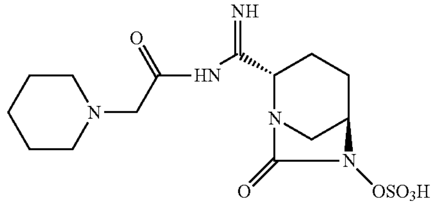
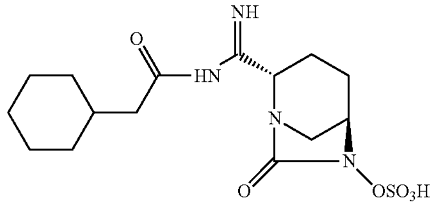

-continued
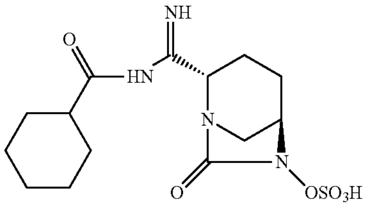
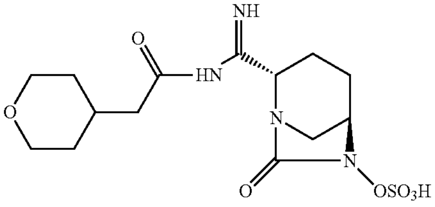
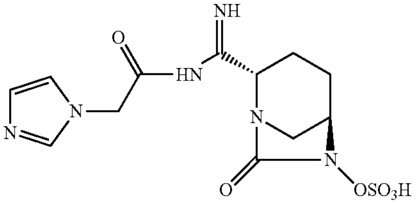
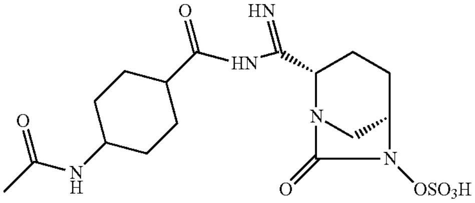
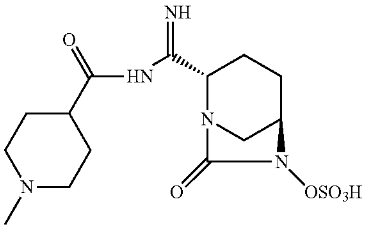
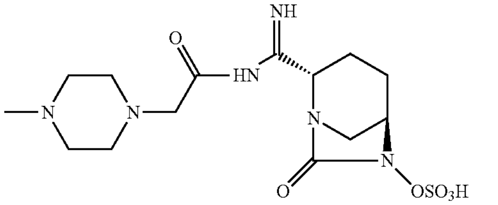
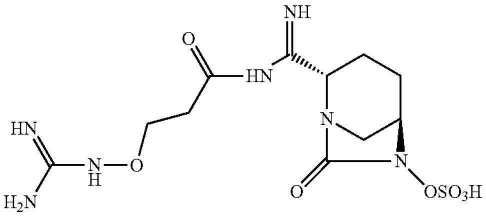
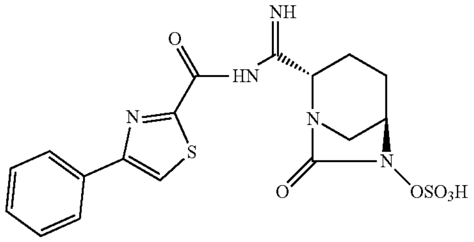
-continued
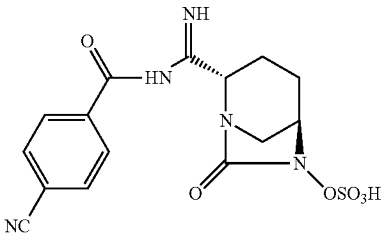
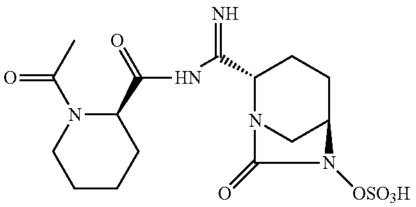
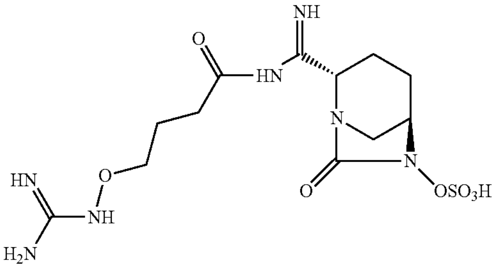
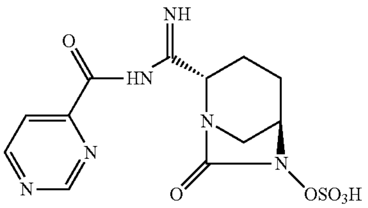
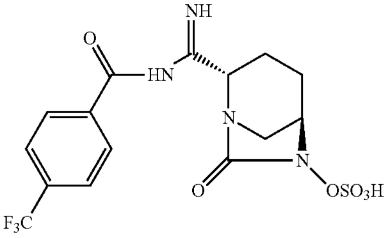
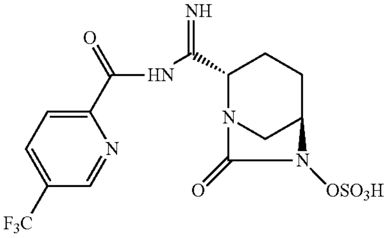
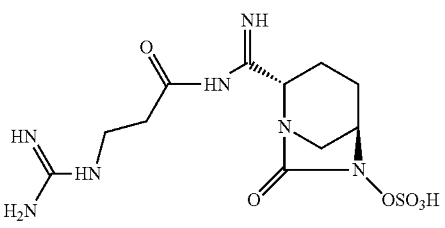

-continued

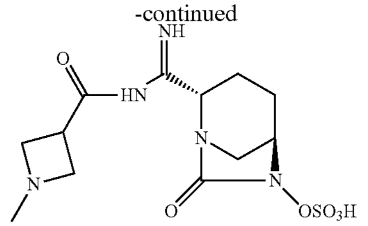

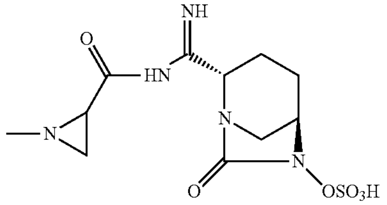

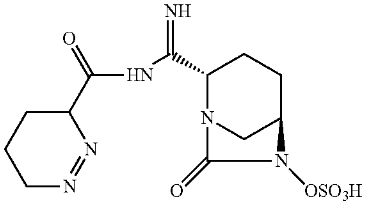

and pharmaceutically acceptable salts of such compounds, or deuterated compounds of such compounds and salts.

3. A method of treating a Gram-negative bacterial infection which comprises administering to a mammal in need thereof a pharmaceutical composition containing an antibacterially effective amount of a compound as recited in claim 1.

4. A pharmaceutical composition containing an antibacterially effective amount of, as an active ingredient, at least one compound as recited in claim 1, and a pharmaceutically acceptable carrier.

5. A pharmaceutical composition containing an antibacterially effective amount of, as an active ingredient, (i) at least one compound as recited in claim 1 and (ii) at least one β-lactam antibiotic, at least one salt of a β-lactam antibiotic, at least one hydrate of a β-lactam antibiotic or at least one prodrug of a β-lactam antibiotic, and a pharmaceutically acceptable carrier.

6. The pharmaceutical composition of claim 5, wherein a ratio of the weight of (i) the compound as recited in claim 4 to the weight of (ii) at least one β-lactam antibiotic, at least one salt of a β-lactam antibiotic, at least one hydrate of a β-lactam antibiotic or at least one prodrug of a β-lactam antibiotic, is in the range of 1:30 to 30:1.

7. A pharmaceutical composition containing an antibacterially effective amount of, as an active ingredient, (i) at least one compound as recited in claim 1 and (ii) at least one antibiotic, at least one salt of an antibiotic, at least one hydrate of an antibiotic or at least one prodrug of an antibiotic, and a pharmaceutically acceptable carrier.

8. The pharmaceutical composition of claim 7, wherein a ratio of the weight of (i) the compound as recited in claim 1 to the weight of (ii) at least one antibiotic, at least one salt of an antibiotic, at least one hydrate of an antibiotic or at least one prodrug of an antibiotic, is in the range of 1:30 to 30:1.

9. A method of treating a Gram-negative bacterial infection, which comprises administering to a mammal in need thereof a combination of (i) an antibacterially effective amount of a compound as recited in claim 1 and (ii) an effective amount of at least one β-lactam antibiotic, at least one salt of a β-lactam antibiotic, at least one hydrate of a β-lactam antibiotic or at least one prodrug of a β-lactam antibiotic.

10. The method of claim 9, wherein a ratio of the weight of (i) the compound as recited in claim 1 to the weight of (ii) at least one β-lactam antibiotic, at least one salt of a β-lactam antibiotic, at least one hydrate of a β-lactam antibiotic or at least one prodrug of a β-lactam antibiotic, is in the range of 1:30 to 30:1.

11. A method of treating a Gram-negative bacterial infection, comprising administering to a mammal in need thereof a combination of (i) an antibacterially effective amount of a compound as recited in claim 1 and (ii) an effective amount of at least one antibiotic, at least one salt of an antibiotic, at least one hydrate of an antibiotic or at least one prodrug of an antibiotic.

12. The method of claim 11, wherein a ratio of the weight of (i) the compound as recited in claim 1 to the weight of (ii) at least one antibiotic, at least one salt of an antibiotic, at least one hydrate of an antibiotic or at least one prodrug of an antibiotic, is in the range of 1:30 to 30:1.

13. A molecular complex comprising a compound as recited in claim 1 and at least one solvent wherein the solvent comprises water.

* * * * *